US007956216B2

(12) United States Patent
Lessene et al.

(10) Patent No.: US 7,956,216 B2
(45) Date of Patent: Jun. 7, 2011

(54) ALPHA-HELICAL MIMETICS

(75) Inventors: Guillaume Laurent Lessene, Coburg (AU); Jonathan Baell, Ivanhoe (AU)

(73) Assignee: The Walter and Eliza Hall Institute of Medical Research, Parkville, Victoria (AU)

( * ) Notice: Subject to any disclaimer, the term of this patent is extended or adjusted under 35 U.S.C. 154(b) by 975 days.

(21) Appl. No.: 11/642,591

(22) Filed: Dec. 21, 2006

(65) Prior Publication Data

US 2008/0153802 A1    Jun. 26, 2008

(51) Int. Cl.
*C07C 229/00* (2006.01)
*A61K 31/195* (2006.01)

(52) U.S. Cl. .......... 562/426; 560/34; 548/250; 548/251; 514/381; 514/562; 514/563; 514/564

(58) Field of Classification Search ............... 560/34; 548/250, 251; 514/381, 563, 564, 562; 562/426
See application file for complete search history.

(56) References Cited

U.S. PATENT DOCUMENTS

| | | | | |
|---|---|---|---|---|
| 4,016,282 A * | 4/1977 | Konig et al. | ................. | 514/197 |
| 4,298,605 A * | 11/1981 | Oi et al. | ........................ | 514/204 |
| 2003/0195209 A1 | 10/2003 | Dellaria et al. | | |
| 2004/0152743 A1* | 8/2004 | Schoenafinger et al. | ..... | 514/357 |

OTHER PUBLICATIONS

RN 106135-34-6, 1987.*
Carter et al, John Wiley & Sons, Chemotherapy of Cancer, 1981, 362-365.*
Driver, et al., "Further Studies on Bisnorpenicillins", The Journal of Antibiotics, Apr. 1985, pp. 550-553, vol. 38, No. 4.
Ohi, et al., "Semisynthetic B-Lactam Antibiotics. IV. Synthesis and Antibacterial . . . or Its Acetate", Chem. Pharm. Bull., 1987, pp. 1903-1909, vol. 35 (5).
Ohi, et al "Semisynthetic B-Lactam Antibiotics I. Synthesis and Antibacterial . . . Catechol Moieties", The Journal of Antibiotics, Feb. 1986, pp. 230-241, vol. 39 (2).
Chugai Pharmaceutical KK, Alpha-benzoyl:ureido:phenylacetic acid cpds . . . antimicrobial penicillin(s), Abstract, pp. 1-2.
Adams, et al., "Highly Specific in Vivo Tumor Targeting by Monovalent . . . Sincle-Chain Fv1", Cancer Research, 1993, pp. 4026-4034, vol. 53.
Baell, et al., "Prospects for targeting the Bcl-2 family of proteins to develop novel cytotoxic drugs", Biochemical Pharmacology, 2002, pp. 851-863, vol. 64.
Bouillet, et al., "Degenerative Disorders Caused by Bcl-2 Deficiency Prevented by Loss of Its BH3-Only antagonist Bim", Developmental Cell, 2001, pp. 645-653, vol. 1.
Brewis, et al., "Particle Assembly Incorporating a VP22-BH3 Fusion Protein . . . and Apoptosis", Molecular Therapy, 2003, pp. 262-270, vol. 7 (2).
Cory, et al., "The BCL2 Family: Regulators of the Cellular Life-or-Death Switch", Nature Reviews/Cancer, 2002, pp. 647-655, vol. 2.

Cumber, et al., "Comparative Stabilities in Vitro and In Vivo of a Recombinant . . . and a bisFvCys Conjugate", The Journal of Immunology, 1992, pp. 120-126, vol. 149.
Davies, et al., "'Camelising'" human antibody fragments: NMR studies on VH domains, FEBS Letters, 1994, pp. 285-290, vol. 339.
Dearden, "Monolclonal Antibody Therapy of Haematological Malignancies", Therapy Review, Bic drugs, 2002, pp. 283-301, vol. 16(4).
Dunican, et al., "Designing Cell-Permeant Phosphopeptides to Modulate Intracellular Signaling Pathways", Biopolymers (Peptide Science), 2001, pp. 45-60, vol. 60.
Dharap, et al., "Targeted Proapoptotic LHRH-BH3 Peptide", Pharmaceutical Research, 2003, pp. 889-896, vol. 20 (6).
Galfre, et al., "Antibodies to major histocompatibility antigens produced by hybrid cell lines", Nature, 1977, pp. 550-552, vol. 266.
Glockshuber, et al., "A Comparison of Strategies to Stabilize Immunoglobulin Fv-Fragments", Biochemistry, 1990, pp. 1362-1367, vol. 29.
Goulet, et al., "Conjugation of Blocked Ricin to an Anti-CD19 Monoclonal Antibody . . . and CD19 Internalization", Blood, 1997, pp. 2364-2375, vol. 90(6).
Hamers-Casterman, et al., "Naturally occurring antibodies devoid of light chains", Nature, 1993, pp. 446-448, vol. 363.
Jue, et al., "Addition of Sulfhydryl Groups to Escherichia . . . (Methyl 4-Mercaptobutyrimidate)", Iminothiolane Modification of Ribosomes, 1978, pp. 5399-5406, vol. 17(25).
Kohler, et al., "Continuous cultures of fused cells secreting antibody of predefined specificity", Nature, 1975, pp. 495-497, vol. 256.
Kostelny, et al., "Formation of a Bispecific Antibody by the Use of Leucine Zippers", The Journal of Immunology, 1992, pp. 1547-1553, vol. 148(5).
Krebber, et al., "Reliable cloning of functional antibody variable domains from hybridomas . . . phage display system", Journal of Immunological Methods, 1997, pp. 35-55, vol. 201.
Ku, et al., "Alternate Protein Frameworks for Molecular Recognition", Proc. Natl. Acad. Sci., 1995, pp. 6552-6556, vol. 92.
Letai et al., "Distinct BH3 domains either sensitize or activate mitochondrial . . . cancer therapeutics", Cancer Cell, 2002, pp. 183-192, vol. 2.
Ludwig, et al., "Monoclonal antibody therapeutics and apoptosis", Oncogene, 2003, pp. 9097-9106, vol. 22.
Marks, et al., "Targeted Therapy with an Amphipathic . . . Lymphocytic Leukemia Cells", Blood, 2003, pp. 1, vol. 247.
Pack et al., "Miniantibodies: Use of Amphipathis Helices . . . with High Avidity in *Escherichia coli*", Biochemistry, 1992, pp. 1579-1584, vol. 31.
Patani, et al., "Bioisosterism: A Rational Approach in Drug Design", Chem. Rev., 1996, pp. 3147-3176, vol. 96.
Petros, et al., Rationale for Bcl-Xl/Bad Peptide Complex Formation from Structure, Mutagenesis, and Biophysical Studies, Protein Science, 2000, pp. 2528-2534, vol. 9.

(Continued)

*Primary Examiner* — Shailendra Kumar
(74) *Attorney, Agent, or Firm* — Perkins Coie LLP

(57) ABSTRACT

Benzoyl urea derivatives that are alpha helical peptides mimetics that mimic BH3-only proteins, compositions containing them, their conjugation to cell-targeting-moieties, and their use in the regulation of cell death are disclosed. The benzoyl urea derivatives are capable of binding to and neutralizing pro-survival Bcl-2 proteins. Use of benzoyl urea derivatives in the treatment and/or prophylaxis of diseases or conditions associated with deregulation of cell death are also described.

28 Claims, No Drawings

OTHER PUBLICATIONS

Reiter, et al., "Improved Binding and Antitumor Activity of a Recombinant . . . of the Fv Fragment", The Journal of Biological Chemistry, 1994, pp. 18327-18331, vol. 26(28).

Reiter, et al., "Stabilization of the Fv Fragments in Recombinant Immunotixins . . . Framework Regions", Biochemistry, 1994, pp. 5451-5459, vol. 33.

Reiter, at al., "Antitumor Activity and Pharmacolienetics in Mice of a . . . Disulfide-stabilized Fv Fragments", Cancer Research, 1994, pp. 2714-2718, vol. 54.

Sapra, et al., "Internalizing Antibodies Are Necessary for Improved . . . of Antibody-targeted Liposomal Drugs", Cancer Research, 2002, pp. 7190-7194, vol. 62.

Sattler, et al., Structure of Bcl-xl-Bak Peptide Complex: . . . Regulators of Apoptosis, Science, 1997, pp, 983-986, vol. 275.

Schimmer, et al., The BH3 domain of BAD fused to the Antennapedia peptide . . . independent of Bcl-2, Cell Death and Differnitation, 2001, pp. 725-733, vol. 8.

Shangary, et al., "Peptides Derived from BH3 of Bcl-2 Family Members: A comparative . . . and activation of Cell Death", Biochemistry, 2002, pp. 9485-9495, vol. 41.

Snyder, et al., Treatment of Terminal Peritoneal Carcinomatosis by a . . . p53-Activating Peptide, PLOS Biology, 2004, pp. 0186-0193, vol. 2(2).

Thorpe, et al., "New Coupling Agents for the Synthesis fo Immunotixins . . . with Improved Stability in Vivo", Cancer Research, 1987, pp. 5924-5931, vol. 47.

Uckun, et al., "Biotherapy of B-cell percursor leukemia by targeting genistein to . . . kinases" , Science, 1995, pp. 886-891, vol. 267.

Wang, et al., "Polyspermine-Ribonuclease Prepared by Cross-linkage with Dimethyl Suberimidate", Biochemistry, 1977, pp. 2937-2942, vol. 16(13).

Wang, et al., "Generation and Characterization of an Anti-CD19 Single-Chain . . . disulfide-Linked dgRTA", Bioconjugate Chem., 1997, pp. 878-884, vol. 8.

Wang, et al., "Cell Permeable Bcl-2 Binding Peptides: A Chemical . . . Induction in Tumor Cells", Cancer Research, 2000, pp. 1498-1502, vol. 60.

Ward, et al., "Binding Activities of a Repertoire of Single Immunoglobulin . . . from *Escherichia coli*", Letter to Nature, 1989, pp. 544-546, vol. 341.

Webber, et al., "Preparation and Characterization of a Disulfide-Stabilized . . . its Single-Chain Analog", Molecular Immunology, 1995, pp. 249-258, vol. 32(4).

Worrell, et al., "Effect of Linkage Variation on Pharmacokinetics of Ricin . . . Conjugates in Normal Rats", Anti-Cancer Drug Design, 1986, pp. 179-188, vol. 1.

Yin, at al., "Terephthalamide Derivatives as Mimetics of . . . Target Bcl-xL Protein", Bioorganic & Medicinal Chemistry Letters, 2004, pp. 1375-1379, vol. 14.

Yoshitake, et al., "Conjugation of Glucose Oxidase from . . . Ester of N-(4-Carboxycyclohexylmethyl)-Maleimide", Eur. J. Biochem, 1979, pp. 395-399, vol. 101.

Brunner et al. "Enanthioselective Catalysis; 123:[1] Octaaldehyde Type Chelating Ligands—A Divergent Synthesis Approach to Easily Tunable Expanded Ligands for Enantioselective Catalysis"; Synthesis, Dec. 1998, pp. 1742-1749.

Carlsson et al. "Protein Thiolation and Reversible Protein-Protein Conjugation"; Biochem, vol. 173, 1978, pp. 723-737.

Chen et al. "An Efficient and Scalable Synthesis of Methyl 3-Hydroxymethylbenzoate"; OPPI Briefs, vol. 32, Nov. 4, 2000, pp. 381-384.

Egle et al. "[465] *Bim* Acts as a Haploinsufficient and Anti-Leukemic Turner Suppressor in Myc-Induced Lymphoma"; Dec. 8, 2003 file://C:\Documents and Settings\KXG\Local Settings\Temporary Internet Files\OLK . . . , M.

Green et al. "A matter of life and death"; Cancer Cell, vol. 1, Feb. 2002, pp. 19-30.

Hinds et al. "The structure of Bcl-w reveals a role for the C-terminal residues in modulating biological activity"; The EMBO Journal, vol. 22, 2003, pp. 1497-1507.

Horner et al. "Absolute Kinetics of Amidyl Radical Reactions"; American Chemical Society, vol. 120, 1998, pp. 7738-7748.

Kaufmann et al. "Programmed cell death: alive and well in the new millennium"; Trends in Cell Biology, vol. 11, No. 12, Dec. 2001; pp. 526-534.

Liu et al. "The Structure of a $Bcl-x_L$/Bim Fragment Complex: Implications for Bim Function"; Immunity, vol. 19, Sep. 2003, pp. 341-352.

Muchmore et al. "X-ray and NMR structure of human $Bcl-x_L$, and inhibitor of programmed cell death"; Nature; vol. 381, May 1996, pp. 335-341.

Negishi et al. "Palladium-Catalyzed Alkynylation"; American Chemical Society, vol. 103, 2003, pp. 1979-2017.

Oltersdorf et al. "An inhibitor of Bcl-2 family proteins induces regression of solid tumours"; Nature, vol. 435, Jun. 2, 2005, pp. 677-681.

Poznansky et al. "Insulin: Carrier Potential for Enzyme and Drug Therapy"; Science, New Series, vol. 223, No. 4642, Mar. 23, 1984, pp. 1304-1306.

Seko et al. "Structure-Activity Study of L-Amino Acid-Based N-Type Calcium Channel Blockers"; Bioorganic & Medicinal Chemistry 11, 2003, pp. 1901-1913.

van Herwijnen et al. "*Meta* Selectivity in the Friedel-Crafts Reaction Induced by a Faujasite-Type Zeolite"; American Chemical Society, vol. 66, 2001, pp. 2874-2876.

Winter et al. "Man-made antibodies"; Nature, vol. 349, Jan. 24, 1991, pp. 293-299.

Zhang "Apoptosis-based anticancer drugs"; Nature Reviews, vol. 1, Feb. 2002, pp. 101-102.

* cited by examiner

ALPHA-HELICAL MIMETICS

This application is a 371 of PCT/AU2005/000968, filed on Jul. 1, 2005, which claims priority to Australian Patent Application No. 60/584,473, filed on Jul. 2, 2004, the entireties of which are hereby incorporated by reference.

FIELD OF THE INVENTION

The invention relates generally to compounds that mimic alpha-helical sequences of peptides and proteins, to compositions containing them and to their use. In particular, the invention relates to compounds that mimic the alpha-helical sequences of BH3-only proteins and are capable of binding to and neutralising pro-survival Bcl-2 proteins. The invention also relates to processes of preparing the compounds that mimic alpha-helical portions of peptides and proteins, and to the use of such compounds in the regulation of cell death and the treatment and/or prophylaxis of diseases or conditions associated with the deregulation of cell death.

BACKGROUND OF THE INVENTION

Bibliographical details of various publications referred to in this specification are collected at the end of the description.

The reference to any prior art in this specification is not, and should not be taken as, an acknowledgment or any form of suggestion that that prior art forms part of the common general knowledge in Australia.

Apoptosis is now recognized as an essential biological process in the tissue homeostasis of all living species [Kaufmann and Hengartner, 2001]. In mammals in particular, it has been shown to regulate embryonic development. Later in life, cell death is a default mechanism that removes potentially dangerous cells (e.g. cells carrying cancerous defects). Several apoptotic pathways have been uncovered and one of the most important involves the Bcl-2 family of proteins [Cory and Adams, 2002]. The structural homology domains BH1 to BH4 are characteristic of this family. Further classification into of three subfamilies depends on how many of these homology domains a protein contains and on its biological activity (pro- or anti-apoptotic).

The first subgroup contains proteins having all 4 homology domains BH1 to BH4. Their general effect is anti-apoptotic thus preserving the cell from starting a cell death process. Proteins such as Bcl-2, Bcl-w and BCl-$x_L$ are members of this first subgroup. Proteins belonging to the second subgroup have a pro-apoptotic effect and contain the three homology domains BH1 to BH3. The two main representative proteins of this second subgroup are Bax and Bak. Finally, the third subgroup is composed of protein containing only the BH3 domain and members of this subgroup are usually referred to as "BH3-only proteins". Their biological effect on the cell is pro-apoptotic. Bim, Bad, Bmf, and Bid are examples of this third subfamily of proteins.

The delicate balance between the three subgroups is the key to homeostasis of the cells. Recent studies have tried to elucidate the mechanisms involving the Bcl-2 family of proteins that allow a cell to undergo programmed cell death upon receiving intra- or extra-cellular signal. Such a signal induces the activation (post translational or transcriptional) of BH3 only proteins. These proteins are the primary inducers of the cascade that leads to cell death. The BH3-only proteins mainly interact with the Bcl-2 subgroup and stop proteins such as Bcl-2, BCl-$x_L$ or Bcl-w from inhibiting the Bax/Bak subgroup. These later proteins are either already anchored to the mitochondrial membrane or migrate to this membrane. Their activation leads to membrane swelling, release of cytochrome C and downstream activation of effector caspases.

As already mentioned the balance between these proteins is essential to the correct cellular response to various stimuli. Any perturbation of this balance will instigate or worsen major diseases. Thus apoptosis perturbations have been shown to be at the origin of important diseases such as neurodegenerative conditions (up-regulated apoptosis [Bouillet et. al., 2001]) for example, Alzheimer's disease, or proliferative diseases (down-regulated apoptosis [Cory and Adams, 2002]) for example, cancer and autoimmune diseases.

The discovery that several proteins of the Bcl-2 family are involved in the onset of cancerous malignancy has unveiled a completely novel way of targeting this still elusive disease [Baell and Huang, 2002]. It has been shown in particular that pro-survival proteins such as Bcl-2 are over-expressed in many cancer types (see Table 1) [Zhang, 2002]. The effect of this deregulation is the survival of altered cells which would have undergone apoptosis in normal conditions. The repetition of these defects associated with unregulated proliferation is thought to be the starting point of cancerous evolution [Green and Evan, 2002]. In other experiments, results have shown that BH3-only proteins can act as tumor suppressors when expressed in diseased animals [Egle et. al., 2003].

TABLE 1

| Bcl-2 over-expression in cancer | |
|---|---|
| Cancer type | Bcl-2 over-expression |
| Hormone-refractory prostate cancer | 90-100% |
| Malignant melanoma | 90% |
| Oestrogen-receptor-positive breast cancer | 80-90% |
| Non-Hodgkin's lymphoma | 50% |
| Colon Cancer | 30-50% |
| Chronic lymphocytic leukaemia | 25-50% |

These findings as well as numerous others have made possible the emergence of new concept in anti-cancer strategies and drug discovery. Indeed, if an entity mimicking the effect of BH3-only proteins were able to enter the cell and overcome the pro-survival protein over-expression, it could be possible to reset the apoptotic process [Baell and Huang, 2002]. This strategy presents several advantages, it does not involve the use of DNA damaging agents that are prescribed in classical chemotherapies therefore avoiding undesirable side effects, and it would also alleviate the problem of drug resistance which is usually a consequence of apoptotic deregulation (abnormal survival).

A considerable effort has been made to understand the structural details of the key interactions between BH3-only proteins and the pro-survival subgroup. Fesik and co-workers have demonstrated in the case of the dimer Bad/BCl-$x_L$ the importance of some structural elements [Muchmore et. al., 1996; Sattler et. al., 1997 and Petros et. al., 2000]:

Binding occurs between a hydrophobic groove located on Bcl-$x_L$ and the BH3 domain of Bad.

The BH3-only protein Bad adopts a helix structure upon binding to the hydrophobic groove of BCl-$x_L$.

Four hydrophobic amino-acids of the BH3 domain located at i, i+3, i+7 and i+11 intervals are essential to the binding of Bad to Bcl-$x_L$ and interact in four hydrophobic pockets situated in the Bcl-$x_L$ binding groove. Moreover, studies of members of the BH3-only subgroups have shown that these four hydrophobic amino-acids are conserved through the subgroup.

Recently the structure of the pro-survival protein Bcl-w [Hinds et. al., 2003] and the structure of BH3-only protein Bim in interaction with Bcl-$x_L$ [Liu et. al., 2003] have been published. This latter structure confirms the findings of the Bad/Bcl-$x_L$ interaction.

A potential target for new drug therapy is small molecules that mimic the interaction between a BH3-only protein and the Bcl-2 family of proteins.

The alpha-helix is a common recognition motif displayed in peptides and proteins. Alpha-helical sequences are often involved in protein-protein interactions, such as enzyme-receptor and antibody-receptor interactions. Targeting these protein-protein interactions is now recognised as one of the major challenges in drug discovery.

One of the difficulties with the development of drug candidates is that short peptide sequences, that are alpha-helical when part of a protein structure, do not necessarily maintain their alpha-helical conformation when isolated from the protein. Furthermore, peptide sequences are often not suitable drug candidates as they readily undergo hydrolysis under biological conditions and upon exposure to proteolytic enzymes making it difficult to deliver them to the desired site of action.

Small molecules that mimic alpha-helical peptide sequences and act as scaffolds for placing substituents in positions that simulate the side chains of amino acids in alpha-helical sequences in proteins are potential drug candidates.

One such small molecule alpha-helical peptidomimetic scaffold is the terephthalamide scaffold developed by Hamilton and co-workers (Yin and Hamilton, 2004). The terephthalamide scaffold was able to provide substituents that mimic the i, i+3 and i+7 side chains of an alpha-helical sequence. However, the terephthalamide scaffolds require a complex multistep synthesis and are not readily adapted to the easy preparation of analogues.

There is a need for small molecule scaffolds which may be easily synthesised with a versatile array of substituents and which mimic the alpha-helical sequences of proteins.

SUMMARY OF THE INVENTION

The present invention is predicated in part on the discovery that benzoylurea derivatives provide an alpha-helical peptidomimetic scaffold which is able to interact with a Bcl-2 protein. This discovery has been reduced to practice in novel compounds, compositions containing them and in methods for their preparation and use, as described hereafter.

DETAILED DESCRIPTION OF THE INVENTION

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

In a first aspect of the invention, there is provided a compound of formula (I):

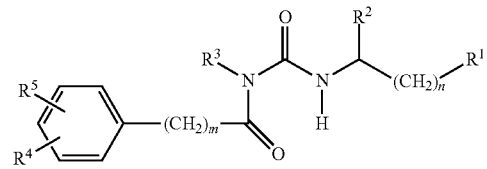

wherein
$R^1$ is selected from $CO_2H$ or a carboxylic acid or carboxylate bioisostere;
$R^2$ is selected from an amino acid side chain, cycloalkyl, cycloalkenyl, aryl, heterocyclyl, heteroaryl and a group

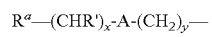

wherein A is a covalent bond or is selected from O, S, SO, $SO_2$ and $NR^6$, $R^a$ is H, cycloalkyl, cycloalkenyl, aryl, heterocyclyl, heteroaryl or $R^b$ where $R^b$ is

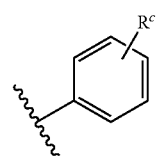

and $R^c$ is selected from heteroaryl, aryl, aryl($C_{2-6}$alkenyl), aryl($C_{2-6}$alkynyl), heteroaryl($C_{2-6}$alkenyl) and heteroaryl ($C_{2-6}$alkynyl), R' is H or $C_{1-6}$alkyl, x and y are independently 0 or an integer from 1 to 6 provided that the sum of x and y is 1 to 6;
$R^3$ is selected from $C_{1-6}$alkyl, $C_{2-6}$alkenyl, $C_{2-6}$alkynyl, cycloalkyl, cycloalkenyl, aryl, heterocyclyl, heteroaryl and a group

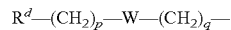

wherein W is selected from a covalent bond, O, S and $NR^6$, $R^d$ is selected from H, cycloalkyl, cycloalkenyl, aryl, heterocyclyl and heteroaryl; p is an integer from 1 to 6, q is 0 or an integer from 1 to 5 provided that the sum of p and q is 1 to 6;
$R^4$ is selected from $C_{1-6}$alkyl, $C_{2-6}$alkenyl, $C_{2-6}$alkynyl, cycloalkyl, $C_{1-6}$alkyloxy, $C_{2-6}$alkenyloxy, $C_{2-6}$alkynyloxy, cycloalkoxy, $C_{1-6}$alkylthio, $C_{2-6}$alkenylthio, $C_{2-6}$alkynylthio, cycloalkylthio, halogen, aryl, aryl($C_{1-6}$alkyl)-, aryl($C_{2-6}$alkenyl), aryl($C_{2-6}$alkynyl), heterocyclyl, heterocyclyl($C_{1-6}$alkyl)-, heterocyclyl($C_{2-6}$alkenyl), heterocyclyl($C_{2-6}$alkynyl), heteroaryl, heteroaryl($C_{1-6}$alkyl)-, heteroaryl($C_{2-6}$ alkenyl) and heteroaryl($C_{2-6}$alkynyl);
$R^5$ is selected from H, halogen, $C_{1-6}$alkyl, $C_{2-6}$alkenyl, $C_{2-6}$alkynyl, $C_{1-6}$alkyloxy, $C_{2-6}$alkenyloxy, $C_{2-6}$alkynyloxy, $C_{1-6}$alkylthio, $C_{2-6}$alkenylthio, $C_{2-6}$alkynylthio, CN and $C(R^7)_3$ or when $R^5$ is in the 2- or 5-position, $R^5$ and $R^3$ taken together may form a 5 to 10 membered ring;
$R^6$ is selected from H, $C_{1-6}$alkyl, $C_{2-6}$alkenyl and $C_{2-6}$alkynyl;
Each $R^7$ is independently selected from H and halogen;
m is 0 or an integer from 1 to 6; and
n is 0 or an integer from 1 to 3;
wherein each alkyl, alkenyl, alkynyl, cycloalkyl, aryl, heterocyclyl and heteroaryl is optionally substituted with one or more optional substituents;
and pharmaceutically acceptable salts and prodrugs thereof;
with the proviso that when $R^1$ is COOH, $R_2$ is $C_6H_5$—$CH_2S$—$CH_2$—, $R^4$ is 3-$C_6H_5$ and $R^5$ is H, $R_3$ is not $CH_3CH_2$—.

In a second aspect of the invention, there is provided a compound of formula (Ia):

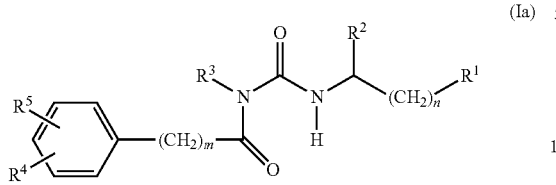

wherein
$R^1$ is selected from $CO_2H$ or a carboxylic acid or carboxylate bioisostere;
$R^2$ is selected from an amino acid side chain, cycloalkyl, cycloalkenyl, aryl, heterocyclyl, heteroaryl and a group

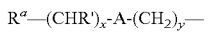

wherein A is a covalent bond or is selected from O, S, SO, $SO_2$ or $NR^6$, $R^a$ is H, cycloalkyl, cycloalkenyl, aryl, heterocyclyl, heteroaryl or $R^b$ where $R^b$ is

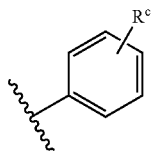

and $R^c$ is selected from heteroaryl, aryl, aryl($C_{2-6}$alkenyl), aryl($C_{2-6}$alkynyl), heteroaryl($C_{2-6}$alkenyl) and heteroaryl ($C_{2-6}$alkynyl), R' is H or $C_{1-6}$alkyl, x and y are independently 0 or an integer from 1 to 6 provided that the sum of x and y is 1 to 6;
$R^3$ is selected from $C_{3-6}$alkyl, $C_{2-6}$alkenyl, $C_{2-6}$alkynyl, cycloalkyl, cycloalkenyl, aryl, heterocyclyl, heteroaryl and a group

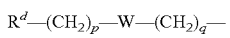

wherein W is selected from a covalent bond, O, S and $NR^6$, $R^d$ is selected from H, cycloalkyl, cycloalkenyl, aryl, heterocyclyl and heteroaryl; p is an integer from 1 to 6, q is 0 or an integer from 1 to 5 provided that the sum of p and q is 1 to 6;
$R^4$ is selected from $C_{1-6}$alkyl, $C_{2-6}$alkenyl, $C_{2-6}$alkynyl, cycloalkyl, $C_{1-6}$alkyloxy, $C_{2-6}$alkenyloxy, $C_{2-6}$alkynyloxy, cycloalkoxy, $C_{1-6}$alkylthio, $C_{2-6}$alkenylthio, $C_{2-6}$alkynylthio, cycloalkylthio, halogen, aryl, aryl($C_{1-6}$alkyl)-, aryl($C_{2-6}$alkenyl), aryl($C_{2-6}$alkynyl), heterocyclyl, heterocyclyl($C_{1-6}$alkyl)-, heterocyclyl($C_{2-6}$alkenyl), heterocyclyl($C_{2-6}$alkynyl), heteroaryl, heteroaryl($C_{1-6}$alkyl)-, heteroaryl($C_{2-6}$ alkenyl) and heteroaryl($C_{2-6}$alkynyl);
$R^5$ is selected from H, halogen, $C_{1-6}$alkyl, $C_{2-6}$alkenyl, $C_{2-6}$alkynyl, $C_{1-6}$alkyloxy, $C_{2-6}$alkenyloxy, $C_{2-6}$alkynyloxy, $C_{1-6}$alkylthio, $C_{2-6}$alkenylthio, $C_{2-6}$alkynylthio, CN and $C(R^7)_3$ or when $R^5$ is in the 2- or 5-position, $R^5$ and $R^3$ taken together may form a 5 to 10 membered ring;
$R^6$ is selected from H, $C_{1-6}$alkyl, $C_{2-6}$alkenyl and $C_{2-6}$alkynyl;
Each $R^7$ is independently selected from H and halogen;
m is 0 or an integer from 1 to 6; and
n is 0 or an integer from 1 to 3;
wherein each alkyl, alkenyl, alkynyl, cycloalkyl, cycloalkenyl, aryl, heterocyclyl and heteroaryl is optionally substituted with one or more optional substituents; and pharmaceutically acceptable salts and prodrugs thereof.

In another aspect of the invention, there is provided a compound of formula (Ib):

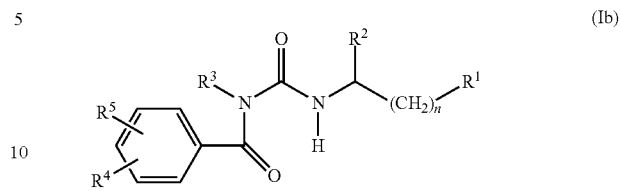

wherein
$R^1$ is selected from $CO_2H$ or a carboxylic acid or carboxylate bioisostere;
$R^2$ is selected from an amino acid side chain, cycloalkyl, cycloalkenyl, aryl, heterocyclyl, heteroaryl and a group

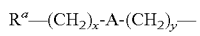

wherein A is a covalent bond or is selected from O, S, SO, $SO_2$ and $NR^6$, $R^a$ is cycloalkyl, cycloalkenyl, aryl, heterocyclyl, heteroaryl or $R^b$ where $R^b$ is

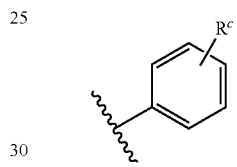

and $R^c$ is selected from heteroaryl, aryl, aryl($C_{2-6}$alkenyl), aryl($C_{2-6}$alkynyl), heteroaryl($C_{2-6}$alkenyl) and heteroaryl ($C_{2-6}$alkynyl), x and y are independently 0 or an integer from 1 to 6 provided that the sum of x and y is 1 to 6;
$R^3$ is selected from $C_{1-6}$alkyl, $C_{2-6}$alkenyl, $C_{2-6}$alkynyl, cycloalkyl, cycloalkenyl, aryl, heterocyclyl, heteroaryl and a group

wherein W is selected from a covalent bond, O, S and $NR^6$, $R^d$ is selected from H, cycloalkyl, cycloalkenyl, aryl, heterocyclyl and heteroaryl; p is an integer from 1 to 6, q is 0 or an integer from 1 to 5 provided that the sum of p and q is 1 to 6;
$R^4$ is selected from $C_{1-6}$alkyl, $C_{2-6}$alkenyl, $C_{2-6}$alkynyl, cycloalkyl, $C_{1-6}$alkyloxy, $C_{2-6}$alkenyloxy, $C_{2-6}$alkynyloxy, cycloalkoxy, $C_{1-6}$alkylthio, $C_{2-6}$alkenylthio, $C_{2-6}$alkynylthio, cycloalkylthio, halogen, aryl, aryl($C_{1-6}$alkyl)-, aryl($C_{2-6}$alkenyl), aryl($C_{2-6}$alkynyl), heterocyclyl, heterocyclyl($C_{1-6}$alkyl)-, heterocyclyl($C_{2-6}$alkenyl), heterocyclyl($C_{2-6}$alkynyl), heteroaryl, heteroaryl($C_{1-6}$alkyl)-, heteroaryl($C_{2-6}$ alkenyl) and heteroaryl($C_{2-6}$alkynyl);
$R^5$ is selected from H, halogen, $C_{1-6}$alkyl, $C_{2-6}$alkenyl, $C_{2-6}$alkynyl, $C_{1-6}$alkyloxy, $C_{2-6}$alkenyloxy, $C_{2-6}$alkynyloxy, $C_{1-6}$alkylthio, $C_{2-6}$alkenylthio, $C_{2-6}$alkynylthio, CN and $C(R^7)_3$;
$R^6$ is selected from H, $C_{1-6}$alkyl, $C_{2-6}$alkenyl and $C_{2-6}$alkynyl;
Each $R^7$ is independently selected from H and halogen; and
n is 0 or an integer from 1 to 3;
wherein each alkyl, alkenyl, alkynyl, cycloalkyl, aryl, heterocyclyl and heteroaryl is optionally substituted with one or more optional substituents;
and pharmaceutically acceptable salts and prodrugs thereof; with the proviso that when $R_1$ is COOH, $R_2$ is $C_6H_5$—$CH_2S$—$CH_2$—, $R^4$ is 3-$C_6H_5$ and $R^5$ is H, $R_3$ is not $CH_3CH_2$—.

In yet another aspect of the invention, there is provided a compound of formula (Ic):

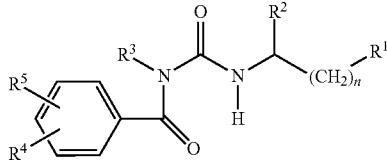
(Ic)

wherein
$R^1$ is selected from $CO_2H$ or a carboxylic acid or carboxylate bioisostere;
$R^2$ is selected from an amino acid side chain, cycloalkyl, cycloalkenyl, aryl, heterocyclyl, heteroaryl and a group $R^a$—$(CH_2)_x$-A-$(CH_2)_y$— wherein A is a covalent bond or is selected from O, S, SO, $SO_2$ or $NR^6$, $R^a$ is cycloalkyl, cycloalkenyl, aryl, heterocyclyl, heteroaryl or $R^b$ where $R^b$ is

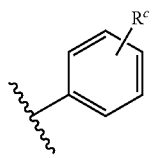

and $R^c$ is selected from heteroaryl, aryl, aryl($C_{2-6}$alkenyl), aryl($C_{2-6}$alkynyl), heteroaryl($C_{2-6}$alkenyl) and heteroaryl ($C_{2-6}$alkynyl), x and y are independently 0 or an integer from 1 to 6 provided that the sum of x and y is 1 to 6;
$R^3$ is selected from $C_{3-6}$alkyl, $C_{2-6}$alkenyl, $C_{2-6}$alkynyl, cycloalkyl, cycloalkenyl, aryl, heterocyclyl, heteroaryl and a group $R^d$—$(CH_2)_p$—W—$(CH_2)_q$— wherein W is selected from a covalent bond, O, S and $NR^6$, $R^d$ is selected from H, cycloalkyl, cycloalkenyl, aryl, heterocyclyl and heteroaryl; p is an integer from 1 to 6, q is 0 or an integer from 1 to 5 provided that the sum of p and q is 1 to 6;
$R^4$ is selected from $C_{1-6}$alkyl, $C_{2-6}$alkenyl, $C_{2-6}$alkynyl, cycloalkyl, $C_{1-6}$alkyloxy, $C_{2-6}$alkenyloxy, $C_{2-6}$alkynyloxy, cycloalkoxy, $C_{1-6}$alkylthio, $C_{2-6}$alkenylthio, $C_{2-6}$alkynylthio, cycloalkylthio, halogen, aryl, aryl($C_{1-6}$alkyl)-, aryl($C_{2-6}$alkenyl), aryl($C_{2-6}$alkynyl), heterocyclyl, heterocyclyl($C_{1-6}$alkyl)-, heterocyclyl($C_{2-6}$alkenyl), heterocyclyl($C_{2-6}$alkynyl), heteroaryl, heteroaryl($C_{1-6}$alkyl)-, heteroaryl($C_{2-6}$ alkenyl) and heteroaryl($C_{2-6}$alkynyl);
$R^5$ is selected from H, halogen, $C_{1-6}$alkyl, $C_{2-6}$alkenyl, $C_{2-6}$alkynyl, $C_{1-6}$alkyloxy, $C_{2-6}$alkenyloxy, $C_{2-6}$alkynyloxy, $C_{1-6}$alkylthio, $C_{2-6}$alkenylthio, $C_{2-6}$alkynylthio, CN and $C(R^7)_3$;
$R^6$ is selected from H, $C_{1-6}$alkyl, $C_{2-6}$alkenyl and $C_{2-6}$alkynyl;
Each $R^7$ is independently selected from H and halogen; and
n is 0 or an integer from 1 to 3;
wherein each alkyl, alkenyl, alkynyl, cycloalkyl, cycloalkenyl, aryl, heterocyclyl and heteroaryl is optionally substituted with one or more optional substituents; and pharmaceutically acceptable salts and prodrugs thereof.

In a further aspect of the invention, there is provided a compound of formula (Id):

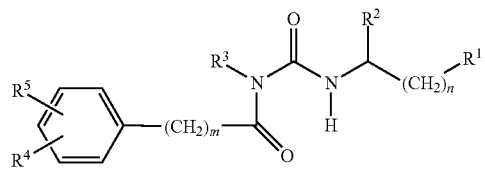
(Id)

wherein
$R^1$ is selected from $CO_2H$ or a carboxylic acid or carboxylate bioisostere;
$R^2$ is selected from an amino acid side chain, cycloalkyl, cycloalkenyl, aryl, heterocyclyl, heteroaryl and a group $R^a$—$(CHR')_x$-A-$(CH_2)_y$— wherein A is a covalent bond or is selected from O, S, SO, $SO_2$ and $NR^6$, $R^a$ is H, cycloalkyl, cycloalkenyl, aryl, heterocyclyl, heteroaryl or $R^b$ where $R^b$ is

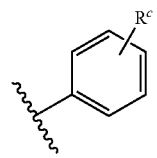

and $R^c$ is selected from heteroaryl, aryl, aryl($C_{2-6}$alkenyl), aryl($C_{2-6}$alkynyl), heteroaryl($C_{2-6}$alkenyl) and heteroaryl ($C_{2-6}$alkynyl), R' is H or $C_{1-6}$alkyl, x and y are independently 0 or an integer from 1 to 6 provided that the sum of x and y is 1 to 6;
$R^3$ is selected from $C_{1-6}$alkyl, $C_{2-6}$alkenyl, $C_{2-6}$alkynyl, cycloalkyl, cycloalkenyl, aryl, heterocyclyl, heteroaryl and a group $R^d$—$(CH_2)_p$—W—$(CH_2)_q$— wherein W is selected from a covalent bond, O, S and $NR^6$, $R^d$ is selected from H, cycloalkyl, cycloalkenyl, aryl, heterocyclyl and heteroaryl; p is an integer from 1 to 6, q is 0 or an integer from 1 to 5 provided that the sum of p and q is 1 to 6;
$R^4$ is selected from $C_{1-6}$alkyl, $C_{2-6}$alkenyl, $C_{2-6}$alkynyl, cycloalkyl, $C_{1-6}$alkyloxy, $C_{2-6}$alkenyloxy, $C_{2-6}$alkynyloxy, cycloalkoxy, $C_{1-6}$alkylthio, $C_{2-6}$alkenylthio, $C_{2-6}$alkynylthio, cycloalkylthio, halogen, aryl, aryl($C_{1-6}$alkyl)-, aryl($C_{2-6}$alkenyl), aryl($C_{2-6}$alkynyl), heterocyclyl, heterocyclyl($C_{1-6}$alkyl)-, heterocyclyl($C_{2-6}$alkenyl), heterocyclyl($C_{2-6}$alkynyl), heteroaryl, heteroaryl($C_{1-6}$alkyl)-, heteroaryl($C_{2-6}$ alkenyl) and heteroaryl($C_{2-6}$alkynyl);
$R^5$ is selected from H, halogen, $C_{1-6}$alkyl, $C_{2-6}$alkenyl, $C_{2-6}$alkynyl, $C_{1-6}$alkyloxy, $C_{2-6}$alkenyloxy, $C_{2-6}$alkynyloxy, $C_{1-6}$alkylthio, $C_{2-6}$alkenylthio, $C_{2-6}$alkynylthio, CN and $C(R^7)_3$ or when $R^5$ is in the 2- or 5-position, $R^5$ and $R^3$ taken together may form a 5 to 10 membered ring;
$R^6$ is selected from H, $C_{1-6}$alkyl, $C_{2-6}$alkenyl and $C_{2-6}$alkynyl;
Each $R^7$ is independently selected from H and halogen;
m is 0 or an integer from 1 to 6; and
n is 0 or an integer from 1 to 3;
wherein each alkyl, alkenyl, alkynyl, cycloalkyl, aryl, heterocyclyl and heteroaryl is optionally substituted with one or more optional substituents;
and pharmaceutically acceptable salts and prodrugs thereof;
with the proviso that (i) when $R^1$ is COOH, $R_2$ is $C_6H_5$—$CH_2S$—$CH_2$—, $R^4$ is 3-$C_6H_5$ and $R^5$ is H, $R_3$ is not $CH_3CH_2$— and (ii) when $R^2$ is $CH_3CH(CH_3)CH_2SCH_2$, $R^4$ is 3-phenethynyl, $R^1$ is $CO_2H$, m and n are 0 and $R^5$ is H, $R^3$ is not n-propyl.

As used herein, the term "alkyl" refers to a straight-chain or branched saturated hydrocarbon group and may have a specified number of carbon atoms. For example, $C_1$-$C_6$ as in "$C_1$-$C_6$alkyl" includes groups having 1, 2, 3, 4, 5 or 6 carbons in a linear or branched arrangement. Examples of suitable alkyl groups include, but are not limited to, methyl, ethyl, n-propyl, i-propyl, i-butyl, i-butyl, t-butyl, n-pentyl, 2-methylbutyl, 3-methylbutyl, 4-methylbutyl, n-hexyl, 2-methylpentyl, 3-methylpentyl, 4-methylpentyl, 5-methylpentyl, 2-ethylbutyl and 3-ethylbutyl.

As used herein, the term "alkenyl" refers to a straight-chain or branched hydrocarbon group having one or more double bonds between carbon atoms and may have a specified number of carbon atoms. For example, $C_2$-$C_6$ as in "$C_2$-$C_6$alkenyl" includes groups having 2, 3, 4, 5 or 6 carbon atoms in a linear or branched arrangement. Examples of suitable alkenyl groups include, but are not limited to, ethenyl, propenyl, isopropenyl, butenyl, pentenyl and hexenyl.

As used herein, the term "alkynyl" refers to a straight-chain or branched hydrocarbon group having one or more triple bonds between carbon atoms, and may have a specified number of carbon atoms. For example, $C_2$-$C_6$ as in "$C_2$-$C_6$alkynyl" includes groups having 2, 3, 4, 5 or 6 carbon atoms in a linear or branched arrangement. Examples of suitable alkynyl groups include, but are not limited to, ethynyl, propynyl, butynyl, pentynyl and hexynyl.

The term "cycloalkyl" as used herein, refers to cyclic hydrocarbon groups and may have a specified number of carbon atoms. For example, $C_3$-$C_{10}$ as in "$C_3$-$C_{10}$cycloalkyl" includes groups having 3, 4, 5, 6, 7, 8, 9 or 10 carbon atoms in the hydrocarbon ring. Examples of suitable cycloalkyl groups include, but are not limited to, cyclopropyl, cyclobutyl, cyclopentyl and cyclohexyl.

The term "cycloalkenyl" as used herein, refers to cyclic hydrocarbon groups having one or more double bonds. Suitable cycloalkenyl groups include, but are not limited to, cyclopentenyl, cyclohexenyl, cyclohexa-1,3-dienyl and cyclohexa-1,4-dienyl.

As used herein the term "halo" or "halogen" refers to fluorine (fluoro), chlorine (chloro), bromine (bromo) and iodine (iodo).

The terms "alkyloxy", "alkenyloxy", "alkynyloxy" and "cycloalkoxy" as used herein represent an alkyl, alkenyl, alkynyl or cycloalkyl group as defined above attached through an oxygen bridge. Examples of suitable alkyloxy, alkenyloxy, alkynyloxy and cycloalkoxy groups include, but are not limited to, methoxy, ethoxy, n-propyloxy, n-butyloxy, n-pentyloxy, n-hexyloxy, ethenyloxy, propenyloxy, butenyloxy, pentenyloxy, hexenyloxy, ethynyloxy, propynyloxy, butynyloxy, pentynyloxy, hexynyloxy, cyclopropyloxy, cyclobutyloxy, cyclopentyloxy and cyclohexyloxy.

The terms "alkylthio", "alkenylthio", "alkynylthio" and "cycloalkylthio" as used herein represent an alkyl, alkenyl, alkynyl or cycloalkyl group as defined above attached through a sulfur bridge. Examples of suitable alkylthio, alkenylthio, alkynylthio and cycloalkylthio include, but are not limited to, methylthio, ethylthio, propylthio, butylthio, pentylthio, hexylthio, ethenylthio, propenylthio, butenylthio, pentenylthio, hexenylthio, ethynylthio, propynylthio, butynylthio, pentynylthio, hexynylthio, cyclopropylthio, cyclobutylthio, cyclopentylthio and cyclohexylthio.

As used herein, the term "aryl" is intended to mean any stable, monocyclic or bicyclic carbon ring of up to 7 atoms in each ring, wherein at least one ring is aromatic. Examples of such aryl groups include, but are not limited to, phenyl, naphthyl, tetrahydronaphthyl, indanyl, biphenyl and binaphthyl.

The term "heterocyclyl" as used herein is intended to mean a 3- to 10-membered nonaromatic heterocycle containing from 1 to 4 heteroatoms selected from the group consisting of O, N and S, and includes bicyclic groups.

The term "heteroaryl" as used herein, represents a stable monocyclic or bicyclic ring of up to 7 atoms in each ring, wherein at least one ring is aromatic and at least one ring contains from 1 to 4 heteroatoms selected from the group consisting of O, N and S. Heteroaryl groups within the scope of this definition include, but are not limited to, acridinyl, carbazolyl, cinnolinyl, quinoxalinyl, pyrrazolyl, indolyl, benzotriazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetrahydroquinoline.

Further examples of "heterocyclyl" and "heteroaryl" include, but are not limited to, the following: benzoimidazolyl, benzofuranyl, benzofurazanyl, benzopyrazolyl, benzotriazolyl, benzothiophenyl, benzoxazolyl, benzopyrrolyl, carbazolyl, carbolinyl, cinnolinyl, furanyl, imidazoyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, aziridinyl, 1,4-dioxanyl, hexahydroazepinyl, piperazinyl, piperidinyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof. Attachment of a heterocyclyl substituent can occur via a carbon atom or via a heteroatom.

The term "amino acid side chain" as used herein includes the α-R group of a naturally occurring α-amino acid and may be selected from —$CH_3$, —$(CH_2)_3NHC(\!\!=\!\!NH)NH_2$, —$CH_2CONH_2$, —$CH_2CO_2H$, —$CH_2SH$, —$(CH_2)_2CO_2NH_2$, —$(CH_2)_2CO_2H$, —$CH_2$(4-imidazole), —$CH(CH_3)CH_2CH_3$, —$CH_2CH(CH_3)_2$, —$(CH_2)_4NH_2$, —$(CH_2)_2SCH_3$, —$CH_2Ph$, —$CH_2OH$, —$CH(CH_3)OH$, —$CH_2$(3-indolyl), —$CH_2$(4-hydroxyphenyl) and —$CH(CH_3)_2$. This term also includes the α-R groups of non-naturally occurring α-amino acid such as those found in homoarginine, homoserine, homocysteine, norvaline, norleucine or amidino derivatives. For example such α-side chains include —$(CH_2)_4$ NHC(=NH)$NH_2$, —$(CH_2)_2OH$, —$(CH_2)_2SH$, —$CH_2CH_2CH_3$, —$(CH_2)_3CH_3$, or $(CH_2)_vC(\!\!=\!\!NH)NH_2$ where v is an integer from 1 to 4. Other derivatives may include α-side chains in which carboxy, hydroxy, thiol or amino groups are protected with suitable carboxy, hydroxy, thiol or amino protecting groups (see "Protective Groups in Organic Synthesis" Theodora Greene and Peter Wuts, third edition, Wiley Interscience, 1999).

Each alkyl, alkenyl, alkynyl, cycloalkyl, cycloalkenyl, aryl, heterocyclyl and heteroaryl may be optionally substituted with one or more optional substituents selected from $C_{1-6}$alkyl, $C_{2-6}$alkenyl, $C_{2-6}$alkynyl, $C_{3-6}$cycloalkyl, $C_{1-6}$alkyloxy$(CH_2)_p$—, $C_{2-6}$alkenyloxy$(CH_2)_p$—, $C_{2-6}$alkynyloxy$(CH_2)_p$—, $C_{3-6}$cycloalkoxy$(CH_2)_p$—, $C_{1-6}$alkylthio$(CH_2)_p$—, $C_{2-6}$alkenylthio$(CH_2)_p$—, $C_{2-6}$alkynylthio$(CH_2)_p$—, $C_{3-6}$cycloalkylthio$(CH_2)_p$—, hydroxy$(CH_2)_p$—, —$(CH_2)_p$SH, —$(CH_2)_p$CO$_2$H, —$(CH_2)_p$CO$_2$C$_{1-6}$alkyl, $C_{2-6}$acyl$(CH_2)_p$—, $C_{2-6}$acyloxy$(CH_2)_p$—, $C_{2-6}$alkylSO$_2$$(CH_2)_p$—, $C_{2-6}$alkenylSO$_2$$(CH_2)_p$—, $C_{2-6}$alkynylSO$_2$$(CH_2)_p$—, aryl-SO$_2$$(CH_2)_p$—, heteroarylSO$_2$$(CH_2)_p$—, heterocyclylSO$_2$$(CH_2)_p$—, —$(CH_2)_p$NH$_2$, —$(CH_2)_p$NH(C$_{1-6}$alkyl), —$(CH_2)_p$N(C$_{1-6}$alkyl)$_2$, —$(CH_2)_p$NH(phenyl), —$(CH_2)_p$N(phenyl)$_2$, —$(CH_2)_p$NH(acyl), —$(CH_2)_p$N(acyl)(phenyl), —$(CH_2)_p$NH—$(CH_2)_p$—S-aryl, —$(CH_2)_p$N=NHC(O)NH$_2$, —$(CH_2)_p$C(R$^7$)$_3$, —$(CH_2)_p$OC(R$^7$)$_3$, —$(CH_2)_p$ SC(R$^7$)$_3$, —$(CH_2)_p$CN, —$(CH_2)_p$NO$_2$, —$(CH_2)_p$ halogen, —$(CH_2)_p$heterocyclyl, heterocyclyloxy$(CH_2)_p$—, —$(CH_2)_p$heteroaryl, heteroaryloxy$(CH_2)_p$—, —$(CH_2)_p$aryl, —$(CH_2)_p$C(O)aryl and aryloxy$(CH_2)_p$— wherein p is 0 or an integer from 1 to 6 and each R$^7$ is independently selected from hydrogen and halogen. Examples of suitable substituents include, but are not limited to, methyl, ethyl, propyl, isopropyl, butyl, sec-butyl, tert-butyl, vinyl, methoxy, ethoxy, propoxy, isopropoxy, butoxy, methylthio, ethylthio, propylthio, isopropylthio, butylthio, hydroxy, hydroxymethyl, hydroxyethyl, hydroxypropyl, hydroxybutyl, fluoro, chloro, bromo, iodo, cyano, nitro, CO$_2$H, CO$_2$CH$_3$, CH$_2$CO$_2$CH$_3$, trifluoromethyl, trifluoromethoxy, trifluoromethylthio, acetyl, amino, methylamino, dimethylamino, phenyl, phenylcarbonyl, —N=NHC(O)NH$_2$, —CH=C(CN)$_2$ and phenoxy. Preferred substituents include fluoro, chloro, methyl, ethyl, propyl, isopropyl, butyl, tert-butyl, methoxy, ethoxy, propoxy, isopropoxy, trifluoromethyl, trifluoromethoxy, cyano, acetyl, amino, methylamino and dimethylamino.

The compounds of the invention may be in the form of pharmaceutically acceptable salts. Suitable pharmaceutically acceptable salts include, but are not limited to, salts of pharmaceutically acceptable inorganic acids such as hydrochloric, sulphuric, phosphoric, nitric, carbonic, boric, sulfamic, and hydrobromic acids, or salts of pharmaceutically acceptable organic acids such as acetic, propionic, butyric, tartaric, maleic, hydroxymaleic, fumaric, maleic, citric, lactic, mucic, gluconic, benzoic, succinic, oxalic, phenylacetic, methanesulphonic, toluenesulphonic, benezenesulphonic, salicyclic sulphanilic, aspartic, glutamic, edetic, stearic, palmitic, oleic, lauric, pantothenic, tannic, ascorbic and valeric acids.

Base salts include, but are not limited to, those formed with pharmaceutically acceptable cations, such as sodium, potassium, lithium, calcium, magnesium, ammonium and alkylammonium.

Basic nitrogen-containing groups may be quaternised with such agents as lower alkyl halide, such as methyl, ethyl, propyl, and butyl chlorides, bromides and iodides; dialkyl sulfates like dimethyl and diethyl sulfate; and others.

It will also be recognised that many compounds of the invention possess asymmetric centres and are therefore capable of existing in more than one stereoisomeric form. The invention thus also relates to compounds in substantially pure isomeric form at one or more asymmetric centres e.g., greater than about 90% ee, such as about 95% or 97% ee or greater than 99% ee, as well as mixtures, including racemic mixtures, thereof. Such isomers may be prepared by asymmetric synthesis, for example using chiral intermediates, or by chiral resolution.

The term "carboxylic acid or carboxylate bioisostere" refers to a group which is physiochemically or topologically similar to carboxylic acid. Examples of suitable carboxylic acid or carboxylate bioisosteres include, but are not limited to, tetrazole, tetrazolate, oxidiazole, acylsulfonamides such as optionally substituted alkyl or optionally substituted aryl acylsulfonamides, especially optionally substituted benzene acylsulfonamides, phosphate (PO$_3$H$_2$) and sulfonic acid (SO$_3$H) [See Patani and LaVoie, 1996].

The term "prodrug" is used in its broadest sense and encompasses those derivatives that are converted in vivo to the compounds of the invention. Such derivatives would readily occur to those skilled in the art, and include N-α-acyloxy amides, N-(acyloxyalkoxy carbonyl) amine derivatives and α-acyloxyalkyl esters of phenols and alcohols. A prodrug may include modifications to one or more of the functional groups of a compound of the invention.

The term "prodrug" also encompasses the use of fusion proteins or peptides comprising cell-permeant proteins or peptides and the compounds of the invention. Such fusion proteins or peptides allow the translocation of the compounds of the invention across a cellular membrane and into a cell cytoplasm or nucleus. Examples of such cell-permeant proteins and peptides include membrane permeable sequences, cationic peptides such as protein transduction domains (PTD), e.g.: antennapedia (penetratin), tat peptide, R7, R8 and R9 and other drug delivery systems. (see Dunican and Doherty, 2001, Shangary and Johnson, 2002; Letai et. al., 2002; Wang et. al., 2000, Schimmer et. al., 2001; Brewis et. al., 2003; Snyder et. al., 2004).

The term "prodrug" also encompasses the combination of lipids with the compounds of the invention. The presence of lipids may assist in the translocation of the compounds across a cellular membrane and into a cell cytoplasm or nucleus. Suitable lipids include fatty acids which may be linked to the compound by formation of a fatty acid ester. Preferred fatty acids include, but are not limited to, lauric acid, caproic acid, palmitic acid and myristic acid.

The phrase "a derivative which is capable of being converted in vivo" as used in relation to another functional group includes all those functional groups or derivatives which upon administration into a mammal may be converted into the stated functional group. Those skilled in the art may readily determine whether a group may be capable of being converted in vivo to another functional group using routine enzymatic or animal studies.

In preferred embodiments at least one of the following applies:

$R^1$ is CO$_2$H, tetrazole, tetrazolate or an optionally substituted benzene acylsulfonamide, especially CO$_2$H;

$R^2$ is $R^6$—(CHR')$_x$-A-(CH$_2$)$_y$—, wherein $R^a$ is H, optionally substituted cycloalkyl or optionally substituted aryl, x is 0 or 1 to 4, R' is H or C$_{1-3}$alkyl, A is O, S or SO and y is 1 to 3, or $R^a$ is optionally substituted aryl or optionally substituted heteroaryl, R' is H, the sum of x and y is 1 to 4 and A is a covalent bond. In some embodiments $R^2$ is $R^a$—(CH$_2$)$_x$-A-(CH$_2$)$_y$— wherein $R^a$ is aryl, x is 1 to 3, y is 1 to 3 and A is selected from O, S and SO; or $R^a$ is aryl, A is a covalent bond, and the sum of x and y is 1 to 4;

$R^3$ is C$_{1-6}$alkyl, optionally substituted cycloalkyl or a group $R^d$—(CH$_2$)$_p$—W—(CH$_2$)$_q$— in which $R^d$ is optionally substituted cycloalkyl, optionally substituted aryl, optionally substituted heterocyclyl or optionally substituted heteroaryl, W is a covalent bond and the sum of p and q is 1 to 3; or $R^d$ is H, W is O or S and the sum of p and q is 2 to 4, especially preferred is C$_{3-6}$alkyl, benzyl and cyclohexylmethyl; and when $R^d$ is aryl, the aryl is preferably optionally substituted with one or more halogen, C$_{1-6}$alkyl or C$_{1-6}$alkoxy groups.

$R^4$ is 3- or 4-aryl, aryl(C$_{1-3}$alkyl)-, aryl(C$_{2-3}$alkenyl) or aryl (C$_{2-3}$alkynyl) wherein aryl is optionally substituted with one or more halogen, C$_{1-6}$alkyl, C$_{1-6}$alkoxy groups, trifluoromethyl groups, hydroxy(C$_{1-6}$alkyl), CN or C$_{1-6}$acyl, especially optionally substituted 3- or 4-phenyl, naphthyl or phenyl (ethynyl), more especially optionally substituted 3-phenyl, naphthyl or phenyl(ethynyl); or $R^4$ is $C_{1-6}$alkyl, $C_{2-6}$alkenyl or $C_{2-6}$alkynyl.

$R^5$ is hydrogen, halogen, methyl or methoxy, especially hydrogen;

m is 0; and n is 0.

Especially preferred compounds are those of formula (II):

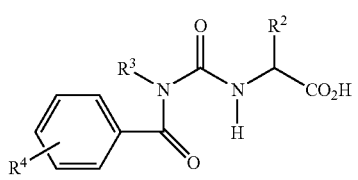

(II)

wherein $R^2$ and $R^3$ are defined as for formulae (I) or (Ib) above and $R^4$ is a 3-phenyl, 3-(2-naphthyl), 3-(1-naphthyl), 3-benzyl, 4-phenyl, 4-benzyl group, 3-(phenylethynyl) or 4-(phenylethynyl), wherein each phenyl, naphthyl or benzyl group is optionally substituted with one or more substituents selected from $C_{1-6}$alkyl, $C_{2-6}$alkenyl, $C_{2-6}$alkynyl, $C_{1-6}$alkoxy, $C_{2-6}$alkenyloxy and halogen; or $R^4$ is $C_{1-6}$alkyl, $C_{2-6}$alkenyl or $C_{2-6}$alkynyl; and pharmaceutically acceptable salts or prodrugs thereof, with the proviso that when $R^2$ is $C_6H_5$—$CH_2S$—$CH_2$— and $R^4$ is 3-phenyl, $R^3$ is not ethyl;

or a compound of formula (IIa):

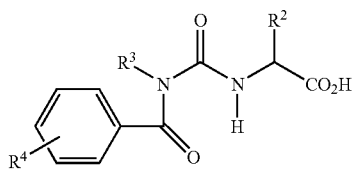

(IIa)

wherein $R^2$ is defined as for formulae (I) or (Ib) above;

$R^3$ is selected from $C_{3-6}$alkyl, $C_{2-6}$alkenyl, $C_{2-6}$alkynyl, cycloalkyl, aryl, heterocyclyl, heteroaryl and a group $R^d$—$(CH_2)_p$—W—$(CH_2)_q$— wherein W is selected from a covalent bond, O, S or $NR^6$, $R^d$ is selected from H, cycloalkyl, cycloalkenyl, aryl, heterocyclyl and heteroaryl; p is an integer from 1 to 6, q is 0 or an integer from 1 to 5 provided that the sum of p and q is 1 to 6;

$R^4$ is a 3-phenyl, 3-(2-naphthyl), 3-(1-naphthyl), 3-benzyl, 4-phenyl, 4-benzyl group, 3-(phenylethynyl) or 4-(phenylethynyl), wherein each phenyl, naphthyl or benzyl group is optionally substituted with one or more substituents selected from $C_{1-6}$alkyl, $C_{2-6}$alkenyl, $C_{2-6}$alkynyl, $C_{1-6}$alkoxy, $C_{2-6}$alkenyloxy and halogen; or $R^4$ is $C_{1-6}$alkyl, $C_{2-6}$alkenyl or $C_{2-6}$alkynyl; and pharmaceutically acceptable salts or prodrugs thereof.

Preferred compounds of the invention include:

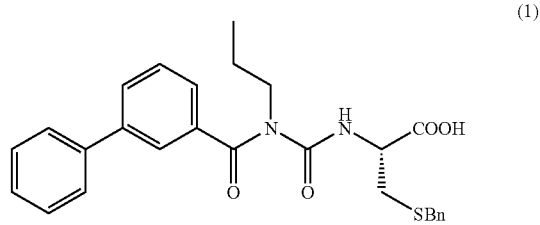

(1)

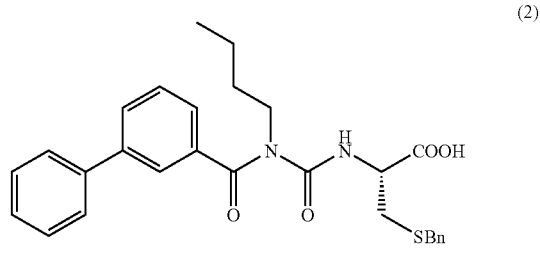

(2)

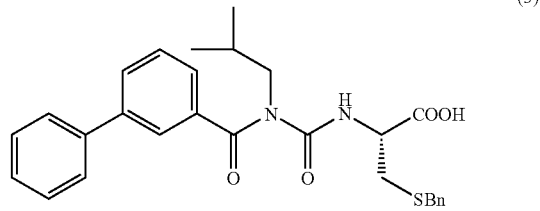

(3)

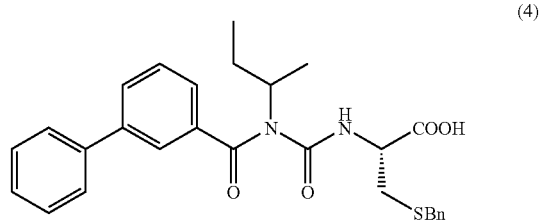

(4)

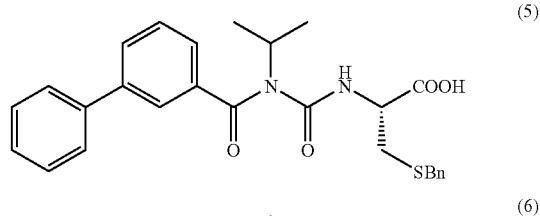

(5)

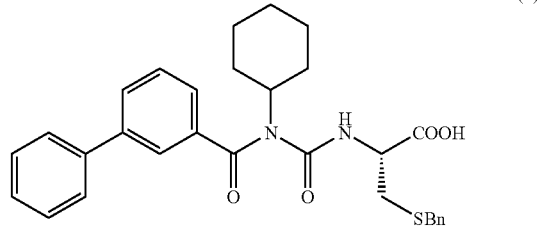

(6)

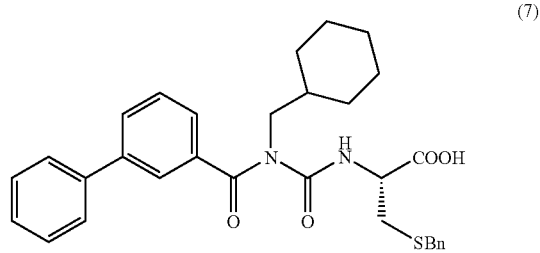

(7)

(8)
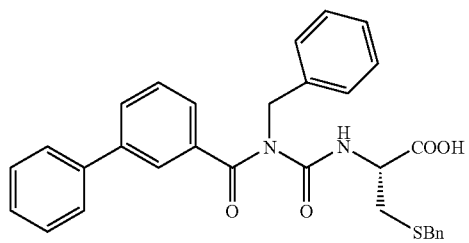
(9)
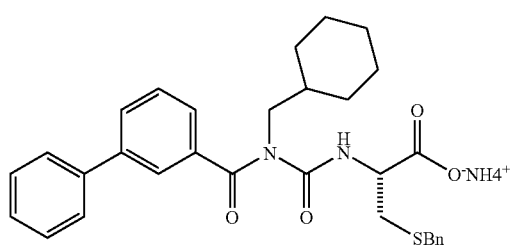
(10)
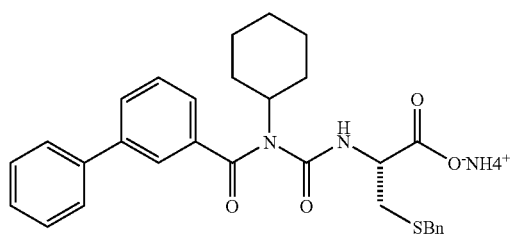
(11)
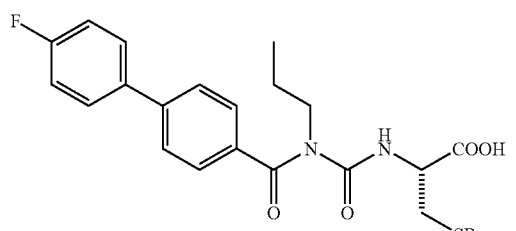
(12)
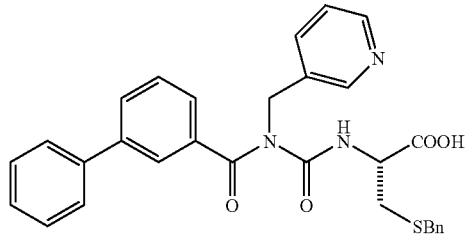
(14)
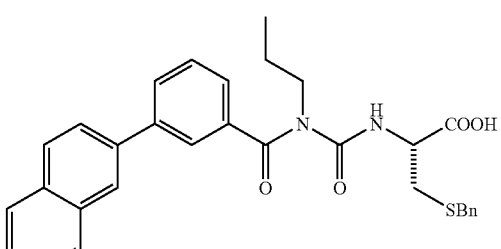
(15)
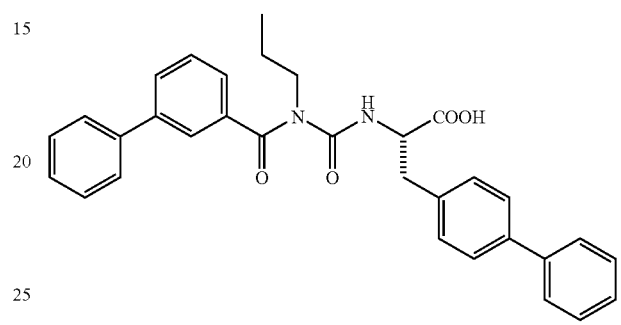
(16)
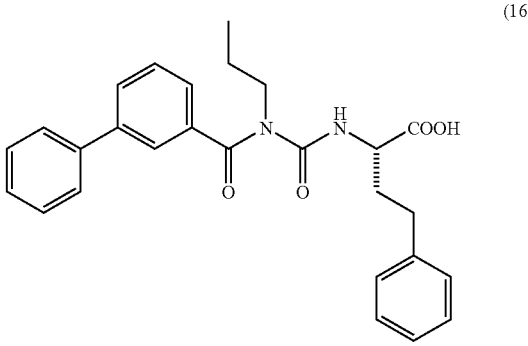
(17)
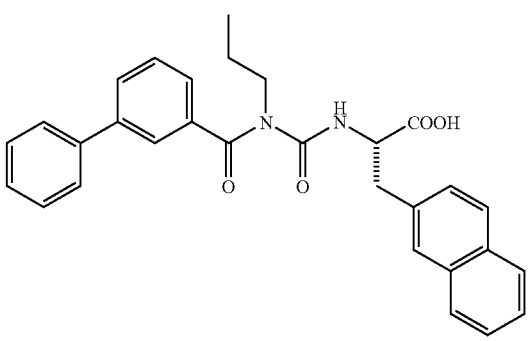
(18)
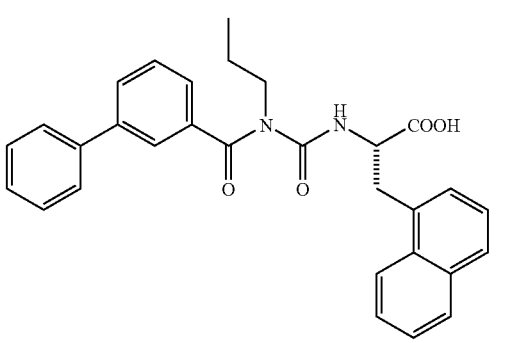
(13)

(19)
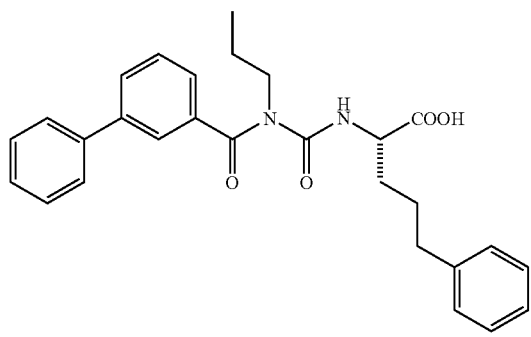
(20)
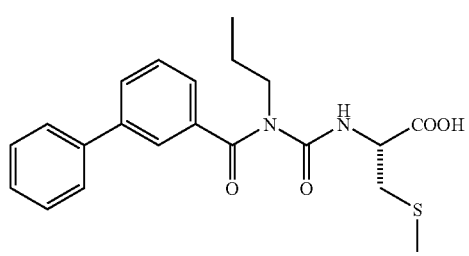
(21)
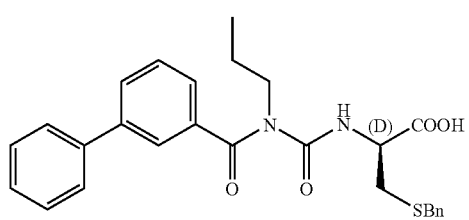
(22)
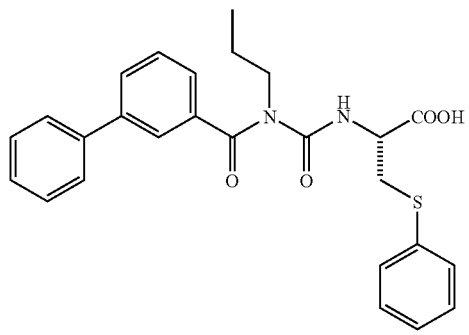
(23)
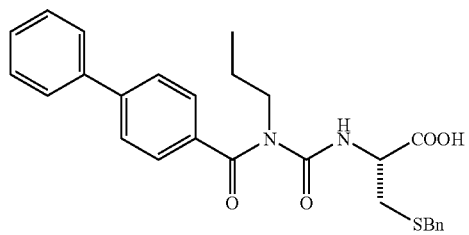
(24)
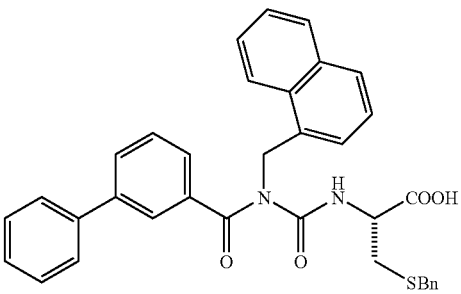
(25)
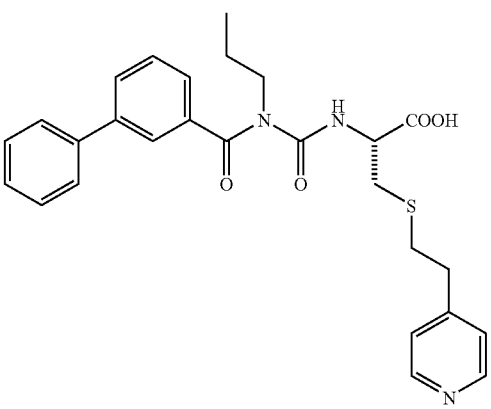
(26)
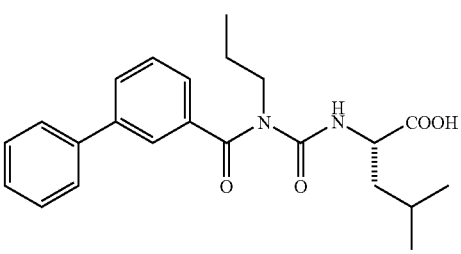
(27)
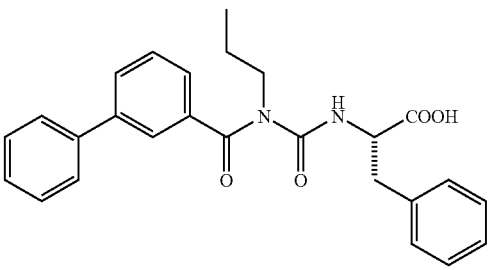
(28)
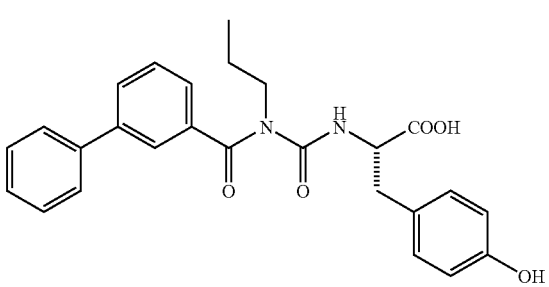

(29)
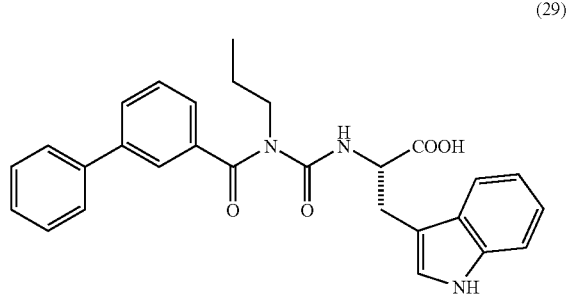
(30)
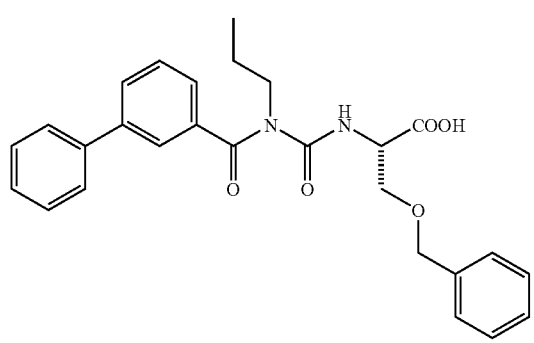
(31)
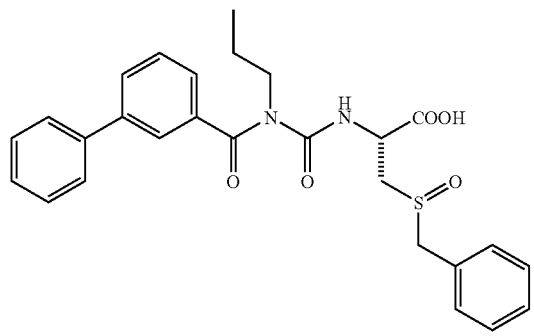
(33)
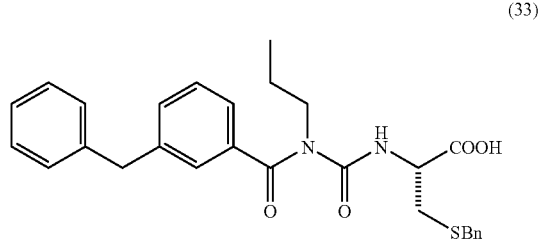
(34)
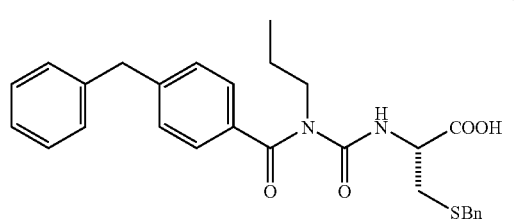
(35)
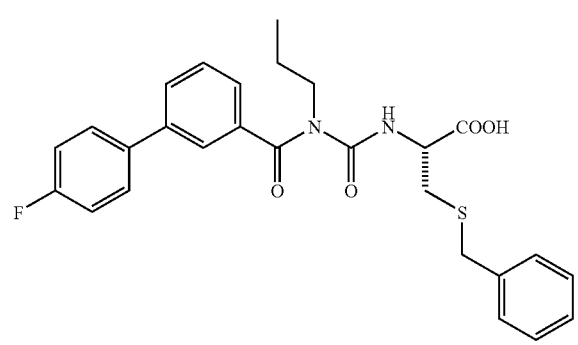
(36)
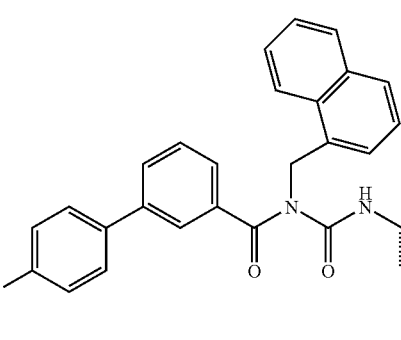
(37)
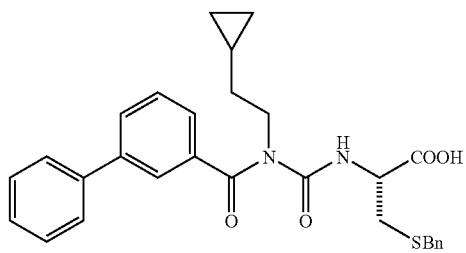
(38)
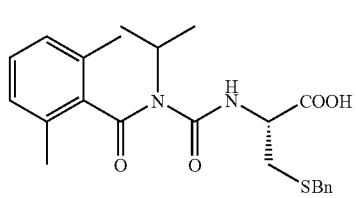
(39)
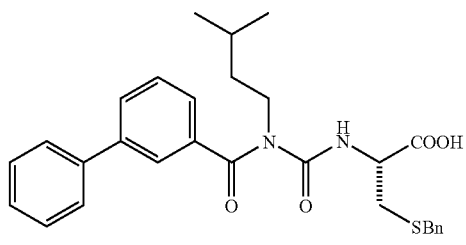

(40)
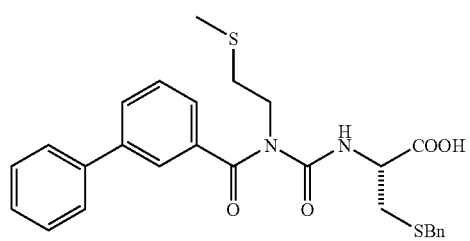
(41)
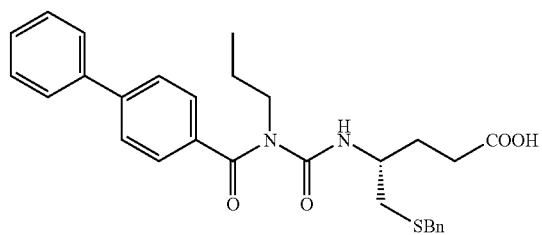
(42)
(43)
(45)
(46)
(47)
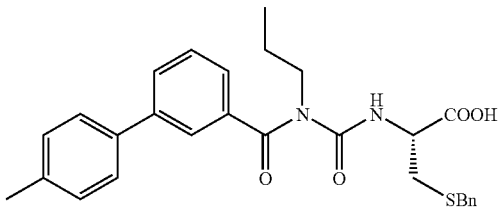
(48)
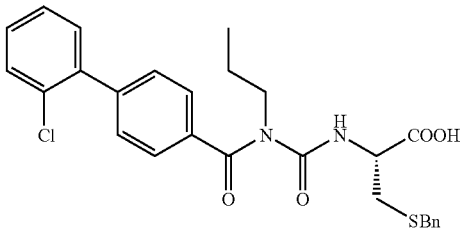
(51)
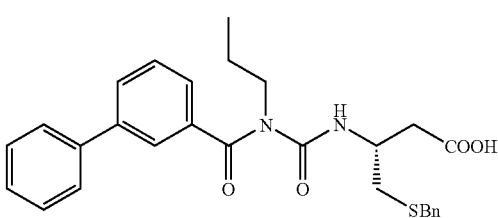
(52)
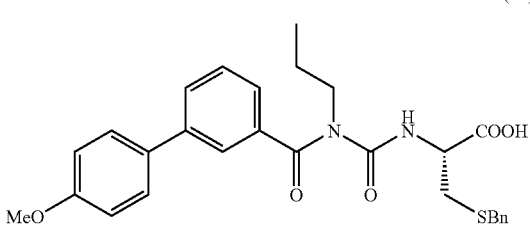
(53)
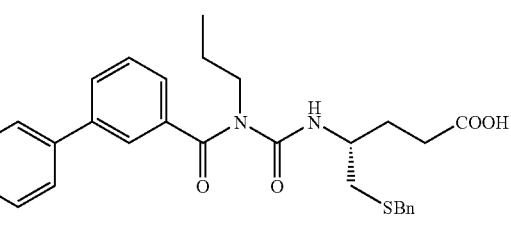
(54)
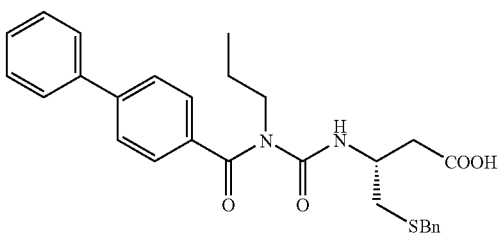

(55)
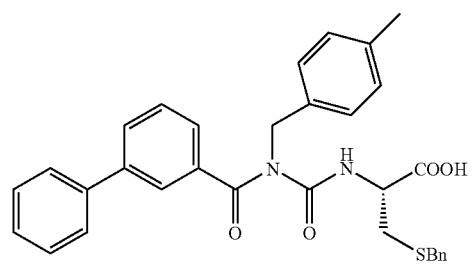
(56)
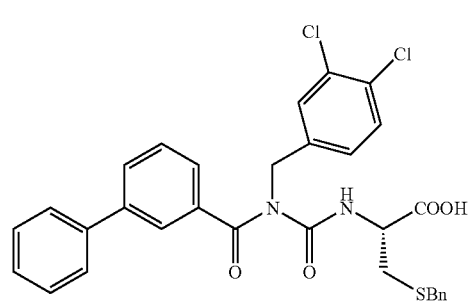
(58)
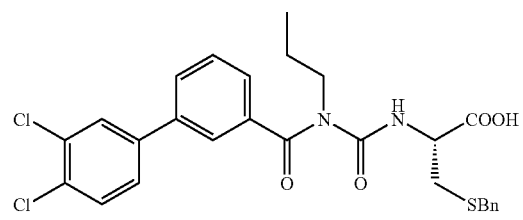
(59)
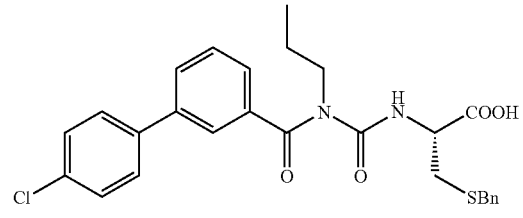
(60)
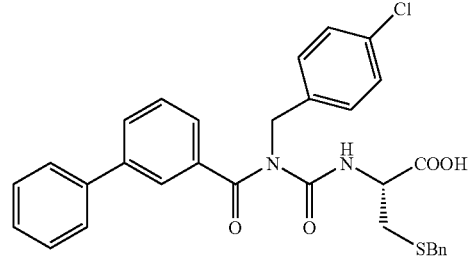
(61)
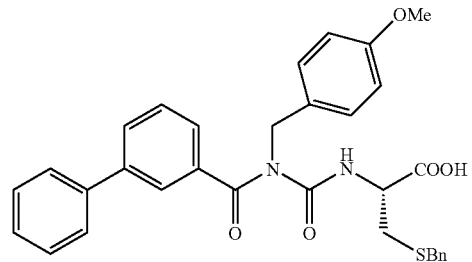
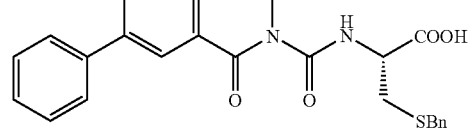
(62)
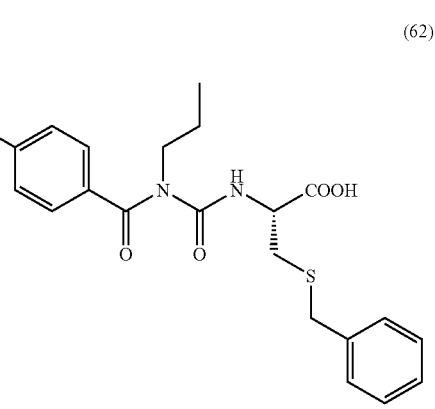
(63)
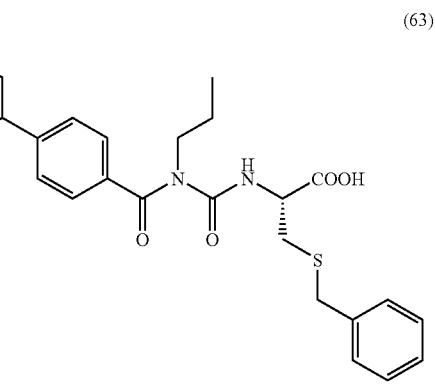
(64)
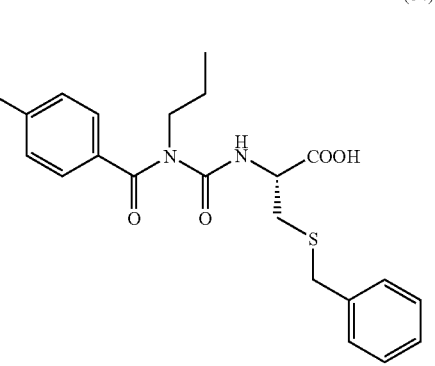
(65)
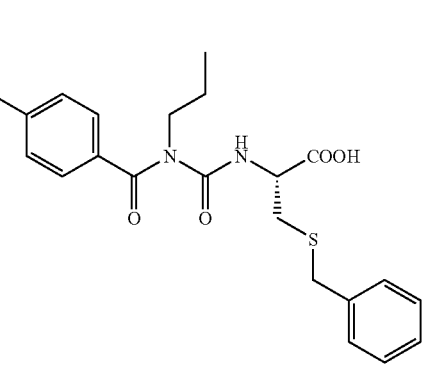

(66)
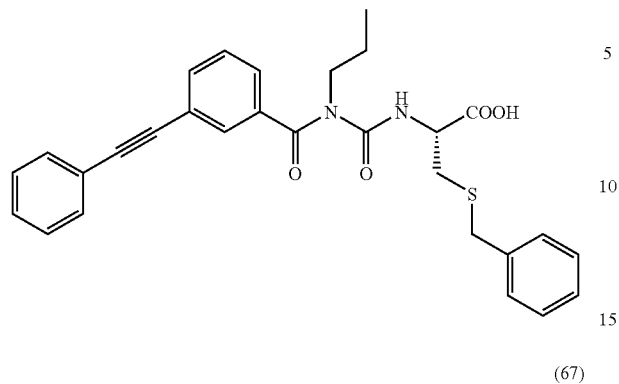
(67)
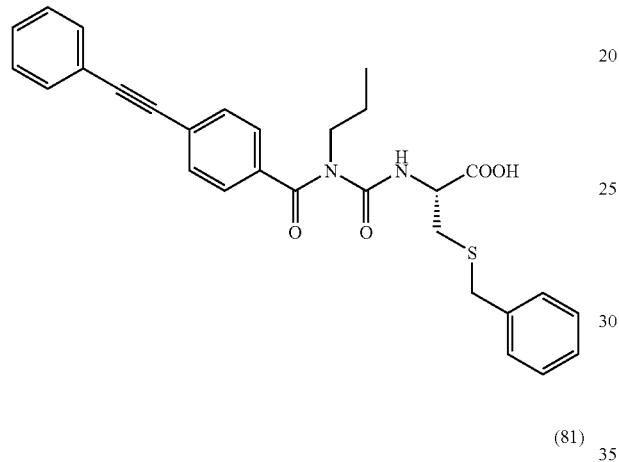
(81)
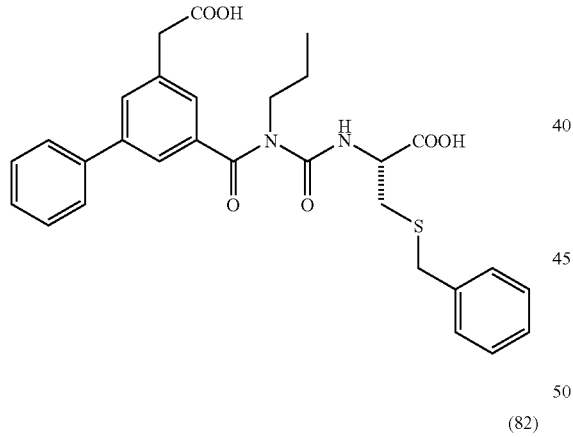
(82)
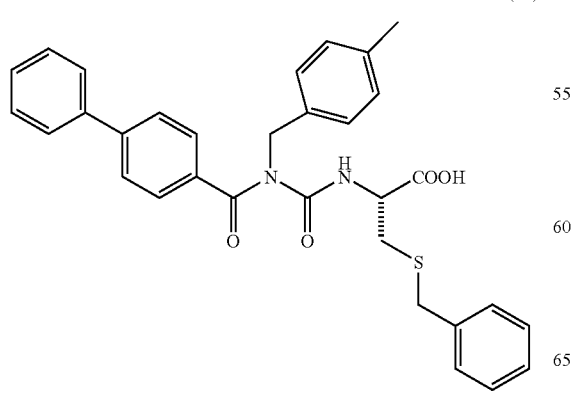
(83)
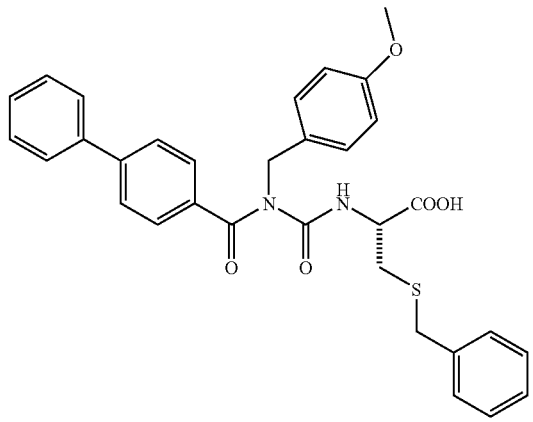
(84)
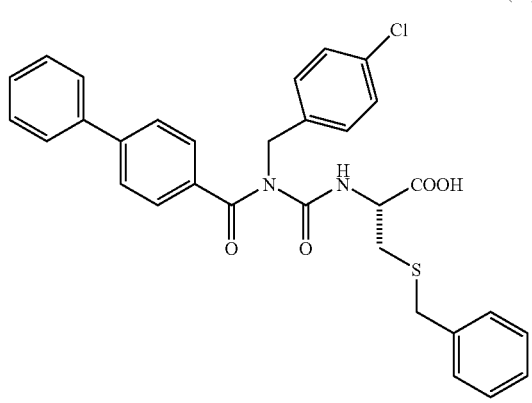
(85)
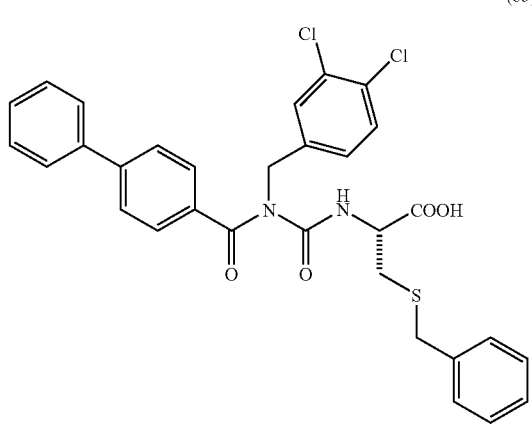
(86)
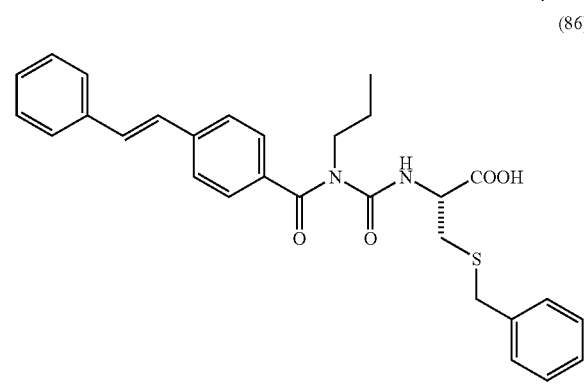

(87)
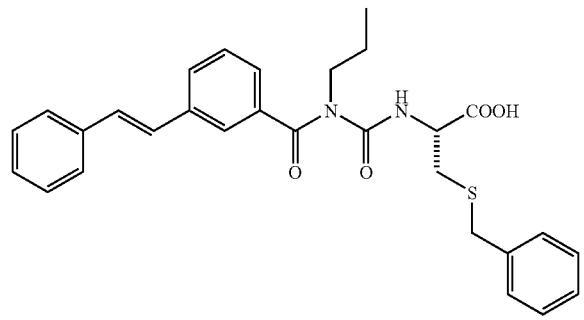
(88)
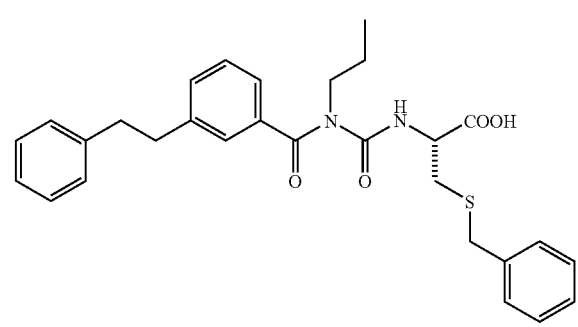
(89)
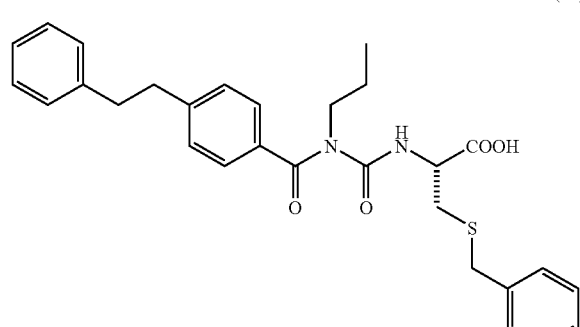
(90)
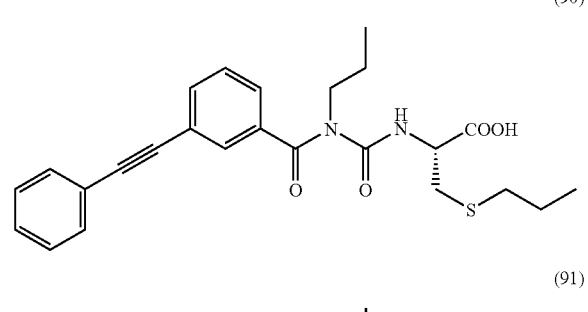
(91)
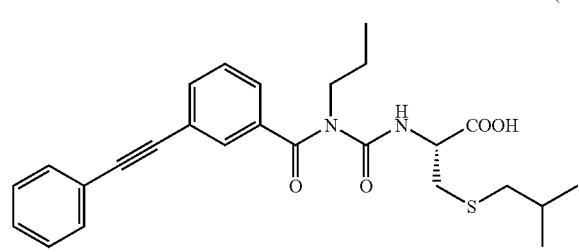
(92)
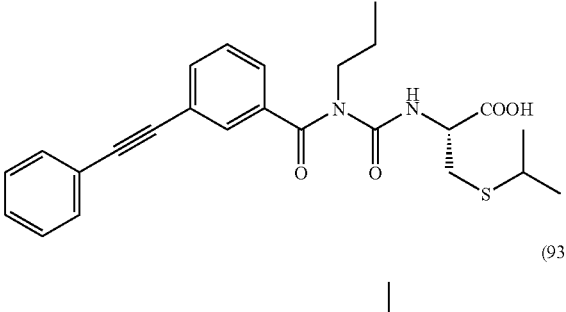
(93)
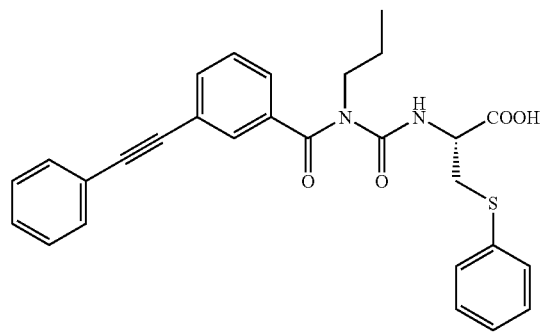
(94)
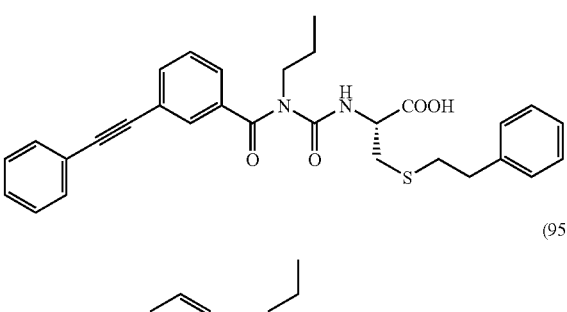
(95)
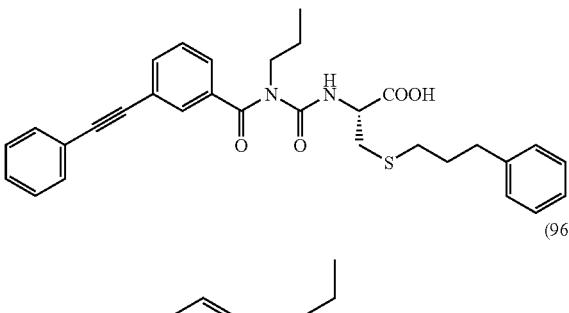
(96)
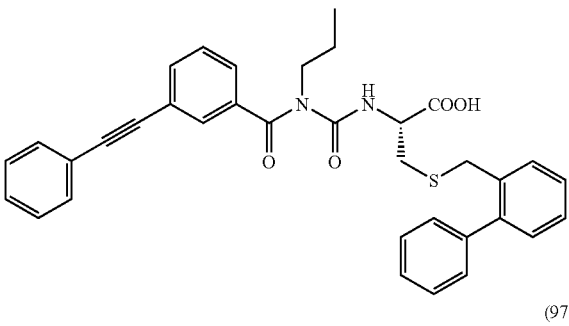
(97)
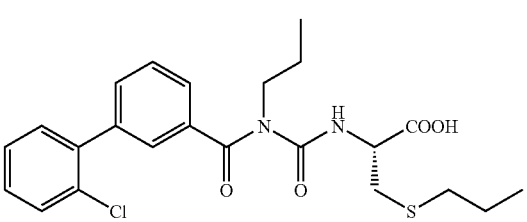

(98) 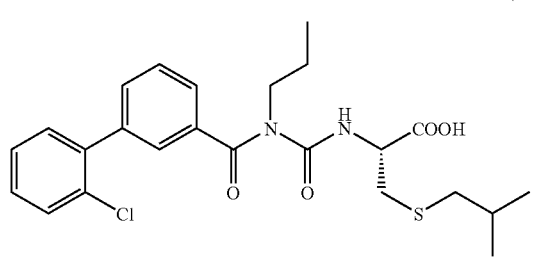
(99) 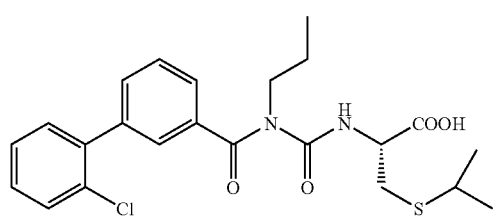
(100) 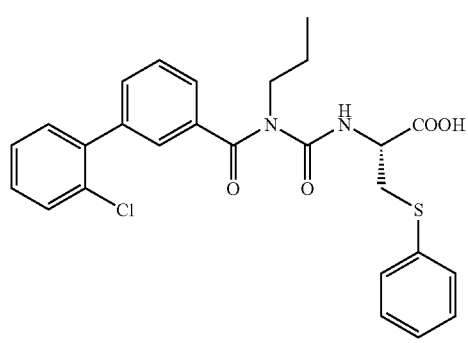
(101) 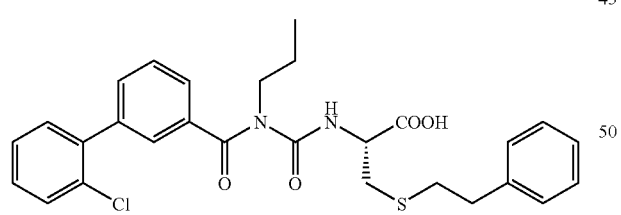
(102) 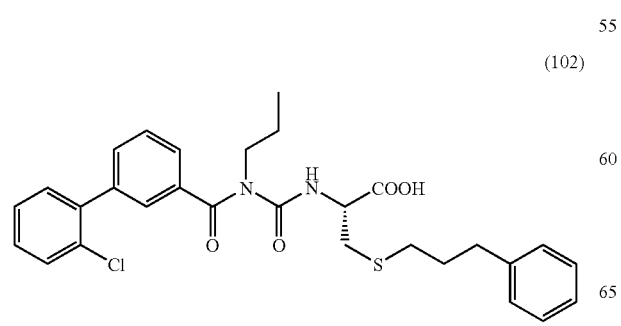
(103) 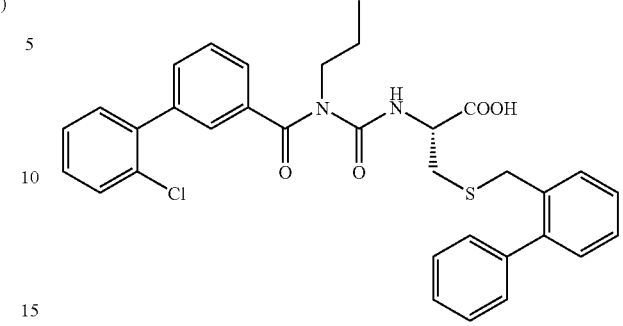
(104) 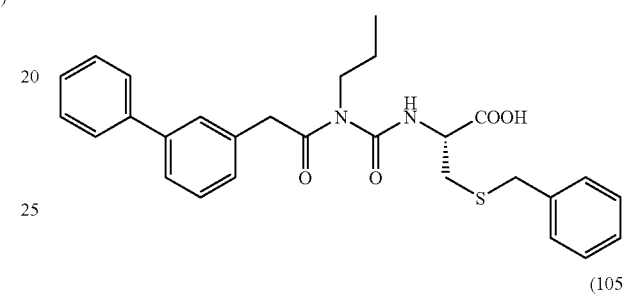
(105) 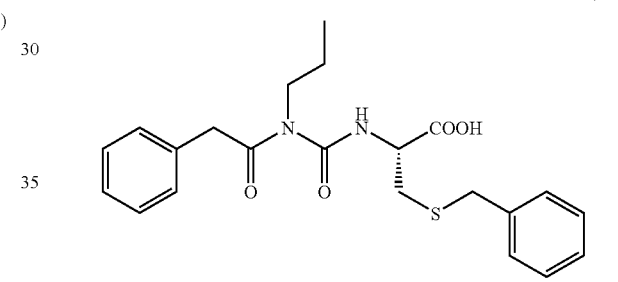
(106) 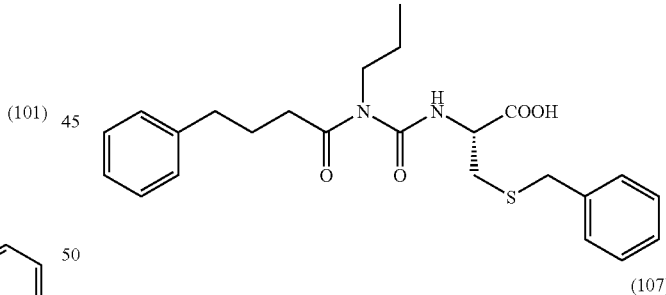
(107) 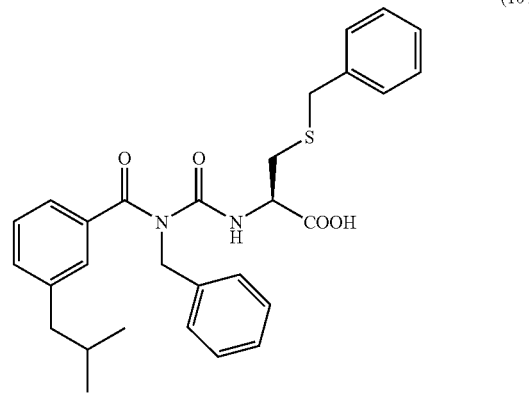

(108) 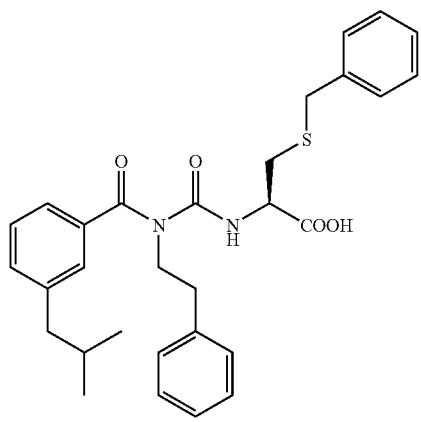
(109) 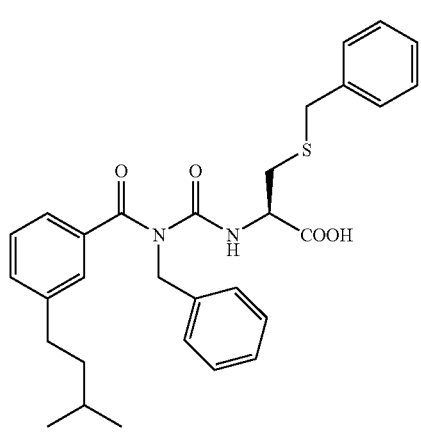
(110) 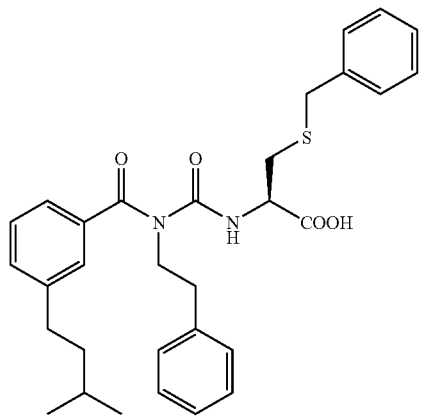
(111) 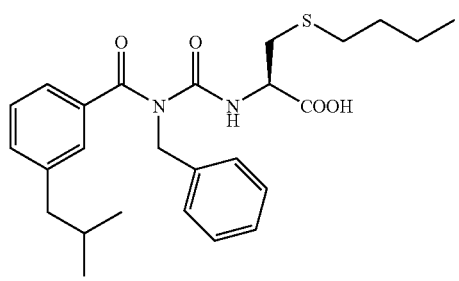
(112) 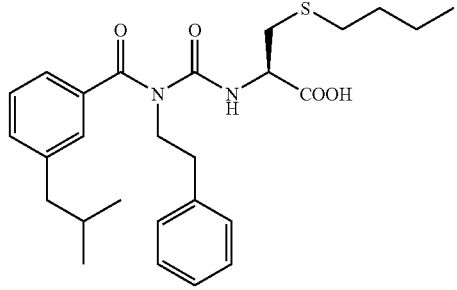
(113) 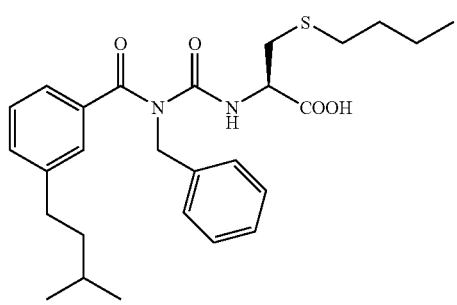
(114) 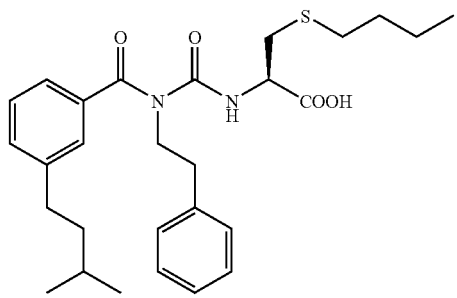
(115) 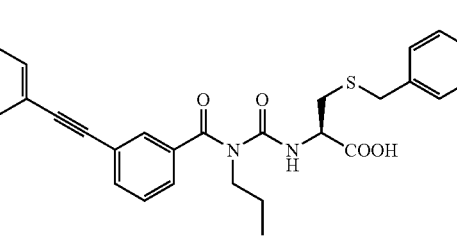
(116) 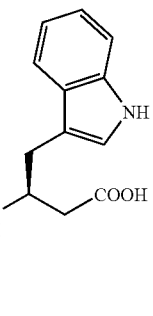

(117)
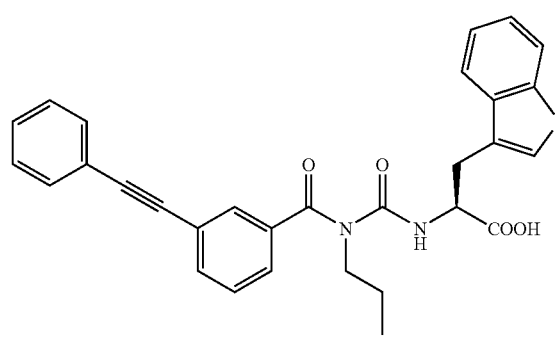
(118)
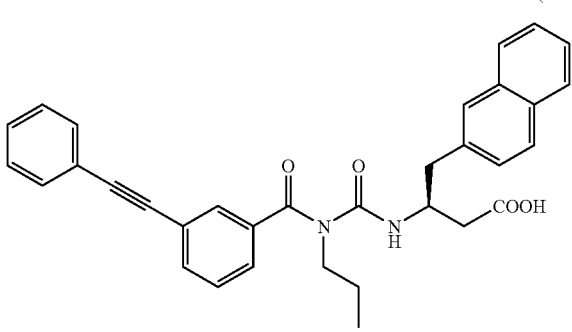
(119)
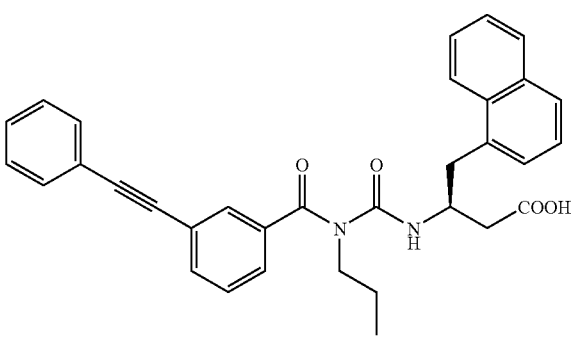
(120)
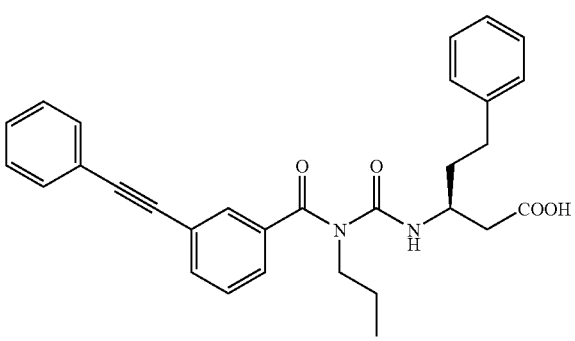
(121)
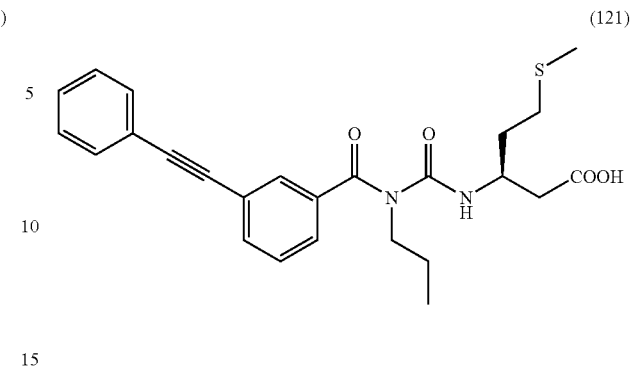
(122)
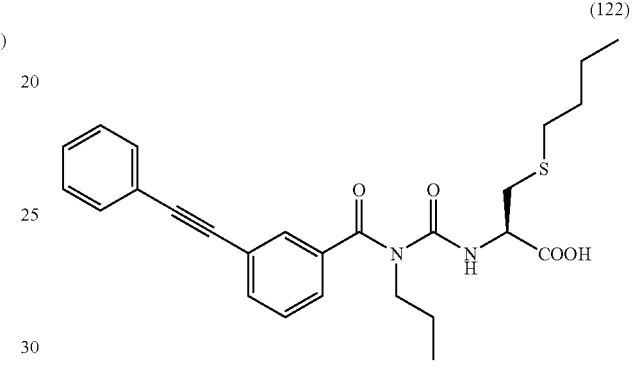
(123)
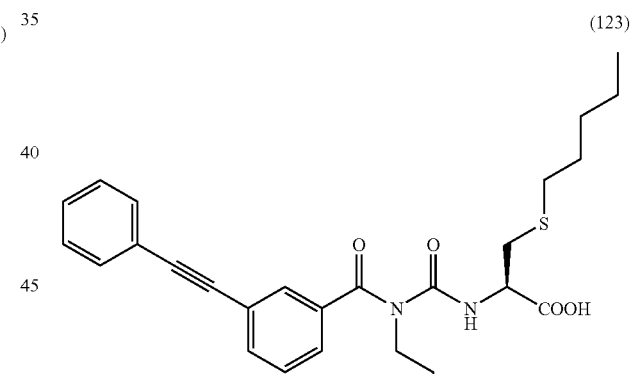
(124)
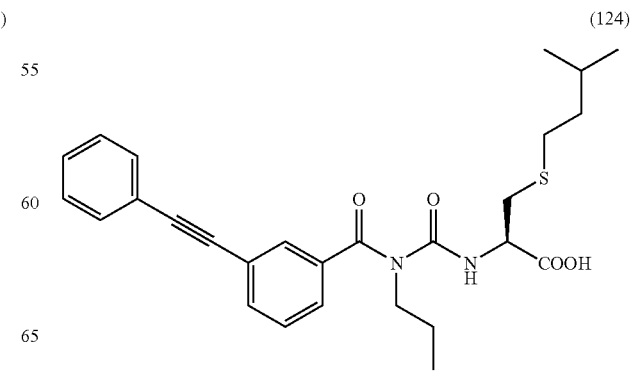

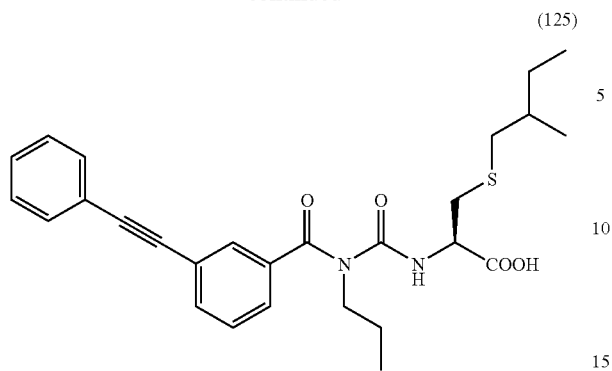
(125)
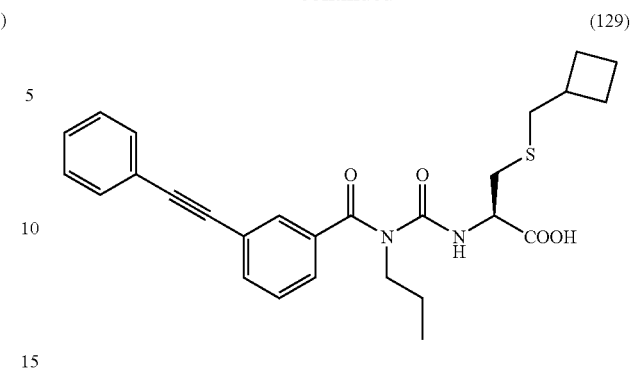
(129)
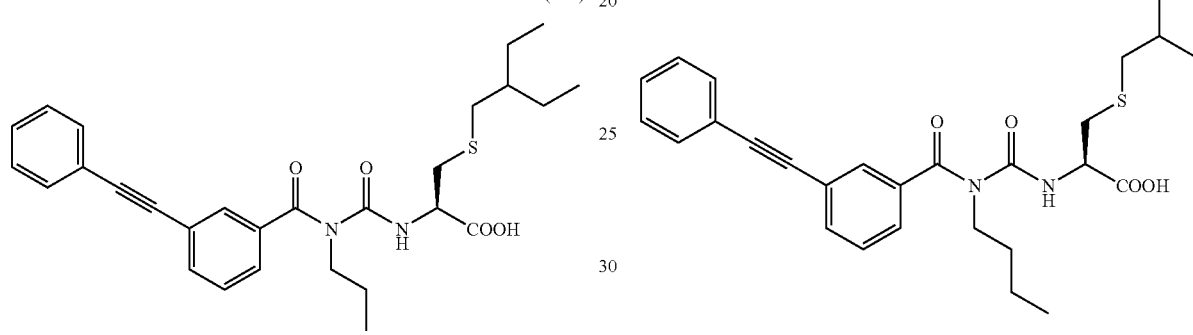
(126)
(130)
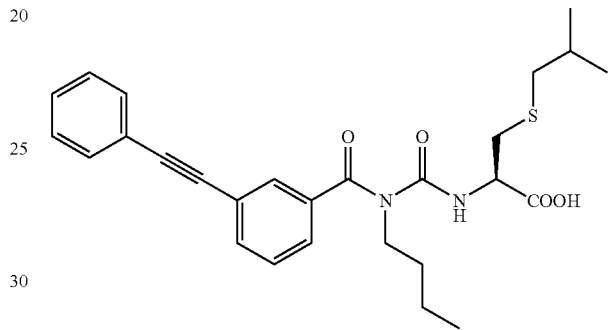
(127)
(131)
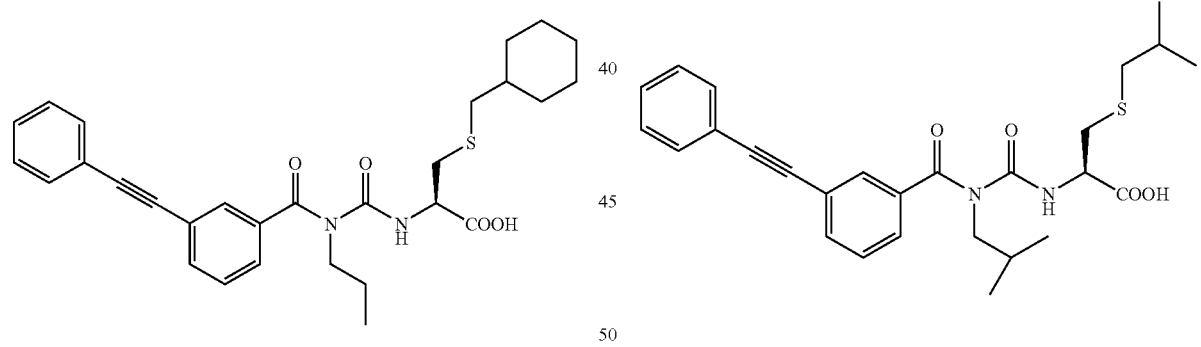
(128)
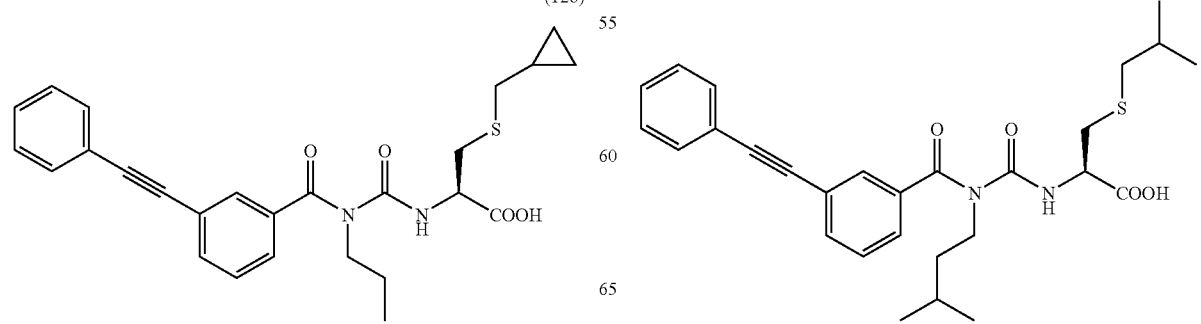
(132)

(133)
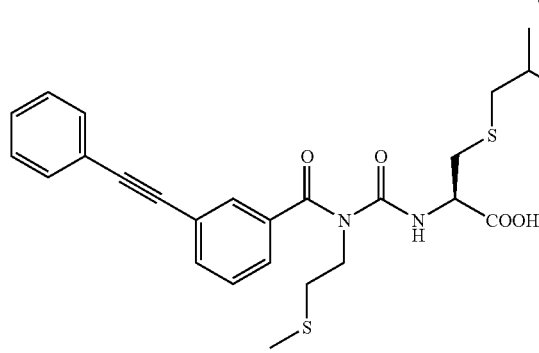
(134)
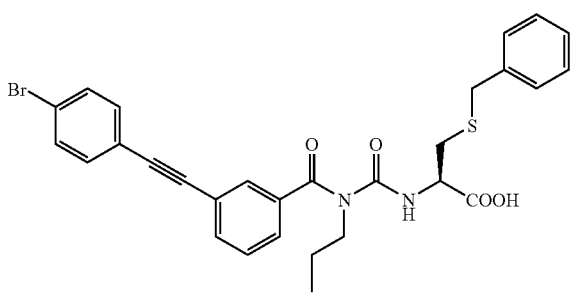
(135)
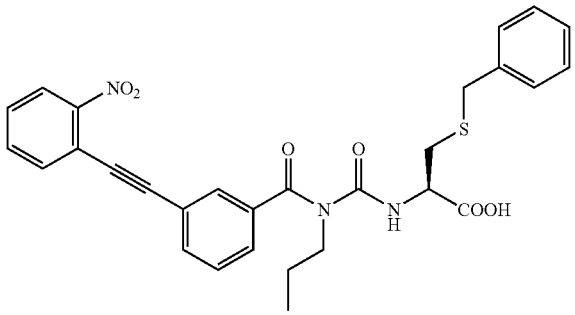
(136)
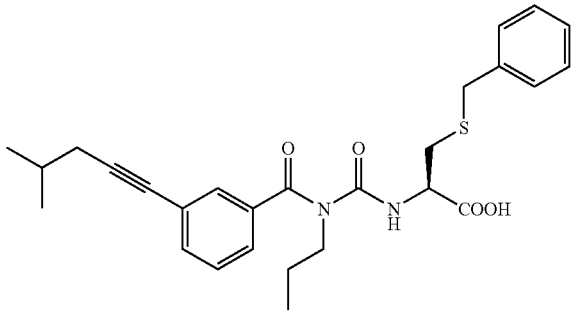
(137)
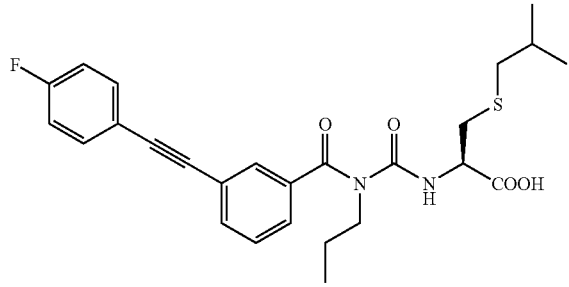
(138)
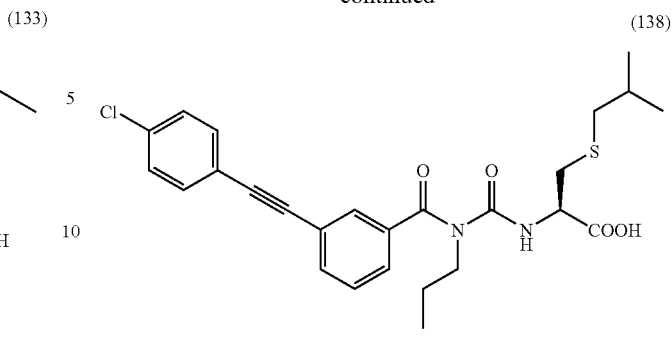
(139)
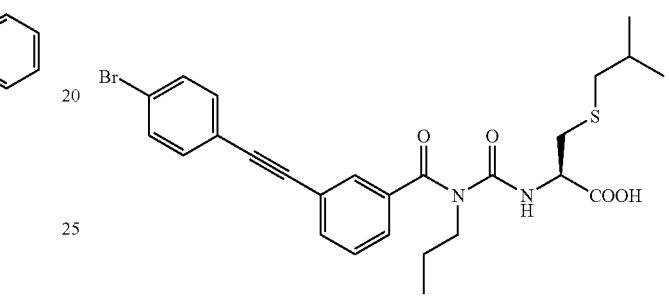
(140)
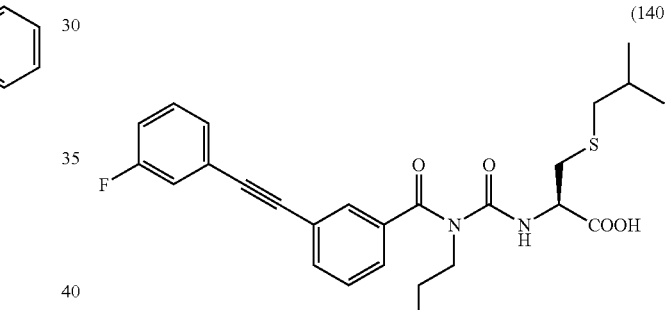
(141)
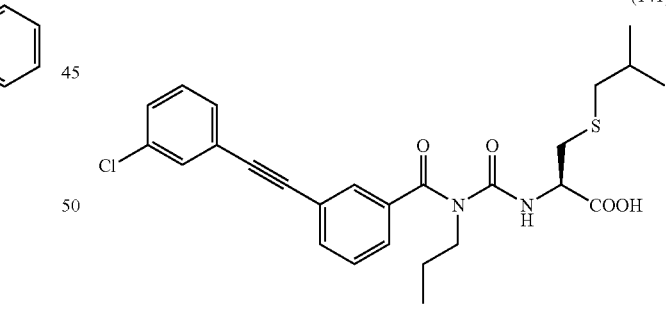
(142)
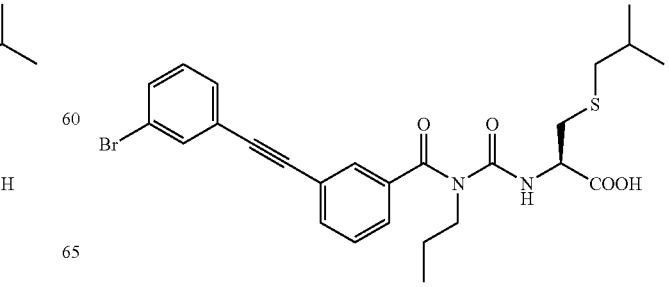

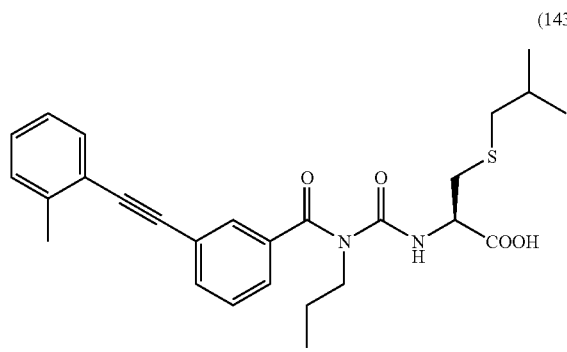
(143)
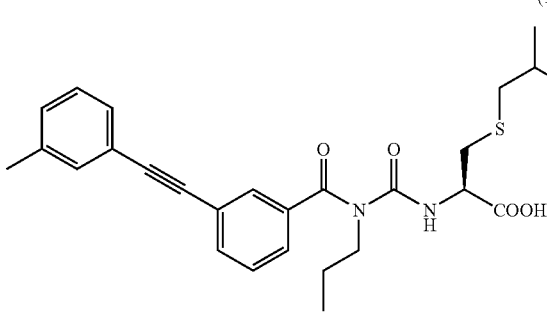
(144)
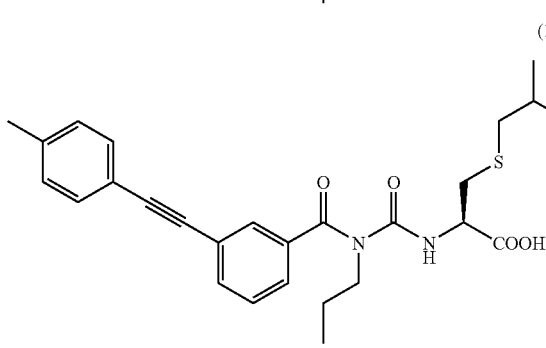
(145)
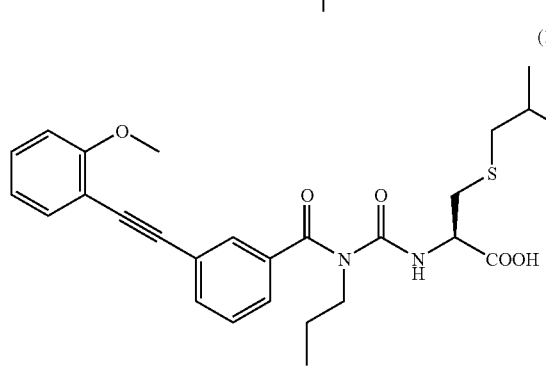
(146)
(147)
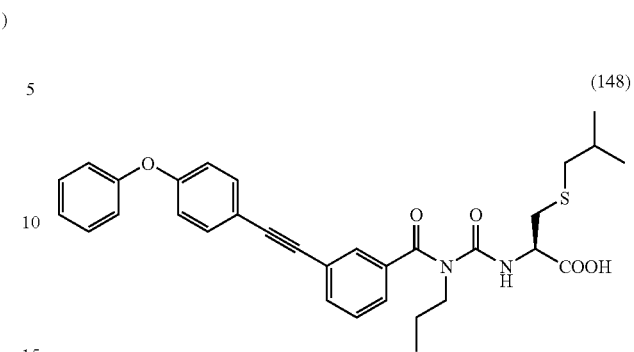
(148)
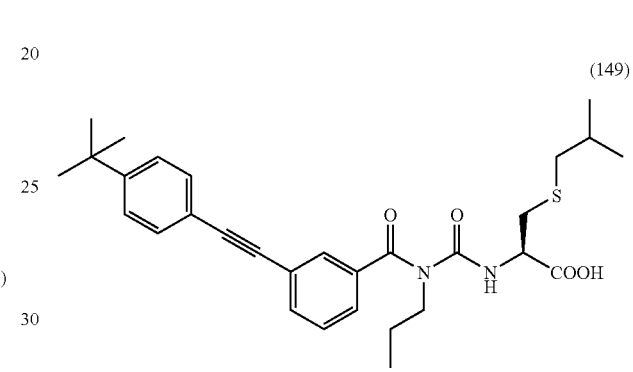
(149)
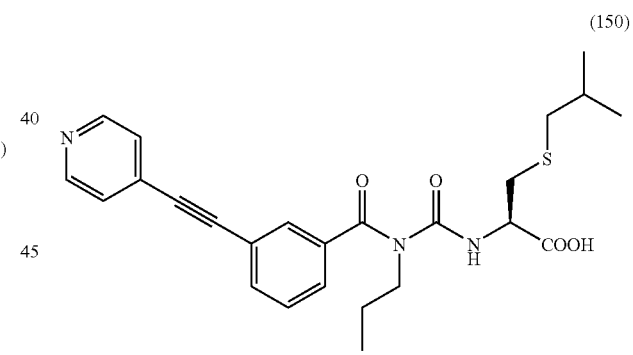
(150)
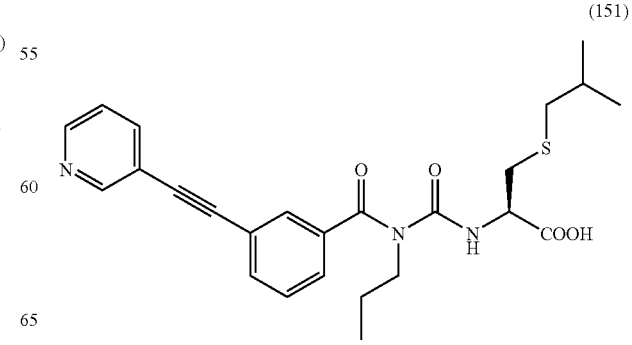
(151)

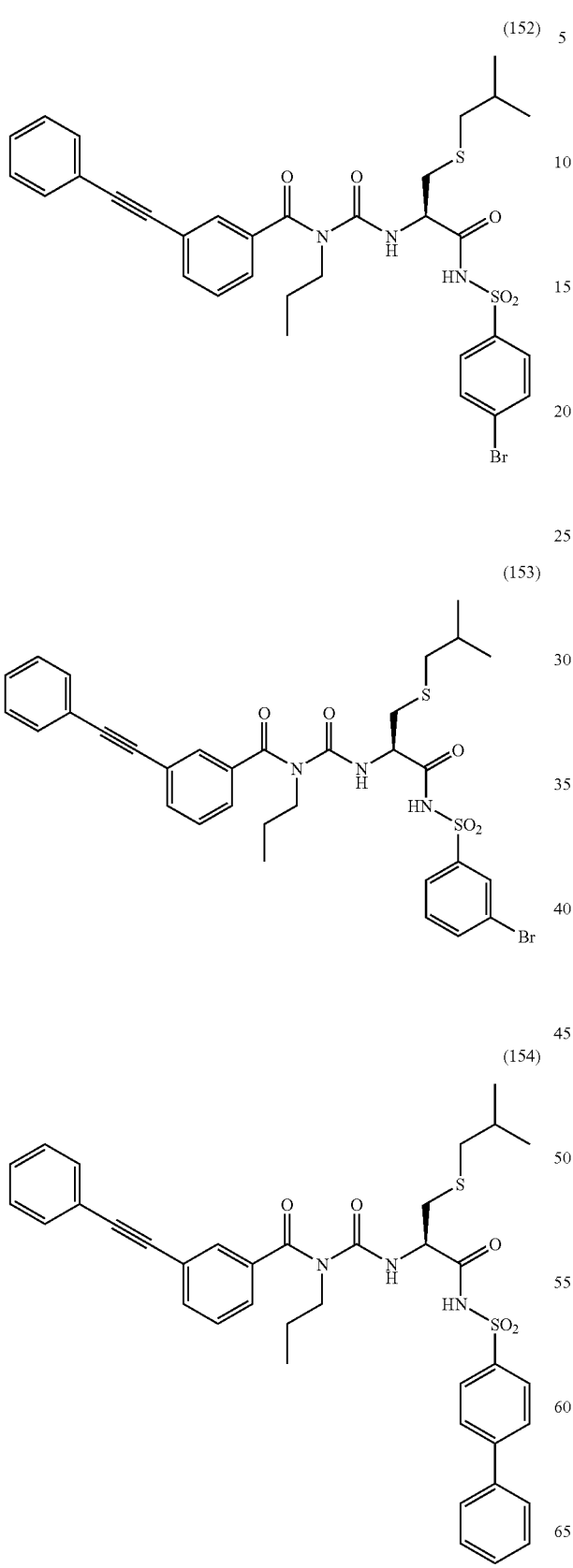
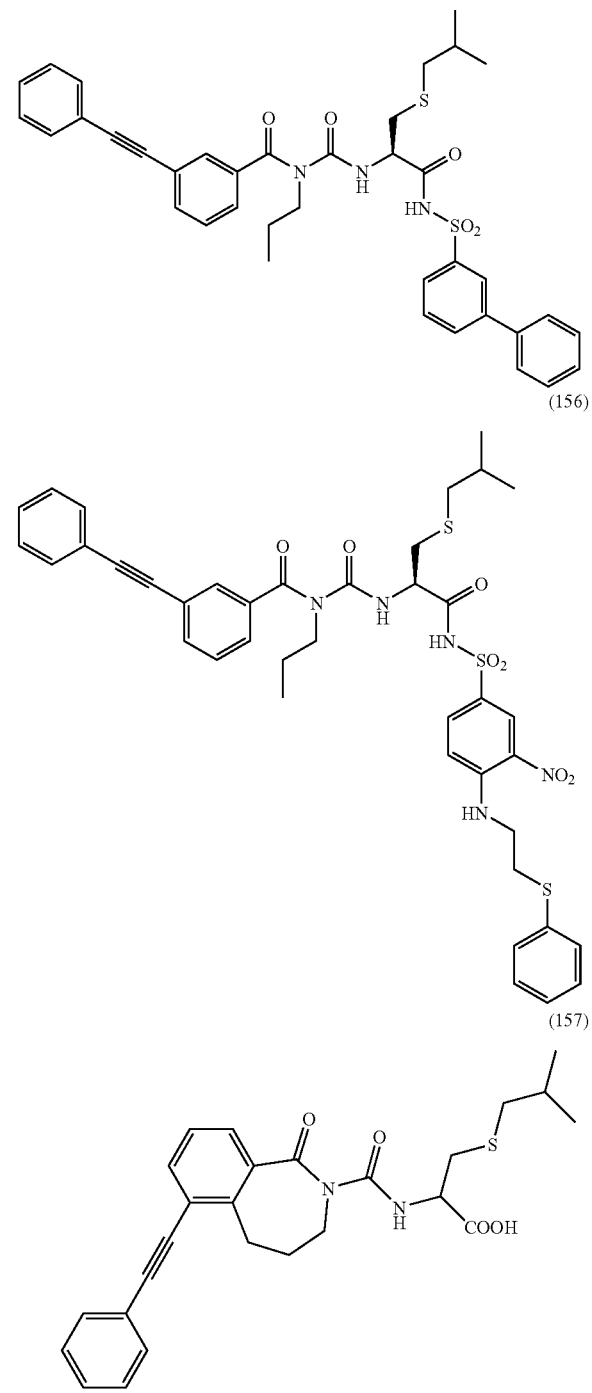
Especially preferred compounds include compounds (1), (2), (3), (6), (7), (8), (9), (10), (11), (12), (13), (14), (15), (17), (18), (21), (22), (23), (24), (29), (33), (34), (35), (36), (37), (39), (40), (42), (43), (45) (46), (47), (48), (52), (58), (59), (62), (64), (65), (66), (67), (82), (83), (84), (85), (86), (87), (88), (89), (90), (91), (92), (93), (94), (95), (96), (97), (98), (99), (100), (101), (102), (103), (105), (107), (108), (109), (110), (111), (112), (113), (114), (115), (116), (117), (118), (119), (120), (122), (123), (124), (125), (126), (127), (128), (129), (130), (131), (132), (133), (134), (135), (136), (137), (138), (139), (140), (141), (142), (143), (144), (145), (146), (147), (148), (149), (152), (153), (154), (155) and (156). Especially compounds (1), (7), (8), (9), (10), (12), (13), (14), (15), (24), (36), (39), (42), (46), (58), (62), (82), (83), (84), (85), (88), (89), (90), (91), (92), (93), (94): (95), (98), (100), (101), (102), (103), (107), (108), (109), (110), (111), (112), (113), (114), (115), (116), (117), (118), (120), (121), (122), (123), (124), (125), (127), (129), (130), (131), (132), (133), (135), (136), (137), (138), (139), (140), (141), (142), (143), (144), (145), (146), (147), (152), (153), (154), (155) and (156). More especially preferred compounds include (9), (83), (84), (91), (94), (100), (101), (102), (103), (116), (131), (137) and (156).

The benzoylurea derivatives of the invention may be prepared by a method adapted from DE 2514020, Eli Lilly & Co., 1975 as shown in Scheme 1 wherein P is a protecting group.

-continued

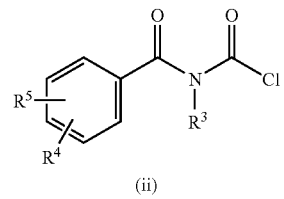

The carbamoylchloride (ii) was readily reacted with a trimethylsilyl (TMS) O-protected amino acid (v) which is prepared and added to the carbamoylchloride (ii) in acetonitrile without purification [Horner et. al., 1998], as shown in Scheme 3.

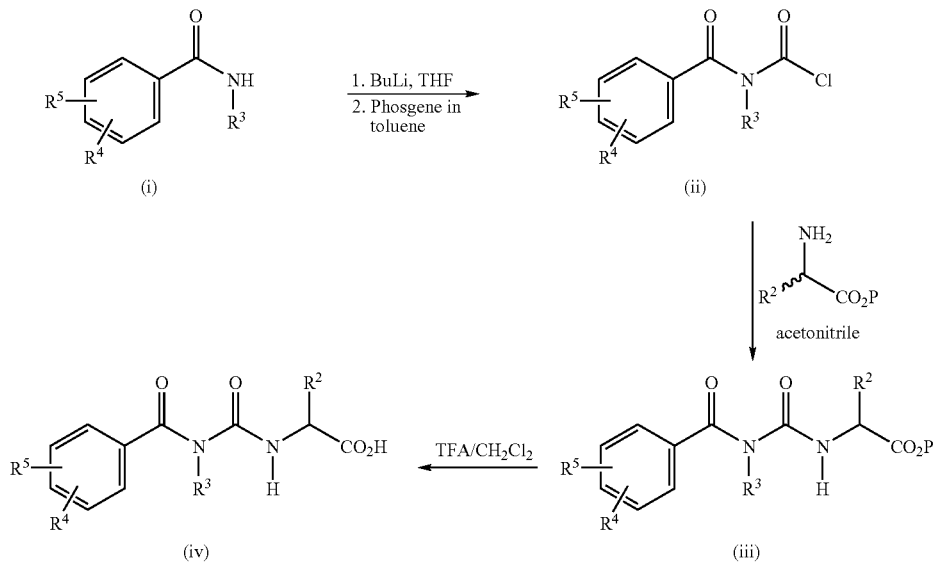

However, the synthetic procedure shown in Scheme 1 is not suitable when $R^3$ is a bulky group which sterically hinders the benzoylamide (i) nitrogen.

A second synthetic strategy which allows the preparation of the carbamoylchloride (ii), even in the presence of a bulky substituent as $R^3$ is shown in Scheme 2. Treatment of an amide with trimethylsilyltriflate (TMSOTf) in ether in the presence of triethylamine provides a silylated intermediate that readily reacts with phosgene to form a carbamoylchloride (ii).

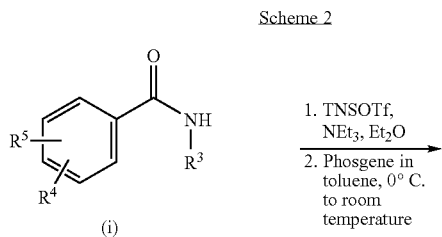

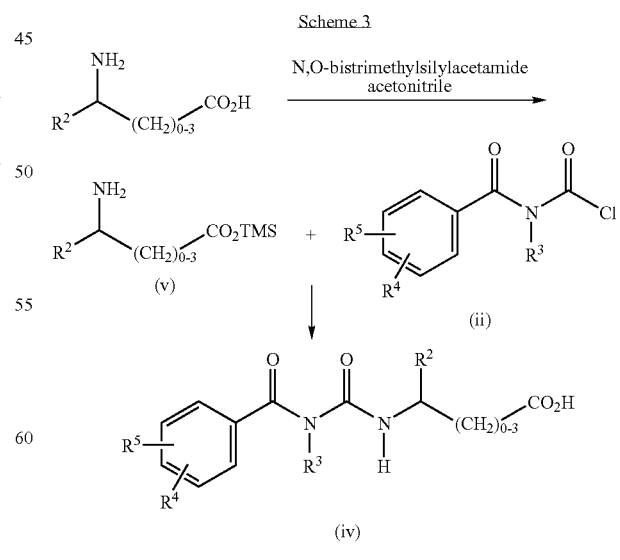

This process allows for a wide diversity of substituents represented by $R^2$, $R^3$, $R^4$ and $R^5$ and provides the benzoylurea derivatives in high yields. Also this process is applicable to both amino acids and amino hydrochlorides.

Although Scheme 3 shows reaction of the carbamoylchloride with a suitably protected amino acid, this may be adapted to allow reaction between any primary amine and the carbamoylchloride. For example, the carboxylic acid may be replaced by a cyano group, which may be further reacted with sodium azide to give a tetrazole. The reaction shown in Scheme 3 may be adapted to allow reaction with a cyano substituted primary amine or a tetrazole substituted primary amine thereby providing means of introducing a carboxylic acid or carboxylate bioisostere as $R^1$.

Another means of preparing the compounds of the invention is by condensation of a nitrosulphonamide with an isocyanate as shown in Scheme 4.

-continued

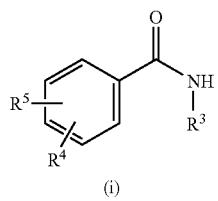

(i)

Arylethynyl substituents may be introduced as $R^4$ using the Sonogashira coupling [Negishi and Anastasia, 2003] as shown in Scheme 6.

Scheme 4

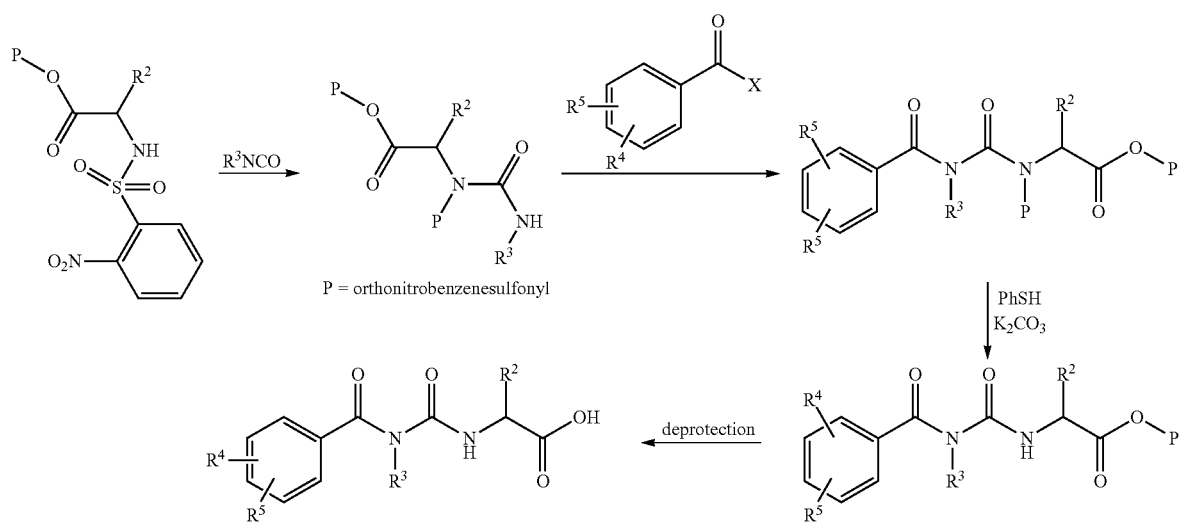

P = orthonitrobenzenesulfonyl

The starting benzoylamide (i) in Scheme 2 may be readily prepared from commercially available starting materials. For example, a range of benzylamides may be prepared from a suitably substituted bromophenylcarboxylic acid by amidation followed by Suzuki coupling as shown in Scheme 5.

Scheme 5

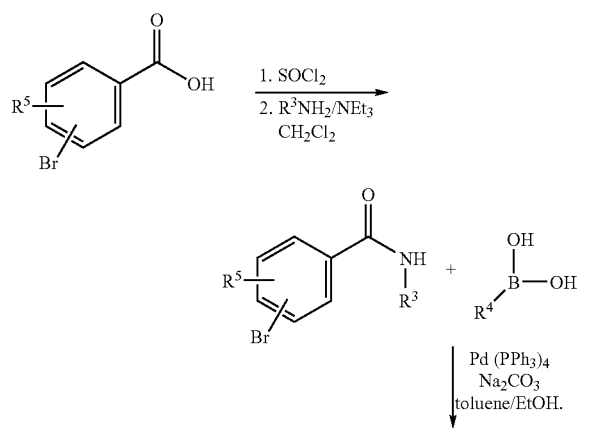

Scheme 6

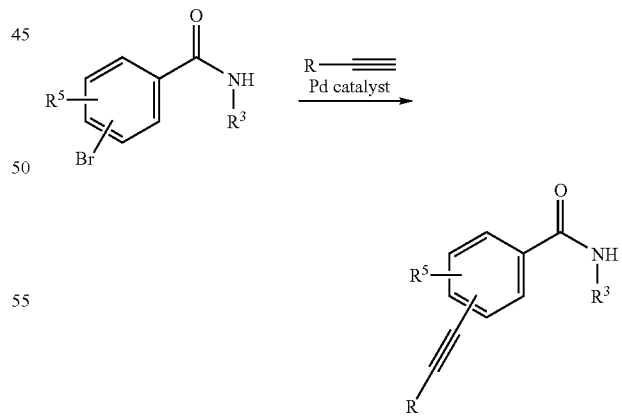

The carbamoylchloride (ii) and compound of the invention (iv) may then be prepared as shown in Schemes 2 and 3. Alternatively, when R is aryl or heteroaryl, it may be introduced using the Sonogashira coupling after preparation of compounds (i) and (iii). For example, the Sonogashira coupling may also be performed as shown in Scheme 7.

Scheme 7

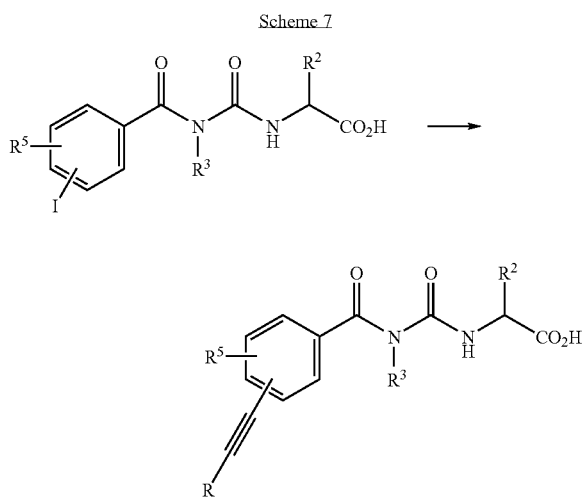

The benzoylurea compounds of the invention in which $R^2$ is $CH_2SR$ may also be prepared from S-derivatised cysteine residues. The carbamoylchloride (ii) prepared as in Scheme 1 or Scheme 2 may be reacted with a S-derivatised cysteine residue as shown in Scheme 8.

Scheme 8

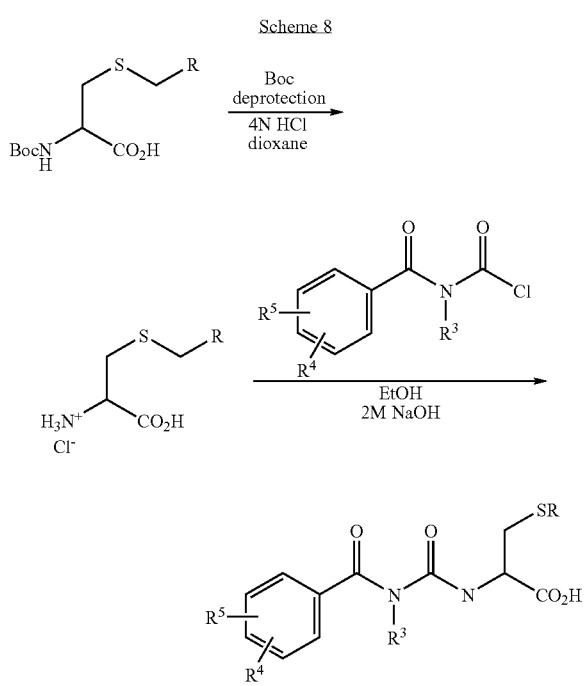

Advantageously, Boc protected unnatural amino acids may be used in this synthesis directly from their preparation. Another advantage is that Boc protected amino acids, both natural or unnatural, used as shown in Scheme 8 provide a very simple and clean method for obtaining an amino acid hydrochloride salt. Suitably derivatised cysteine residues for use in Scheme 8 may be prepared by the method of Seko et. al. (2003) as shown in Scheme 9.

Scheme 9

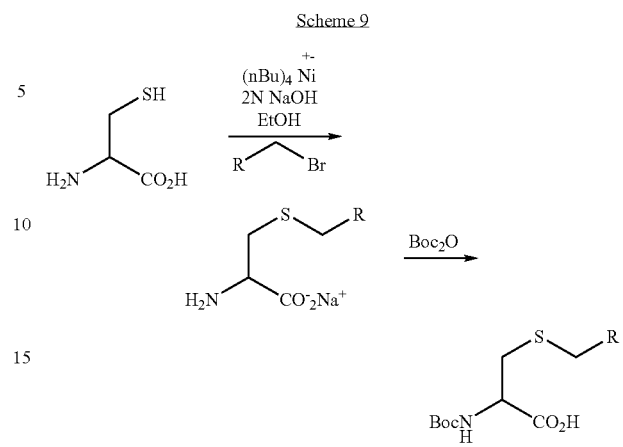

Alternatively the benzoylurea compounds may be prepared directly from unprotected amino acids as shown in Scheme 10.

Scheme 10

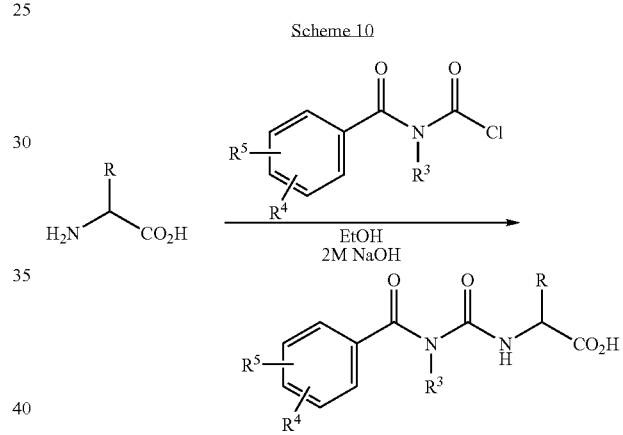

The substituent $R^5$ may be present in the starting benzoic acid or may be introduced later in the synthetic process by procedures known in the art. For example, alkyl groups may be introduced by Friedel-Crafts alkylation, halogens can be introduced by treatment with dihalogen in the presence of a catalyst, alkylthio groups may be introduced by sulfonylation followed by reduction. Suitable methodology may be found in, for example, March J., "Advanced Organic Chemistry", Wiley & Sons, 1985.

Compounds in which $R^1$ is a tetrazole or tetrazolate can be prepared by known methods from a cyano group and sodium azide by cycloaddition [Davies D. T. "Aromatic Heterocyclic Chemistry", Oxford University Press, 1992]. The cyano group may be present in the amine reacted with the carbamoylchloride, or may be reacted with sodium azide before reaction with the carbamoylchloride.

The substituents $R_1$ to $R_5$ may be present during the synthesis in protected or unprotected form. Suitable protecting and deprotecting methods for reactive functional groups such as carboxylic acids, ketones, amines and hydroxy groups are known in the art, for example, in Protective Groups in Organic Synthesis, T. W. Green & P. Wutz; John Wiley & Son, $3^{rd}$ Ed., 1999.

The substituents $R_1$ to $R_5$ may also undergo further manipulation to provide different substituents during or after the synthetic process described above.

In order to prepare large numbers of analogues, the strategy is also compatible with a solid phase synthetic approach. The synthetic process would then be reversed as the amino acid is immobilized onto a solid phase polymer support. Examples of this approach are provided in Schemes 11-17.

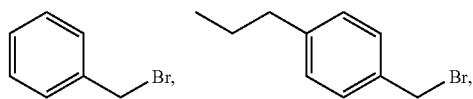

Scheme 11: Solid phase synthesis where the amino acid is a cysteine or derivative thereof.

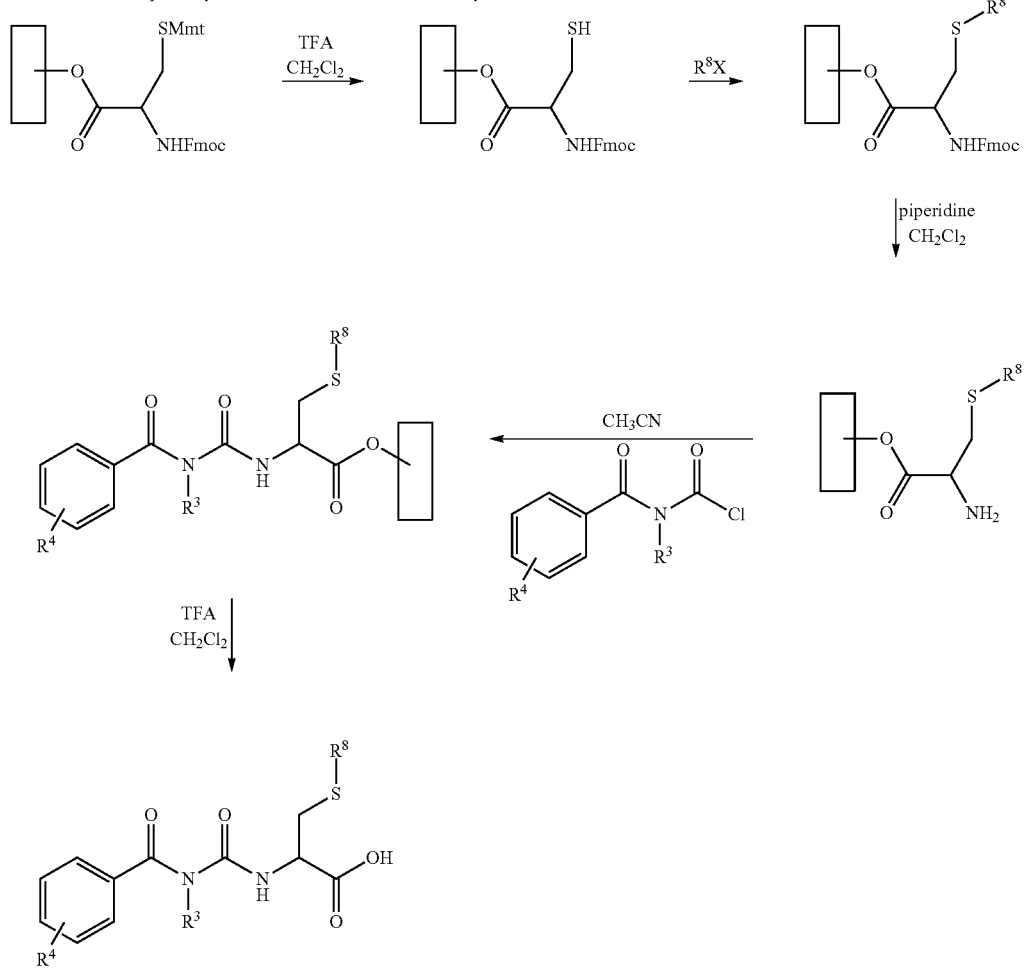

Mmt: 4-methoxytrityl
Fmoc: fluromethyloxycarbonyl
TFA: trifluoroacetic acid

Diversity in the substitution at the cysteine sulfur atom can be introduced by reactions known in the art. For example, the deprotected thiol of the cysteine residue may be alkylated with an alkyl halide or alkyl halide derivative ($R^8$—X). Examples of suitable alkyl halides include, but are not limited to $CH_3Cl$, $CH_3Br$, $CH_3I$, $CH_3CH_2Cl$, $CH_3CH_2Br$, $CH_3CH_2I$, $CH_3(CH_2)_2Cl$, $CH_3(CH_2)_2Br$, $CH_3(CH_2)_2I$, $(CH_3)_2CHCl$, $(CH_3)_2CHBr$, $(CH_3)_2CHI$, $CH_3(CH_2)_3Cl$, $CH_3(CH_2)_3Br$, $CH_3(CH_2)_3I$, $(CH_3)_2CHCH_2Cl$, $(CH_3)_2CHCH_2Br$, $(CH_3)_2CHCH_2I$, $CH_3(CH_2)_4Cl$, $CH_3(CH_2)_4Br$, $CH_3(CH_2)_4I$, $(CH_3)_2CH(CH_2)_2Cl$, $(CH_3)_2CH(CH_2)_2Br$, $(CH_3)_2CH(CH_2)_2I$, $CH_3CH_2CH(CH_3)CH_2Cl$, $CH_3CH_2CH(CH_3)CH_2Br$, $CH_3CH_2CH(CH_3)CH_2I$, $CH_3CH_2CH(CH_3CH_2)CH_2Cl$, $CH_3CH_2CH(CH_3CH_2)CH_2Br$, $CH_3CH_2CH(CH_3CH_2)CH_2I$, -continued

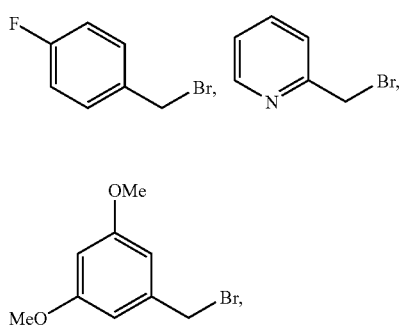

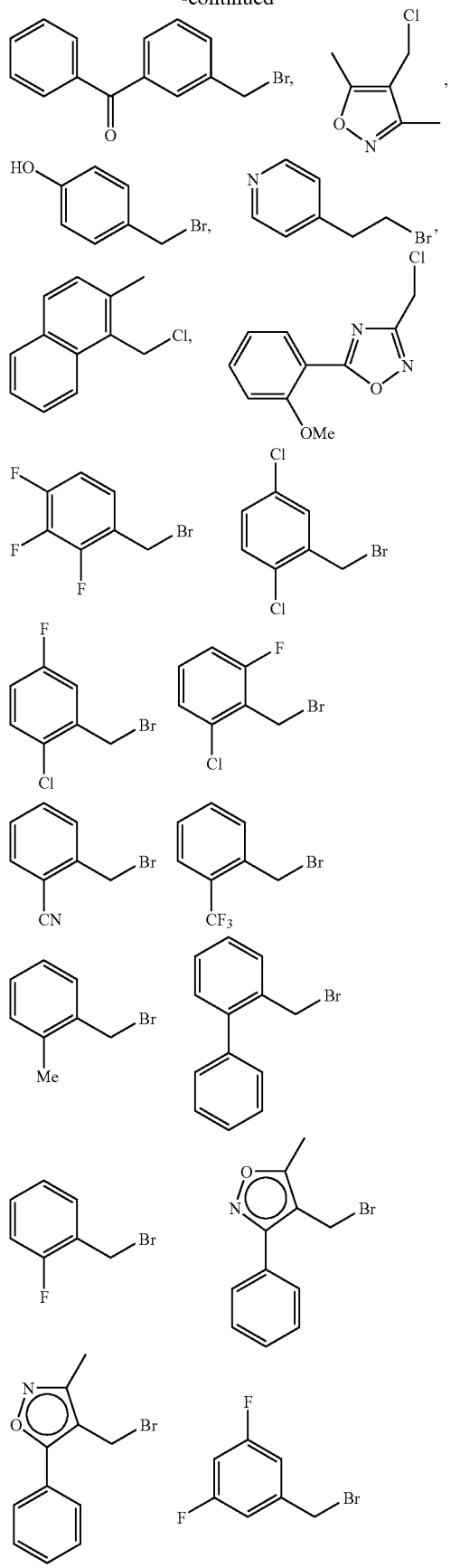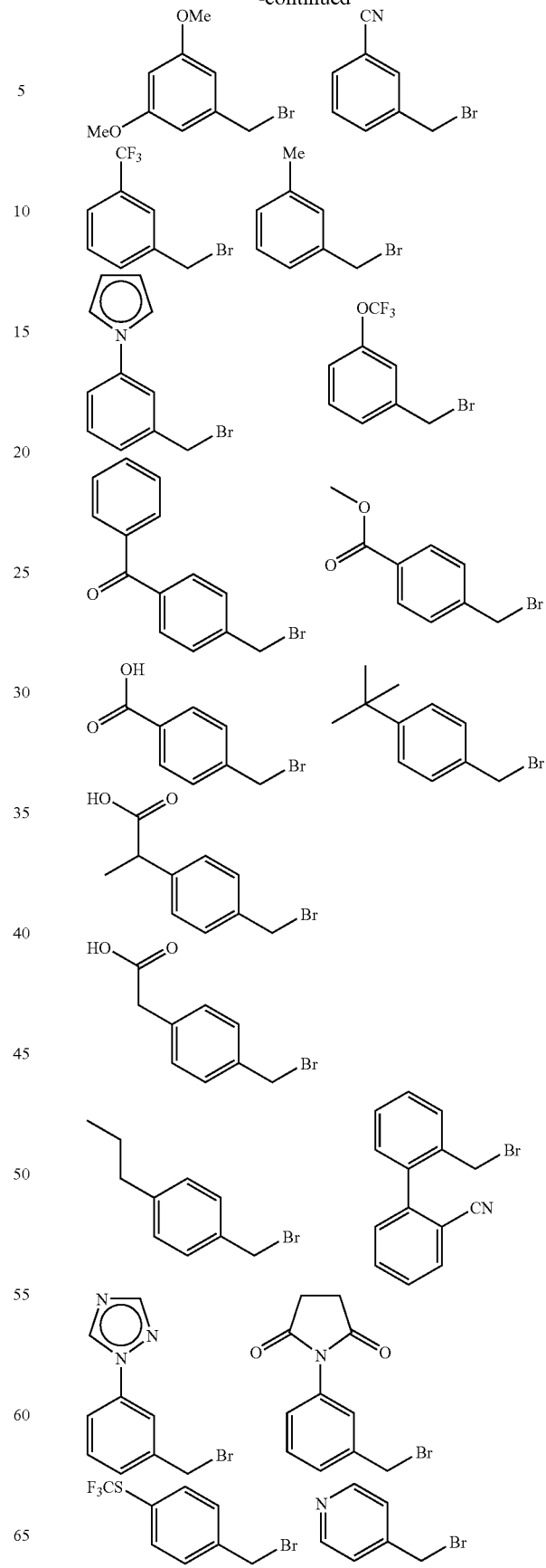

-continued

55
-continued
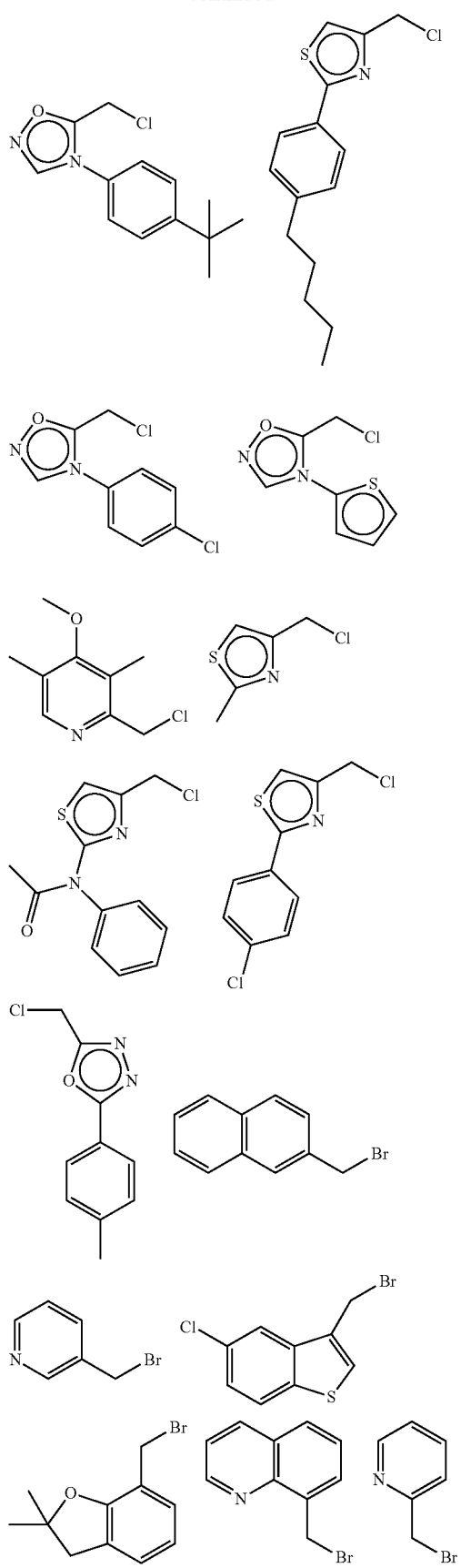
56
-continued
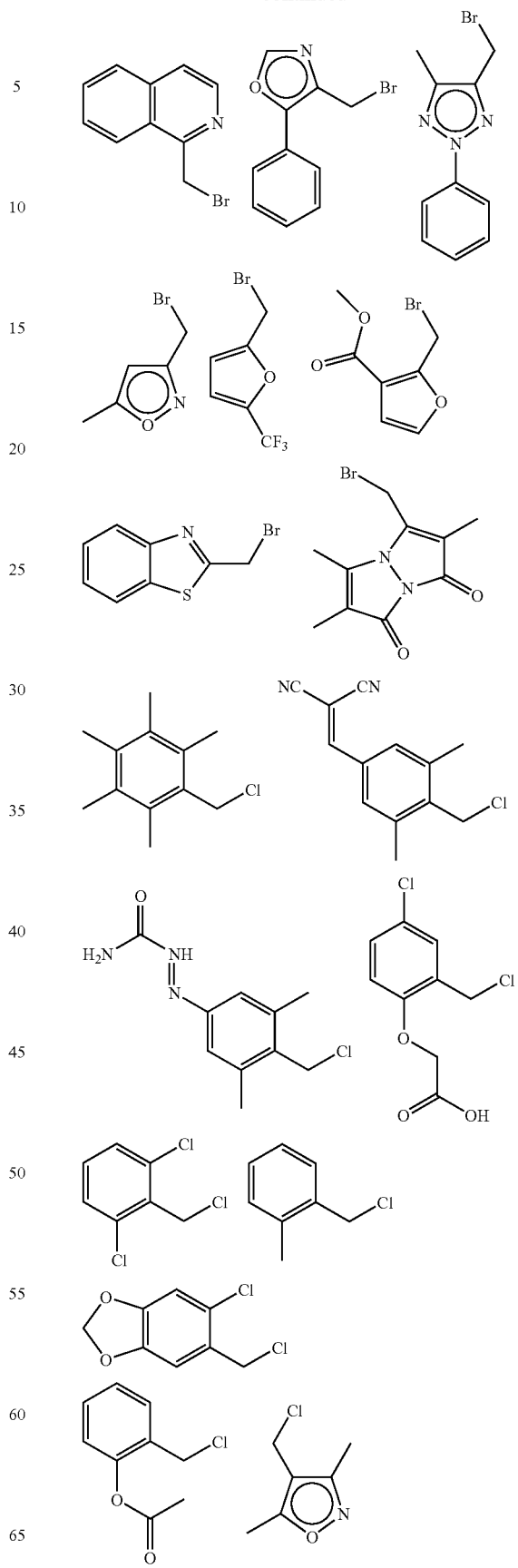

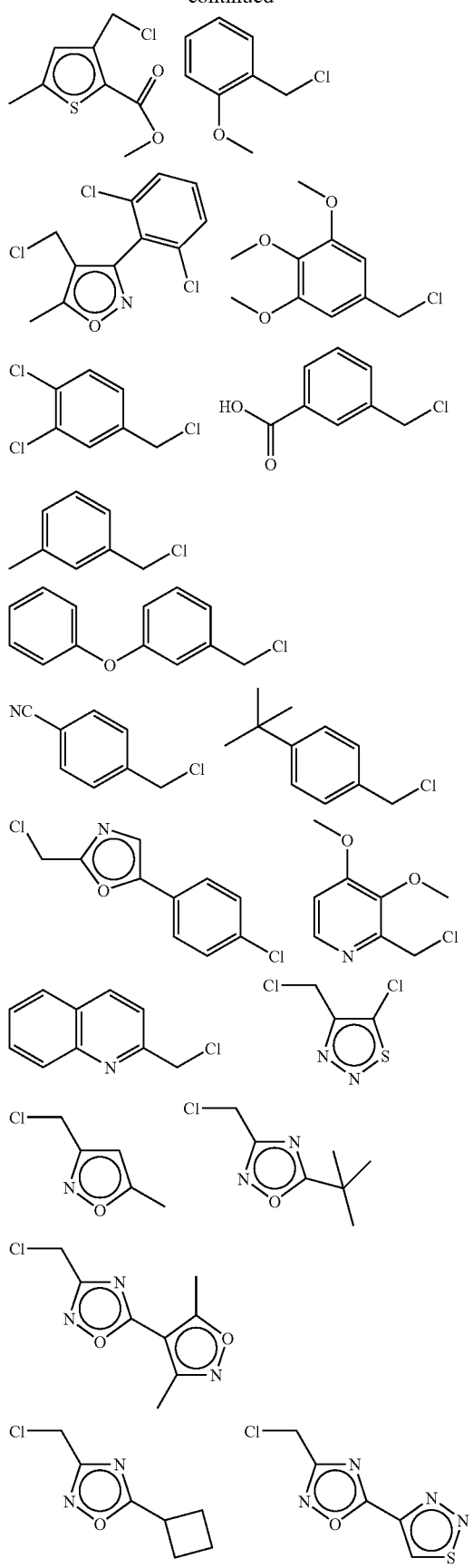
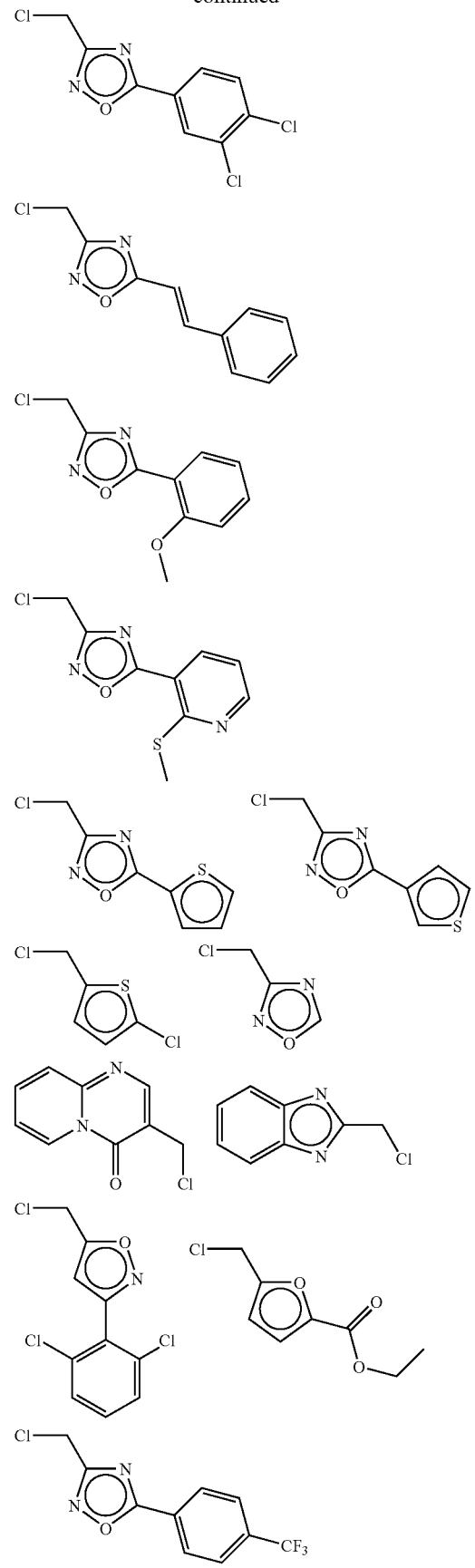

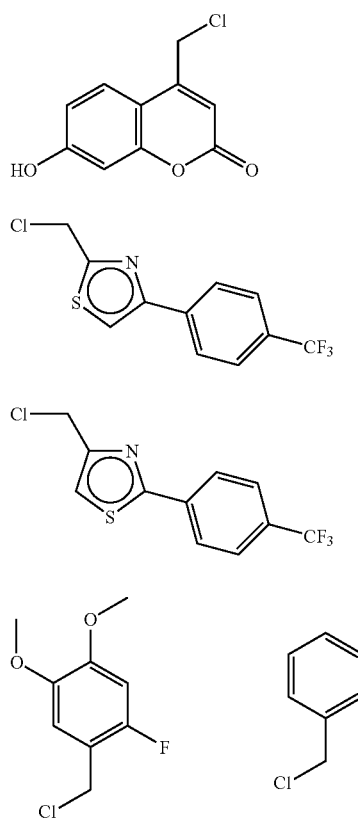
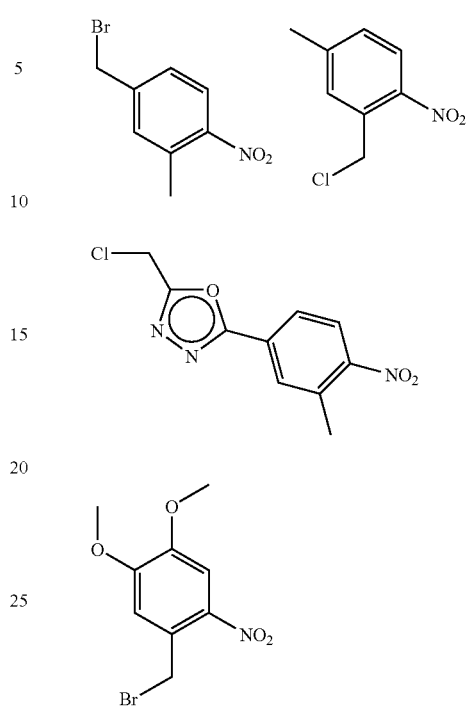
and the like.
Alternatively, thiophenyl substituents at $R^2$ may be prepared from serine derivatives as shown in Scheme 12.
Scheme 12
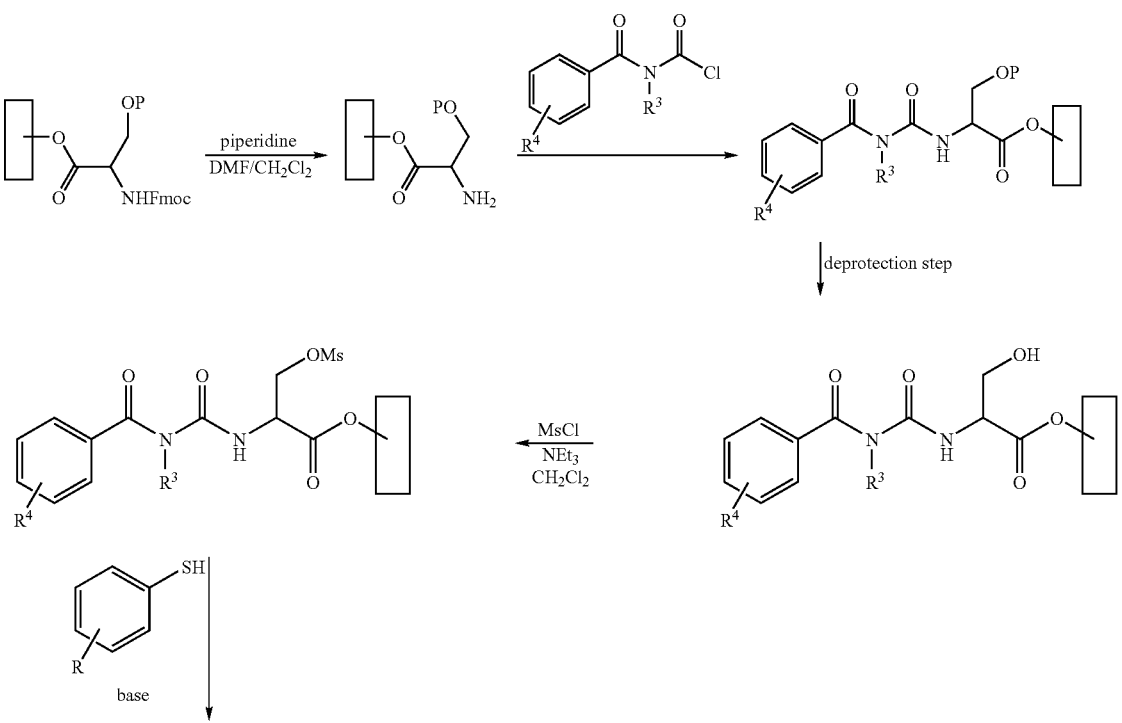

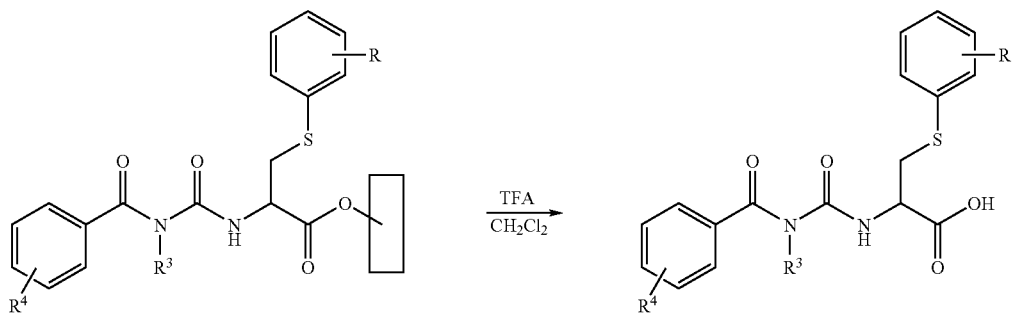
where P is a protecting group (see Green & Wutz, 1999) and R is at least one optional substituent.
Diversity may also be introduced into $R^2$ by use of a halo-substituted phenylamine residue and Suzuki coupling as shown in Scheme 13.
Scheme 13: Introduction of diversity via Suzuki coupling on 4- or 3-iodophenylalanine.
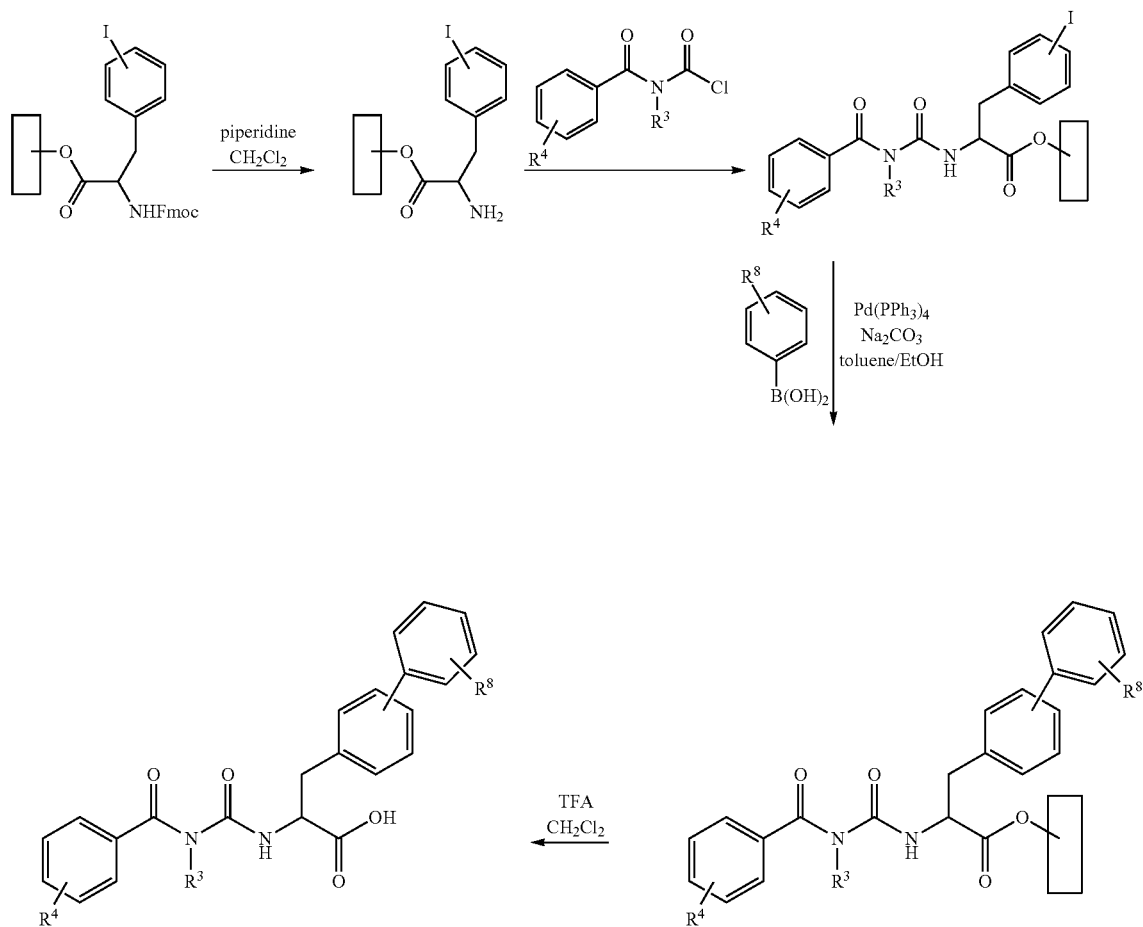

Suzuki coupling may also be used to introduce R⁴ as shown in Scheme 14.

Scheme 14: Introduction of diversity via Suzuki coupling on a 3- or 4-iodobenzoylurea; where R is one or more optional substituents

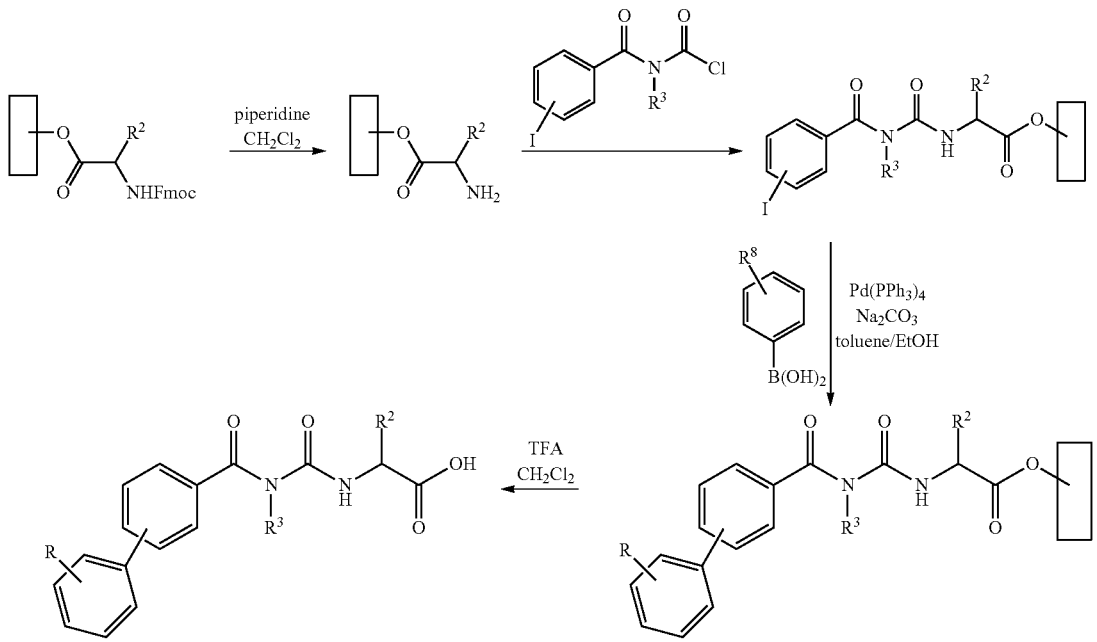

Phenylethynyl substituents may also be introduced at R⁴ using Sonogashira coupling [Negishi and Anastasia, 2003] and a solid phase synthesis approach as shown in Scheme 15.

Scheme 15

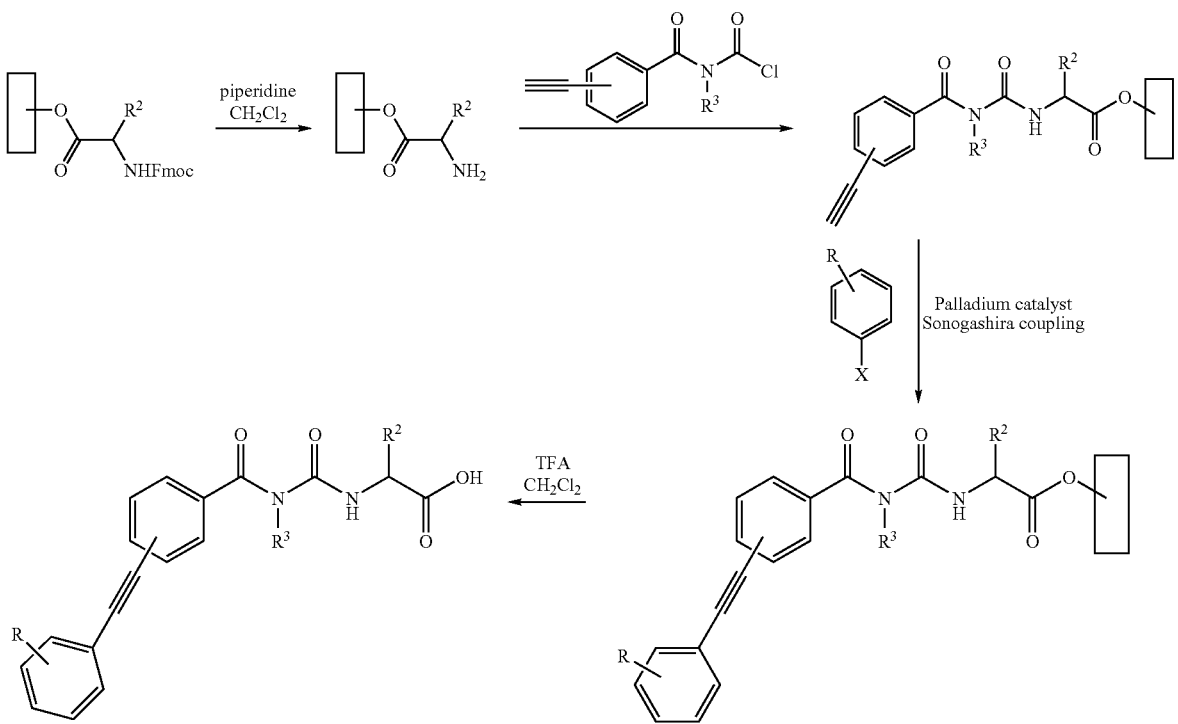

In Scheme 15, R represents one or more optional substituents.

Variation of $R^3$ may also be achieved by substitution at the $N^1$ nitrogen. For example, by using the Mitsunobu reaction, as shown in Scheme 16.

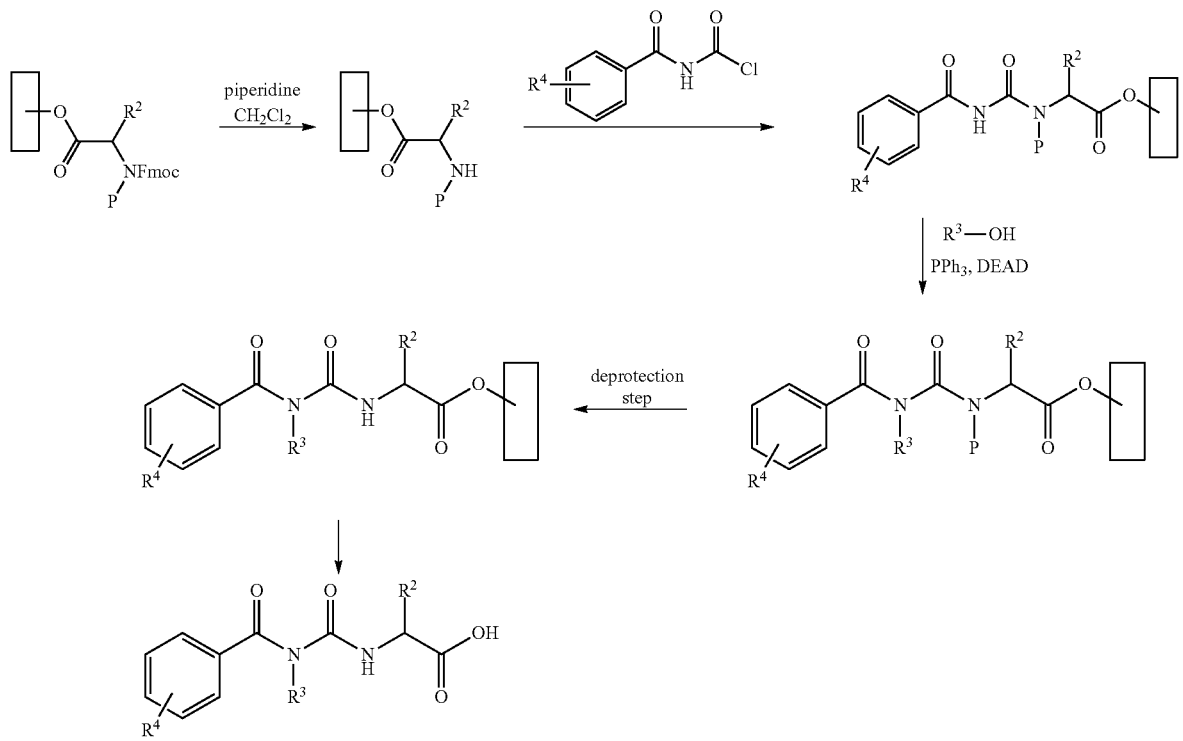

where P is a nitrogen protecting group such as t-butyl, p-methoxybenzyl, benzyl and methylbenzyl.

Another method for use in solid phase synthesis is condensation of a nitrosulphonamide with an isocyanate as shown in Scheme 17.

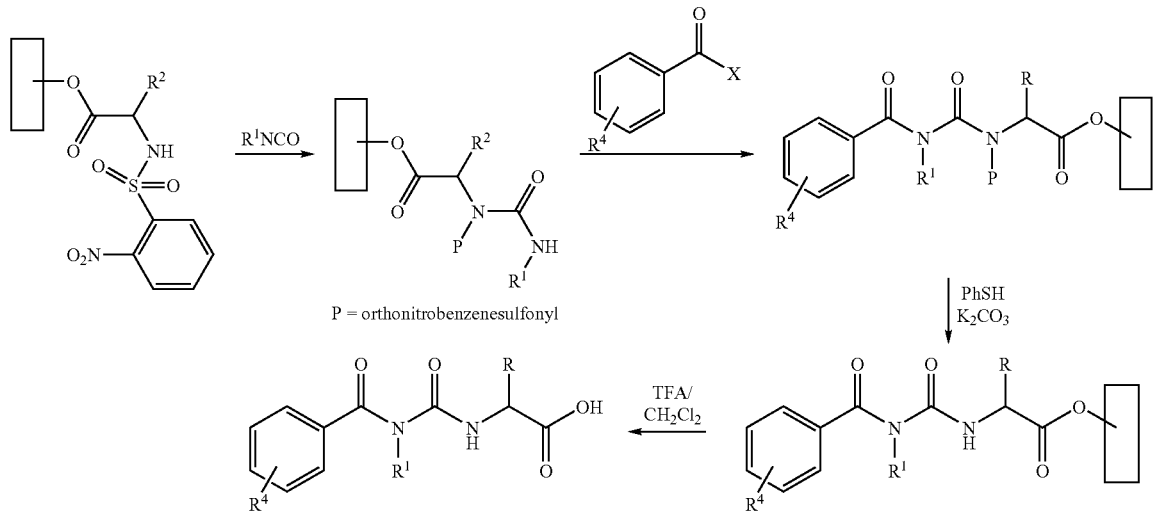

Scheme 17: introduction of diversity via an isocyanate/sulfonamide condensation.
Suitable boronic acids for use in Suzuki couplings, whether in solution phase or solid phase synthesis, include, but are not limited to:
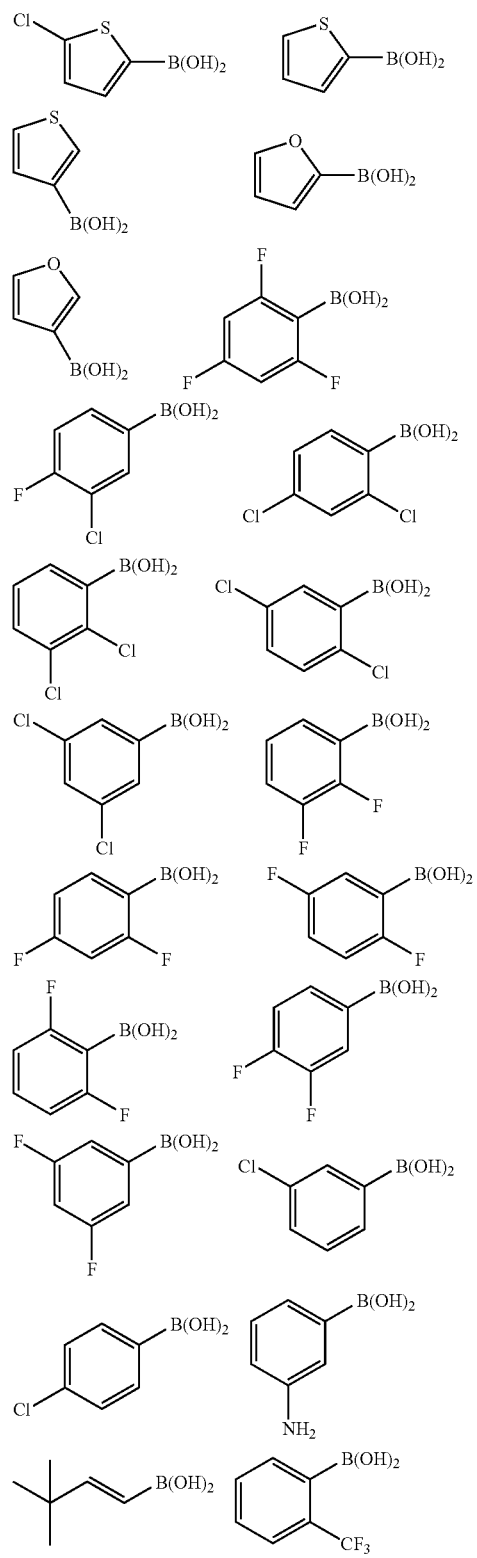
-continued
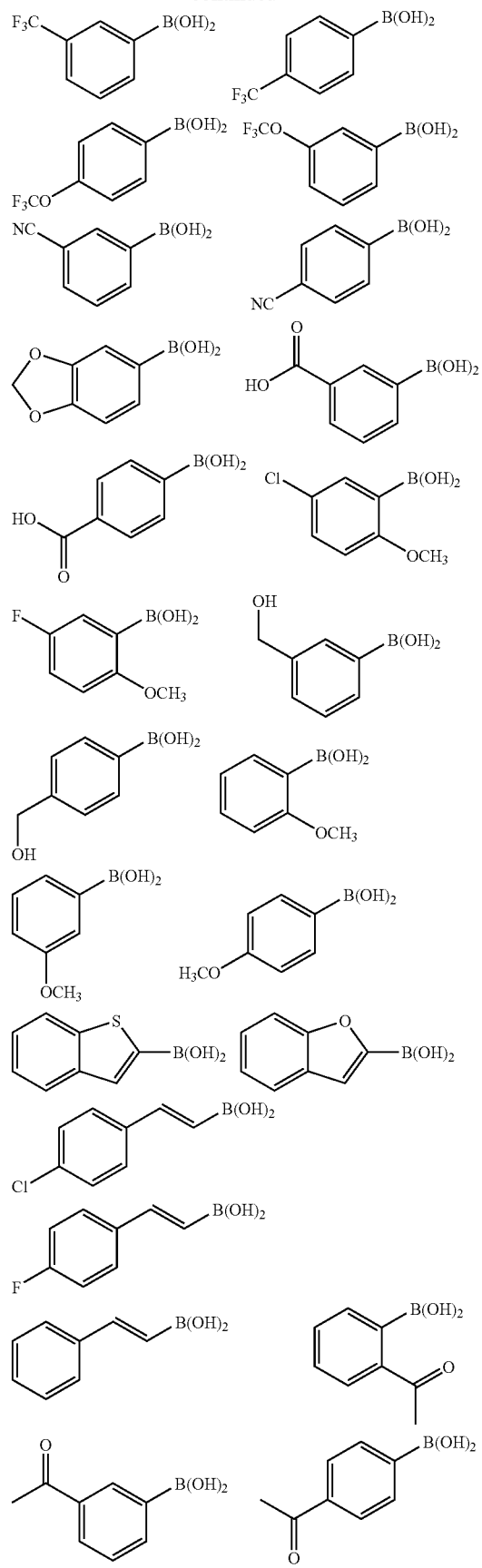

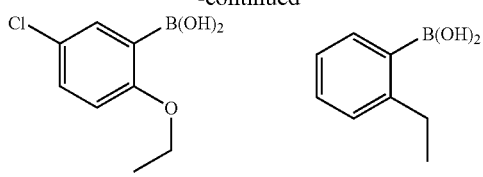
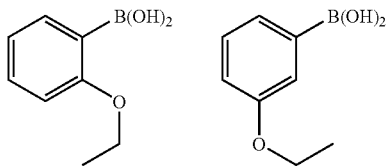
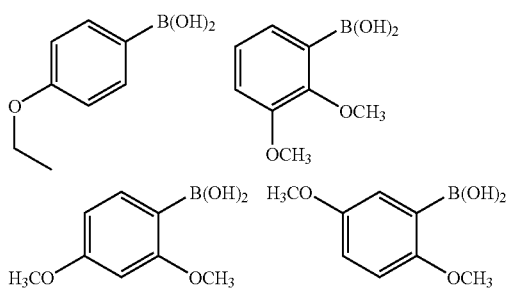
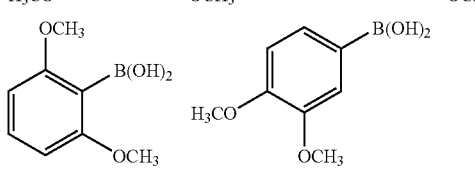
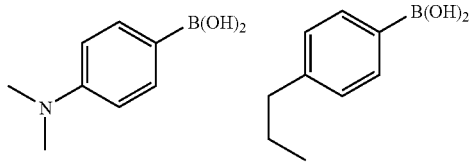
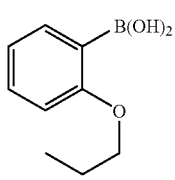
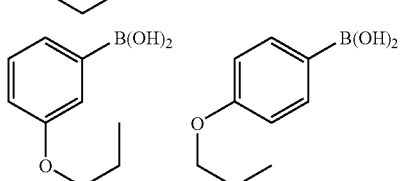
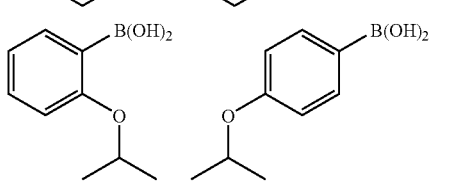
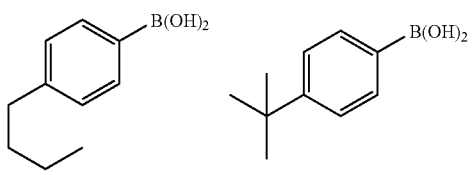

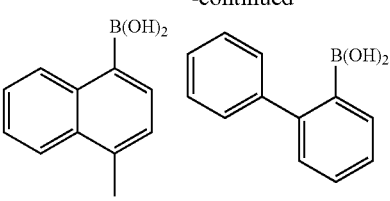

When introducing aryl rings into the molecule, for example as shown in Schemes 11-14, suitable substituents that may be present on the aryl rings are depicted above in relation to the boronic acids and aryl halides used in Suzuki couplings and substitution at the cysteine thiol (Scheme 10) respectively.

Suitable acetylenic derivatives for use in the Sonogashira coupling reactions, whether in solution phase or solid phase synthesis, include but are not limited to:

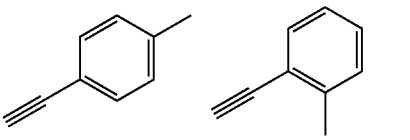
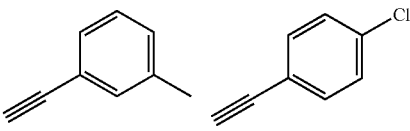
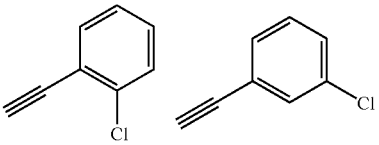
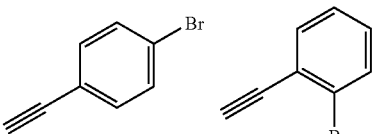
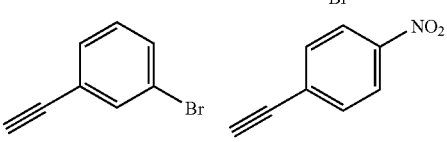
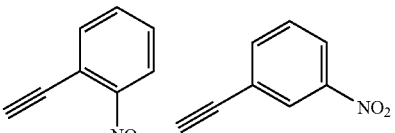
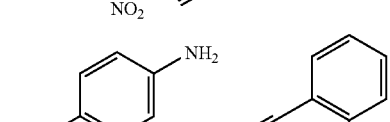
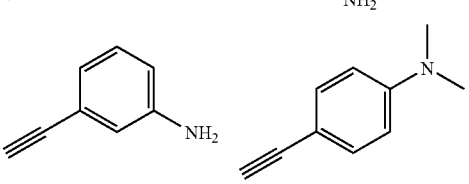

-continued
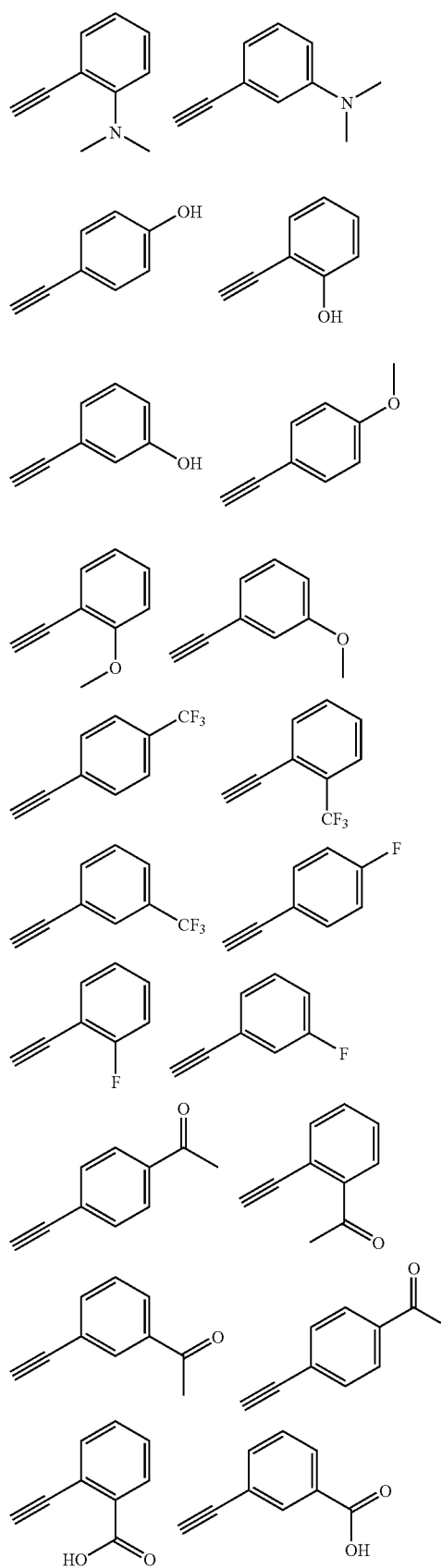
-continued
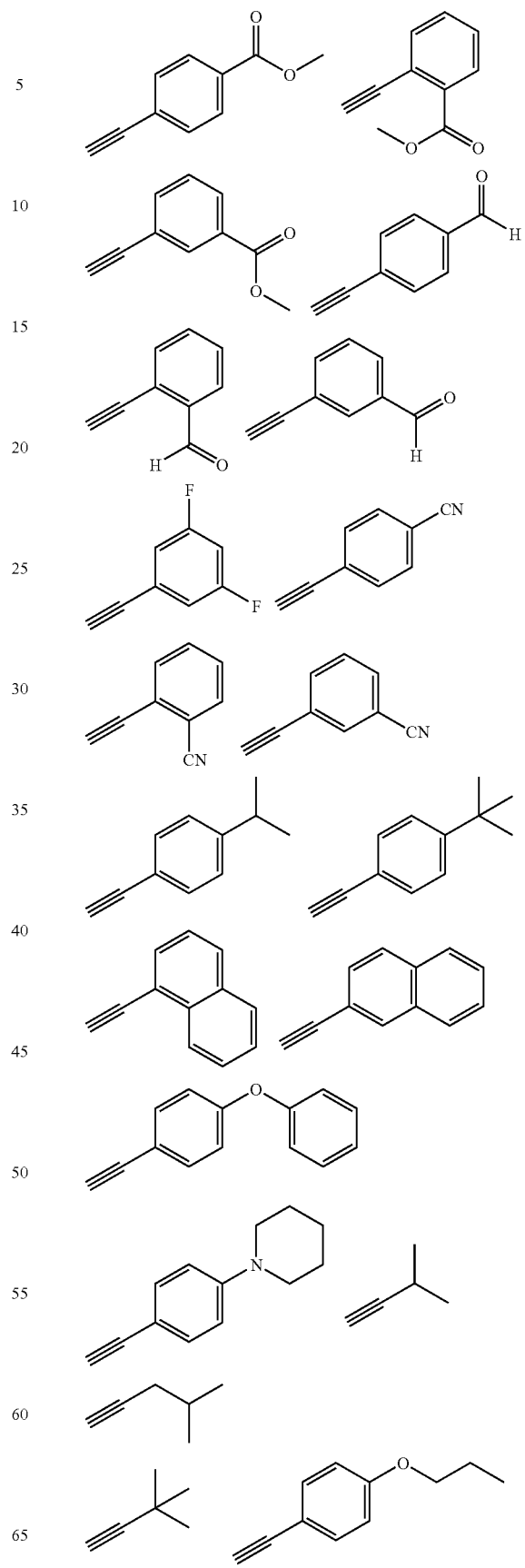

-continued

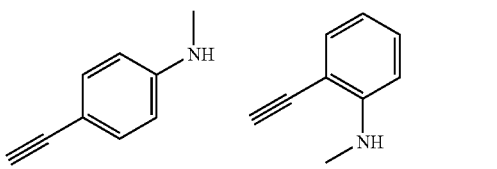

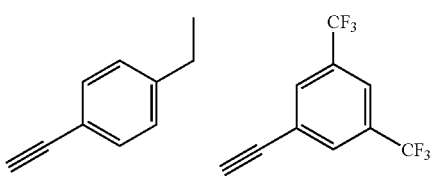

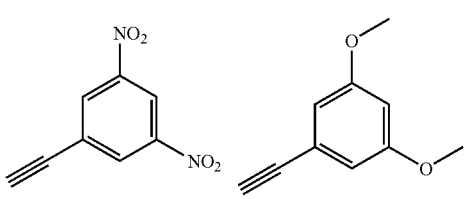

-continued

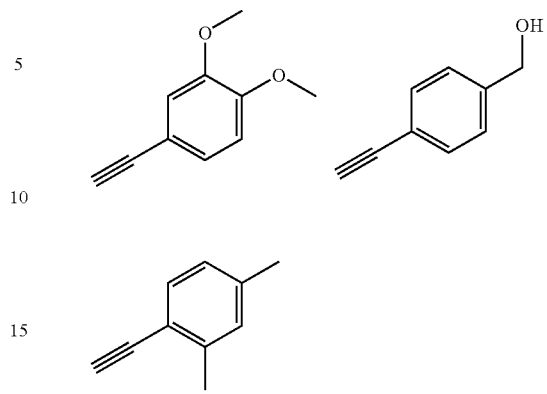

In preferred synthetic procedures, solution phase synthesis is used.

While not wishing to be bound by theory, it appears that the benzoylurea compounds of the invention are able to form an intramolecular hydrogen bond which stabilizes a conformation in which the substituents $R^2$, $R^3$ and $R^4$ simulate the spatial arrangement of the side chains of an alpha helical peptide. The conformation having an intramolecular hydrogen bond is an equilibrium with an open linear conformation as shown in Scheme 18.

Scheme 18

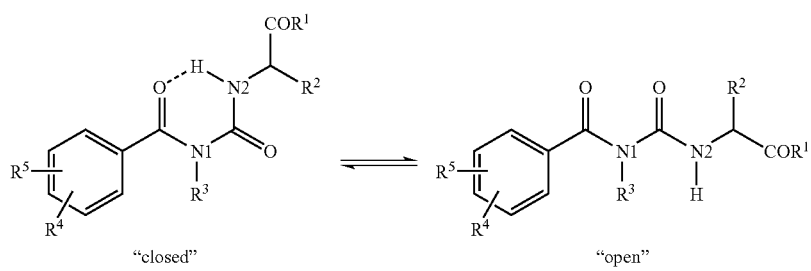

"closed"     "open"

The NMR chemical shift for the $N^2H$ proton showed in general a downfield shifted signal which can be considered as a sign of hydrogen bonding. It was observed that compounds bearing a sterically-hindered substituent at the $N^1$ position had a reduced downfield shift (see Table 2). This difference may be due to the possibility of a change of conformation for these structures where the downfield chemical shift is representative of the closed conformation (consequence of the intramolecular hydrogen bonding) and the more upfield chemical shifts are indicative of the open conformation (hydrogen atom solvent exposed).

The importance of steric hindrance at the $R^3$ position may be observed by $^1$HMR chemical shift of the $N^2$ hydrogen atom. Those compounds in which $R^3$ was linear or in which branching was not directly attached to the $N^1$ nitrogen atom had downfield shifted signals compared to the $N^2$ hydrogen atom signals of compounds in which $R^3$ was a branched or cyclic group directly attached to the $N^1$ nitrogen atom as shown in Table 2.

TABLE 2

| Compound | (62) | (1) | (2) | (5) | (3) | (4) | (6) | (7) | (8) |
|---|---|---|---|---|---|---|---|---|---|
| $R^3$ | Et | n-Pr | n-Bu | i-Pr | i-Bu | sec-Bu | cyclohexyl | cyclohexylmethyl | benzyl |
| δ ($N^2H$) | 9.72 | 9.68 | 9.68 | 8.52 | 9.57 | 8.58 | 7.91 | 9.6 | 9.8 |

It is postulated that the substitution pattern of the benzoylurea compounds affects the position of the equilibrium between the closed and open conformations. However, upon binding in the hydrophobic pocket of the Bcl-2 hydrophobic groove, the closed conformation will be favoured because of the general hydrophobicity of the interaction area (dielectric constant effect) and the specific interactions in the hydrophobic pockets bringing the molecules into the preferred closed conformation and adopting the spatial arrangement required to mimic an alpha helical peptide.

The decrease in binding of compounds bearing a hindered group on the $N^1$ nitrogen (like compound 5) could therefore be explained by the surplus of energy required during the binding event to bring the molecule into the closed conformation. However it is possible that compounds binding with high affinity having the appropriate $N^1$ substituent would adopt an open conformation in the cell medium and the closed conformation in the binding groove and as such constitute a "conformational prodrug". This could be important in terms of selectivity and toxicity. Helical mimetics are known to be able to interact with hydrophobic membranes therefore causing homeostatic disruption via non-selective pathways (e.g. swelling of mitochondrial membrane). The compounds of the present invention in the open conformation do not appear to be a helical mimetic and therefore in such a conformation they are unlikely to interfere with other non-selective pathways.

In another aspect of the invention there is provided a method of regulating the death of a cell, comprising contacting the cell with an effective amount of a compound of formula (I):

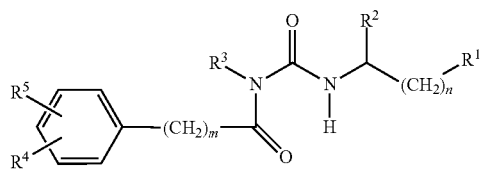

wherein $R^1$ is selected from $CO_2H$ or a carboxylic acid or carboxylate bioisostere;

$R^2$ is selected from an amino acid side chain, cycloalkyl, cycloalkenyl, aryl, heterocyclyl, heteroaryl and a group $$R^a\text{—}(CHR')_x\text{-}A\text{-}(CH_2)_y\text{—}$$

wherein A is a covalent bond or is selected from O, S, SO, $SO_2$ and $NR^6$, $R^a$ is H, cycloalkyl, cycloalkenyl, aryl, heterocyclyl, heteroaryl or $R^b$ where $R^b$ is

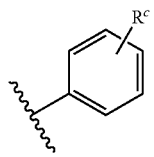

and $R^c$ is selected from heteroaryl, aryl, aryl($C_{2-6}$alkenyl), aryl($C_{2-6}$alkynyl), heteroaryl($C_{2-6}$alkenyl) and heteroaryl($C_{2-6}$alkynyl), R' is H or $C_{1-6}$alkyl, x and y are independently 0 or an integer from 1 to 6 provided that the sum of x and y is 1 to 6;

$R^3$ is selected from $C_{1-6}$alkyl, $C_{2-6}$alkenyl, $C_{2-6}$alkynyl, cycloalkyl, cycloalkenyl, aryl, heterocyclyl, heteroaryl and a group $$R^d\text{—}(CH_2)_p\text{—}W\text{—}(CH_2)_q\text{—}$$

wherein W is selected from a covalent bond, O, S and $NR^6$, $R^d$ is selected from H, cycloalkyl, cycloalkenyl, aryl, heterocyclyl and heteroaryl; p is an integer from 1 to 6, q is 0 or an integer from 1 to 5 provided that the sum of p and q is 1 to 6;

$R^4$ is selected from $C_{1-6}$alkyl, $C_{2-6}$alkenyl, $C_{2-6}$alkynyl cycloalkyl, $C_{1-6}$alkyloxy, $C_{2-6}$alkenyloxy, $C_{2-6}$alkynyloxy, cycloalkoxy, $C_{1-6}$alkylthio, $C_{2-6}$alkenylthio, $C_{2-6}$alkynylthio, cycloalkylthio, halogen, aryl, aryl($C_{1-6}$alkyl)-, aryl($C_{2-6}$alkenyl), aryl($C_{2-6}$alkynyl), heterocyclyl, heterocyclyl($C_{1-6}$alkyl)-, heterocyclyl($C_{2-6}$alkenyl), heterocyclyl($C_{2-6}$alkynyl), heteroaryl, heteroaryl($C_{1-6}$alkyl)-, heteroaryl($C_{2-6}$alkenyl) and heteroaryl($C_{2-6}$alkynyl);

$R^5$ is selected from H, halogen, $C_{1-6}$alkyl, $C_{2-6}$alkenyl, $C_{2-6}$alkynyl, $C_{1-6}$alkyloxy, $C_{2-6}$alkenyloxy, $C_{2-6}$alkynyloxy, $C_{1-6}$alkylthio, $C_{2-6}$alkenylthio, $C_{2-6}$alkynylthio, CN and $C(R^7)_3$ or when $R^5$ is in the 2- or 5-position, $R^5$ and $R^3$ taken together may form a 5 to 10 membered ring;

$R^6$ is selected from H, $C_{1-6}$alkyl, $C_{2-6}$alkenyl and $C_{2-6}$alkynyl;

Each $R^7$ is independently selected from H and halogen;

m is 0 or an integer from 1 to 6; and n is 0 or an integer from 1 to 3;

wherein each alkyl, alkenyl, alkynyl, cycloalkyl, aryl, heterocyclyl and heteroaryl is optionally substituted with one or more optional substituents;

and pharmaceutically acceptable salts and prodrugs thereof; with the proviso that when $R_1$ is COOH, $R_2$ is $C_6H_5$—$CH_2S$—$CH_2$—, $R^4$ is 3-$C_6H_5$ and $R^5$ is H, $R_3$ is not $CH_3CH_2$—.

In another aspect of the invention there is provided a method of regulating the death of a cell, comprising contacting the cell with an effective amount of a compound of formula (Ia):

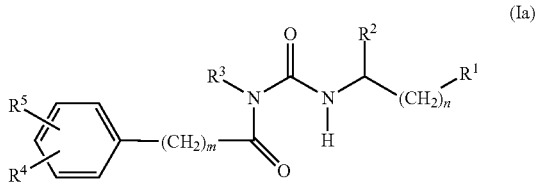

(Ia)

wherein
$R^1$ is selected from $CO_2H$ or a carboxylic acid or carboxylate bioisostere;
$R^2$ is selected from an amino acid side chain, cycloalkyl, cycloalkenyl, aryl, heterocyclyl, heteroaryl and a group $$R^a\text{—}(CHR')_x\text{-A-}(CH_2)_y\text{—}$$

wherein A is a covalent bond or is selected from O, S, SO, $SO_2$ or $NR^6$, $R^a$ is H, cycloalkyl, cycloalkenyl, aryl, heterocyclyl, heteroaryl or $R^b$ where $R^b$ is

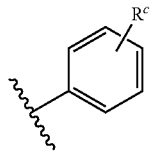

and $R^c$ is selected from heteroaryl, aryl, aryl($C_{2-6}$alkenyl), aryl($C_{2-6}$alkynyl), heteroaryl($C_{2-6}$alkenyl) and heteroaryl ($C_{2-6}$alkynyl), R' is H or $C_{1-6}$alkyl, x and y are independently 0 or an integer from 1 to 6 provided that the sum of x and y is 1 to 6;
$R^3$ is selected from $C_{3-6}$alkyl, $C_{2-6}$alkenyl, $C_{2-6}$alkynyl, cycloalkyl, cycloalkenyl, aryl, heterocyclyl, heteroaryl and a group $$R^d\text{—}(CH_2)_p\text{—W—}(CH_2)_q\text{—}$$

wherein W is selected from a covalent bond, O, S and $NR^6$, $R^d$ is selected from H, cycloalkyl, cycloalkenyl, aryl, heterocyclyl and heteroaryl; p is an integer from 1 to 6, q is 0 or an integer from 1 to 5 provided that the sun of p and q is 1 to 6;
$R^4$ is selected from $C_{1-6}$alkyl, $C_{2-6}$alkenyl, $C_{2-6}$alkynyl, cycloalkyl, $C_{1-6}$alkyloxy, $C_{2-6}$alkenyloxy, $C_{2-6}$alkynyloxy, cycloalkoxy, $C_{1-6}$alkylthio, $C_{1-6}$alkenylthio, $C_{2-6}$alkynylthio, cycloalkylthio, halogen, aryl, aryl($C_{1-6}$alkyl)-, aryl($C_{2-6}$alkenyl), aryl($C_{2-6}$alkynyl), heterocyclyl, heterocyclyl($C_{1-6}$alkyl)-, heterocyclyl($C_{2-6}$alkenyl), heterocyclyl($C_{2-6}$alkynyl), heteroaryl, heteroaryl($C_{1-6}$alkyl)-, heteroaryl($C_{2-6}$ alkenyl) and heteroaryl($C_{2-6}$alkynyl);
$R^5$ is selected from H, halogen, $C_{1-6}$alkyl, $C_{2-6}$alkenyl, $C_{2-6}$alkynyl, $C_{1-6}$alkyloxy, $C_{2-6}$alkenyloxy, $C_{2-6}$alkynyloxy, $C_{1-6}$alkylthio, $C_{2-6}$alkenylthio, $C_{1-6}$alkynylthio, CN and $C(R^7)_3$ or when $R^5$ is in the 2- or 5-position, $R^5$ and $R^3$ taken together may form a 5 to 10 membered ring;
$R^6$ is selected from H, $C_{1-6}$alkyl, $C_{2-6}$alkenyl and $C_{2-6}$alkynyl;
Each $R^7$ is independently selected from H and halogen;
m is 0 or an integer from 1 to 6; and
n is 0 or an integer from 1 to 3;
wherein each alkyl, alkenyl, alkynyl, cycloalkyl, aryl, heterocyclyl and heteroaryl is optionally substituted with one or more optional substituents;
and pharmaceutically acceptable salts and prodrugs thereof.
In another aspect of the invention there is provided a method of regulating the death of a cell, comprising contacting the cell with an effective amount of a compound of formula (Ib):

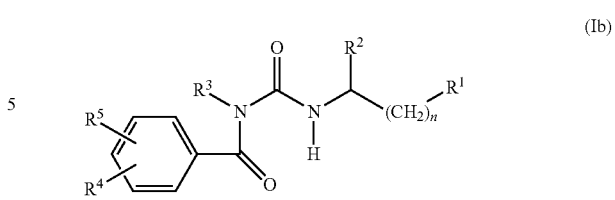

(Ib)

wherein
$R^1$ is selected from $CO_2H$ or a carboxylic acid or carboxylate bioisostere;
$R^2$ is selected from an amino acid side chain, cycloalkyl, cycloalkenyl, aryl, heterocyclyl, heteroaryl and a group $$R^a\text{—}(CH_2)_x\text{-A-}(CH_2)_y\text{—}$$

wherein A is a covalent bond or is selected from O, S, SO, $SO_2$ and $NR_6$, $R^a$ is cycloalkyl, cycloalkenyl, aryl, heterocyclyl, heteroaryl or $R^b$ where $R^b$ is

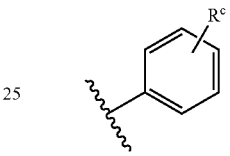

and $R^c$ is selected from heteroaryl, aryl, aryl($C_{2-6}$alkenyl), aryl($C_{2-6}$alkynyl), heteroaryl($C_{2-6}$alkenyl) and heteroaryl ($C_{2-6}$alkynyl), x and y are independently 0 or an integer from 1 to 6 provided that the sum of x and y is 1 to 6;
$R^3$ is selected from $C_{1-6}$alkyl, $C_{2-6}$alkenyl, $C_{2-6}$alkynyl, cycloalkyl, cycloalkenyl, aryl, heterocyclyl, heteroaryl and a group $$R^d\text{—}(CH_2)_p\text{—W—}(CH_2)_q\text{—}$$

wherein W is selected from a covalent bond, O, S and $NR^6$, $R^d$ is selected from H, cycloalkyl, cycloalkenyl, aryl, heterocyclyl and heteroaryl; p is an integer from 1 to 6, q is 0 or an integer from 1 to 5 provided that the sum of p and q is 1 to 6;
$R^4$ is selected from $C_{1-6}$alkyl, $C_{2-6}$alkenyl, $C_{2-6}$alkynyl, cycloalkyl, $C_{1-6}$alkyloxy, $C_{2-6}$alkenyloxy, $C_{2-6}$alkynyloxy, cycloalkoxy, $C_{1-6}$alkylthio, $C_{2-6}$alkenylthio, $C_{2-6}$alkynylthio, cycloalkylthio, halogen, aryl, aryl($C_{1-6}$alkyl)-, aryl($C_{2-6}$alkenyl), aryl($C_{2-6}$alkynyl), heterocyclyl, heterocyclyl($C_{1-6}$alkyl)-, heterocycyl($C_{2-6}$alkenyl), heterocyclyl($C_{2-6}$alkynyl), heteroaryl, heteroaryl($C_{1-6}$alkyl)-, heteroaryl($C_{2-6}$ alkenyl) and heteroaryl($C_{2-6}$alkynyl);
$R^5$ is selected from H, halogen, $C_{1-6}$alkyl, $C_{2-6}$alkenyl, $C_{2-6}$alkynyl, $C_{1-6}$alkyloxy, $C_{2-6}$alkenyloxy, $C_{2-6}$alkynyloxy, $C_{1-6}$alkylthio, $C_{2-6}$alkenylthio, $C_{2-6}$alkynylthio, CN and $C(R^7)_3$;
$R^6$ is selected from H, $C_{1-6}$alkyl, $C_{2-6}$alkenyl and $C_{2-6}$alkynyl;
Each $R^7$ is independently selected from H and halogen; and
n is 0 or an integer from 1 to 3;
wherein each alkyl, alkenyl, alkynyl, cycloalkyl, aryl, heterocyclyl and heteroaryl is optionally substituted with one or more optional substituents;
and pharmaceutically acceptable salts and prodrugs thereof;
with the proviso that when $R_1$ is COOH, $R_2$ is $C_6H_5$—$CH_2S$—$CH_2$—, $R^4$ is 3-$C_6H_5$ and $R^5$ is H, $R_3$ is not $CH_3CH_2$—.
In another aspect of the invention there is provided a method of regulating the death of a cell, comprising contacting the cell with an effective amount of a compound of formula (Ic):

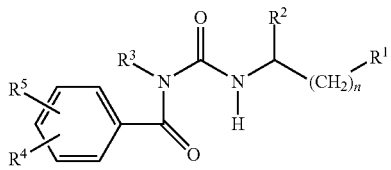 (Ic)

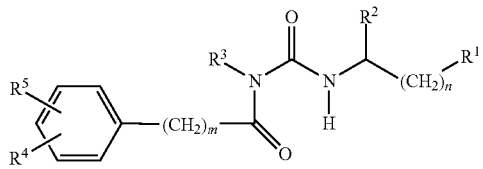 (I)

wherein
$R^1$ is selected from $CO_2H$ or a carboxylic acid or carboxylate bioisostere;
$R^2$ is selected from an amino acid side chain, cycloalkyl, cycloalkenyl, aryl, heterocyclyl, heteroaryl and a group $$R^a\text{—}(CH_2)_x\text{-A-}(CH_2)_y\text{—}$$

wherein A is a covalent bond or is selected from O, S, SO, $SO_2$ or $NR^6$, $R^a$ is cycloalkyl, cycloalkenyl, aryl, heterocyclyl, heteroaryl or $R^b$ where $R^b$ is

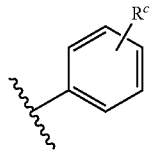

and $R^c$ is selected from heteroaryl, aryl, aryl($C_{2-6}$alkenyl), aryl($C_{2-6}$alkynyl), heteroaryl($C_{2-6}$alkenyl) and heteroaryl ($C_{2-6}$alkynyl), x and y are independently 0 or an integer from 1 to 6 provided that the sum of x and y is 1 to 6;
$R^3$ is selected from $C_{3-6}$alkyl, $C_{2-6}$alkenyl, $C_{2-6}$alkynyl, cycloalkyl, cycloalkenyl, aryl, heterocyclyl, heteroaryl and a group $$R^d\text{—}(CH_2)_p\text{—W—}(CH_2)_q\text{—}$$

wherein W is selected from a covalent bond, O, S and $NR^6$, $R^d$ is selected from H, cycloalkyl, cycloalkenyl, aryl, heterocyclyl and heteroaryl; p is an integer from 1 to 6, q is 0 or an integer from 1 to 5 provided that the sum of p and q is 1 to 6;
$R^4$ is selected from $C_{1-6}$alkyl, $C_{2-6}$alkenyl, $C_{2-6}$alkynyl, cycloalkyl, $C_{1-6}$alkyloxy, $C_{2-6}$alkenyloxy, $C_{2-6}$alkynyloxy, cycloalkoxy, $C_{1-6}$alkylthio, $C_{2-6}$alkenylthio, $C_{2-6}$alkynylthio, cycloalkylthio, halogen, aryl, aryl($C_{1-6}$alkyl)-, aryl($C_{2-6}$alkenyl), aryl($C_{2-6}$alkynyl), heterocyclyl, heterocyclyl($C_{1-6}$alkyl)-, heterocyclyl($C_{2-6}$alkenyl), heterocyclyl($C_{2-6}$alkynyl), heteroaryl, heteroaryl($C_{1-6}$alkyl)-, heteroaryl($C_{2-6}$alkenyl) and heteroaryl($C_{2-6}$alkynyl);
$R^5$ is selected from H, halogen, $C_{1-6}$alkyl, $C_{2-6}$alkenyl, $C_{2-6}$alkynyl, $C_{1-6}$alkyloxy, $C_{2-6}$alkenyloxy, $C_{2-6}$alkynyloxy, $C_{1-6}$alkylthio, $C_{2-6}$alkenylthio, $C_{2-6}$alkynylthio, CN and $C(R^7)_3$;
$R^6$ is selected from H, $C_{1-6}$alkyl, $C_{2-6}$alkenyl and $C_{2-6}$alkynyl;
Each $R^7$ is independently selected from H and halogen; and
n is 0 or an integer from 1 to 3;
wherein each alkyl, alkenyl, alkynyl, cycloalkyl, aryl, heterocyclyl and heteroaryl is optionally substituted with one or more optional substituents;
and pharmaceutically acceptable salts and prodrugs thereof.
In another aspect of the invention there is provided a method of inducing apoptosis in unwanted or damaged cells comprising contacting said damaged or unwanted cells with an effective amount of a compound of formula (I):

wherein
$R^1$ is selected from $CO_2H$ or a carboxylic acid or carboxylate bioisostere;
$R^2$ is selected from an amino acid side chain, cycloalkyl, cycloalkenyl, aryl, heterocyclyl, heteroaryl and a group $$R^a\text{—}(CHR')_x\text{-A-}(CH_2)_y\text{—}$$

wherein A is a covalent bond or is selected from O, S, SO, $SO_2$ and $NR^6$, $R^a$ is H, cycloalkyl, cycloalkenyl, aryl, heterocyclyl, heteroaryl or $R^b$ where $R^b$ is

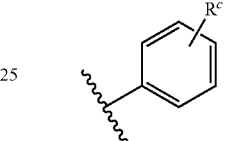

and $R^c$ is selected from heteroaryl, aryl, aryl($C_{2-6}$alkenyl), aryl($C_{2-6}$alkynyl), heteroaryl($C_{2-6}$alkenyl) and heteroaryl ($C_{2-6}$alkynyl), R' is H or $C_{1-6}$alkyl, x and y are independently 0 or an integer from 1 to 6 provided that the sum of x and y is 1 to 6;
$R^3$ is selected from $C_{1-6}$alkyl, $C_{2-6}$alkenyl, $C_{2-6}$alkynyl, cycloalkyl, cycloalkenyl, aryl, heterocyclyl, heteroaryl and a group $$R^d\text{—}(CH_2)_p\text{—W—}(CH_2)_q\text{—}$$

wherein W is selected from a covalent bond, O, S and $NR^6$, $R^d$ is selected from H, cycloalkyl, cycloalkenyl, aryl, heterocyclyl and heteroaryl; p is an integer from 1 to 6, q is 0 or an integer from 1 to 5 provided that the sum of p and q is 1 to 6;
$R^4$ is selected from $C_{1-6}$alkyl, $C_{2-6}$alkenyl, $C_{2-6}$alkynyl, cycloalkyl, $C_{1-6}$alkyloxy, $C_{2-6}$alkenyloxy, $C_{2-6}$alkynyloxy, cycloalkoxy, $C_{1-6}$alkylthio, $C_{2-6}$alkenylthio, $C_{2-6}$alkynylthio, cycloalkylthio, halogen, aryl, aryl($C_{1-6}$alkyl)-, aryl($C_{2-6}$alkenyl), aryl($C_{2-6}$alkynyl), heterocyclyl, heterocyclyl($C_{1-6}$alkyl)-, heterocyclyl($C_{2-6}$alkenyl), heterocyclyl($C_{2-6}$alkynyl), heteroaryl, heteroaryl($C_{1-6}$alkyl)-, heteroaryl($C_{2-6}$alkenyl) and heteroaryl($C_{2-6}$alkynyl);
$R^5$ is selected from H, halogen, $C_{1-6}$alkyl, $C_{2-6}$alkenyl, $C_{2-6}$alkynyl, $C_{1-6}$alkyloxy, $C_{2-6}$alkenyloxy, $C_{2-6}$alkynyloxy, $C_{1-6}$alkylthio, $C_{2-6}$alkenylthio, $C_{2-6}$alkynylthio, CN and $C(R^7)_3$ or when $R^5$ is in the 2- or 5-position, $R^5$ and $R^3$ taken together may form a 5 to 10 membered ring;
$R^6$ is selected from H, $C_{1-6}$alkyl, $C_{2-6}$alkenyl and $C_{2-6}$alkynyl;
Each $R^7$ is independently selected from H and halogen;
m is 0 or an integer from 1 to 6; and
n is 0 or an integer from 1 to 3;
wherein each alkyl, alkenyl, alkynyl, cycloalkyl, aryl, heterocyclyl and heteroaryl is optionally substituted with one or more optional substituents;
and pharmaceutically acceptable salts and prodrugs thereof;
with the proviso that when $R^1$ is COOH, $R_2$ is $C_6H_5$—$CH_2S$—$CH_2$—, $R^4$ is 3-$C_6H_5$ and $R^5$ is H, $R_3$ is not $CH_3CH_2$—.

In another aspect of the invention there is provided a method of inducing apoptosis in unwanted or damaged cells comprising contacting said damaged or unwanted cells with an effective amount of a compound of formula (Ia):

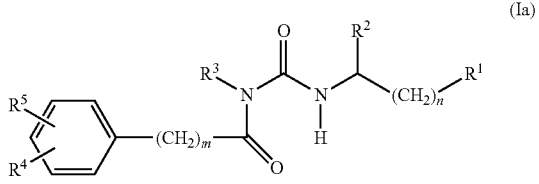

(Ia)

wherein
$R^1$ is selected from $CO_2H$ or a carboxylic acid or carboxylate bioisostere;
$R^2$ is selected from an amino acid side chain, cycloalkyl, cycloalkenyl, aryl, heterocyclyl, heteroaryl and a group $$R^a\text{---}(CHR')_x\text{-}A\text{-}(CH_2)_y\text{---}$$

wherein A is a covalent bond or is selected from O, S, SO, $SO_2$ or $NR^6$, $R^a$ is H, cycloalkyl, cycloalkenyl, aryl, heterocyclyl heteroaryl or $R^b$ where $R^b$ is

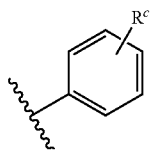

and $R^c$ is selected from heteroaryl, aryl, aryl($C_{2-6}$alkenyl), aryl($C_{2-6}$alkynyl), heteroaryl($C_{2-6}$alkenyl) and heteroaryl ($C_{2-6}$alkynyl), R' is H or $C_{1-6}$alkyl, x and y are independently 0 or an integer from 1 to 6 provided that the sum of x and y is 1 to 6;
$R^3$ is selected from $C_{3-6}$alkyl, $C_{2-6}$alkenyl, $C_{2-6}$alkynyl, cycloalkyl, cycloalkenyl, aryl, heterocyclyl, heteroaryl and a group $$R^d\text{---}(CH_2)_p\text{---}W\text{---}(CH_2)_q\text{---}$$

wherein W is selected from a covalent bond, O, S and $NR^6$, $R^d$ is selected from H, cycloalkyl, cycloalkenyl, aryl, heterocyclyl and heteroaryl; p is an integer from 1 to 6, q is 0 or an integer from 1 to 5 provided that the sum of p and q is 1 to 6;
$R^4$ is selected from $C_{1-6}$alkyl, $C_{2-6}$alkenyl, $C_{2-6}$alkynyl, cycloalkyl, $C_{1-6}$alkyloxy, $C_{2-6}$alkenyloxy, $C_{2-6}$alkynyloxy, cycloalkoxy, $C_{1-6}$alkylthio, $C_{2-6}$alkenylthio, $C_{2-6}$alkynylthio, cycloalkylthio, halogen, aryl, aryl($C_{1-6}$alkyl)-, aryl($C_{2-6}$alkenyl), aryl($C_{2-6}$alkynyl), heterocyclyl, heterocyclyl($C_{1-6}$alkyl)-, heterocyclyl($C_{2-6}$alkenyl), heterocyclyl($C_{2-6}$alkynyl), heteroaryl, heteroaryl($C_{1-6}$alkyl)-, heteroaryl($C_{2-6}$alkenyl) and heteroaryl($C_{2-6}$alkynyl);
$R^5$ is selected from H, halogen, $C_{1-6}$alkyl, $C_{2-6}$alkenyl, $C_{2-6}$alkynyl, $C_{1-6}$alkyloxy, $C_{2-6}$alkenyloxy, $C_{2-6}$alkynyloxy, $C_{1-6}$alkylthio, $C_{2-6}$alkenylthio, $C_{2-6}$alkynylthio, CN and $C(R^7)_3$ or when $R^5$ is in the 2- or 5-position, $R^5$ and $R^3$ taken together may form a 5 to 10 membered ring;
$R^6$ is selected from H, $C_{1-6}$alkyl, $C_{2-6}$alkenyl and $C_{2-6}$alkynyl;
Each $R^7$ is independently selected from H and halogen;
m is 0 or an integer from 1 to 6; and
n is 0 or an integer from 1 to 3;
wherein each alkyl, alkenyl, alkynyl, cycloalkyl, aryl, heterocyclyl and heteroaryl is optionally substituted with one or more optional substituents;

and pharmaceutically acceptable salts and prodrugs thereof.

In yet another aspect of the invention there is provided a method of inducing apoptosis in unwanted or damaged cells comprising contacting said damaged or unwanted cells with an effective amount of a compound of formula (Ib):

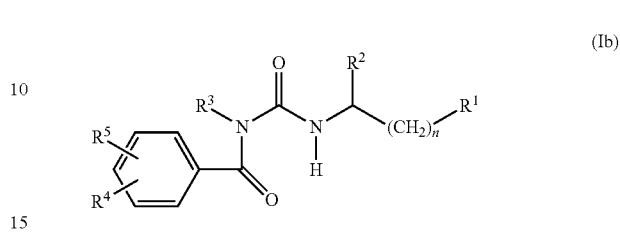

(Ib)

wherein
$R^1$ is selected from $CO_2H$ or a carboxylic acid or carboxylate bioisostere;
$R^2$ is selected from an amino acid side chain, cycloalkyl, cycloalkenyl, aryl, heterocyclyl, heteroaryl and a group $$R^a\text{---}(CH_2)_x\text{-}A\text{-}(CH_2)_y\text{---}$$

wherein A is a covalent bond or is selected from O, S, SO, $SO_2$ and $NR^6$, $R^a$ is cycloalkyl, cycloalkenyl, aryl, heterocyclyl, heteroaryl or $R^b$ where $R^b$ is

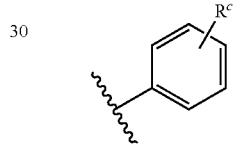

and $R^c$ is selected from heteroaryl, aryl, aryl($C_{2-6}$alkenyl), aryl($C_{2-6}$alkynyl), heteroaryl($C_{2-6}$alkenyl) and heteroaryl ($C_{2-6}$alkynyl), x and y are independently 0 or an integer from 1 to 6 provided that the sum of x and y is 1 to 6;
$R^3$ is selected from $C_{1-6}$alkyl, $C_{2-6}$alkenyl, $C_{2-6}$alkynyl, cycloalkyl, cycloalkenyl, aryl, heterocyclyl, heteroaryl and a group $$R^d\text{---}(CH_2)_p\text{---}W\text{---}(CH_2)_q\text{---}$$

wherein W is selected from a covalent bond, O, S and $NR^6$, $R^d$ is selected from H, cycloalkyl, cycloalkenyl, aryl, heterocyclyl and heteroaryl; p is an integer from 1 to 6, q is 0 or an integer from 1 to 5 provided that the sum of p and q is 1 to 6;
$R^4$ is selected from $C_{1-6}$alkyl, $C_{2-6}$alkenyl, $C_{2-6}$alkynyl, cycloalkyl, $C_{1-6}$alkyloxy, $C_{2-6}$alkenyloxy, $C_{2-6}$alkynyloxy, cycloalkoxy, $C_{1-6}$alkylthio, $C_{2-6}$alkenylthio, $C_{2-6}$alkynylthio, cycloalkylthio, halogen, aryl, aryl($C_{1-6}$alkyl)-, aryl($C_{2-6}$alkenyl), aryl($C_{2-6}$alkynyl), heterocyclyl, heterocyclyl($C_{1-6}$alkyl)-, heterocyclyl($C_{2-6}$alkenyl), heterocyclyl($C_{2-6}$alkynyl), heteroaryl, heteroaryl($C_{1-6}$alkyl)-, heteroaryl($C_{2-6}$alkenyl) and heteroaryl($C_{2-6}$alkynyl);
$R^5$ is selected from H, halogen, $C_{1-6}$alkyl, $C_{2-6}$alkenyl, $C_{2-6}$alkynyl, $C_{1-6}$alkyloxy, $C_{2-6}$alkenyloxy, $C_{2-6}$alkynyloxy, $C_{1-6}$alkylthio, $C_{2-6}$alkenylthio, $C_{2-6}$alkynylthio, CN and $C(R^7)_3$;
$R^6$ is selected from H, $C_{1-6}$alkyl, $C_{2-6}$alkenyl and $C_{2-6}$alkynyl;
Each $R^7$ is independently selected from H and halogen; and
n is 0 or an integer from 1 to 3;
wherein each alkyl, alkenyl, alkynyl, cycloalkyl, aryl, heterocyclyl and heteroaryl is optionally substituted with one or more optional substituents;

and pharmaceutically acceptable salts and prodrugs thereof; with the proviso that when $R_1$ is COOH, $R_2$ is $C_6H_5$—$CH_2S$—$CH_2$—, $R^4$ is 3-$C_6H_5$ and $R^5$ is H, $R_3$ is not $CH_3CH_2$—.

In another aspect of the invention there is provided a method of inducing apoptosis in unwanted or damaged cells comprising contacting said damaged or unwanted cells with an effective amount of a compound of formula (Ic):

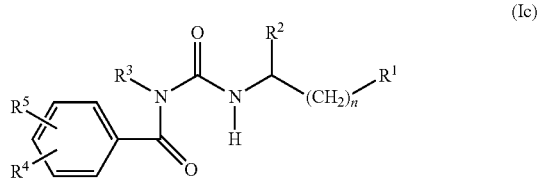

(Ic)

wherein
$R^1$ is selected from $CO_2H$ or a carboxylic acid or carboxylate bioisostere;
$R^2$ is selected from an amino acid side chain, cycloalkyl, cycloalkenyl, aryl, heterocyclyl, heteroaryl and a group

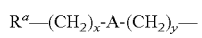

wherein A is a covalent bond or is selected from O, S, SO, $SO_2$ or $NR^6$, $R^a$ is cycloalkyl, cycloalkenyl, aryl, heterocyclyl, heteroaryl or $R^b$ where $R^b$ is

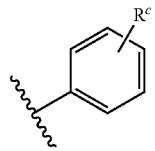

and $R^c$ is selected from heteroaryl, aryl, aryl($C_{2-6}$alkenyl), aryl($C_{2-6}$alkynyl), heteroaryl($C_{2-6}$alkenyl) and heteroaryl ($C_{2-6}$alkynyl), x and y are independently 0 or an integer from 1 to 6 provided that the sum of x and y is 1 to 6;
$R^3$ is selected from $C_{3-6}$alkyl, $C_{2-6}$alkenyl, $C_{2-6}$alkynyl, cycloalkyl, cycloalkenyl, aryl, heterocyclyl, heteroaryl and a group

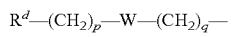

wherein W is selected from a covalent bond, O, S and $NR^6$, $R^d$ is selected from H, cycloalkyl, cycloalkenyl, aryl, heterocyclyl and heteroaryl; p is an integer from 1 to 6, q is 0 or an integer from 1 to 5 provided that the sum of p and q is 1 to 6;
$R^4$ is selected from $C_{1-6}$alkyl, $C_{2-6}$alkenyl, $C_{2-6}$alkynyl, cycloalkyl, $C_{1-6}$alkyloxy, $C_{2-6}$alkenyloxy, $C_{2-6}$alkynyloxy, cycloalkoxy, $C_{1-6}$alkylthio, $C_{2-6}$alkenylthio, $C_{2-6}$alkynylthio, cycloalkylthio, halogen, aryl, aryl($C_{1-6}$alkyl)-, aryl($C_{2-6}$alkenyl), aryl($C_{2-6}$alkynyl), heterocyclyl, heterocyclyl($C_{1-6}$alkyl)-, heterocyclyl($C_{2-6}$alkenyl), heterocyclyl($C_{2-6}$alkynyl), heteroaryl, heteroaryl($C_{1-6}$alkyl)-, heteroaryl($C_{2-6}$ alkenyl) and heteroaryl($C_{2-6}$alkynyl);
$R^5$ is selected from H, halogen, $C_{1-6}$alkyl, $C_{2-6}$alkenyl, $C_{2-6}$alkynyl, $C_{1-6}$alkyloxy, $C_{2-6}$alkenyloxy, $C_{2-6}$alkynyloxy, $C_{1-6}$alkylthio, $C_{2-6}$alkenylthio, $C_{2-6}$alkynylthio, CN and $C(R^7)_3$;
$R^6$ is selected from H, $C_{1-6}$alkyl, $C_{2-6}$alkenyl and $C_{2-6}$alkynyl;
Each $R^7$ is independently selected from H and halogen; and n is 0 or an integer from 1 to 3;

wherein each alkyl, alkenyl, alkynyl, cycloalkyl, aryl, heterocyclyl and heteroaryl is optionally substituted with one or more optional substituents;
and pharmaceutically acceptable salts and prodrugs thereof.

It should be understood that the cell which is treated according to a method of the present invention may be located ex vivo or in vivo. By "ex vivo" is meant that the cell has been removed from the body of a subject wherein the modulation of its activity will be initiated in vitro. For example, the cell may be a cell which is to be used as a model for studying any one or more aspects of the pathogenesis of conditions which are characterised by aberrant cell death signalling. In a preferred embodiment, the subject cell is located in vivo.

In another aspect of the invention there is provided a method of treatment and/or prophylaxis of a pro-survival Bcl-2 family member-mediated disease or condition, in a mammal, comprising administering to said mammal an effective amount of a compound of formula (I):

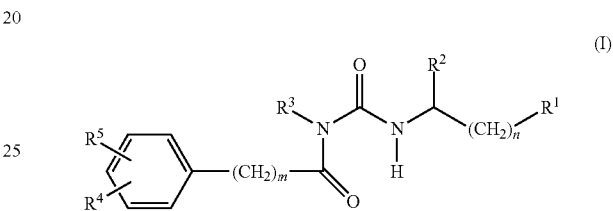

(I)

wherein
$R^1$ is selected from $CO_2H$ or a carboxylic acid or carboxylate bioisostere;
$R^2$ is selected from an amino acid side chain, cycloalkyl, cycloalkenyl, aryl, heterocyclyl, heteroaryl and a group

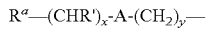

wherein A is a covalent bond or is selected from O, S, SO, $SO_2$ and $NR^6$, $R^a$ is H, cycloalkyl, cycloalkenyl, aryl, heterocyclyl, heteroaryl or $R^b$ where $R^b$ is

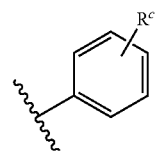

and $R^c$ is selected from heteroaryl, aryl, aryl($C_{2-6}$alkenyl), aryl($C_{2-6}$alkynyl), heteroaryl($C_{2-6}$alkenyl) and heteroaryl ($C_{2-6}$alkynyl), R' is H or $C_{1-6}$alkyl, x and y are independently 0 or an integer from 1 to 6 provided that the sum of x and y is 1 to 6;
$R^3$ is selected from $C_{1-6}$alkyl, $C_{2-6}$alkenyl, $C_{2-6}$alkynyl, cycloalkyl, cycloalkenyl, aryl, heterocyclyl, heteroaryl and a group

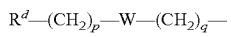

wherein W is selected from a covalent bond, O, S and $NR^6$, $R^d$ is selected from H, cycloalkyl, cycloalkenyl, aryl, heterocyclyl and heteroaryl; p is an integer from 1 to 6, q is 0 or an integer from 1 to 5 provided that the sum of p and q is 1 to 6;
$R^4$ is selected from $C_{1-6}$alkyl, $C_{2-6}$alkenyl, $C_{2-6}$alkynyl, cycloalkyl, $C_{1-6}$alkyloxy, $C_{2-6}$alkenyloxy, $C_{2-6}$alkynyloxy, cycloalkoxy, $C_{1-6}$alkylthio, $C_{2-6}$alkenylthio, $C_{1-6}$alkynylthio, cycloalkylthio, halogen, aryl, aryl($C_{1-6}$alkyl)-, aryl($C_{2-6}$alkenyl), aryl($C_{2-6}$alkynyl), heterocyclyl, heterocyclyl($C_{1-6}$ alkyl)-, heterocyclyl($C_{2-6}$alkenyl), heterocycyl($C_{2-6}$alkynyl), heteroaryl, heteroaryl($C_{1-6}$alkyl)-, heteroaryl($C_{2-6}$alkenyl) and heteroaryl($C_{2-6}$alkynyl);

$R^5$ is selected from H, halogen, $C_{1-6}$alkyl, $C_{2-6}$alkenyl, $C_{2-6}$alkynyl, $C_{1-6}$alkyloxy, $C_{2-6}$alkenyloxy, $C_{2-6}$alkynyloxy, $C_{1-6}$alkylthio, $C_{2-6}$alkenylthio, $C_{2-6}$alkynylthio, CN and $C(R^7)_3$ or when $R^5$ is in the 2- or 5-position, $R^5$ and $R^3$ taken together may form a 5 to 10 membered ring;

$R^6$ is selected from H, $C_{1-6}$alkyl, $C_{2-6}$alkenyl and $C_{2-6}$alkynyl;

Each $R^7$ is independently selected from H and halogen;

m is 0 or an integer from 1 to 6; and n is 0 or an integer from 1 to 3;

wherein each alkyl, alkenyl, alkynyl, cycloalkyl, aryl, heterocyclyl and heteroaryl is optionally substituted with one or more optional substituents;

and pharmaceutically acceptable salts and prodrugs thereof, with the proviso that when $R_1$ is COOH, $R_2$ is $C_6H_5$—$CH_2S$—$CH_2$—, $R^4$ is 3-$C_6H_5$ and $R^5$ is H, $R_3$ is not $CH_3CH_2$—.

In another aspect of the invention there is provided a method of treatment and/or prophylaxis of a pro-survival Bcl-2 family member-mediated disease or condition, in a mammal, comprising administering to said mammal an effective amount of a compound of formula (Ia):

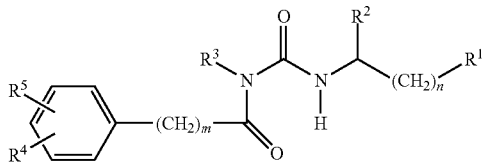

(Ia)

wherein $R^1$ is selected from $CO_2H$ or a carboxylic acid or carboxylate bioisostere;

$R^2$ is selected from an amino acid side chain, cycloalkyl, cycloalkenyl, aryl, heterocyclyl, heteroaryl and a group $R^a$—(CHR')$_x$-A-(CH$_2$)$_y$— wherein A is a covalent bond or is selected from O, S, SO, $SO_2$ or $NR^6$, $R^a$ is H, cycloalkyl, cycloalkenyl, aryl, heterocyclyl, heteroaryl or $R^b$ where $R^b$ is

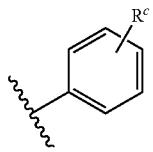

and $R^c$ is selected from heteroaryl, aryl, aryl($C_{2-6}$alkenyl), aryl($C_{2-6}$alkynyl), heteroaryl($C_{2-6}$alkenyl) and heteroaryl ($C_{2-6}$alkynyl), R' is H or $C_{1-6}$alkyl, x and y are independently 0 or an integer from 1 to 6 provided that the sum of x and y is 1 to 6;

$R^3$ is selected from $C_{3-6}$alkyl, $C_{2-6}$alkenyl, $C_{2-6}$alkynyl, cycloalkyl, cycloalkenyl, aryl, heterocyclyl, heteroaryl and a group $R^d$—(CH$_2$)$_p$—W—(CH$_2$)$_q$— wherein W is selected from a covalent bond, O, S and $NR^6$, $R^d$ is selected from H, cycloalkyl, cycloalkenyl, aryl, heterocyclyl and heteroaryl; p is an integer from 1 to 6, q is 0 or an integer from 1 to 5 provided that the sum of p and q is 1 to 6;

$R^4$ is selected from $C_{1-6}$alkyl, $C_{2-6}$alkenyl, $C_{2-6}$alkynyl, cycloalkyl, $C_{1-6}$alkyloxy, $C_{2-6}$alkenyloxy, $C_{2-6}$alkynyloxy, cycloalkoxy, $C_{1-6}$alkylthio, $C_{2-6}$alkenylthio, $C_{2-6}$alkynylthio, cycloalkylthio, halogen, aryl, aryl($C_{1-6}$alkyl)-, aryl($C_{2-6}$alkenyl), aryl($C_{2-6}$alkynyl), heterocyclyl, heterocyclyl($C_{1-6}$alkyl)-, heterocyclyl($C_{2-6}$alkenyl), heterocyclyl($C_{2-6}$alkynyl), heteroaryl, heteroaryl($C_{1-6}$alkyl)-, heteroaryl($C_{2-6}$alkenyl) and heteroaryl($C_{2-6}$alkynyl);

$R^5$ is selected from H, halogen, $C_{1-6}$alkyl, $C_{2-6}$alkenyl, $C_{2-6}$alkynyl, $C_{1-6}$alkyloxy, $C_{2-6}$alkenyloxy, $C_{2-6}$alkynyloxy, $C_{1-6}$alkylthio, $C_{2-6}$alkenylthio, $C_{2-6}$alkynylthio, CN and $C(R^7)_3$ or when $R^5$ is in the 2- or 5-position, $R^5$ and $R^3$ taken together may form a 5 to 10 membered ring;

$R^6$ is selected from H, $C_{1-6}$alkyl, $C_{2-6}$alkenyl and $C_{2-6}$alkynyl;

Each $R^7$ is independently selected from H and halogen;

m is 0 or an integer from 1 to 6; and n is 0 or an integer from 1 to 3;

wherein each alkyl, alkenyl, alkynyl, cycloalkyl, aryl, heterocyclyl and heteroaryl is optionally substituted with one or more optional substituents;

and pharmaceutically acceptable salts and prodrugs thereof.

In another aspect of the invention there is provided a method of treatment and/or prophylaxis of a pro-survival Bcl-2 family member-mediated disease or condition, in a mammal, comprising administering to said mammal an effective amount of a compound of formula (Ib):

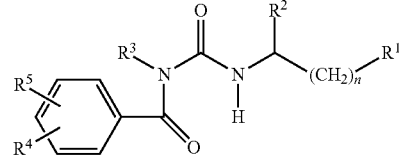

(Ib)

wherein $R^1$ is selected from $CO_2H$ or a carboxylic acid or carboxylate bioisostere;

$R^2$ is selected from an amino acid side chain, cycloalkyl, cycloalkenyl, aryl, heterocyclyl, heteroaryl and a group $R^a$—(CH$_2$)$_x$-A-(CH$_2$)$_y$— wherein A is a covalent bond or is selected from O, S, SO, $SO_2$ and $NR^6$, $R^a$ is cycloalkyl, cycloalkenyl, aryl, heterocyclyl, heteroaryl or $R^b$ where $R^b$ is

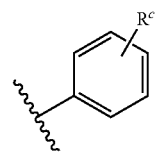

and $R^c$ is selected from heteroaryl, aryl, aryl($C_{2-6}$alkenyl), aryl($C_{2-6}$alkynyl), heteroaryl($C_{2-6}$alkenyl) and heteroaryl ($C_{2-6}$alkynyl), x and y are independently 0 or an integer from 1 to 6 provided that the sum of x and y is 1 to 6;

$R^3$ is selected from $C_{1-6}$alkyl, $C_{2-6}$alkenyl, $C_{2-6}$alkynyl, cycloalkyl, cycloalkenyl, aryl, heterocyclyl, heteroaryl and a group $R^d$—(CH$_2$)$_p$—W—(CH$_2$)$_q$— wherein W is selected from a covalent bond, O, S and $NR^6$, $R^d$ is selected from H, cycloalkyl, cycloalkenyl, aryl, heterocyclyl and heteroaryl; p is an integer from 1 to 6, q is 0 or an integer from 1 to 5 provided that the sum of p and q is 1 to 6;

$R^4$ is selected from $C_{1-6}$alkyl, $C_{2-6}$alkenyl, $C_{2-6}$alkynyl, cycloalkyl, $C_{1-6}$alkyloxy, $C_{2-6}$alkenyloxy, $C_{2-6}$alkynyloxy, cycloalkoxy, $C_{1-6}$alkylthio, $C_{2-6}$alkenylthio, $C_{2-6}$alkynylthio, cycloalkylthio, halogen, aryl, aryl($C_{1-6}$alkyl)-, aryl($C_{2-6}$alkenyl), aryl($C_{2-6}$alkynyl), heterocyclyl, heterocyclyl($C_{1-6}$alkyl)-, heterocyclyl($C_{2-6}$alkenyl), heterocyclyl($C_{2-6}$alkynyl), heteroaryl, heteroaryl($C_{1-6}$alkyl)-, heteroaryl($C_{2-6}$alkenyl) and heteroaryl($C_{2-6}$alkynyl);

$R^5$ is selected from H, halogen, $C_{1-6}$alkyl, $C_{2-6}$alkenyl, $C_{2-6}$alkynyl, $C_{1-6}$alkyloxy, $C_{2-6}$alkenyloxy, $C_{2-6}$alkynyloxy, $C_{1-6}$alkylthio, $C_{2-6}$alkenylthio, $C_{2-6}$alkynylthio, CN and $C(R^7)_3$;

$R^6$ is selected from H, $C_{1-6}$alkyl, $C_{2-6}$alkenyl and $C_{2-6}$alkynyl; Each $R^7$ is independently selected from H and halogen; and n is 0 or an integer from 1 to 3;

wherein each alkyl, alkenyl, alkynyl, cycloalkyl, aryl, heterocyclyl and heteroaryl is optionally substituted with one or more optional substituents;

and pharmaceutically acceptable salts and prodrugs thereof, with the proviso that when $R_1$ is COOH, $R_2$ is $C_6H_5$—$CH_2S$—$CH_2$—, $R^4$ is 3-$C_6H_5$ and $R^5$ is H, $R_3$ is not $CH_3CH_2$—.

In yet another aspect of the invention there is provided a method of treatment and/or prophylaxis of a pro-survival Bcl-2 family member-mediated disease or condition, in a mammal, comprising administering to said mammal an effective amount of a compound of formula (Ic):

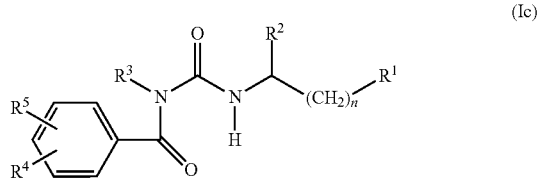

(Ic)

wherein $R^1$ is selected from $CO_2H$ or a carboxylic acid or carboxylate bioisostere;

$R^2$ is selected from an amino acid side chain, cycloalkyl, cycloalkenyl, aryl, heterocyclyl, heteroaryl and a group

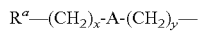

$R^a$—$(CH_2)_x$-A-$(CH_2)_y$— wherein A is a covalent bond or is selected from O, S, SO, $SO_2$ or $NR^6$, $R^a$ is cycloalkyl, cycloalkenyl, aryl, heterocyclyl, heteroaryl or $R^b$ where $R^b$ is

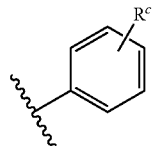

and $R^c$ is selected from heteroaryl, aryl, aryl($C_{2-6}$alkenyl), aryl($C_{2-6}$alkynyl), heteroaryl($C_{2-6}$alkenyl) and heteroaryl ($C_{2-6}$alkynyl), x and y are independently 0 or an integer from 1 to 6 provided that the sum of x and y is 1 to 6;

$R^3$ is selected from $C_{3-6}$alkyl, $C_{2-6}$alkenyl, $C_{2-6}$alkynyl, cycloalkyl, cycloalkenyl, aryl, heterocyclyl, heteroaryl and a group

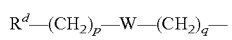

$R^d$—$(CH_2)_p$—W—$(CH_2)_q$— wherein W is selected from a covalent bond, O, S and $NR^6$, $R^d$ is selected from H, cycloalkyl, cycloalkenyl, aryl, heterocyclyl and heteroaryl; p is an integer from 1 to 6, q is 0 or an integer from 1 to 5 provided that the sum of p and q is 1 to 6;

$R^4$ is selected from $C_{1-6}$alkyl, $C_{2-6}$alkenyl, $C_{2-6}$alkynyl, cycloalkyl, $C_{1-6}$alkyloxy, $C_{2-6}$alkenyloxy, $C_{2-6}$alkynyloxy, cycloalkoxy, $C_{1-6}$alkylthio, $C_{2-6}$alkenylthio, $C_{2-6}$alkynylthio, cycloalkylthio, halogen, aryl, aryl($C_{1-6}$alkyl)-, aryl($C_{2-6}$alkenyl), aryl($C_{2-6}$alkynyl), heterocyclyl, heterocyclyl($C_{1-6}$alkyl)-, heterocyclyl($C_{2-6}$alkenyl), heterocyclyl($C_{2-6}$alkynyl), heteroaryl, heteroaryl($C_{1-6}$alkyl)-, heteroaryl($C_{2-6}$alkenyl) and heteroaryl($C_{2-6}$alkynyl);

$R^5$ is selected from H, halogen, $C_{1-6}$alkyl, $C_{2-6}$alkenyl, $C_{2-6}$alkynyl, $C_{1-6}$alkyloxy, $C_{2-6}$alkenyloxy, $C_{2-6}$alkynyloxy, $C_{1-6}$alkylthio, $C_{2-6}$alkenylthio, $C_{2-6}$alkynylthio, CN and $C(R^7)_3$;

$R^6$ is selected from H, $C_{1-6}$alkyl, $C_{2-6}$alkenyl and $C_{2-6}$alkynyl; Each $R^7$ is independently selected from H and halogen; and n is 0 or an integer from 1 to 3;

wherein each alkyl, alkenyl, alkynyl, cycloalkyl, aryl, heterocyclyl and heteroaryl is optionally substituted with one or more optional substituents;

and pharmaceutically acceptable salts and prodrugs thereof.

In yet another aspect of the invention there is provided a method of treatment and/or prophylaxis of a disease or condition characterised by the inappropriate persistence or proliferation of unwanted or damaged cells in a mammal, comprising administering to said mammal an effective amount of a compound of formula (I):

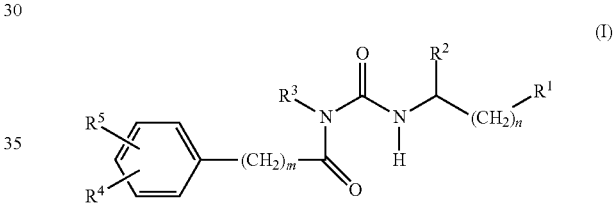

(I)

wherein $R^1$ is selected from $CO_2H$ or a carboxylic acid or carboxylate bioisostere;

$R^2$ is selected from an amino acid side chain, cycloalkyl, cycloalkenyl, aryl, heterocyclyl, heteroaryl and a group

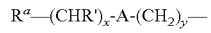

$R^a$—$(CHR')_x$-A-$(CH_2)_y$— wherein A is a covalent bond or is selected from O, S, SO, $SO_2$ and $NR^6$, $R^a$ is H, cycloalkyl, cycloalkenyl, aryl, heterocyclyl, heteroaryl or $R^b$ where $R^b$ is

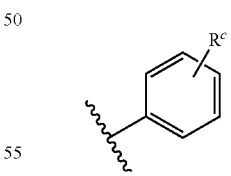

and $R^c$ is selected from heteroaryl, aryl, aryl($C_{2-6}$alkenyl), aryl($C_{2-6}$alkynyl), heteroaryl($C_{2-6}$alkenyl) and heteroaryl ($C_{2-6}$alkynyl), R' is H or $C_{1-6}$alkyl, x and y are independently 0 or an integer from 1 to 6 provided that the sum of x and y is 1 to 6;

$R^3$ is selected from $C_{1-6}$alkyl, $C_{2-6}$alkenyl, $C_{2-6}$alkynyl, cycloalkyl, cycloalkenyl, aryl, heterocyclyl, heteroaryl and a group

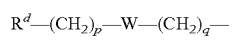

$R^d$—$(CH_2)_p$—W—$(CH_2)_q$— wherein W is selected from a covalent bond, O, S and $NR^6$, $R^d$ is selected from H, cycloalkyl, cycloalkenyl, aryl, heterocyclyl and heteroaryl; p is an integer from 1 to 6, q is 0 or an integer from 1 to 5 provided that the sum of p and q is 1 to 6; $R^4$ is selected from $C_{1-6}$alkyl, $C_{2-6}$alkenyl, $C_{2-6}$alkynyl, cycloalkyl, $C_{1-6}$alkyloxy, $C_{2-6}$alkenyloxy, $C_{2-6}$alkynyloxy, cycloalkoxy, $C_{1-6}$alkylthio, $C_{2-6}$alkenylthio, $C_{2-6}$alkynylthio, cycloalkylthio, halogen, aryl, aryl($C_{1-6}$alkyl)-, aryl($C_{2-6}$alkenyl), aryl($C_{2-6}$alkynyl), heterocyclyl, heterocyclyl($C_{1-6}$alkyl)-, heterocyclyl($C_{2-6}$alkenyl), heterocyclyl($C_{2-6}$alkynyl), heteroaryl, heteroaryl($C_{1-6}$alkyl)-, heteroaryl($C_{2-6}$alkenyl) and heteroaryl($C_{2-6}$alkynyl);

$R^5$ is selected from H, halogen, $C_{1-6}$alkyl, $C_{2-6}$alkenyl, $C_{2-6}$alkynyl, $C_{1-6}$alkyloxy, $C_{2-6}$alkenyloxy, $C_{2-6}$alkynyloxy, $C_{1-6}$alkylthio, $C_{2-6}$alkenylthio, $C_{2-6}$alkynylthio, CN and $C(R^7)_3$ or when $R^5$ is in the 2- or 5-position, $R^5$ and $R^3$ taken together may form a 5 to 10 membered ring;

$R^6$ is selected from H, $C_{1-6}$alkyl, $C_{2-6}$alkenyl and $C_{2-6}$alkynyl;

Each $R^7$ is independently selected from H and halogen;

m is 0 or an integer from 1 to 6; and n is 0 or an integer from 1 to 3;

wherein each alkyl, alkenyl, alkynyl, cycloalkyl, aryl, heterocyclyl and heteroaryl is optionally substituted with one or more optional substituents;

and pharmaceutically acceptable salts and prodrugs thereof; with the proviso that when $R_1$ is COOH, $R_2$ is $C_6H_5$—$CH_2S$—$CH_2$—, $R^4$ is 3-$C_6H_5$ and $R^5$ is H, $R_3$ is not $CH_3CH_2$—.

In yet another aspect of the invention there is provided a method of treatment and/or prophylaxis of a disease or condition characterised by the inappropriate persistence or proliferation of unwanted or damaged cells in a mammal, comprising administering to said mammal an effective amount of a compound of formula (Ia):

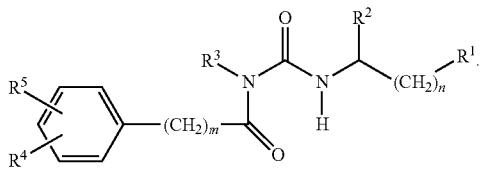

(Ia)

wherein $R^1$ is selected from $CO_2H$ or a carboxylic acid or carboxylate bioisostere;

$R^2$ is selected from an amino acid side chain, cycloalkyl, cycloalkenyl, aryl, heterocyclyl, heteroaryl and a group $R^a$—(CHR')$_x$-A-(CH$_2$)$_y$— wherein A is a covalent bond or is selected from O, S, SO, SO$_2$ or $NR^6$, $R^a$ is H, cycloalkyl, cycloalkenyl, aryl, heterocyclyl, heteroaryl or $R^b$ where $R^b$ is

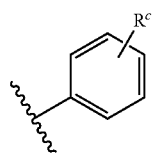

and $R^c$ is selected from heteroaryl, aryl, aryl($C_{2-6}$alkenyl), aryl($C_{2-6}$alkynyl), heteroaryl($C_{2-6}$alkenyl) and heteroaryl ($C_{2-6}$alkynyl), R' is H or $C_{1-6}$alkyl, x and y are independently 0 or an integer from 1 to 6 provided that the sum of x and y is 1 to 6;

$R^3$ is selected from $C_{3-6}$alkyl, $C_{2-6}$alkenyl, $C_{2-6}$alkynyl, cycloalkyl, cycloalkenyl, aryl, heterocyclyl, heteroaryl and a group $R^d$—(CH$_2$)$_p$—W—(CH$_2$)$_q$— wherein W is selected from a covalent bond, O, S and $NR^6$, $R^d$ is selected from H, cycloalkyl, cycloalkenyl, aryl, heterocyclyl and heteroaryl; p is an integer from 1 to 6, q is 0 or an integer from 1 to 5 provided that the sum of p and q is 1 to 6;

$R^4$ is selected from $C_{1-6}$alkyl, $C_{2-6}$alkenyl, $C_{2-6}$alkynyl, cycloalkyl, $C_{1-6}$alkyloxy, $C_{2-6}$alkenyloxy, $C_{2-6}$alkynyloxy, cycloalkoxy, $C_{1-6}$alkylthio, $C_{2-6}$alkenylthio, $C_{2-6}$alkynylthio, cycloalkylthio, halogen, aryl, aryl($C_{1-6}$alkyl)-, aryl($C_{2-6}$alkenyl), aryl($C_{2-6}$alkynyl), heterocyclyl, heterocyclyl($C_{1-6}$alkyl)-, heterocyclyl($C_{2-6}$alkenyl), heterocyclyl($C_{2-6}$alkynyl), heteroaryl, heteroaryl($C_{1-6}$alkyl)-, heteroaryl($C_{2-6}$alkenyl) and heteroaryl($C_{2-6}$alkynyl);

$R^5$ is selected from H, halogen, $C_{1-6}$alkyl, $C_{2-6}$alkenyl, $C_{2-6}$alkynyl, $C_{1-6}$alkyloxy, $C_{2-6}$alkenyloxy, $C_{2-6}$alkynyloxy, $C_{1-6}$alkylthio, $C_{2-6}$alkenylthio, $C_{2-6}$alkynylthio, CN and $C(R^7)_3$ or when $R^5$ is in the 2- or 5-position, $R^5$ and $R^3$ taken together may form a 5 to 10 membered ring;

$R^6$ is selected from H, $C_{1-6}$alkyl, $C_{2-6}$alkenyl and $C_{2-6}$alkynyl;

Each $R^7$ is independently selected from H and halogen;

m is 0 or an integer from 1 to 6; and n is 0 or an integer from 1 to 3;

wherein each alkyl, alkenyl, alkynyl, cycloalkyl, aryl, heterocyclyl and heteroaryl is optionally substituted with one or more optional substituents;

and pharmaceutically acceptable salts and prodrugs thereof.

In yet another aspect of the invention there is provided a method of treatment and/or prophylaxis of a disease or condition characterised by the inappropriate persistence or proliferation of unwanted or damaged cells in a mammal, comprising administering to said mammal an effective amount of a compound of formula (Ib):

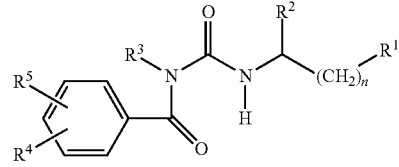

(Ib)

wherein $R^1$ is selected from $CO_2H$ or a carboxylic acid or carboxylate bioisostere;

$R^2$ is selected from an amino acid side chain, cycloalkyl, cycloalkenyl, aryl, heterocyclyl, heteroaryl and a group $R^a$—(CH$_2$)$_x$-A-(CH$_2$)$_y$— wherein A is a covalent bond or is selected from O, S, SO, SO$_2$ and $NR^6$, $R^a$ is cycloalkyl, cycloalkenyl, aryl, heterocyclyl, heteroaryl or $R^b$ where $R^b$ is

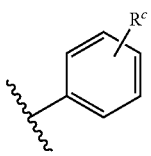

and $R^c$ is selected from heteroaryl, aryl, aryl($C_{2-6}$alkenyl), aryl($C_{2-6}$alkynyl), heteroaryl($C_{2-6}$alkenyl) and heteroaryl ($C_{2-6}$alkynyl), x and y are independently 0 or an integer from 1 to 6 provided that the sum of x and y is 1 to 6;

$R^3$ is selected from $C_{1-6}$alkyl, $C_{2-6}$alkenyl, $C_{2-6}$alkynyl, cycloalkyl, cycloalkenyl, aryl, heterocyclyl, heteroaryl and a group $$R^d\text{—}(CH_2)_p\text{—}W\text{—}(CH_2)_q\text{—}$$

wherein W is selected from a covalent bond, O, S and $NR^6$, $R^d$ is selected from H, cycloalkyl, cycloalkenyl, aryl, heterocyclyl and heteroaryl; p is an integer from 1 to 6, q is 0 or an integer from 1 to 5 provided that the sum of p and q is 1 to 6; $R^4$ is selected from $C_{1-6}$alkyl, $C_{2-6}$alkenyl, $C_{2-6}$alkynyl, cycloalkyl, $C_{1-6}$alkyloxy, $C_{2-6}$alkenyloxy, $C_{2-6}$alkynyloxy, cycloalkoxy, $C_{1-6}$alkylthio, $C_{2-6}$alkenylthio, $C_{2-6}$alkynylthio, cycloalkylthio, halogen, aryl, aryl($C_{1-6}$alkyl)-, aryl($C_{2-6}$alkenyl), aryl($C_{2-6}$alkynyl), heterocyclyl, heterocyclyl($C_{1-6}$alkyl)-, heterocyclyl($C_{2-6}$alkenyl), heterocyclyl($C_{2-6}$alkynyl), heteroaryl, heteroaryl($C_{1-6}$alkyl)-, heteroaryl($C_{2-6}$ alkenyl) and heteroaryl($C_{2-6}$alkynyl);

$R^5$ is selected from H, halogen, $C_{1-6}$alkyl, $C_{2-6}$alkenyl, $C_{2-6}$alkynyl, $C_{1-6}$alkyloxy, $C_{2-6}$alkenyloxy, $C_{2-6}$alkynyloxy, $C_{1-6}$alkylthio, $C_{2-6}$alkenylthio, $C_{2-6}$alkynylthio, CN and $C(R^7)_3$;

$R^6$ is selected from H, $C_{1-6}$alkyl, $C_{2-6}$alkenyl and $C_{2-6}$alkynyl; Each $R^7$ is independently selected from H and halogen; and n is 0 or an integer from 1 to 3;

wherein each alkyl, alkenyl, alkynyl, cycloalkyl, aryl, heterocyclyl and heteroaryl is optionally substituted with one or more optional substituents;

and pharmaceutically acceptable salts and prodrugs thereof; with the proviso that when $R^1$ is COOH, $R_2$ is $C_6H_5$—$CH_2S$—$CH_2$—, $R^4$ is 3-$C_6H_5$ and $R^5$ is H, $R_3$ is not $CH_3CH_2$—.

In yet another aspect of the invention there is provided a method of treatment and/or prophylaxis of a disease or condition characterised by the inappropriate persistence or proliferation of unwanted or damaged cells in a mammal, comprising administering to said mammal an effective amount of a compound of formula (Ic):

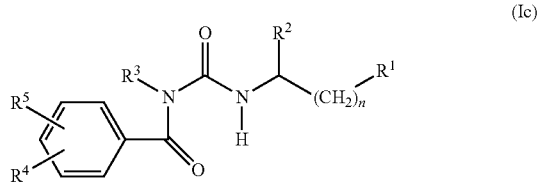

(Ic)

wherein
$R^1$ is selected from $CO_2H$ or a carboxylic acid or carboxylate bioisostere;
$R^2$ is selected from an amino acid side chain, cycloalkyl, cycloalkenyl, aryl, heterocyclyl, heteroaryl and a group $$R^a\text{—}(CHR')_x\text{-}A\text{-}(CH_2)_y\text{—}$$

wherein A is a covalent bond or is selected from O, S, SO, $SO_2$ or $NR^6$, $R^a$ is cycloalkyl, cycloalkenyl, aryl, heterocyclyl, heteroaryl or $R^b$ where $R^b$ is

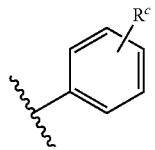

and $R^c$ is selected from heteroaryl, aryl, aryl($C_{2-6}$alkenyl), aryl($C_{2-6}$alkynyl), heteroaryl($C_{2-6}$alkenyl) and heteroaryl ($C_{2-6}$alkynyl), x and y are independently 0 or an integer from 1 to 6 provided that the sum of x and y is 1 to 6;

$R^3$ is selected from $C_{3-6}$alkyl, $C_{2-6}$alkenyl, $C_{2-6}$alkynyl, cycloalkyl, cycloalkenyl, aryl, heterocyclyl, heteroaryl and a group $$R^d\text{—}(CH_2)_p\text{—}W\text{—}(CH_2)_q\text{—}$$

wherein W is selected from a covalent bond, O, S and $NR^6$, $R^d$ is selected from H, cycloalkyl, cycloalkenyl, aryl, heterocyclyl and heteroaryl; p is an integer from 1 to 6, q is 0 or an integer from 1 to 5 provided that the sum of p and q is 1 to 6; $R^4$ is selected from $C_{1-6}$alkyl, $C_{2-6}$alkenyl, $C_{2-6}$alkynyl, cycloalkyl, $C_{1-6}$alkyloxy, $C_{2-6}$alkenyloxy, $C_{2-6}$alkynyloxy, cycloalkoxy, $C_{1-6}$alkylthio, $C_{2-6}$alkenylthio, $C_{2-6}$alkynylthio, cycloalkylthio, halogen, aryl, aryl($C_{1-6}$alkyl)-, aryl($C_{2-6}$alkenyl), aryl($C_{2-6}$alkynyl), heterocyclyl, heterocyclyl($C_{1-6}$alkyl)-, heterocyclyl($C_{2-6}$alkenyl), heterocyclyl($C_{2-6}$alkynyl), heteroaryl, heteroaryl($C_{1-6}$alkyl)-, heteroaryl($C_{2-6}$ alkenyl) and heteroaryl($C_{2-6}$alkynyl);

$R^5$ is selected from H, halogen, $C_{1-6}$alkyl, $C_{2-6}$alkenyl, $C_{2-6}$alkynyl, $C_{1-6}$alkyloxy, $C_{2-6}$alkenyloxy, $C_{2-6}$alkynyloxy, $C_{1-6}$alkylthio, $C_{2-6}$alkenylthio, $C_{2-6}$alkynylthio, CN and $C(R^7)_3$;

$R^6$ is selected from H, $C_{1-6}$alkyl, $C_{2-6}$alkenyl and $C_{2-6}$alkynyl; Each $R^7$ is independently selected from H and halogen; and n is 0 or an integer from 1 to 3;

wherein each alkyl, alkenyl, alkynyl, cycloalkyl, aryl, heterocyclyl and heteroaryl is optionally substituted with one or more optional substituents;

and pharmaceutically acceptable salts and prodrugs thereof.

In yet another aspect of the present invention there is provided a use of a compound of formula (I):

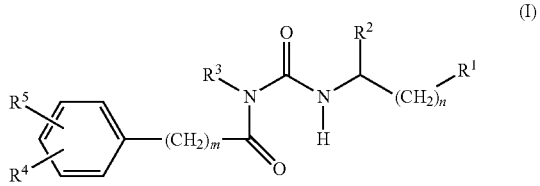

(I)

wherein
$R^3$ is selected from $CO_2H$ or a carboxylic acid or carboxylate bioisostere;
$R^2$ is selected from an amino acid side chain, cycloalkyl, cycloalkenyl, aryl, heterocyclyl, heteroaryl and a group $$R^a\text{—}(CHR')_x\text{-}A\text{-}(CH_2)_y\text{—}$$

wherein A is a covalent bond or is selected from O, S, SO, $SO_2$ and $NR^6$, $R^a$ is H, cycloalkyl, cycloalkenyl, aryl, heterocyclyl, heteroaryl or $R^b$ where $R^b$ is

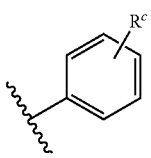

and $R^c$ is selected from heteroaryl, aryl, aryl($C_{2-6}$alkenyl), aryl($C_{2-6}$alkynyl), heteroaryl($C_{2-6}$alkenyl) and heteroaryl ($C_{2-6}$alkynyl), R' is H or $C_{1-6}$alkyl, x and y are independently 0 or an integer from 1 to 6 provided that the sum of x and y is 1 to 6;

$R^3$ is selected from $C_{1-6}$alkyl, $C_{2-6}$alkenyl, $C_{2-6}$alkynyl, cycloalkyl, cycloalkenyl, aryl, heterocyclyl, heteroaryl and a group $$R^d-(CH_2)_p-W-(CH_2)_q-$$

wherein W is selected from a covalent bond, O, S and $NR^6$, $R^d$ is selected from H, cycloalkyl, cycloalkenyl, aryl, heterocyclyl and heteroaryl; p is an integer from 1 to 6, q is 0 or an integer from 1 to 5 provided that the sum of p and q is 1 to 6;

$R^4$ is selected from $C_{1-6}$alkyl, $C_{2-6}$alkenyl, $C_{2-6}$alkynyl, cycloalkyl, $C_{1-6}$alkyloxy, $C_{2-6}$alkenyloxy, $C_{2-6}$alkynyloxy, cycloalkoxy, $C_{1-6}$alkylthio, $C_{2-6}$alkenylthio, $C_{2-6}$alkynylthio, cycloalkylthio, halogen, aryl, aryl($C_{1-6}$alkyl)-, aryl($C_{2-6}$alkenyl), aryl($C_{2-6}$alkynyl), heterocyclyl, heterocyclyl($C_{1-6}$alkyl)-, heterocyclyl($C_{2-6}$alkenyl), heterocyclyl($C_{2-6}$alkynyl), heteroaryl, heteroaryl($C_{1-6}$alkyl)-, heteroaryl($C_{2-6}$alkenyl) and heteroaryl($C_{2-6}$alkynyl);

$R^5$ is selected from H, halogen, $C_{1-6}$alkyl, $C_{2-6}$alkenyl, $C_{2-6}$alkynyl, $C_{1-6}$alkyloxy, $C_{2-6}$alkenyloxy, $C_{2-6}$alkynyloxy, $C_{1-6}$alkylthio, $C_{2-6}$alkenylthio, $C_{2-6}$alkynylthio, CN and $C(R^7)_3$ or when $R^5$ is in the 2- or 5-position, $R^5$ and $R^3$ taken together may form a 5 to 10 membered ring;

$R^6$ is selected from H, $C_{1-6}$alkyl, $C_{2-6}$alkenyl and $C_{2-6}$alkynyl;

Each $R^7$ is independently selected from H and halogen;

m is 0 or an integer from 1 to 6; and n is 0 or an integer from 1 to 3;

wherein each alkyl, alkenyl, alkynyl, cycloalkyl, aryl, heterocyclyl and heteroaryl is optionally substituted with one or more optional substituents;

and pharmaceutically acceptable salts and prodrugs thereof; with the proviso that when $R_1$ is COOH, $R_2$ is $C_6H_5$—$CH_2S$—$CH_2$—, $R^4$ is 3-$C_6H_5$ and $R^5$ is H, $R_3$ is not $CH_3CH_2$—, in the manufacture of a medicament for regulating the death of a cell, or for inducing apoptosis in unwanted or damaged cells, or for the treatment and/or prophylaxis of a pro-survival Bcl-2 family member-mediated disease or condition, or for the treatment and/or prophylaxis of a disease or condition characterised by the inappropriate persistence or proliferation of unwanted or damaged cells.

In yet another aspect of the present invention there is provided a use of a compound of formula (Ia):

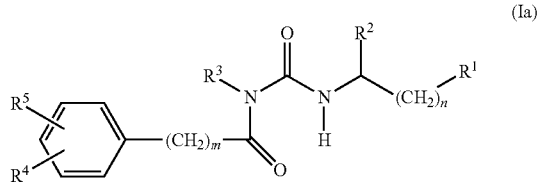

(Ia)

wherein $R^1$ is selected from $CO_2H$ or a carboxylic acid or carboxylate bioisostere;

$R^2$ is selected from an amino acid side chain, cycloalkyl, cycloalkenyl, aryl, heterocyclyl, heteroaryl and a group $$R^a-(CHR')_x-A-(CH_2)_y-$$

wherein A is a covalent bond or is selected from O, S, SO, $SO_2$ or $NR^6$, $R^a$ is H, cycloalkyl, cycloalkenyl, aryl, heterocyclyl, heteroaryl or $R^b$ where $R^b$ is

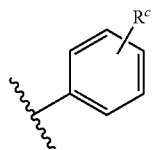

and $R^c$ is selected from heteroaryl, aryl, aryl($C_{2-6}$alkenyl), aryl($C_{2-6}$alkynyl), heteroaryl($C_{2-6}$alkenyl) and heteroaryl ($C_{2-6}$alkynyl), R' is H or $C_{1-6}$alkyl, x and y are independently 0 or an integer from 1 to 6 provided that the sum of x and y is 1 to 6;

$R^3$ is selected from $C_{3-6}$alkyl, $C_{2-6}$alkenyl, $C_{2-6}$alkynyl, cycloalkyl, cycloalkenyl, aryl, heterocyclyl, heteroaryl and a group $$R^d-(CH_2)_p-W-(CH_2)_q-$$

wherein W is selected from a covalent bond, O, S and $NR^6$, $R^d$ is selected from H, cycloalkyl, cycloalkenyl, aryl, heterocyclyl and heteroaryl; p is an integer from 1 to 6, q is 0 or an integer from 1 to 5 provided that the sum of p and q is 1 to 6;

$R^4$ is selected from $C_{1-6}$alkyl, $C_{2-6}$alkenyl, $C_{2-6}$alkynyl, cycloalkyl, $C_{1-6}$alkyloxy, $C_{2-6}$alkenyloxy, $C_{2-6}$alkynyloxy, cycloalkoxy, $C_{1-6}$alkylthio, $C_{2-6}$alkenylthio, $C_{2-6}$alkynylthio, cycloalkylthio, halogen, aryl, aryl($C_{1-6}$alkyl)-, aryl($C_{2-6}$alkenyl), aryl($C_{2-6}$alkynyl), heterocyclyl, heterocyclyl($C_{1-6}$alkyl)-, heterocyclyl($C_{2-6}$alkenyl), heterocyclyl($C_{2-6}$alkynyl), heteroaryl, heteroaryl($C_{1-6}$alkyl)-, heteroaryl($C_{2-6}$alkenyl) and heteroaryl($C_{2-6}$alkynyl);

$R^5$ is selected from H, halogen, $C_{1-6}$alkyl, $C_{2-6}$alkenyl, $C_{2-6}$alkynyl, $C_{1-6}$alkyloxy, $C_{2-6}$alkenyloxy, $C_{2-6}$alkynyloxy, $C_{1-6}$alkylthio, $C_{2-6}$alkenylthio, $C_{2-6}$alkynylthio, CN and $C(R^7)_3$ or when $R^5$ is in the 2- or 5-position, $R^5$ and $R^3$ taken together may form a 5 to 10 membered ring;

$R^6$ is selected from H, $C_{1-6}$alkyl, $C_{2-6}$alkenyl and $C_{2-6}$alkynyl;

Each $R^7$ is independently selected from H and halogen;

m is 0 or an integer from 1 to 6; and n is 0 or an integer from 1 to 3;

wherein each alkyl, alkenyl, alkynyl, cycloalkyl, aryl, heterocyclyl and heteroaryl is optionally substituted with one or more optional substituents;

and pharmaceutically acceptable salts and prodrugs thereof, in the manufacture of a medicament for regulating the death of a cell, or for inducing apoptosis in unwanted or damaged cells, or for the treatment and/or prophylaxis of a pro-survival Bcl-2 family member-mediated disease or condition, or for the treatment and/or prophylaxis of a disease or condition characterised by the inappropriate persistence or proliferation of unwanted or damaged cells.

In yet another aspect of the present invention there is provided a use of a compound of formula (Ib):

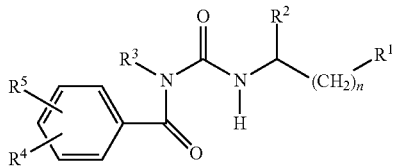

(Ib)

wherein
$R^1$ is selected from $CO_2H$ or a carboxylic acid or carboxylate bioisostere;
$R^2$ is selected from an amino acid side chain, cycloalkyl, cycloalkenyl, aryl, heterocyclyl, heteroaryl and a group $$R^a—(CH_2)_x\text{-}A\text{-}(CH_2)_y—$$

wherein A is a covalent bond or is selected from O, S, SO, $SO_2$ and $NR^6$, $R^a$ is cycloalkyl, cycloalkenyl, aryl, heterocyclyl, heteroaryl or $R^b$ where $R^b$ is

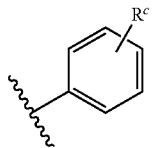

and $R^c$ is selected from heteroaryl, aryl, aryl($C_{2-6}$alkenyl), aryl($C_{2-6}$alkynyl), heteroaryl($C_{2-6}$alkenyl) and heteroaryl ($C_{2-6}$alkynyl), x and y are independently 0 or an integer from 1 to 6 provided that the sum of x and y is 1 to 6;
$R^3$ is selected from $C_{1-6}$alkyl, $C_{2-6}$alkenyl, $C_{2-6}$alkynyl, cycloalkyl, cycloalkenyl, aryl, heterocyclyl, heteroaryl and a group $$R^d—(CH_2)_p—W—(CH_2)_q—$$

wherein W is selected from a covalent bond, O, S and $NR^6$, $R^d$ is selected from H, cycloalkyl, cycloalkenyl, aryl, heterocyclyl and heteroaryl; p is an integer from 1 to 6, q is 0 or an integer from 1 to 5 provided that the sum of p and q is 1 to 6;
$R^4$ is selected from $C_{1-6}$alkyl, $C_{2-6}$alkenyl, $C_{2-6}$alkynyl, cycloalkyl, $C_{1-6}$alkyloxy, $C_{2-6}$alkenyloxy, $C_{2-6}$alkynyloxy, cycloalkoxy, $C_{1-6}$alkylthio, $C_{2-6}$alkenylthio, $C_{2-6}$alkynylthio, cycloalkylthio, halogen, aryl, aryl($C_{1-6}$alkyl)-, aryl($C_{2-6}$alkenyl), aryl($C_{2-6}$alkynyl), heterocyclyl, heterocyclyl($C_{1-6}$alkyl)-, heterocyclyl($C_{2-6}$alkenyl), heterocyclyl($C_{2-6}$alkynyl), heteroaryl, heteroaryl($C_{1-6}$alkyl)-, heteroaryl($C_{2-6}$ alkenyl) and heteroaryl($C_{2-6}$alkynyl);
$R^5$ is selected from H, halogen, $C_{1-6}$alkyl, $C_{2-6}$alkenyl, $C_{2-6}$alkynyl, $C_{1-6}$alkyloxy, $C_{2-6}$alkenyloxy, $C_{2-6}$alkynyloxy, $C_{1-6}$alkylthio, $C_{2-6}$alkenylthio, $C_{2-6}$alkynylthio, CN and $C(R^7)_3$;
$R^6$ is selected from H, $C_{1-6}$alkyl, $C_{2-6}$alkenyl and $C_{2-6}$alkynyl;
Each $R^7$ is independently selected from H and halogen; and
n is 0 or an integer from 1 to 3;
wherein each alkyl, alkenyl, alkynyl, cycloalkyl, aryl, heterocyclyl and heteroaryl is optionally substituted with one or more optional substituents;
and pharmaceutically acceptable salts and prodrugs thereof;
with the proviso that when $R_1$ is COOH, $R_2$ is $C_6H_5$—$CH_2S$—$CH_2$—, $R^4$ is 3-$C_6H_5$ and $R^5$ is H, $R_3$ is not $CH_3CH_2$—, in the manufacture of a medicament for regulating the death of a cell, or for inducing apoptosis in unwanted or damaged cells, or for the treatment and/or prophylaxis of a pro-survival Bcl-2 family member-mediated disease or condition, or for the treatment and/or prophylaxis of a disease or condition characterised by the inappropriate persistence or proliferation of unwanted or damaged cells.

In yet another aspect of the present invention there is provided a use of a compound of formula (Ic):

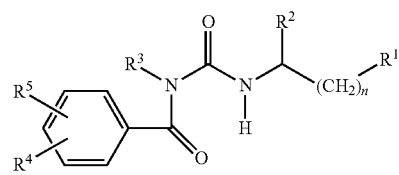

(Ic)

wherein
$R^1$ is selected from $CO_2H$ or a carboxylic acid or carboxylate bioisostere;
$R^2$ is selected from an amino acid side chain, cycloalkyl, cycloalkenyl, aryl, heterocyclyl, heteroaryl and a group $$R^a—(CH_2)_x\text{-}A\text{-}(CH_2)_y—$$

wherein A is a covalent bond or is selected from O, S, SO, $SO_2$ or $R^6$, $R^a$ is cycloalkyl, cycloalkenyl, aryl, heterocyclyl, heteroaryl or $R^b$ where $R^b$ is

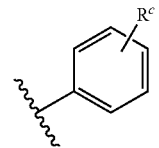

and $R^c$ is selected from heteroaryl, aryl, aryl($C_{2-6}$alkenyl), aryl($C_{2-6}$alkynyl), heteroaryl($C_{2-6}$alkenyl) and heteroaryl ($C_{2-6}$alkynyl), x and y are independently 0 or an integer from 1 to 6 provided that the sum of x and y is 1 to 6;
$R^3$ is selected from $C_{3-6}$alkyl, $C_{2-6}$alkenyl, $C_{2-6}$alkynyl, cycloalkyl, cycloalkenyl, aryl, heterocyclyl, heteroaryl and a group $$R^d—(CH_2)_p—W—(CH_2)_q—$$

wherein W is selected from a covalent bond, O, S and $NR^6$, $R^d$ is selected from H, cycloalkyl, cycloalkenyl, aryl, heterocyclyl and heteroaryl; p is an integer from 1 to 6, q is 0 or an integer from 1 to 5 provided that the sum of p and q is 1 to 6;
$R^4$ is selected from $C_{1-6}$alkyl, $C_{2-6}$alkenyl, $C_{2-6}$alkynyl, cycloalkyl, $C_{1-6}$alkyloxy, $C_{2-6}$alkenyloxy, $C_{2-6}$alkynyloxy, cycloalkoxy, $C_{1-6}$alkylthio, $C_{2-6}$alkenylthio, $C_{2-6}$alkynylthio, cycloalkylthio, halogen, aryl, aryl($C_{1-6}$alkyl)-, aryl($C_{2-6}$alkenyl), aryl($C_{2-6}$alkynyl), heterocyclyl, heterocyclyl($C_{1-6}$alkyl)-, heterocyclyl($C_{2-6}$alkenyl), heterocyclyl($C_{2-6}$alkynyl), heteroaryl, heteroaryl($C_{1-6}$alkyl)-, heteroaryl($C_{2-6}$ alkenyl) and heteroaryl($C_{2-6}$alkynyl);
$R^5$ is selected from H, halogen, $C_{1-6}$alkyl, $C_{2-6}$alkenyl, $C_{2-6}$alkynyl, $C_{1-6}$alkyloxy, $C_{2-6}$alkenyloxy, $C_{2-6}$alkynyloxy, $C_{1-6}$alkylthio, $C_{2-6}$alkenylthio, $C_{2-6}$alkynylthio, CN and $C(R^7)_3$;
$R^6$ is selected from H, $C_{1-6}$alkyl, $C_{2-6}$alkenyl and $C_{2-6}$alkynyl;
Each $R^7$ is independently selected from H and halogen; and
n is 0 or an integer from 1 to 3;
wherein each alkyl, alkenyl, alkynyl, cycloalkyl, aryl, heterocyclyl and heteroaryl is optionally substituted with one or more optional substituents;
and pharmaceutically acceptable salts and prodrugs thereof,
in the manufacture of a medicament for regulating the death of a cell, or for inducing apoptosis in unwanted or damaged cells, or for the treatment and/or prophylaxis of a pro-survival Bcl-2 family member-mediated disease or condition, or for the treatment and/or prophylaxis of a disease or condition characterised by the inappropriate persistence or proliferation of unwanted or damaged cells.

A compound of formula (Id) may also be used in the above methods and uses.

The term "mammal" as used herein includes humans, primates, livestock animals (e.g. sheep, pigs, cattle, horses, donkeys), laboratory test animals (e.g. mice, rabbits, rats, guinea pigs), companion animals (e.g. dogs, cats) and captive wild animals (e.g. foxes, kangaroos, deer). Preferably, the mammal is human or a laboratory test animal. Even more preferably, the mammal is a human.

As used herein, the term "pro-survival Bcl-2 family member-mediated disease or condition" refers to diseases or conditions where unwanted or damaged cells are not removed by normal cellular process, or diseases or conditions in which cells undergo aberrant, unwanted or inappropriate proliferation. Such diseases include those related to inactivation of apoptosis (cell death), including disorders characterised by inappropriate cell proliferation. Disorders characterised by inappropriate cell proliferation include, for example, inflammatory conditions such as inflammation arising from acute tissue injury including, for example, acute lung injury, cancer including lymphomas, such as prostate hyperplasia, genotypic tumours, autoimmune disorders, tissue hypertrophy etc. For example, diseases or conditions associated with or characterised by inappropriate persistence or proliferation of unwanted or damaged cells include those relating to unwanted or damaged B cells, for example B cell non-Hodgkin's lymphoma, B cell acute lymphoblastic leukemia; rheumatoid arthritis, systemic Lupus erythematosis and related arthropathies. Diseases and conditions associated with or characterised by the inappropriate persistence of unwanted or damaged T cells include T cell acute lymphoblastic leukemia, T cell non-Hodgkin's lymphoma and graft vs Host disease. Diseases and conditions associated with or characterised by the inappropriate persistence of unwanted or damaged myeloid cells include acute myelogenous leukemia, chronic myelogenous leukemia and chronic myelomonocytic leukemia. Diseases and conditions associated with or characterised by the inappropriate persistence of unwanted or damaged plasma cells include multiple myeloma. Diseases and conditions associated with or characterised by the inappropriate persistence of unwanted or damaged cancer cells, include cancers, especially ovarian cancer, breast cancer and prostate cancer cells.

An "effective amount" means an amount necessary at least partly to attain the desired response, or to delay the onset or inhibit progression or halt altogether, the onset or progression of a particular condition being treated. The amount varies depending upon the health and physical condition of the individual to be treated, the taxonomic group of individual to be treated, the degree of protection desired, the formulation of the composition, the assessment of the medical situation, and other relevant factors. It is expected that the amount will fall in a relatively broad range that can be determined through routine trials. An effective amount in relation to a human patient, for example, may lie in the range of about 0.1 ng per kg of body weight to 1 g per kg of body weight per dosage. The dosage is preferably in the range of 1 µg to 1 g per kg of body weight per dosage, such as is in the range of 1 mg to 1 g per kg of body weight per dosage. In one embodiment, the dosage is in the range of 1 mg to 500 mg per kg of body weight per dosage. In another embodiment, the dosage is in the range of 1 mg to 250 mg per kg of body weight per dosage. In yet another embodiment, the dosage is in the range of 1 mg to 100 mg per kg of body weight per dosage, such as up to 50 mg per kg of body weight per dosage. In yet another embodiment, the dosage is in the range of 1 µg to 1 mg per kg of body weight per dosage. Dosage regimes may be adjusted to provide the optimum therapeutic response. For example, several divided doses may be administered daily, weekly, monthly or other suitable time intervals, or the dose may be proportionally reduced as indicated by the exigencies of the situation.

Reference herein to "treatment" and "prophylaxis" is to be considered in its broadest context. The term "treatment" does not necessarily imply that a subject is treated until total recovery. Similarly, "prophylaxis" does not necessarily mean that the subject will not eventually contract a disease condition. Accordingly, treatment and prophylaxis include amelioration of the symptoms of a particular condition or preventing or otherwise reducing the risk of developing a particular condition. The term "prophylaxis" may be considered as reducing the severity or onset of a particular condition. "Treatment" may also reduce the severity of an existing condition.

The present invention further contemplates a combination of therapies, such as the administration of the compounds of the invention or pharmaceutically acceptable salts or prodrugs thereof together with the subjection of the mammal to other agents or procedures which are useful in the treatment of diseases and conditions characterised by the inappropriate persistence or proliferation of unwanted or damaged cells. For example, the compounds of the present invention may be administered in combination with other chemotherapeutic drugs, or with other treatments such as radiotherapy. Suitable chemotherapeutic drugs include, but are not limited to, cyclophosphamide, doxorubicine, etoposide phosphate, paclitaxel and vincristine.

While it is possible that, for use in therapy, a compound of the invention may be administered as a neat chemical, it is preferable to present the active ingredient as a pharmaceutical composition.

Thus, in a further aspect of the invention, there is provided a pharmaceutical composition comprising a compound of formula (I):

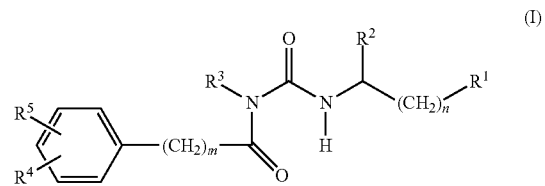

wherein
$R^1$ is selected from $CO_2H$ or a carboxylic acid or carboxylate bioisostere;
$R^2$ is selected from an amino acid side chain, cycloalkyl, cycloalkenyl, aryl, heterocyclyl, heteroaryl and a group $$R^a-(CHR')_x-A-(CH_2)_y-$$

wherein A is a covalent bond or is selected from O, S, SO, $SO_2$ and $NR^6$, $R^a$ is H, cycloalkyl, cycloalkenyl, aryl, heterocyclyl, heteroaryl or $R^b$ where $R^b$ is

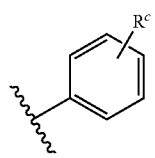

and $R^c$ is selected from heteroaryl, aryl, aryl($C_{2-6}$alkenyl), aryl($C_{2-6}$alkynyl), heteroaryl($C_{2-6}$alkenyl) and heteroaryl($C_{2-6}$alkynyl), R' is H or $C_{1-6}$alkyl, x and y are independently 0 or an integer from 1 to 6 provided that the sum of x and y is 1 to 6;

$R^3$ is selected from $C_{1-6}$alkyl, $C_{2-6}$alkenyl, $C_{2-6}$alkynyl, cycloalkyl, cycloalkenyl, aryl, heterocyclyl, heteroaryl and a group

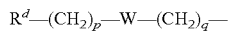

wherein W is selected from a covalent bond, O, S and $NR^6$, $R^d$ is selected from H, cycloalkyl, cycloalkenyl, aryl, heterocyclyl and heteroaryl; p is an integer from 1 to 6, q is 0 or an integer from 1 to 5 provided that the sum of p and q is 1 to 6;

$R^4$ is selected from $C_{1-6}$alkyl, $C_{2-6}$alkenyl, $C_{2-6}$alkynyl, cycloalkyl, $C_{1-6}$alkyloxy, $C_{2-6}$alkenyloxy, $C_{2-6}$alkynyloxy, cycloalkoxy, $C_{1-6}$alkylthio, $C_{2-6}$alkenylthio, $C_{2-6}$alkynylthio, cycloalkylthio, halogen, aryl, aryl($C_{1-6}$alkyl)-, aryl($C_{2-6}$alkenyl), aryl($C_{2-6}$alkynyl), heterocyclyl, heterocyclyl($C_{1-6}$alkyl)-, heterocyclyl($C_{2-6}$alkenyl), heterocyclyl($C_{2-6}$alkynyl), heteroaryl, heteroaryl($C_{1-6}$alkyl)-, heteroaryl($C_{2-6}$alkenyl) and heteroaryl($C_{2-6}$alkynyl);

$R^5$ is selected from H, halogen, $C_{1-6}$alkyl, $C_{2-6}$alkenyl, $C_{2-6}$alkynyl, $C_{1-6}$alkyloxy, $C_{2-6}$alkenyloxy, $C_{2-6}$alkynyloxy, $C_{1-6}$alkylthio, $C_{2-6}$alkenylthio, $C_{2-6}$alkynylthio, CN and $C(R^7)_3$ or when $R^5$ is in the 2- or 5-position, $R^5$ and $R^3$ taken together may form a 5 to 10 membered ring;

$R^6$ is selected from H, $C_{1-6}$alkyl, $C_{2-6}$alkenyl and $C_{2-6}$alkynyl;

Each $R^7$ is independently selected from H and halogen;

m is 0 or an integer from 1 to 6; and n is 0 or an integer from 1 to 3;

wherein each alkyl, alkenyl, alkynyl, cycloalkyl, aryl, heterocyclyl and heteroaryl is optionally substituted with one or more optional substituents;

and pharmaceutically acceptable salts and prodrugs thereof; with the proviso that when $R_1$ is COOH, $R_2$ is $C_6H_5$—$CH_2S$—$CH_2$—, $R^4$ is 3-$C_6H_5$ and $R^5$ is H, $R_3$ is not $CH_3CH_2$—, together with one or more pharmaceutically acceptable carriers and optionally, other therapeutic and/or prophylactic ingredients.

In a further aspect of the invention, there is provided a pharmaceutical composition comprising a compound of formula (Ia):

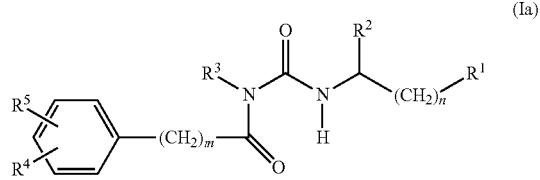

(Ia)

wherein $R^1$ is selected from $CO_2H$ or a carboxylic acid or carboxylate bioisostere;

$R^2$ is selected from an amino acid side chain, cycloalkyl, cycloalkenyl, aryl, heterocyclyl, heteroaryl and a group

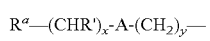

wherein A is a covalent bond or is selected from O, S, SO, $SO_2$ or $NR^6$, $R^a$ is H, cycloalkyl, cycloalkenyl, aryl, heterocyclyl, heteroaryl or $R^b$ where $R^b$ is

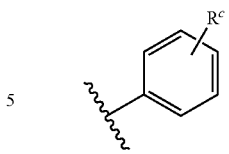

and $R^c$ is selected from heteroaryl, aryl, aryl($C_{2-6}$alkenyl), aryl($C_{2-6}$alkynyl), heteroaryl($C_{2-6}$alkenyl) and heteroaryl($C_{2-6}$alkynyl), R' is H or $C_{1-6}$alkyl, x and y are independently 0 or an integer from 1 to 6 provided that the sum of x and y is 1 to 6;

$R^3$ is selected from $C_{3-6}$alkyl, $C_{2-6}$alkenyl, $C_{2-6}$alkynyl, cycloalkyl, cycloalkenyl, aryl, heterocyclyl, heteroaryl and a group

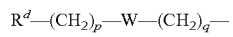

wherein W is selected from a covalent bond, O, S and $NR^6$, $R^d$ is selected from H, cycloalkyl, cycloalkenyl, aryl, heterocyclyl and heteroaryl; p is an integer from 1 to 6, q is 0 or an integer from 1 to 5 provided that the sum of p and q is 1 to 6;

$R^4$ is selected from $C_{1-6}$alkyl, $C_{2-6}$alkenyl, $C_{2-6}$alkynyl, cycloalkyl, $C_{1-6}$alkyloxy, $C_{2-6}$alkenyloxy, $C_{2-6}$alkynyloxy, cycloalkoxy, $C_{1-6}$alkylthio, $C_{2-6}$alkenylthio, $C_{2-6}$alkynylthio, cycloalkylthio, halogen, aryl, aryl($C_{1-6}$alkyl)-, aryl($C_{2-6}$alkenyl), aryl($C_{2-6}$alkynyl), heterocyclyl, heterocyclyl($C_{1-6}$alkyl)-, heterocyclyl($C_{2-6}$alkenyl), heterocyclyl($C_{2-6}$alkynyl), heteroaryl, heteroaryl($C_{1-6}$alkyl)-, heteroaryl($C_{2-6}$alkenyl) and heteroaryl($C_{2-6}$alkynyl);

$R^5$ is selected from H, halogen, $C_{1-6}$alkyl, $C_{2-6}$alkenyl, $C_{2-6}$alkynyl, $C_{1-6}$alkyloxy, $C_{2-6}$alkenyloxy, $C_{2-6}$alkynyloxy, $C_{1-6}$alkylthio, $C_{2-6}$alkenylthio, $C_{2-6}$alkynylthio, CN and $C(R^7)_3$ or when $R^5$ is in the 2- or 5-position, $R^5$ and $R^3$ taken together may form a 5 to 10 membered ring;

$R^6$ is selected from H, $C_{1-6}$alkyl, $C_{2-6}$alkenyl and $C_{2-6}$alkynyl;

Each $R^7$ is independently selected from H and halogen;

m is 0 or an integer from 1 to 6; and n is 0 or an integer from 1 to 3;

wherein each alkyl, alkenyl, alkynyl, cycloalkyl, aryl, heterocyclyl and heteroaryl is optionally substituted with one or more optional substituents;

and pharmaceutically acceptable salts and prodrugs thereof, together with one or more pharmaceutically acceptable carriers and optionally, other therapeutic and/or prophylactic ingredients.

In a further aspect of the invention, there is provided a pharmaceutical composition comprising a compound of formula (Ib):

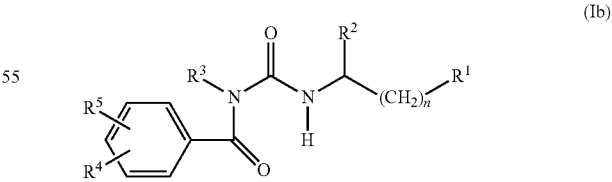

(Ib)

wherein $R^1$ is selected from $CO_2H$ or a carboxylic acid or carboxylate bioisostere;

$R^2$ is selected from an amino acid side chain, cycloalkyl, cycloalkenyl, aryl, heterocyclyl, heteroaryl and a group

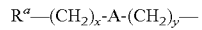

wherein A is a covalent bond or is selected from O, S, SO, SO$_2$ and NR$^6$, R$^a$ is cycloalkyl, cycloalkenyl, aryl, heterocyclyl, heteroaryl or R$^b$ where R$^b$ is

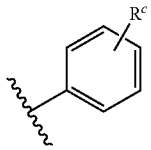

and R$^c$ is selected from heteroaryl, aryl, aryl(C$_{2-6}$alkenyl), aryl(C$_{2-6}$alkynyl), heteroaryl(C$_{2-6}$alkenyl) and heteroaryl (C$_{2-6}$alkynyl), x and y are independently 0 or an integer from 1 to 6 provided that the sum of x and y is 1 to 6;

R$^3$ is selected from C$_{1-6}$alkyl, C$_{2-6}$alkenyl, C$_{2-6}$alkynyl, cycloalkyl, cycloalkenyl, aryl, heterocyclyl, heteroaryl and a group

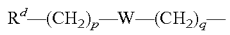

wherein W is selected from a covalent bond, O, S and NR$^6$, R$^d$ is selected from H, cycloalkyl, cycloalkenyl, aryl, heterocyclyl and heteroaryl; p is an integer from 1 to 6, q is 0 or an integer from 1 to 5 provided that the sum of p and q is 1 to 6; R$^4$ is selected from C$_{1-6}$alkyl, C$_{2-6}$alkenyl, C$_{2-6}$alkynyl, cycloalkyl, C$_{1-6}$alkyloxy, C$_{2-6}$alkenyloxy, C$_{2-6}$alkynyloxy, cycloalkoxy, C$_{1-6}$alkylthio, C$_{2-6}$alkenylthio, C$_{2-6}$alkynylthio, cycloalkylthio, halogen, aryl, aryl(C$_{1-6}$alkyl)-, aryl(C$_{2-6}$alkenyl), aryl(C$_{2-6}$alkynyl), heterocyclyl, heterocyclyl(C$_{1-6}$alkyl)-, heterocyclyl(C$_{2-6}$alkenyl), heterocyclyl(C$_{2-6}$alkynyl), heteroaryl, heteroaryl(C$_{1-6}$alkyl)-, heteroaryl(C$_{2-6}$ alkenyl) and heteroaryl(C$_{2-6}$alkynyl);

R$^5$ is selected from H, halogen, C$_{1-6}$alkyl, C$_{2-6}$alkenyl, C$_{2-6}$alkynyl, C$_{1-6}$alkyloxy, C$_{2-6}$alkenyloxy, C$_{2-6}$alkynyloxy, C$_{1-6}$alkylthio, C$_{2-6}$alkenylthio, C$_{2-6}$alkynylthio, CN and C(R$^7$)$_3$;

R$^6$ is selected from H, C$_{1-6}$alkyl, C$_{2-6}$alkenyl and C$_{2-6}$alkynyl; Each R$^7$ is independently selected from H and halogen; and n is 0 or an integer from 1 to 3;

wherein each alkyl, alkenyl, alkynyl, cycloalkyl, aryl, heterocyclyl and heteroaryl is optionally substituted with one or more optional substituents;

and pharmaceutically acceptable salts and prodrugs thereof; with the proviso that when R$^1$ is COOH, R$_2$ is C$_6$H$_5$—CH$_2$S—CH$_2$—, R$^4$ is 3-C$_6$H$_5$ and R$^5$ is H, R$_3$ is not CH$_3$CH$_2$—, together with one or more pharmaceutically acceptable carriers and optionally, other therapeutic and/or prophylactic ingredients.

In a further aspect of the invention, there is provided a pharmaceutical composition comprising a compound of formula (Ic):

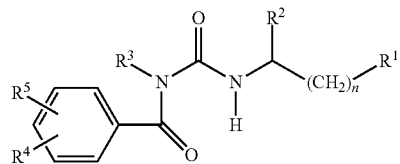

wherein
R$^1$ is selected from CO$_2$H or a carboxylic acid or carboxylate bioisostere;
R$^2$ is selected from an amino acid side chain, cycloalkyl, cycloalkenyl, aryl, heterocyclyl, heteroaryl and a group

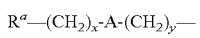

wherein A is a covalent bond or is selected from O, S, SO, SO$_2$ or NR$^6$, R$^a$ is cycloalkyl, cycloalkenyl, aryl, heterocyclyl, heteroaryl or R$^b$ where R$^b$ is

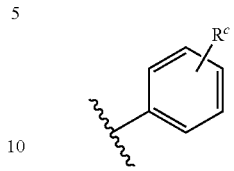

and R$^c$ is selected from heteroaryl, aryl, aryl(C$_{2-6}$alkenyl), aryl(C$_{2-6}$alkynyl), heteroaryl(C$_{2-6}$alkenyl) and heteroaryl (C$_{2-6}$alkynyl), x and y are independently 0 or an integer from 1 to 6 provided that the sum of x and y is 1 to 6;

R$^3$ is selected from C$_{3-6}$alkyl, C$_{2-6}$alkenyl, C$_{2-6}$alkynyl, cycloalkyl, cycloalkenyl, aryl, heterocyclyl, heteroaryl and a group

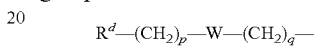

wherein W is selected from a covalent bond, O, S and NR$^6$, R$^d$ is selected from H, cycloalkyl, cycloalkenyl, aryl, heterocyclyl and heteroaryl; p is an integer from 1 to 6, q is 0 or an integer from 1 to 5 provided that the sum of p and q is 1 to 6; R$^4$ is selected from C$_{1-6}$alkyl, C$_{2-6}$alkenyl, C$_{2-6}$alkynyl, cycloalkyl, C$_{1-6}$alkyloxy, C$_{2-6}$alkenyloxy, C$_{2-6}$alkynyloxy, cycloalkoxy, C$_{1-6}$alkylthio, C$_{2-6}$alkenylthio, C$_{2-6}$alkynylthio, cycloalkylthio, halogen, aryl, aryl(C$_{1-6}$alkyl)-, aryl(C$_{2-6}$alkenyl), aryl(C$_{2-6}$alkynyl), heterocyclyl, heterocyclyl(C$_{1-6}$alkyl)-, heterocyclyl(C$_{2-6}$alkenyl), heterocyclyl(C$_{2-6}$alkynyl), heteroaryl, heteroaryl(C$_{1-6}$alkyl)-, heteroaryl(C$_{2-6}$ alkenyl) and heteroaryl(C$_{2-6}$alkynyl);

R$^5$ is selected from H, halogen, C$_{1-6}$alkyl, C$_{2-6}$alkenyl, C$_{2-6}$alkynyl, C$_{1-6}$alkyloxy, C$_{2-6}$alkenyloxy, C$_{2-6}$alkynyloxy, C$_{1-6}$alkylthio, C$_{2-6}$alkenylthio, C$_{2-6}$alkynylthio, CN and C(R$^7$)$_3$;

R$^6$ is selected from H, C$_{1-6}$alkyl, C$_{2-6}$alkenyl and C$_{2-6}$alkynyl; Each R$^7$ is independently selected from H and halogen; and n is 0 or an integer from 1 to 3;

wherein each alkyl, alkenyl, alkynyl, cycloalkyl, aryl, heterocyclyl and heteroaryl is optionally substituted with one or more optional substituents;

and pharmaceutically acceptable salts and prodrugs thereof, together with one or more pharmaceutically acceptable carriers and optionally, other therapeutic and/or prophylactic ingredients.

The pharmaceutical compositions may also comprise a compound of formula (Id).

The carrier(s) must be "acceptable" in the sense of being compatible with the other ingredients of the composition and not deleterious to the recipient thereof.

Pharmaceutical formulations include those suitable for oral, rectal, nasal, topical (including buccal and sub-lingual), vaginal or parenteral (including intramuscular, sub-cutaneous and intravenous) administration or in a form suitable for administration by inhalation or insufflation. The compounds of the invention, together with a conventional adjuvant, carrier, or diluent, may thus be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed. Formulations containing ten (10) milligrams of active ingredient or, more broadly, 0.1 to two hundred (200) milligrams, per tablet, are accordingly suitable representative unit dosage forms. The compounds of the present invention can be administered in a wide variety of oral and parenteral dosage forms. It will be obvious to those skilled in the art that the following dosage forms may comprise, as the active component, either a compound of the invention or a pharmaceutically acceptable salt or derivative of the compound of the invention.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding capacity in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as admixture of fatty acid glycerides or cocoa butter, is first melted and the active component is dispersed homogeneously therein, as by stirring. The molten homogenous mixture is then poured into convenient sized molds, allowed to cool, and thereby to solidify.

Formulations suitable for vaginal administration may be presented as pessaries, tampons, creams, gels, pastes, foams or sprays containing in addition to the active ingredient such carriers as are known in the art to be appropriate.

Liquid form preparations include solutions, suspensions, and emulsions, for example, water or water-propylene glycol solutions. For example, parenteral injection liquid preparations can be formulated as solutions in aqueous polyethylene glycol solution.

The compounds according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilising and/or dispersing agents. Alternatively, the active ingredient may be in powder form, obtained by aseptic isolation of sterile solid or by lyophilisation from solution, for constitution with a suitable vehicle, e.g. sterile, pyrogen-free water, before use.

Aqueous solutions suitable for oral use can be prepared by dissolving the active component in water and adding suitable colorants, flavours, stabilizing and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavours, stabilizers, buffers, artificial and natural sweeteners, dispersants, thickeners, solubilizing agents, and the like.

For topical administration to the epidermis the compounds according to the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Formulations suitable for topical administration in the mouth include lozenges comprising active agent in a flavoured base, usually sucrose and acacia or tragacanth; pastilles comprising the active ingredient in an inert base such as gelatin and glycerin or sucrose and acacia; and mouthwashes comprising the active ingredient in a suitable liquid carrier.

Solutions or suspensions are applied directly to the nasal cavity by conventional means, for example with a dropper, pipette or spray. The formulations may be provided in single or multidose form. In the latter case of a dropper or pipette, this may be achieved by the patient administering an appropriate, predetermined volume of the solution or suspension. In the case of a spray, this may be achieved for example by means of a metering atomising spray pump. To improve nasal delivery and retention the compounds according to the invention may be encapsulated with cyclodextrins, or formulated with their agents expected to enhance delivery and retention in the nasal mucosa.

Administration to the respiratory tract may also be achieved by means of an aerosol formulation in which the active ingredient is provided in a pressurised pack with a suitable propellant such as a chlorofluorocarbon (CFC) for example dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP).

Conveniently the powder carrier will form a gel in the nasal cavity. The powder composition may be presented in unit dose form for example in capsules or cartridges of, e.g., gelatin, or blister packs from which the powder may be administered by means of an inhaler.

In formulations intended for administration to the respiratory tract, including intranasal formulations, the compound will generally have a small particle size for example of the order of 1 to 10 microns or less. Such a particle size may be obtained by means known in the art, for example by micronization.

When desired, formulations adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Liquids or powders for intranasal administration, tablets or capsules for oral administration and liquids for intravenous administration are preferred compositions.

Bcl-2 proteins are not only present in persistent damaged or unwanted cells related to disease states such as malignant disease and autoimmunity. In order to minimise the risk of apoptosis of healthy cells caused by compounds that bind to Bcl-2 proteins, it is desirable to target delivery of the compounds to specific unwanted cells.

The use of certain antibodies to target particular cell types is an active area of research, particularly where the antibody is conjugated to the cell active agent (Wang et. al., 1997; Goulet et. al., 1997; Sapra and Allen, 2002; Marks et. al., 2003; Deardon, 2002; Ludwig et. al., 2003; Uckun et. al., 1995). For example, CD19, as a pan B-cell antigen, is an ideal target for immunotoxin therapy of B-lineage leukemia and lymphomas (Wang et. al., 1997; Goulet et. al., 1997; Sapra and Allen, 2002; Marks et. al., 2003; Deardon, 2002). Various cytotoxic agents, such as genistein, ricin analogues, doxorubicin, and cytotoxic peptides have been conjugated to anti-CD19 antibodies (Wang et. al., 1997; Goulet et. al., 1997; Sapra and Allen, 2002; Marks et. al., 2003; Deardon, 2002; Uckun et. al., 1995), in order to target and kill B-cells and treat B-cell associated cancer.

A $BH_3$ peptide has been conjugated to leutinising hormone releasing hormone (LHRH) to target LHRH receptors, which are overexpressed in several cancer cell lines but are not expressed in healthy human visceral organs (Dharap and Minko, 2003).

In a further aspect of the invention there is provided a conjugate comprising at least one cell targeting moiety and at least one compound of formula (I):

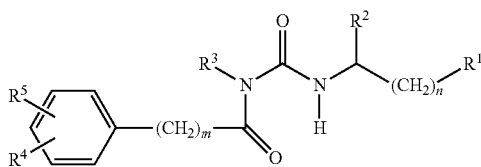
(I)

wherein
$R^1$ is selected from $CO_2H$ or a carboxylic acid or carboxylate bioisostere;
$R^2$ is selected from an amino acid side chain, cycloalkyl, cycloalkenyl, aryl, heterocyclyl, heteroaryl and a group $$R^a\text{—}(CHR')_x\text{-A-}(CH_2)_y\text{—}$$

wherein A is a covalent bond or is selected from O, S, SO, $SO_2$ and $NR^6$, $R^a$ is H, cycloalkyl, cycloalkenyl, aryl, heterocyclyl, heteroaryl or $R^b$ where $R^b$ is

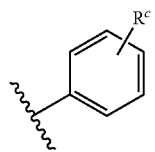

and $R^c$ is selected from heteroaryl, aryl, aryl($C_{2-6}$alkenyl), aryl($C_{2-6}$alkynyl), heteroaryl($C_{2-6}$alkenyl) and heteroaryl($C_{2-6}$alkynyl), R' is H or $C_{1-6}$alkyl, x and y are independently 0 or an integer from 1 to 6 provided that the sum of x and y is 1 to 6;

$R^3$ is selected from $C_{1-6}$alkyl, $C_{2-6}$alkenyl, $C_{2-6}$alkynyl, cycloalkyl, cycloalkenyl, aryl, heterocyclyl, heteroaryl and a group $$R^d\text{—}(CH_2)_p\text{—W—}(CH_2)_q\text{—}$$

wherein W is selected from a covalent bond, O, S and $NR^6$, $R^d$ is selected from H, cycloalkyl, cycloalkenyl, aryl, heterocyclyl and heteroaryl; p is an integer from 1 to 6, q is 0 or an integer from 1 to 5 provided that the sum of p and q is 1 to 6;
$R^4$ is selected from $C_{1-6}$alkyl, $C_{2-6}$alkenyl, $C_{2-6}$alkynyl, cycloalkyl, $C_{1-6}$alkyloxy, $C_{2-6}$alkenyloxy, $C_{2-6}$alkynyloxy, cycloalkoxy, $C_{1-6}$alkylthio, $C_{2-6}$alkenylthio, $C_{2-6}$alkynylthio, cycloalkylthio, halogen, aryl, aryl($C_{1-6}$alkyl)-, aryl($C_{2-6}$alkenyl), aryl($C_{2-6}$alkynyl), heterocyclyl, heterocyclyl($C_{1-6}$alkyl)-, heterocyclyl($C_{2-6}$alkenyl), heterocyclyl($C_{2-6}$alkynyl), heteroaryl, heteroaryl($C_{1-6}$alkyl)-, heteroaryl($C_{2-6}$alkenyl) and heteroaryl($C_{2-6}$alkynyl);
$R^5$ is selected from H, halogen, $C_{1-6}$alkyl, $C_{2-6}$alkenyl, $C_{2-6}$alkynyl, $C_{1-6}$alkyloxy, $C_{2-6}$alkenyloxy, $C_{2-6}$alkynyloxy, $C_{1-6}$alkylthio, $C_{2-6}$alkenylthio, $C_{2-6}$alkynylthio, CN and $C(R^7)_3$ or when $R^5$ is in the 2- or 5-position, $R^5$ and $R^3$ taken together may form a 5 to 10 membered ring;
$R^6$ is selected from H, $C_{1-6}$alkyl, $C_{2-6}$alkenyl and $C_{2-6}$alkynyl;
Each $R^7$ is independently selected from H and halogen;
m is 0 or an integer from 1 to 6; and
n is 0 or an integer from 1 to 3;
wherein each alkyl, alkenyl, alkynyl, cycloalkyl, aryl, heterocyclyl and heteroaryl is optionally substituted with one or more optional substituents;
and pharmaceutically acceptable salts and prodrugs thereof;
with the proviso that when $R_1$ is COOH, $R_2$ is $C_6H_5$—$CH_2S$—$CH_2$—, $R^4$ is 3-$C_6H_5$ and $R^5$ is H, $R_3$ is not $CH_3CH_2$—.

In yet a further aspect of the invention there is provided a conjugate comprising at least one cell targeting moiety and at least one compound of formula (Ia):

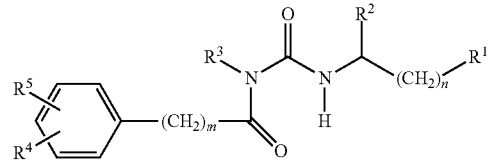
(Ia)

wherein
$R^1$ is selected from $CO_2H$ or a carboxylic acid or carboxylate bioisostere;
$R^2$ is selected from an amino acid side chain, cycloalkyl, cycloalkenyl, aryl, heterocyclyl, heteroaryl and a group $$R^a\text{—}(CHR')_x\text{-A-}(CH_2)_y\text{—}$$

wherein A is a covalent bond or is selected from O, S, SO, SO$_2$ or NR$^6$, R$^a$ is H, cycloalkyl, cycloalkenyl, aryl, heterocyclyl, heteroaryl or R$^b$ where R$^b$ is

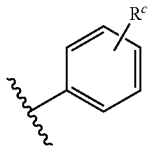

and R$^c$ is selected from heteroaryl, aryl, aryl(C$_{2-6}$alkenyl), aryl(C$_{2-6}$alkynyl), heteroaryl(C$_{2-6}$alkenyl) and heteroaryl (C$_{2-6}$alkynyl), R' is H or C$_{1-6}$alkyl, x and y are independently 0 or an integer from 1 to 6 provided that the sum of x and y is 1 to 6;
R$^3$ is selected from C$_{3-6}$alkyl, C$_{2-6}$alkenyl, C$_{2-6}$alkynyl, cycloalkyl, cycloalkenyl, aryl, heterocyclyl, heteroaryl and a group

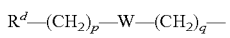

wherein W is selected from a covalent bond, O, S and NR$^6$, R$^d$ is selected from H, cycloalkyl, cycloalkenyl, aryl, heterocyclyl and heteroaryl; p is an integer from 1 to 6, q is 0 or an integer from 1 to 5 provided that the sum of p and q is 1 to 6;
R$^4$ is selected from C$_{1-6}$alkyl, C$_{2-6}$alkenyl, C$_{2-6}$alkynyl, cycloalkyl, C$_{1-6}$alkyloxy, C$_{2-6}$alkenyloxy, C$_{2-6}$alkynyloxy, cycloalkoxy, C$_{1-6}$alkylthio, C$_{2-6}$alkenylthio, C$_{2-6}$alkynylthio, cycloalkylthio, halogen, aryl, aryl(C$_{1-6}$alkyl)-, aryl(C$_{2-6}$alkenyl), aryl(C$_{2-6}$alkynyl), heterocyclyl, heterocyclyl(C$_{1-6}$ alkyl)-, heterocyclyl(C$_{2-6}$alkenyl), heterocyclyl(C$_{2-6}$alkynyl), heteroaryl, heteroaryl(C$_{1-6}$alkyl)-, heteroaryl(C$_{2-6}$ alkenyl) and heteroaryl(C$_{2-6}$alkynyl);
R$^5$ is selected from H, halogen, C$_{1-6}$alkyl, C$_{2-6}$alkenyl, C$_{2-6}$alkynyl, C$_{1-6}$alkyloxy, C$_{2-6}$alkenyloxy, C$_{2-6}$alkynyloxy, C$_{1-6}$alkylthio, C$_{2-6}$alkenylthio, C$_{2-6}$alkynylthio, CN and C(R$^7$)$_3$ or when R$^5$ is in the 2- or 5-position, R$^5$ and R$^3$ taken together may form a 5 to 10 membered ring;
R$^6$ is selected from H, C$_{1-6}$alkyl, C$_{2-6}$alkenyl and C$_{2-6}$alkynyl;
Each R$^7$ is independently selected from H and halogen;
m is 0 or an integer from 1 to 6; and
n is 0 or an integer from 1 to 3;
wherein each alkyl, alkenyl, alkynyl, cycloalkyl, aryl, heterocyclyl and heteroaryl is optionally substituted with one or more optional substituents;
and pharmaceutically acceptable salts and prodrugs thereof.

In a further aspect of the invention there is provided a conjugate comprising at least one cell targeting moiety and at least one compound of formula (Ib):

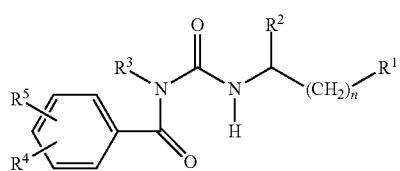

wherein
R$^1$ is selected from CO$_2$H or a carboxylic acid or carboxylate bioisostere;
R$^2$ is selected from an amino acid side chain, cycloalkyl, cycloalkenyl, aryl, heterocyclyl, heteroaryl and a group

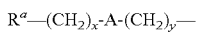

wherein A is a covalent bond or is selected from O, S, SO, SO$_2$ and NR$^6$, R$^a$ is cycloalkyl, cycloalkenyl, aryl, heterocyclyl, heteroaryl or R$^b$ where R$^b$ is

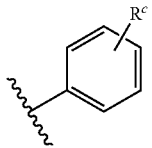

and R$^c$ is selected from heteroaryl, aryl, aryl(C$_{2-6}$alkenyl), aryl(C$_{2-6}$alkynyl), heteroaryl(C$_{2-6}$alkenyl) and heteroaryl (C$_{2-6}$alkynyl), x and y are independently 0 or an integer from 1 to 6 provided that the sum of x and y is 1 to 6;
R$^3$ is selected from C$_{1-6}$alkyl, C$_{2-6}$alkenyl, C$_{2-6}$alkynyl, cycloalkyl, cycloalkenyl, aryl, heterocyclyl, heteroaryl and a group

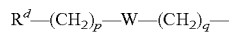

wherein W is selected from a covalent bond, O, S and NR$^6$, R$^d$ is selected from H, cycloalkyl, cycloalkenyl, aryl, heterocyclyl and heteroaryl; p is an integer from 1 to 6, q is 0 or an integer from 1 to 5 provided that the sum of p and q is 1 to 6;
R$^4$ is selected from C$_{1-6}$alkyl, C$_{2-6}$alkenyl, C$_{2-6}$alkynyl, cycloalkyl, C$_{1-6}$alkyloxy, C$_{2-6}$alkenyloxy, C$_{2-6}$alkynyloxy, cycloalkoxy, C$_{1-6}$alkylthio, C$_{2-6}$alkenylthio, C$_{2-6}$alkynylthio, cycloalkylthio, halogen, aryl, aryl(C$_{1-6}$alkyl)-, aryl(C$_{2-6}$alkenyl), aryl(C$_{2-6}$alkynyl), heterocyclyl, heterocyclyl(C$_{1-6}$ alkyl)-, heterocycyl(C$_{2-6}$alkenyl), heterocyclyl(C$_{2-6}$alkynyl), heteroaryl, heteroaryl(C$_{1-6}$alkyl)-, heteroaryl(C$_{2-6}$ alkenyl) and heteroaryl(C$_{2-6}$alkynyl);
R$^5$ is selected from H, halogen, C$_{1-6}$alkyl, C$_{2-6}$alkenyl, C$_{2-6}$alkynyl, C$_{1-6}$alkyloxy, C$_{2-6}$alkenyloxy, C$_{2-6}$alkynyloxy, C$_{1-6}$alkylthio, C$_{2-6}$alkenylthio, C$_{2-6}$alkynylthio, CN and C(R$^7$)$_3$;
R$^6$ is selected from H, C$_{1-6}$alkyl, C$_{2-6}$alkenyl and C$_{2-6}$alkynyl;
Each R$^7$ is independently selected from H and halogen; and
n is 0 or an integer from 1 to 3;
wherein each alkyl, alkenyl, alkynyl, cycloalkyl, aryl, heterocyclyl and heteroaryl is optionally substituted with one or more optional substituents;
and pharmaceutically acceptable salts and prodrugs thereof; with the proviso that when R$^1$ is COOH, R$_2$ is C$_6$H$_5$—CH$_2$S—CH$_2$—, R$^4$ is 3-C$_6$H$_5$ and R$^5$ is H, R$_3$ is not CH$_3$CH$_2$—.

In yet a further aspect of the invention there is provided a conjugate comprising at least one cell targeting moiety and at least one compound of formula (Ic):

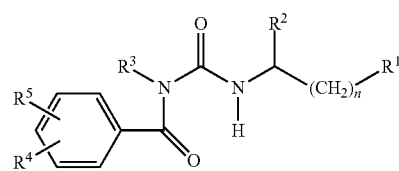

wherein
R$^1$ is selected from CO$_2$H or a carboxylic acid or carboxylate bioisostere;
R$^2$ is selected from an amino acid side chain, cycloalkyl, cycloalkenyl, aryl, heterocyclyl, heteroaryl and a group

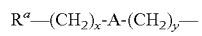

wherein A is a covalent bond or is selected from O, S, SO, SO$_2$ or NR$^6$, R$^a$ is cycloalkyl, cycloalkenyl, aryl, heterocyclyl, heteroaryl or R$^b$ where R$^b$ is

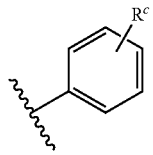

and R$^c$ is selected from heteroaryl, aryl, aryl(C$_{2-6}$alkenyl), aryl(C$_{2-6}$alkynyl), heteroaryl(C$_{2-6}$alkenyl) and heteroaryl (C$_{2-6}$alkynyl), x and y are independently 0 or an integer from 1 to 6 provided that the sum of x and y is 1 to 6;
R$^3$ is selected from C$_{3-6}$alkyl, C$_{2-6}$alkenyl, C$_{2-6}$alkynyl, cycloalkyl, cycloalkenyl, aryl, heterocyclyl, heteroaryl and a group

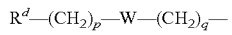

wherein W is selected from a covalent bond, O, S and NR$^6$, R$^d$ is selected from H, cycloalkyl, cycloalkenyl, aryl, heterocyclyl and heteroaryl; p is an integer from 1 to 6, q is 0 or an integer from 1 to 5 provided that the sum of p and q is 1 to 6;
R$^4$ is selected from C$_{1-6}$alkyl, C$_{2-6}$alkenyl, C$_{2-6}$alkynyl, cycloalkyl, C$_{1-6}$alkyloxy, C$_{2-6}$alkenyloxy, C$_{2-6}$alkynyloxy, cycloalkoxy, C$_{1-6}$alkylthio, C$_{2-6}$alkenylthio, C$_{2-6}$alkynylthio, cycloalkylthio, halogen, aryl, aryl(C$_{1-6}$alkyl)-, aryl(C$_{2-6}$alkenyl), aryl(C$_{2-6}$alkynyl), heterocyclyl, heterocyclyl(C$_{1-6}$ alkyl)-, heterocyclyl(C$_{2-6}$alkenyl), heterocyclyl(C$_{2-6}$alkynyl), heteroaryl, heteroaryl(C$_{1-6}$alkyl)-, heteroaryl(C$_{2-6}$ alkenyl) and heteroaryl(C$_{2-6}$alkynyl);
R$^5$ is selected from H, halogen, C$_{1-6}$alkyl, C$_{2-6}$alkenyl, C$_{2-6}$alkynyl, C$_{1-6}$alkyloxy, C$_{2-6}$alkenyloxy, C$_{2-6}$alkynyloxy, C$_{1-6}$alkylthio, C$_{2-6}$alkenylthio, C$_{2-6}$alkynylthio, CN and C(R$^7$)$_3$;
R$^6$ is selected from H, C$_{1-6}$alkyl, C$_{2-6}$alkenyl and C$_{2-6}$alkynyl;
Each R$^7$ is independently selected from H and halogen; and n is 0 or an integer from 1 to 3;
wherein each alkyl, alkenyl, alkynyl, cycloalkyl, aryl, heterocyclyl and heteroaryl is optionally substituted with one or more optional substituents;
and pharmaceutically acceptable salts and prodrugs thereof.

The conjugates of the invention may also comprise compounds of formula (Id).

As used herein, the term "conjugate" refers to a molecule composed of at least two moieties, at least one cell targeting moiety coupled to at least one compound of formula (I) or formula (Ia). The at least two moieties are releasably coupled, preferably by a covalent bond, more preferably a covalent bond that is able to be hydrolysed under specific cellular conditions to release the compound of formula (I) or formula (Ia) within a damaged or unwanted cell at its site of action. Examples of suitable covalent bonds able to be hydrolysed intracellularly include disulfide bonds, ester bonds and amide bonds. The conformationally constrained peptide moiety or a spacer, which may be present between the compound of the invention and the cell targeting moiety, may include an enzyme, for example, a protease, recognition sequence to provide hydrolysis of a bond under specific conditions thereby releasing the compound of formula (I) or formula (Ia).

As used herein, the term "cell targeting moiety" refers to a moiety which is able to interact with a target molecule expressed by an unwanted or damaged cell, preferably on the cell surface. Preferably, the target molecule is overexpressed in the unwanted or damaged cell and is not expressed in healthy cells. Suitable cell targeting moieties include proteins and antigen-binding molecules, which interact with target molecules in the damaged or unwanted cells. Suitable cell targeting moieties include, but are not limited to, hormones such as leutinising hormone receptor hormone and cytokines such as VEGF and EGF, and antibodies such as CD19, CD20, CD22, CD79a, CD2, CD3, CD7, CD5, CD13, CD33 and CD138, or antibodies targeting receptors such as Erb1 (also called EGFR), Erb2 (also called HER2 and NEU), Erb3 and Erb4. In a preferred embodiment the cell targeting moiety is an antibody that targets B-cells, for example, CD19, CD20, CD22 and CD79a.

The conjugate may include one cell targeting moiety and one compound of formula (I) or formula (Ia), one cell targeting moiety and multiple compounds of formula (I) or formula (Ia), more than one cell targeting moiety and one compound of formula (I) or formula (Ia) or more than one cell targeting moiety and multiple compounds of formula (I) or formula (Ia). In some embodiments, the conjugate comprises one cell targeting moiety and between one and 100 compounds of formula (I) or formula (Ia), preferably one and 50, more preferably one and 20, most preferably 3 and 15. In other embodiments the conjugate may have more than one cell targeting moiety. The two or more cell targeting moieties may be the same or different. If the two or more cell targeting moieties are different, the conjugate may be used to target cells which express target molecules for each cell targeting moiety, thereby increasing cell specificity.

As used herein, the term "antigen-binding molecule" refers to a molecule that has binding affinity for a target antigen, and extends to immunoglobulins, immunoglobulin fragments and non-immunoglobulin derived protein frameworks that exhibit antigen-binding activity.

In some embodiments, the cell-targeting moiety is an antigen-binding molecule that is immuno-interactive with a target molecule, typically a cell surface protein (e.g., a receptor), expressed by a cell that is the subject of targeting. Reference herein to "immuno-interactive" includes reference to any interaction, reaction, or other form of association between molecules and in particular where one of the molecules is, or mimics, a component of the immune system.

The antigen-binding molecule may be selected from immunoglobulin molecules such as whole polyclonal antibodies and monoclonal antibodies as well as sub-immunoglobulin-sized antigen-binding molecules. Polyclonal antibodies may be prepared, for example, by injecting a target molecule of the invention into a production species, which may include mice or rabbits, to obtain polyclonal antisera. Methods of producing polyclonal antibodies are well known to those skilled in the art. Exemplary protocols which may be used are described for example in Coligan et al., "Current Protocols In Immunology", (John Wiley & Sons, Inc, 1991), and Ausubel et al., "Current Protocols In Molecular Biology" (1994-1998), in particular Section III of Chapter 11.

In lieu of the polyclonal antisera obtained in the production species, monoclonal antibodies may be produced using the standard method as described, for example, by Köhler and Milstein, 1975, or by more recent modifications thereof as described, for example, in Coligan et al, 1991, by immortalising spleen or other antibody-producing cells derived from a production species which has been inoculated with target molecule of the invention. Suitable sub-immunoglobulin-sized antigen binding molecules include, but are not restricted to, Fv, Fab, Fab' and F(ab')$_2$ immunoglobulin fragments. In some embodiments, the sub-immunoglobulin-sized antigen-binding molecule does not comprise the Fc portion of an immunoglobulin molecule.

In some embodiments, the sub-immunoglobulin-sized antigen-binding molecule comprises a synthetic Fv fragment. Suitably, the synthetic Fv fragment is stabilised. Exemplary synthetic stabilised Fv fragments include single chain Fv fragments (sFv, frequently termed scFv) in which a peptide linker is used to bridge the N terminus or C terminus of a $V_H$ domain with the C terminus or N-terminus, respectively, of a $V_L$ domain. ScFv lack all constant parts of whole antibodies and are not able to activate complement. Suitable peptide linkers for joining the $V_H$ and $V_L$ domains are those which allow the $V_H$ and $V_L$ domains to fold into a single polypeptide chain having an antigen binding site with a three dimensional structure similar to that of the antigen binding site of a whole antibody from which the Fv fragment is derived. Linkers having the desired properties may be obtained by the method disclosed in U.S. Pat. No. 4,946,778. However, in some cases a linker is absent.

ScFvs may be prepared, for example, in accordance with methods outlined in Krebber et. al., 1997. Alternatively, they may be prepared by methods described in U.S. Pat. No. 5,091,513, European Patent No 239,400 or the articles by Winter and Milstein, 1991 and Pluckthun et. al., 1996, *Antibody engineering. A practical approach.* 203-252.

Alternatively, the synthetic stabilised Fv fragment comprises a disulphide stabilised Fv (dsFv) in which cysteine residues are introduced into the $V_H$ and $V_L$ domains such that in the fully folded Fv molecule the two residues will form a disulphide bond therebetween. Suitable methods of producing dsFv are described for example in Glockshuber et. al. 1990, Reiter et. al. 1994a, Reiter et al. 1994b, Reiter et. al. 1994c, Webber et al. 1995.

Also contemplated as sub-immunoglobulin-sized antigen binding molecules are single variable region domains (termed dAbs) as for example disclosed in Ward et. al. 1989, Hamers-Castennan et al 1993, Davies & Riechmann, 1994.

In other embodiments, the sub-immunoglobulin-sized antigen-binding molecule is a "minibody". In this regard, minibodies are small versions of whole antibodies, which encode in a single chain the essential elements of a whole antibody. Suitably, the minibody is comprised of the $V_H$ and $V_L$ domains of a native antibody fused to the hinge region and CH3 domain of the immunoglobulin molecule as, for example, disclosed in U.S. Pat. No. 5,837,821.

In still other embodiments, the sub-immunoglobulin-sized antigen binding molecule comprises non-immunoglobulin derived, protein frameworks. For example, reference may be made to Ku & Schultz, 1995, which discloses a four-helix bundle protein cytochrome b562 having two loops randomised to create complementarity determining regions (CDRs), which have been selected for antigen binding.

In some embodiments, the sub-immunoglobulin-sized antigen-binding molecule comprises a modifying moiety. In illustrative examples of this type, the modifying moiety modifies the effector function of the molecule. For instance, the modifying moiety may comprise a peptide for detection of the antigen-binding molecule, for example in an immunoassay. Alternatively, the modifying moiety may facilitate purification of the antigen-binding molecule. In this instance, the modifying moiety includes, but is not limited to, glutathione-S-transferase (GST), maltose binding protein (MBP) and hexahistidine ($HIS_6$), which are particularly useful for isolation of the antigen-binding molecule by affinity chromatography. For the purposes of purification by affinity chromatography, relevant matrices for affinity chromatography are glutathione-, amylose-, and nickel- or cobalt-conjugated resins respectively as is well known in the art.

The sub-immunoglobulin-sized antigen binding molecule may be multivalent (i.e., having more than one antigen binding site). Such multivalent molecules may be specific for one or more antigens (e.g., two target molecules expressed by a targeted cell). Multivalent molecules of this type may be prepared by dimerisation of two antibody fragments through a cysteinyl-containing peptide as, for example disclosed by Adams et. al., 1993 and Cumber et. al., 1992. Alternatively, dimerisation may be facilitated by fusion of the antibody fragments to amphiphilic helices that naturally dimerise (Pack and Plückthun, 1992) or by use of domains (such as the leucine zippers jun and fos) that preferentially heterodimerise (Kostelny et. al., 1992). In other embodiments, the multivalent molecule comprises a multivalent single chain antibody (multi-scFv) comprising at least two scFvs linked together by a peptide linker. For example, non-covalently or covalently linked scFv dimers termed "diabodies" may be used in this regard. Multi-scFvs may be bispecific or greater depending on the number of scFvs employed having different antigen binding specificities. Multi-scFvs may be prepared for example by methods disclosed in U.S. Pat. No. 5,892,020.

The compounds of formula (I) and formula (Ia) may be coupled to the cell targeting moiety by any suitable means known in the art. For example an amino or carboxy substituent on the compound of the invention may be coupled to a carboxy or amino substituent on the cell targeting moiety using general means for coupling carboxylic acids and amines. If the cell targeting moiety is an antibody or protein, care must be taken during any reaction steps, such as deprotection, to avoid denaturation of the antibody or protein.

Conjugates that comprise a compound of formula (I) or formula (Ia) and a cell-targeting moiety can be produced by any suitable technique known to persons of skill in the art. The present invention, therefore, is not dependent on, and not directed to, any one particular technique for conjugating these moieties.

The manner of attachment of a compound of formula (I) or formula (Ia) to a cell-targeting moiety should be such that the biological activity of each moiety is not substantially inhibited or impaired. A linker or spacer may be included between the moieties to spatially separate them. The linker or spacer molecule may be from about 1 to about 100 atoms in length. In some embodiments, the linker or spacer molecule comprises one or more amino acid residues (e.g., from about 1 to about 50 amino acid residues and desirably 1, 2, 3, 4, 5, 6, 7, 8, 9, 10, 15, 20 amino acid residues). Such linkers or spacers may facilitate the proper folding of the cell targeting moiety and the adoption of a desired conformation of the compound of formula (I) or formula (Ia).

Suitably, the compound of formula (I) or formula (Ia) is covalently attached to the cell-targeting moiety. Covalent attachment may be achieved by any suitable means known to persons of skill in the art. For example, a conjugate may be prepared by linking the cell targeting moiety and the compound of formula (I) or formula (Ia) using crosslinking reagents. Examples of such crosslinking agents include carbodiimides such as, but not limited to, 1-cyclohexyl-3-(2-morpholinyl-(4-ethyl)carbodiimide (CMC), 1-ethyl-3-(3-dimethylaminopropyl)carbodiimide (EDC) and 1-ethyl-3-(4-azonia-4,4-dimethylpentyl) carbodiimide. Exemplary crosslinking agents of this type are selected from the group consisting of 1-cyclohexyl-3-(2-morpholinyl-(4-ethyl)carbodiimide, (1-ethyl-3-(3-dimethylaminopropyl carbodiimide (EDC) and 1-ethyl-3-(4-azonia-4,4-dimethylpentyl)carbodiimide. Examples of other suitable crosslinking agents are cyanogen bromide, glutaraldehyde and succinic anhydride.

In general, any of a number of homobifunctional agents including a homobifunctional aldehyde, a homobifunctional epoxide, a homobifunctional imidoester, a homobifunctional N-hydroxysuccinimide ester, a homobifunctional maleimide, a homobifunctional alkyl halide, a homobifunctional pyridyl disulfide, a homobifunctional aryl halide, a homobifunctional hydrazide, a homobifunctional diazonium derivative and a homobifunctional photoreactive compound may be used. Also included are heterobifunctional compounds, for example, compounds having an amine-reactive and a sulfhydryl-reactive group, compounds with an amine-reactive and a photoreactive group and compounds with a carbonyl-reactive and a sulfhydryl-reactive group.

Homobifunctional reagents are molecules with at least two identical functional groups. The functional groups of the reagent generally react with one of the functional groups on a protein, typically an amino group. Specific examples of such homobifunctional crosslinking reagents include the bifunctional N-hydroxysuccinimide esters dithiobis(succinimidylpropionate), disuccinimidyl suberate, and disuccinimidyl tartrate; the bifunctional imidoesters dimethyl adipimidate, dimethyl pimelimidate, and dimethyl suberimidate; the bifunctional sulfhydryl-reactive crosslinkers 1,4-di-[3'-(2'-pyridyldithio)propionamido]butane, bismaleimidohexane, and bis-N-maleimido-1,8-octane; the bifunctional aryl halides 1,5-difluoro-2,4-dinitrobenzene and 4,4'-difluoro-3,3'-dinitrophenylsulfone; bifunctional photoreactive agents such as bis-[b-(4-azidosalicylamido)ethyl]disulfide; the bifunctional aldehydes formaldehyde, malondialdehyde, succinaldehyde, glutaraldehyde, and adipaldehyde; a bifunctional epoxide such as 1,4-butanediol diglycidyl ether, the bifunctional hydrazides adipic acid dihydrazide, carbohydrazide, and succinic acid dihydrazide; the bifunctional diazoniums o-toluidine, diazotized and bis-diazotized benzidine; the bifunctional alkylhalides N,N'-ethylene-bis(iodoacetamide), N,N'-hexamethylene-bis(iodoacetamide), N,N'-undecamethylene-bis(iodoacetamide), as well as benzylhalides and halomustards, such as α,α'-diiodo-p-xylene sulfonic acid and tri(2-chloroethyl)amine, respectively. Methods of using homobifunctional crosslinking reagents are known to practitioners in the art. For instance, the use of glutaraldehyde as a cross-linking agent is described for example by Poznansky et. al., 1984. The use of diimidates as a cross-linking agent is described for example by Wang, et. al., 1977.

Although it is possible to use homobifunctional crosslinking reagents for the purpose of forming a conjugate molecule according to the invention, skilled practitioners in the art will appreciate that it is more difficult to attach proteins and molecules in an ordered fashion with these reagents. In this regard, in attempting to link a protein with a compound of formula (I) or formula (Ia) by means of a homobifunctional reagent, one cannot prevent the linking of the protein to each other rather than the compound of formula (I) or formula (Ia). Accordingly, heterobifunctional crosslinking reagents are preferred because one can control the sequence of reactions, and combine proteins at will. Heterobifunctional reagents thus provide a more sophisticated method for linking two moieties. These reagents require one of the molecules to be joined, hereafter called Partner B, to possess a reactive group not found on the other, hereafter called Partner A, or else require that one of the two functional groups be blocked or otherwise greatly reduced in reactivity while the other group is reacted with Partner A. In a typical two-step process for forming heteroconjugates, Partner A is reacted with the heterobifunctional reagent to form a derivatised Partner A molecule. If the unreacted functional group of the crosslinker is blocked, it is then deprotected. After deprotecting, Partner B is coupled to derivatised Partner A to form the conjugate. Primary amino groups on Partner A are reacted with an activated carboxylate or imidate group on the crosslinker in the derivatisation step. A reactive thiol or a blocked and activated thiol at the other end of the crosslinker is reacted with an electrophilic group or with a reactive thiol, respectively, on Partner B. When the crosslinker possesses a reactive thiol, the electrophile on Partner B preferably will be a blocked and activated thiol, a maleimide, or a halomethylene carbonyl (e.g. bromoacetyl or iodoacetyl) group. Because biological macromolecules do not naturally contain such electrophiles, they must be added to Partner B by a separate derivatisation reaction. When the crosslinker possesses a blocked and activated thiol, the thiol on Partner B with which it reacts may be native to Partner B.

An example of a heterobifunctional reagent is N-succinimidyl 3-(2-pyridyldithio)propionate (SPDP) (see for example Carlsson et. al., 1978). Other heterobifunctional reagents for linking proteins include for example succinimidyl 4-(N-maleimidomethyl)cyclohexane-1-carboxylate (SMCC) (Yoshitake et. al., 1979), 2-iminothiolane (IT) (Ju et. al., 1978), and S-acetyl mercaptosuccinic anhydride (SAMSA) (Klotz and Heiney, 1962). All three react preferentially with primary amines (e.g., lysine side chains) to form an amide or amidine group which links a thiol to the derivatised molecule via a connecting short spacer arm, one to three carbon atoms long.

Another example of a heterobifunctional reagent is N-succinimidyl 3-(2-pyridyldithio)butyrate (SPDB) (Worrell et. al., 1986), which is identical in structure to SPDP except that it contain a single methyl-group branch alpha to the sulfur atom which is blocked and activated by 2-thiopyridine. SMPT and SMBT described by Thorpe et al. 1987, contain a phenylmethyl spacer arm between an N-hydroxysuccinimide-activated carboxyl group and the blocked thiol; both the thiol and a single methyl-group branch are attached to the aliphatic carbon of the spacer arm. These heterobifunctional reagents result in less easily cleaved disulfide bonds than do unbranched crosslinkers.

Some other examples of heterobifunctional reagents containing reactive disulfide bonds include sodium S-4-succinimidyloxycarbonyl-α-methylbenzylthiosulfate, 4-succinimidyl-oxycarbony-α-methyl-(2-pyridyldithio)toluene.

Examples of heterobifunctional reagents comprising reactive groups having a double bond that reacts with a thiol group include SMCC mentioned above, succinimidyl m-maleimidobenzoate, succinimidyl 3-(maleimido)propionate, sulfosuccinimidyl 4-(p-maleimidophenyl)butyrate, sulfosuccinimidyl 4-(N-maleimidomethylcyclohexane-1-carboxylate and maleimidobeiizoyl-N-hydroxysuccinimide ester (MBS).

Other heterobifunctional reagents for forming conjugates of two molecules are described for example by Rodwell et al. in U.S. Pat. No. 4,671,958 and by Moreland et al. in U.S. Pat. No. 5,241,078.

Crosslinking of the cell-targeting moiety and the compound of formulae (I), (Ia), (Ib), (Ic) or (Id) may be accomplished by coupling a carbonyl group to an amine group or to a hydrazide group by reductive amination.

Specific antibodies may be used to target specific cells and therefore diseases or conditions that are related to unwanted or damaged cells that are targeted or the proliferation of such cells. For example, antibodies CD19, CD20, CD22 and CD79a are able to target B cells, therefore can be used to deliver the compound of formulae (I), (Ia), (Ib), (Ic) or (Id) to a B cell to regulate apoptosis in unwanted or damaged B cells. Disorders and conditions that are characterised by unwanted or damaged B cells or the unwanted proliferation of B cells include B cell non-Hodgkins Lymphoma, B cell acute lymphoblastic leukemia (B-ALL) and autoimmune diseases related to B cells such as rheumatoid arthritis, systemic Lupus erythematosis and related arthropathies. Antibodies such as CD2, CD3, CD7 and CD5 are able to target T cells and therefore can be used to deliver the compound of formulae (I), (Ia), (Ib), (Ic) or (Id) to a T cell to regulate apoptosis in unwanted or damaged T cells. Disorders and conditions that are characterised by unwanted or damaged T cells or the unwanted proliferation of T cells include T cell acute lymphoblastic leukemia (T-ALL), T cell non-Hodgkins Lymphoma and T cell mediated autoimmune diseases such as Graft vs Host disease. Antibodies CD13 and CD33 are able to target myeloid cells and therefore can be used to deliver the compound of formulae (I), (Ia), (Ib), (Ic) or (Id) to a myeloid cell to regulate apoptosis in unwanted or damaged myeloid cells. Diseases and conditions that are characterised by unwanted or damaged myeloid cells or the unwanted proliferation of myeloid cells include acute myelogenous leukemia (AML), chronic myelogenous leukemia (CML) and chronic myelomonocytic leukemia (CMML). The antibody CD138 is able to target plasma cells therefore can be used to deliver the compound of formulae (I), (Ia), (Ib), (Ic) or (Id) to plasma cells to regulate apoptosis in unwanted or damaged plasma cells. Diseases and conditions that are characterised by unwanted or damaged plasma cells or the unwanted proliferation of plasma cells include multiple myeloma.

Other cell targeting moieties can also be used to target specific cells. Luteinizing hormone-releasing hormone (LHRH) receptor is expressed in several types of cancer cells, such as ovarian cancer cells, breast cancer cells and prostate cancer cells, but is not expressed in healthy human viceral organs. LHRH can be used as a cell targeting moiety to deliver the compound of formulae (I), (Ia), (Ib), (Ic) or (Id) to cells expressing LHRH receptor. Disorders or conditions that are able to be treated with a conjugate comprising an LHRH-cell-targeting moiety and a compound of formulae (I), (Ia), (Ib), (Ic) or (Id) include ovarian cancer, breast cancer and prostate cancer.

The invention will now be described with reference to the following examples which illustrate some preferred aspects of the present invention. However, it is to be understood that the particularity of the following description of the invention is not to supersede the generality of the preceding description of the invention.

EXAMPLES

General Synthetic Procedures

Preparation Method 1:

Amides (1) were prepared by the method shown in Scheme 4. An appropriately substituted benzoic acid was refluxed in neat $SOCl_2$ (150 µL for 1 mmol of acid). The resulting acid chloride was dissolved in dichloromethane and treated at 0° C. successively with triethylamine (1.2 equivalents) and an amine substituted with $R^3$ (1.2 equivalents). The reaction was stirred at room temperature for 16 hours. The resulting amide was washed with 2M HCl, followed by saturated $NaHCO_3$, then brine. The resulting solution was then dried over $MgSO_4$.

Preparation Method 2: Biphenyl Compounds Prepared by Suzuki Coupling

Biphenyl compounds at $R^3$ and $R^4$ may be introduced using Suzuki coupling between para- or meta-halogenated phenyl derivatives and substituted phenyl boronic acids. The two starting materials (1.1 equivalent of phenyl boronic acid) are dissolved in toluene (2.2 mL for 1 mmol of halogenated phenyl derivative). Ethanol (530 µL for 1 mmol of halogenated phenyl derivative), 2N $Na_2CO_3$ (1 mL for 1 mmol of halogenated phenyl derivative) and 5 mol % $Pd(PPh_3)_4$ were added successively to the starting mixture. The reaction was stirred at 80° C. until the palladium precipitates. The resulting reaction mixture was dissolved with ethyl acetate and poured onto water. The aqueous phase was extracted three times with ethyl acetate. The combined organic layers were washed with water and brine, dried over $MgSO_4$ and concentrated under vacuum.

Preparation Method 3: Preparation of Carbamoyl Chloride

To a stirred solution or suspension of amide from Preparation Method 1 in ether (2 mL for 0.5 mmol) was added dry triethylamine (1.1 equivalent/amide). Trimethylsilyltriflate was then added (1.1 equivalent/amide). The reaction was stirred under nitrogen atmosphere at room temperature for 16 hours. After that time, an orange oil formed and was removed via a syringe. To the clear remaining solution was added at 0° C. a solution of phosgene in toluene (20% in toluene, 100 µL for 0.1 mmol). The reaction was then slowly warmed up to room temperature and stirred over a 4 hour period. After this time the reaction flask was connected to a vacuum line and the reaction was concentrated leaving the carbamoylchloride as a thick oil residue. The compound was then used directly in the next step without further purification.

Preparation method 4: General Method for In-Situ Protection of Amino Acids

To a suspension of amino acid or amino acid hydrochloride in acetonitrile (4 mL per 1 mmol amino acid) was added successively propylene oxide (2 mL per 1 mmol amino acid) and N,O-bistrimethylsilylacetamide (1.5 equivalent per 1 mmol amino acid). The reaction mixture was stirred at room temperature under nitrogen for 30 minutes after which time it was used directly in the following step.

Preparation Method 5: General Reaction Between Carbamoylchloride and Protected Amino Acid To a solution of carbamoylchloride from Preparation Method 3 in acetonitrile (1 mL for 0.5 mmol) was added a mixture of in-situ protected amino-acid from Preparation Method 4 (1.2 equivalent amino-acid/carbamoylchloride) in acetonitrile at 0° C. The ice bath was then removed and the reaction was stirred at room temperature for 1 hour. After completion of the reaction as shown by TLC ($CH_2Cl_2$), the reaction mixture was diluted with ethyl acetate and poured onto 2N HCl (5 mL for 1 mmol carbamoylchloride). The aqueous phase was extracted three-times with ethyl acetate and the combined organic phases were washed with brine, dried over $MgSO_4$ and concentrated. The compounds were purified using silica gel ($SiO_2$) and $CH_2Cl_2$/MeOH/AcOH 99:0.5:0.5. The purified product was dissolved in toluene, then concentrated three times before drying under high vacuum.

Preparation Method 6: Synthesis of Boc-Protected Cysteine Derivatives.

According to Seko et al., (2003), cysteine was reacted in EtOH (1 mL per mmol) with 2 equivalents of NaOH 2M, 3% of tetrabutylammonium iodide and an alkyl halide (in case of alkyl iodide, tetrabutylammonium iodide was omitted) for three days at room temperature. After this time $Boc_2O$ was added (250 µL per mmol) and the reaction was stirred at room temperature for a further 24 hours. The reaction mixture was then concentrated. Cold 1N HCl was added (1.65 mL per mmol) followed by AcOEt and water. The aqueous phase was extracted 3 times with AcOEt. The combined organic layers were washed with water and brine and dried over $MgSO_4$. Concentration of the organic phase afforded compounds which were pure enough to be engaged in following step without further purification.

Preparation Method 7: Synthesis of Benzoylurea from Boc-Protected Cysteine Derivatives.

The Boc-protected cysteine derivatives were dissolved in 1,4-dioxane (1.43 mL per mmol) and HCl 4N in dioxane (1.43 mL per mmol) was added. The deprotection reaction was followed by TLC and upon completion of the reaction, the mixture were concentrated. The residue was dried in vacuo and redissolved in EtOH (1 mL per mmol) and treated with 1 equivalent of NaOH 2M. To this reaction mixture was added 1.1 equivalent of a $CH_3CN$ solution of carbamoylchloride prepared according to preparation method 3. The mixtures were concentrated down. At this stage compounds can be redissolved in MeOH and purified HPLC semi-preparative (see detail for each compound). Alternatively, the residue was dissolved in dichloromethane and treated two times with 2N HCl. The organic solution was purified directly by flash chromatography (see detail for each compound).

Preparation Method 8: Synthesis of Benzoylurea from Unprotected Amino-Acids.

The amino acid is suspended in EtOH (1 mL per mmol) and treated with 1 equivalent of NaOH 2M (in the case of an amino acid hydrochloride salt, 2 equivalents of NaOH 2M are used). To this reaction mixture was added 1.1 equivalent of a $CH_3CN$ solution of carbamoylchloride prepared according to preparation method 3. The mixtures were concentrated down and purified either by flash chromatography of HPLC semi-preparative (see detail for each compound).

Preparation Method 9: Parallel Synthesis of S-Substituted Cysteine Derived Benzoylureas.

Cysteine was reacted in EtOH (1-mL per mmol) with 2 equivalents of NaOH 2M, 3% of tetrabutylammonium iodide and 1 equivalent of an alkyl halide (in case of alkyl iodide, tetrabutylammonium iodide was omitted) for three days at room temperature. To this reaction mixture was added 1 equivalent of carbamoylchloride prepared according to preparation method 3 in $CH_3CN$ (4 mL per mmol). Stirring was applied for thirty minutes. The mixture was concentrated down. The residue was dissolved in EtOAc and treated two times with 2N HCl. The organic solution can be purified by flash chromatography (see detail for each compound). Alternatively, the desired compound may be isolated by passing through a SAX Acetate solid phase extraction column.

Preparation Method 10: Synthesis of Ethynylbenzoylureas.

(3-iodobenzoyl)urea or derivative thereof was dissolved in $DMF/Et_3N$ 80:20 (5 mL per mmol) along with CuI (0.2 equivalent) and a substituted ethyne (1.5 equivalent). $Pd(PPh_3)_2Cl_2$ (0.1 equivalent) was added and stirring at room temperature was applied for 16 hours. The reaction mixture was diluted with EtOAc then filtered. The solution was washed twice with HCl 2N, then once with water, then once with brine. The organic phase was dried over $MgSO_4$, filtered and concentrated. The residue was passed through a SAX Acetate solid phase extraction column with MeOH 100% then MeOH/AcOH 85:15 to obtain the desired compound.

Preparation Method 11: Coupling Amino Acid-Derived Benzoylureas to Sulfonamides.

A substituted benzoylurea derived from an amino acid was dissolved in $CH_2Cl_2$ (10 mL per mmol) with an arenesulfonamide (1 equivalent), DMAP (2 equivalents), and EDAC (2 equivalents). Stirring was applied at room temperature for 24 hours. The reaction mixture was diluted with EtOAc then washed twice with HCl 2N, then washed twice with water, then washed once with brine. The organic solution was dried over $MgSO_4$, filtered, and concentrated to yield the desired product. Reaction conditions and work up procedures were similar to those used by Oltersdorf et. al., 2005 and in US Patent Application No. 20020086887.

Example 1

Compound (1)

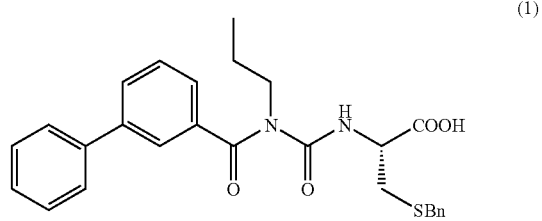

(1)

1A: N-n-propyl-3-bromobenzamide

Using Preparation Method 1,3-bromobenzoic acid was reacted with n-propylamine. The resulting reaction mixture was purified using $SiO_2$ with $CH_2Cl_2$ (100%) to $CH_2Cl_2$/MeOH 99:1 to give N-n-propyl-3-bromobenzamide as an off-white solid (79%). NMR $^1H$ (ppm, $CDCl_3$): 7.86 (s, 1H), 7.63 (d, $J^3$=7.74 Hz, 1H), 7.50 (d, $J^3$=7.00 Hz, 1H), 7.19-7.13 (m, 1H), 7.02 (br. s., 1H), 3.33-3.27 (m, 2H), 1.54 (sext., $J^3$=7.34 Hz, 2H), 0.88 (t, $J^3$=7.42 Hz, 3H).

1B: N-n-propyl-3-phenylbenzamide

Using Preparation Method 2, N-n-propyl-3-bromobenzamide from Example 1A was reacted with phenyl boronic acid. The resulting reaction mixture was purified using $SiO_2$ with $CH_2Cl_2$ (100%) to $CH_2Cl_2$/MeOH 90:10 to give N-n-propyl-3-phenylbenzamide as a white solid (96%). NMR $^1H$ (ppm, $CDCl_3$): 7.97 (t, $J^4$=1.53 Hz, 1H), 7.69 (dd, $J^3$=7.91 Hz, $J^4$=1.84 Hz, 2H), 7.61-7.58 (m, 2H), 7.51-7.24 (m, 4H), 6.17 (br. s., 1H), 3.47-3.40 (m, 2H), 1.65 (sext., $J^3$=7.32 Hz, 2H), 0.98 (t, $J^3$=7.38 Hz, 3H).

1C: Compound (1)

Using Preparation Method 3, N-n-propyl-3-phenylbenzamide was reacted with phosgene to provide a carbamoylchloride. Using Preparation Method 4, Trimethylsilyl (TMS) protected S-benzyl-(L)-cysteine was prepared. The carbamoylchloride and TMS-protected S-benzyl-(L)-cysteine were reacted using Preparation Method 5 to provide compound (1) as a colourless glassy oil (44%). NMR $^1H$ (ppm, $CDCl_3$): 9.68 (d, $J^3$=6.98 Hz, 1H), 7.72-7.66 (m, 2H), 7.60-7.56 (m, 2H), 7.53-7.19 (m, 10H), 6.4 (br. s., 1H), 4.74 (m, 1H), 3.78 (s, 2H), 3.70 (m, 2H), 3.03-2.87 (m, 2H), 1.56 (sext., $J^3$=7.5 Hz, 2H), 0.73 (t, $J^3$=7.4 Hz, 3H).

Example 2

Compound (2)

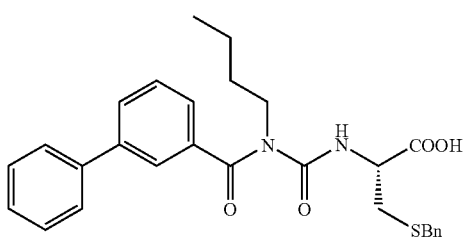

(2)

2A: N-n-butyl 3-phenylbenzamide

Oxalyl chloride (132 µL, 1.5 mmol) was added over a 10 minute period to a mixture of 3-phenylbenzoic acid (200 mg, 1 mmol) dissolved in a mixture THF/DMF (3.5 mL/58 µL). After the addition, the reaction was stirred at room temperature for 2.5 hours. n-Butylamine (247 µL, 2.5 mmol) was then added into half of the acid chloride solution at 0° C. The reaction was then stirred at room temperature for 18 hours. The reaction was concentrated and water was added to the residue. The aqueous phase was extracted 3 times with $CH_2Cl_2$. The combined organic layers were washed with 2N HCl, saturated $NaHCO_3$, brine, dried over $Na_2SO_4$ and concentrated. Diethyl ether was added to the residue and a white solid precipitated. It was collected by filtration and rinsed with a small amount of diethyl ether. The white solid was then dried under vacuum (88 mg, 70%). NMR $^1$H (ppm, $CDCl_3$): 7.96 (s, 1H), 7.69 (d, $J^3$=8.01 Hz, 2H), 7.59 (d, $J^3$=7.16 Hz, 2H), 7.51-7.34 (m, 4H), 6.11 (br. s., 1H), 3.51-3.44 (m, 2H), 1.64 (sext., $J^3$=7.59 Hz, 2H), 1.43 (quint., $J^3$=7.98 Hz, 2H), 0.96 (t, $J^3$=7.32 Hz, 3H).

2B: Compound (2)

Using Preparation Method 3, N-n-butyl 3-phenylbenzamide was reacted with phosgene to provide a carbamoylchloride. Using Preparation Method 4, trimethylsilyl (TMS) protected S-benzyl-(L)-cysteine was prepared. The carbamoylchloride and TMS protected S-benzyl-(L)-cysteine were reacted using Preparation Method 5 to provide compound (2) as a colourless glassy oil (44%). NMR $^1$H (ppm, $CDCl_3$): 9.68 (d, $J^3$=6.92 Hz, 1H), 7.73-7.66 (m, 2H), 7.59-7.58 (m, 2H), 7.49-7.37 (m, 5H), 7.33-7.23 (m, 5H), 4.75 (m, 1H), 3.77 (s, 2H), 3.66 (m, 2H), 3.04-2.87 (m, 2H), 1.52 (q., $J^3$=7.8 Hz, 2H), 1.12 (sext., $J^3$=7.4 Hz, 2H), 0.72 (t, $J^3$=7.3 Hz, 3H).

Example 3

Compound (3)

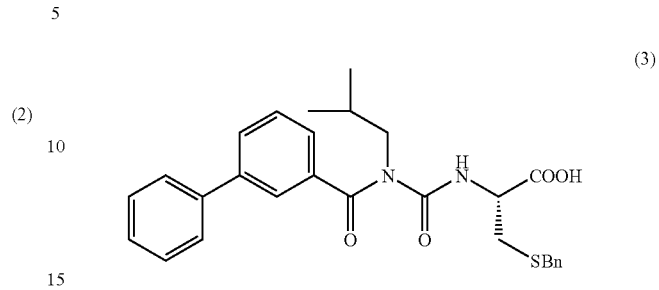

(3)

3A: N-isobutyl 3-phenylbenzamide

Oxalyl chloride (132 µL, 1.5 mmol) was added over a 10 minute period to a mixture of 3-phenylbenzoic acid (200 mg, 1 mmol) dissolved in a mixture THF/DMF (3.5 mL/58 µL). After the addition, the reaction was stirred at room temperature for 2.5 hours. Isobutylamine (247 µL, 2.5 mmol) was then added into half of the acid chloride solution at 0° C. The reaction was then stirred at room temperature for 18 hours. The reaction was concentrated and water was added to the residue. The aqueous phase was extracted 3 times with $CH_2Cl_2$. The combined organic layers were washed with 2N HCl, saturated $NaHCO_3$, brine, dried over $Na_2SO_4$ and concentrated. Diethyl ether was added to the residue and a white solid precipitated. It was collected by filtration and rinsed with a small amount of diethyl ether. The white solid was then dried under vacuum (102 mg, 71%). NMR $^1$H (ppm, $CDCl_3$): 7.97 (t, $J^4$=1.71 Hz, 1H), 7.70 (dd, $J^3$=7.65 Hz, $J^4$=1.77 Hz, 2H), 7.62-7.58 (m, 2H), 7.51-7.34 (m, 4H), 6.18 (br. s., 1H), 3.33-3.29 (m, 2H), 1.91 (n, $J^3$=6.71 Hz, 1H), 0.98 (d, $J^3$=6.68 Hz, 6H).

3B: Compound (3)

Using Preparation Method 3, N-isobutyl 3-phenylbenzamide was reacted with phosgene to provide a carbamoylchloride. Using Preparation Method 4, TMS protected S-benzyl-(L)-cysteine was prepared. The carbamoylchloride and TMS protected S-benzyl-(L)-cysteine were reacted using Preparation Method 5 to provide compound (3) as a colourless glassy oil (73%). NMR $^1$H (ppm, $CDCl_3$): 9.57 (d, $J^3$=5.91 Hz, 1H), 7.67 (s, 2H), 7.57-7.55 (m, 2H), 7.49-7.36 (m, 5H), 7.31-7.19 (m, 5H), 4.72 (m, 1H), 3.75 (s, 2H), 3.67 (m, 2H), 3.03-2.86 (m, 2H), 1.87 (n., $J^3$=6.8 Hz, 1H), 0.73 (d, $J^3$=6.4 Hz, 6H).

Example 4

Compound (4)

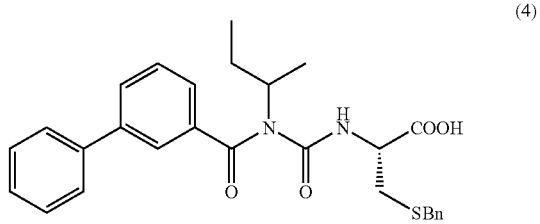

(4)

4A: N-(+/−)-sec-butyl 3-phenylbenzamide

Oxalyl chloride (132 μL, 1.5 mmol) was added over a 10 minute period to a mixture of 3-phenylbenzoic acid (200 mg, 1 mmol) dissolved in a mixture THF/DMF (3.5 mL/58 μL). After the addition, the reaction was stirred at room temperature for 2.5 hours. Sec-butylamine (253 μL, 2.5 mmol) was then added into half of the acid chloride solution at 0° C. The reaction was then stirred at room temperature for 18 hours. The reaction was concentrated and water was added to the residue. The aqueous phase was extracted 3 times with $CH_2Cl_2$. The combined organic layers were washed with 2N HCl, saturated $NaHCO_3$, brine, dried over $Na_2SO_4$ and concentrated. Diethyl ether was added to the residue and a white solid precipitated. It was collected by filtration and rinsed with a small amount of diethyl ether. The white solid was then dried under vacuum (89 mg, 70%). NMR $^1$H (ppm, $CDCl_3$): 7.95 (s, 1H), 7.68 (d, $J^3$=7.51 Hz, 2H), 7.59 (d, $J^3$=7.63 Hz, 2H), 7.50-7.33 (m, 4H), 5.97 (br. s., 1H), 4.30 (hept., $J^3$=6.86 Hz, 1H), 1.58 (quint., $J^3$=7.26 Hz, 1H), 1.23 (d, $J^3$=6.56 Hz, 3H), 0.97 (t, $J^3$=7.36 Hz, 3H).

4B: Compound (4)

Using Preparation Method 3, N-(+/−)-sec-butyl 3-phenylbenzamide was reacted with phosgene to provide a carbamoylchloride. Using Preparation Method 4, TMS protected S-benzyl-(L)-cysteine was prepared. The carbamoylchloride and TMS protected S-benzyl-(L)-cysteine were reacted using Preparation Method 5 to provide compound (4) as a colourless glassy solid (86%). NMR $^1$H (ppm, $CDCl_3$), mixture of diastereoisomers: 9.39 (br. s., 1H), 8.63 and 8.54 (d, $J^3$=6.98 and 7.03 Hz, 1H), 7.73 (s, 1H), 7.69-7.67 (m, 1H), 7.59-7.56 (m, 2H), 7.52-7.34 (m, 5H), 7.29-7.13 (m, 5H), 4.64 (m, 1H), 4.14-4.02 (m, 1H), 3.70 (s, 2H), 2.86-2.79 (m, 2H), 2.13-2.00 (m, 1H), 1.76-1.63 (m, 1H), 1.48 and 1.46 (d, $J^3$=6.6 and 6.63 Hz, 3H), 0.87 and 0.86 (d, $J^3$=7.4 and 7.4 Hz, 3H).

Example 5

Compound (5)

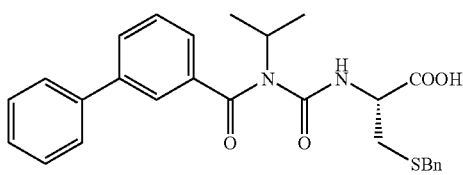

(5)

5A: N-isopropyl 3-phenylbenzamide

Oxalyl chloride (132 μL, 1.5 mmol) was added over a 10 minute period to a mixture of 3-phenylbenzoic acid (200 mg, 1 mmol) dissolved in a mixture THF/DMF (3.5 mL/58 μL). After the addition, the reaction was stirred at room temperature for 2.5 hours. Isopropylamine (511 μL, 6 mmol) was then added into the acid chloride solution at 0° C. The reaction was then stirred at room temperature for 18 hours. The reaction was concentrated and water was added to the residue. The aqueous phase was extracted 3 times with $CH_2Cl_2$. The combined organic layers were washed with 2N HCl, saturated $NaHCO_3$, brine, dried over $Na_2SO_4$ and concentrated. The residue was purified by flash chromatography: $SiO_2$, $CH_2Cl_2$/AcOEt 95:5 to give a white solid (167 mg, 58%). NMR $^1$H (ppm, $CDCl_3$): 7.96 (s, 1H), 7.69 (d, $J^3$=7.68 Hz, 2H), 7.59 (d, $J^3$=7.14 Hz, 2H), 7.50-7.33 (m, 4H), 5.93 (br. s., 1H), 4.14 (oct., $J^3$=6.66 Hz, 1H), 1.27 (d, $J^-$6.43 Hz, 6H).

5B: Compound (5)

Using Preparation Method 3, N-isopropyl 3-phenylbenzamide was reacted with phosgene to provide a carbamoylchloride. Using Preparation Method 4, TMS protected S-benzyl-(L)-cysteine was prepared. The carbamoylchloride and TMS protected S-benzyl-(L)-cysteine were reacted using Preparation Method 5 to provide compound (5) as a colourless glassy oil (63%). NMR $^1$H (ppm, $CDCl_3$): 8.73 (br. s., 1H), 8.52 (d, $J^3$=7.01 Hz, 1H), 7.73 (s, 1H), 7.71-7.63 (m, 1H), 7.59-7.56 (m, 5H), 7.28-7.09 (m, 5H), 4.67-4.60 (m, 1H), 4.37 (h., $J^3$=6.77 Hz, 1H), 3.68 (s, 2H), 2.80 (d, $J^3$=5.8 Hz, 2H), 1.48-1.44 (m, 6H).

Example 6

Compound (6)

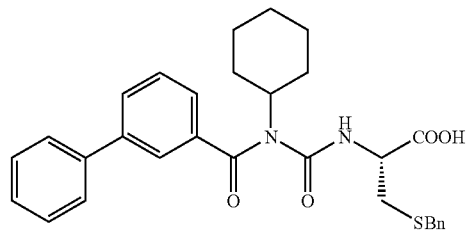

(6)

6A: N-cyclohexyl 3-phenylbenzamide

Oxalyl chloride (132 μL, 1.5 mmol) was added over a 10 minute period to a mixture of 3-phenylbenzoic acid (200 mg, 1 mmol) dissolved in a mixture THF/DMF (3.5 mL/58 μL). After the addition, the reaction was stirred at room temperature for 2.5 hours. Cyclohexylamine (286 μL, 2.5 mmol) was then added into half of the acid chloride solution at 0° C. The reaction was then stirred at room temperature for 18 hours. The reaction was concentrated and water was added to the residue. The aqueous phase was extracted 3 times with $CH_2Cl_2$ and the combined organic layers were washed with 2N HCl, saturated $NaHCO_3$, brine, dried over $Na_2SO_4$ and concentrated. Diethyl ether was added to the residue and a white solid precipitated which was collected by filtration and rinsed with a small amount of diethyl ether. The white solid was then dried under vacuum (108 mg, 80%). NMR $^1$H (ppm, $CDCl_3$): 7.95 (s, 1H), 7.68 (d, $J^3$=7.82 Hz, 2H), 7.59 (d, $J^3$=7.13 Hz, 2H), 7.49-7.33 (m, 4H), 6.05 (br. d., $J^3$=6.58 Hz, 1H), 3.75-3.70 (m, 1H), 2.06-2.01 (m, 2H), 1.78-1.61 (m, 3H), 1.49-1.36 (m, 2H), 1.30-1.14 (m, 3H).

6B: Compound (6)

Using Preparation Method 3, N-cyclohexyl 3-phenylbenzamide was reacted with phosgene to provide a carbamoylchloride. Using Preparation Method 4, TMS protected S-benzyl-(L)-cysteine was prepared. The carbamoylchloride and TMS protected S-benzyl-(L)-cysteine were reacted using Preparation Method 5 to provide compound (6) as a white solid (60%). NMR $^1$H (ppm, CDCl$_3$): 8.8 (br. s., 1H), 7.92 (d, J$^3$=7.09 Hz, 1H), 7.74 (m, 1H), 7.66 (d.t., J$^3$=7.15 Hz, J$^4$=1.7 Hz, 2H), 7.55 (d, J=6.95 Hz, 2H), 7.50-7.33 (m, 5H), 7.29-7.12 (m, 5H), 4.58-4.52 (m, 1H), 4.05-3.98 (m, 1H), 3.61 (s, 2H), 2.76-2.64 (m, 2H), 2.19-2.12 (m, 2H), 1.84-1.77 (m, 4H), 1.56 (br. s., 1H), 1.34 (br. s., 3H).

Example 7

Compound (7)

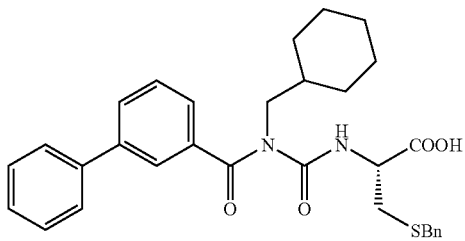

(7)

7A: N-cyclohexylmethyl 3-phenylbenzamide

Oxalyl chloride (132 µL, 1.5 mmol) was added over a 10 minute period to a mixture of 3-phenylbenzoic acid (200 mg, 1 mmol) dissolved in a mixture THF/DMF (3.5 mL/58 µL). After the addition, the reaction was stirred at room temperature for 2.5 hours. Cyclohexylmethylamine (325 µL, 2.5 mmol) was then added into half of the acid chloride solution at 0° C. The reaction mixture was then stirred at room temperature for 18 hours. The reaction mixture was concentrated and water was added to the residue. The aqueous phase was extracted 3 times with CH$_2$Cl$_2$. The combined organic layers were washed with 2N HCl, saturated NaHCO$_3$, brine, dried over Na$_2$SO$_4$ and concentrated. Diethyl ether was added to the residue and a white solid precipitated which was collected by filtration and rinsed with a small amount of diethyl ether. The white solid was then dried under vacuum (115 mg, 78%). NMR $^1$H (ppm, CDCl$_3$): 7.95 (s, 1H), 7.69 (d, J$^3$=7.80 Hz, 2H), 7.59 (d, J$^3$=8.22 Hz, 2H), 7.50-7.33 (m, 4H), 6.22 (br. s., 1H), 3.31 (t, J$^3$=6.29 Hz, 2H), 1.80-1.53 (m, 6H), 1.31-1.10 (m, 3H), 1.05-0.84 (m, 2H).

7B: Compound (7)

Using Preparation Method 3, N-cyclohexylmethyl 3-phenylbenzamide was reacted with phosgene to provide a carbamoylchloride. Using Preparation Method 4, TMS protected S-benzyl-(L)-cysteine was prepared. The carbamoylchloride and TMS protected S-benzyl-(L)-cysteine were reacted using Preparation Method 5 to provide compound (7) as a glassy colourless oil (86%). NMR $^1$H (ppm, CDCl$_3$): 9.92 (br. s., 1H), 9.60 (d, J$^3$=7.07 Hz, 1H), 7.72-7.70 (m, 2H), 7.62-7.59 (m, 2H), 7.54-7.44 (m, 4H), 7.41-7.21 (m, 6H), 4.83-4.77 (m, 1H), 3.79 (s, 2H), 3.72 (d, J$^3$=6.84 Hz, 2H), 3.06-2.89 (m, 2H), 1.62-1.59 (m, 6H), 1.22-0.99 (m, 3H), 0.76-0.64 (m, 2H).

Example 8

Compound (8)

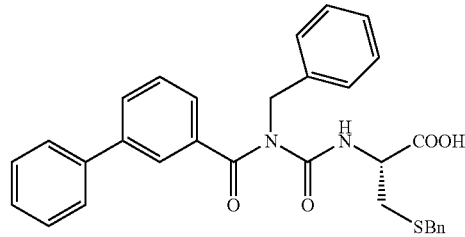

(8)

8A: N-benzyl 3-phenylbenzamide

Oxalyl chloride (132 µL, 1.5 mmol) was added over a 10 minute period to a mixture of 3-phenylbenzoic acid (200 mg, 1 mmol) dissolved in a mixture THF/DMF (3.5 mL/58 µL). After the addition, the reaction was stirred at room temperature for 2.5 hours. Benzylamine (268 µL, 2.5 mmol) was then added into half of the acid chloride solution at 0° C. The reaction mixture was then stirred at room temperature for 18 hours. The reaction mixture was concentrated and water was added to the residue. The aqueous phase was extracted 3 times with CH$_2$Cl$_2$ and the combined organic layers were washed with 2N HCl, saturated NaHCO$_3$, brine, dried over Na$_2$SO$_4$ and concentrated. Diethyl ether was added to the residue and a white solid precipitated which was collected by filtration and rinsed with a small amount of diethyl ether. The white solid was then dried under vacuum (105 mg, 73%). NMR $^1$H (ppm, CDCl$_3$): 8.01 (s, 1H), 7.72 (t, J$^3$=7.89 Hz, 2H), 7.58 (d, J$^3$=7.14 Hz, 2H), 7.49-7.24 (m, 9H), 6.57 (br. s., 1H), 4.64 (d, J$^3$=5.29 Hz, 2H).

8B: Compound (8)

Using Preparation Method 3, N-benzyl 3-phenylbenzamide was reacted with phosgene to provide a carbamoylchloride. Using Preparation Method 4, TMS protected S-benzyl-(L)-cysteine was prepared. The carbamoylchloride and TMS protected S-benzyl-(L)-cysteine were reacted using Preparation Method 5 to provide compound (8) as a colourless glassy oil (66%). NMR $^1$H (ppm, CDCl$_3$): 9.81 (d, J$^3$=7.15 Hz, 1H), 9.33 (br. s., 1H), 7.66 (d.t., J$^3$=7.86 Hz, J$^4$=1.44 Hz, 1H), 7.49 (t, J$^4$=1.54 Hz, 1H), 7.46-7.16 (m, 10H), 7.05 (d.d., J$^3$=7.91 Hz, J$^4$=1.97 Hz, 2H), 5.02 (s, 2H), 4.86-4.79 (m, 1H), 3.79 (s, 2H), 3.07-2.90 (m, 2H).

Example 9

Compound (11)

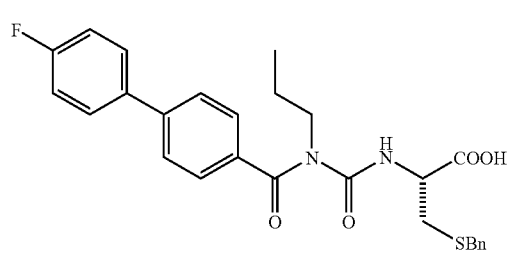

(11)

9A: N-n-propyl 4-bromobenzamide

Using Preparation Method 1, 4-bromobenzoic acid was reacted with n-propylamine. The resulting reaction mixture was purified using SiO$_2$ With 100% CH$_2$Cl$_2$ to give a white solid (67%). NMR $^1$H (ppm, CDCl$_3$): 7.61 (d, J$^3$=8.60 Hz, 2H), 7.54 (d, J$^3$=8.57 Hz, 2H), 6.06 (br. s., 1H), 3.43-3.37 (m, 2H), 1.62 (sext., J$^3$=7.25 Hz, 2H), 0.97 (t, J$^3$=7.39 Hz, 3H).

9B: N-n-propyl 4-(4'-fluoro)-phenylbenzamide

Using Preparation Method 2, N-n-propyl 4-bromobenzamide was reacted with 4-fluorophenylboronic acid. The resulting reaction mixture was purified using SiO$_2$ with CH$_2$Cl$_2$/Petroleum Ether 80:20 to CH$_2$Cl$_2$/AcOH 80:20 to give a white solid (89%). NMR $^1$H (ppm, CDCl$_3$): 7.81 (d, J$^3$=8.18 Hz, 2H), 7.58 (d, J$^3$=8.09 Hz, 2H), 7.56-7.53 (m, 2H), 7.13 (t, J$^3$=8.54 Hz, 2H), 6.12 (br. s., 1H), 3.47-3.40 (m, 2H), 1.65 (sext., J$^3$=7.26 Hz, 2H), 0.99 (t, J$^3$=7.44 Hz, 3H).

9C: Compound (11)

Using Preparation Method 3, N-n-propyl 4-(4'-fluoro)-phenylbenzamide was reacted with phosgene to provide a carbamoylchloride. Using Preparation Method 4, TMS protected S-benzyl-(L)-cysteine was prepared. The carbamoylchloride and TMS protected S-benzyl-(L)-cysteine were reacted using Preparation Method 5 to provide compound (11) as a colourless glassy oil (81%). NMR $^1$H (ppm, CDCl$_3$): 9.63 (d, J$^3$=7.04 Hz, 1H), 9.43 (br. s., 1H), 7.62-7.52 (m, 6H), 7.35-7.23 (m, 5H), 7.14 (t, J$^3$=8.64 Hz, 2H), 4.80-4.74 (m, 1H), 3.78 (s, 2H), 3.73 (m, 2H), 3.04-2.87 (m, 2H), 1.57 (sext., J$^3$=7.45 Hz, 2H), 0.75 (t, J$^3$=7.34 Hz, 3H).

Example 10

Compound (12)

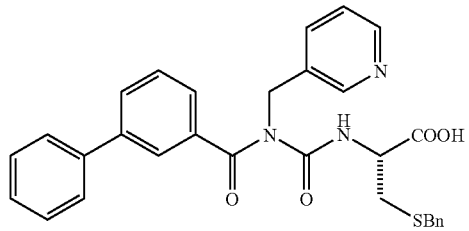

(12)

10A: N-(3-pyridylmethyl)-3-bromobenzamide

Using Preparation Method 1, 3-bromobenzoic acid was reacted with 3-pyridylmethylamine. The resulting reaction mixture was purified using SiO$_2$ with CH$_2$Cl$_2$/MeOH 95:5 to give N-(3-pyridylmethyl)-3-bromobenzamide as thick yellow oil (73%). NMR $^1$H (ppm, CDCl$_3$): 8.44 (s, 1H), 8.41 (d, J$^4$=3.9 Hz, 1H), 7.92 (s, 1H), 7.69 (d, J$^3$=7.8 Hz, 1H), 7.64 (d, J$^3$=7.8 Hz, 1H), 7.57-7.54 (m, 2H), 7.24-7.18 (m, 2H), 4.55 (d, J$^3$=5.9 Hz, 2H).

10B: N-(3-pyridylmethyl)-3-phenylbenzamide

Using Preparation Method 2, N-(3-pyridylmethyl)-3-bromobenzamide was reacted with phenylboronic acid. The resulting reaction mixture was purified using SiO$_2$ with CH$_2$Cl$_2$/MeOH 98:2 to 90:10. A colourless oil was obtained (87%). NMR $^1$H (ppm, CDCl$_3$): 8.87 (s, 1H), 8.73 (d, J$^4$=4.5 Hz, 1H), 8.28 (t, J$^4$=2.0 Hz, 1H), 8.03-7.94 (m, 3H), 7.89 (d, J$^3$=6.9 Hz, 2H), 7.75-7.50 (m, 5H), 6.17 (br. t., 1H), 4.91 (d, J$^3$=5.9 Hz, 2H).

10C: Compound (12)

Using Preparation Method 3, N-(3-pyridylmethyl)-3-phenylbenzamide was reacted with phosgene to provide a carbamoylchloride. Using Preparation Method 4, TMS protected S-benzyl-(L)-cysteine was prepared. The carbamoylchloride and TMS protected S-benzyl-(L)-cysteine were reacted using Preparation Method 5. Work-up was followed without washing with HCl 2N. Compound (12) was obtained as a white solid (14%). NMR $^1$H (ppm, CDCl$_3$): 9.35 (br. s., 1H), 8.45 (br. s., 2H), 7.65-7.24 (m, 16H), 5.15-4.90 (m, 2H), 4.68 (br. s., 1H), 3.71 (br. s., 2H), 2.95 (br. s., 2H).

Example 11

Compound (13)

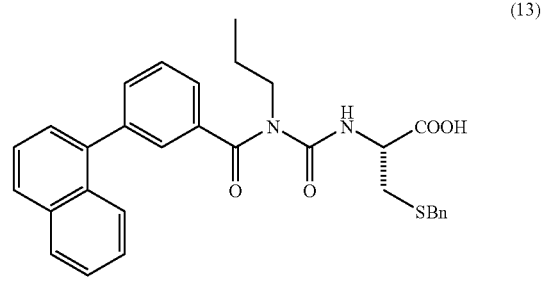

(13)

11A: N-n-propyl-3-(1-naphthyl)-benzamide

Using Preparation Method 2, N-n-propyl-3-bromobenzamide from Example 1A was reacted with 1-naphthylboronic acid. The resulting reaction mixture was purified using SiO$_2$ with CH$_2$Cl$_2$/Petroleum ether 80:20 to CH$_2$Cl$_2$/AcOH 80:20 to give a thick yellow oil (75%). NMR $^1$H (ppm, CDCl$_3$): 7.92-7.78 (m, 5H), 7.67-7.40 (m, 6H), 6.16 (br. s., 1H), 3.50-3.36 (m, 2H), 1.64 (sext., J$^3$=7.33 Hz, 2H), 0.97 (t, J$^3$=7.38 Hz, 3H).

11B: Compound (13)

Using Preparation Method 3, N-n-propyl-3-(1-naphthyl)-benzamide was reacted with phosgene to provide a carbamoylchloride. Using Preparation Method 4, TMS protected S-benzyl-(L)-cysteine was prepared. The carbamoylchloride and TMS protected S-benzyl-(L)-cysteine were reacted using Preparation Method 5 to provide compound (13) as a colourless glassy oil (87%). NMR $^1$H (major stereoisomer, ppm, CDCl$_3$): 10.76 (br. s., 1H), 9.72 (d, J$^3$=6.99 Hz, 1H), 7.91 (t, J$^3$=8.05 Hz, 2H), 7.82 (d, J$^3$=8.18 Hz, 1H), 7.64-7.48 (m, 5H), 7.43 (t, J$^3$=6.68 Hz, 2H), 7.34-7.21 (m, 4H), 7.17 (t, J$^3$=7.57 Hz, 2H), 4.82-4.76 (m, 1H), 3.78 (s, 2H), 3.77 (m, 2H), 3.04-2.88 (m, 2H), 1.61 (sext., J$^3$=7.46 Hz, 2H), 0.79 (t, J$^3$=7.33 Hz, 3H).

Example 12

Compound (14)

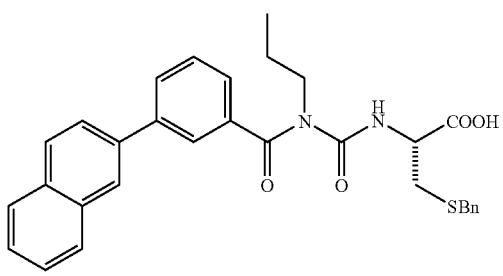

(14)

12A: N-n-propyl-3-(2-naphthyl)-benzamide

Using Preparation Method 2, N-n-propyl-3-bromobenzamide from Example 1A was reacted with 2-naphthylboronic acid. The resulting reaction mixture was purified using SiO$_2$ with CH$_2$Cl$_2$/Petroleum ether 80:20 to CH$_2$Cl$_2$/AcOH 80:20 to give a white solid (57%). NMR $^1$H (ppm, CDCl$_3$): 8.12 (t, J$^4$=1.65 Hz, 1H), 8.06 (s, 1H), 7.91 (t, J$^3$=8.37 Hz, 2H), 7.83 (d, J$^3$=7.81 Hz, 2H), 7.73 (td, J$^3$=8.51 Hz, J$^4$=1.79 Hz, 2H), 7.55-7.46 (m, 3H), 6.18 (br. s., 1H), 3.49-3.43 (m, 2H), 1.67 (sext., J$^3$=7.31 Hz, 2H), 1.00 (t, J$^3$=7.37 Hz, 3H).

12B: Compound (14)

Using Preparation Method 3, N-n-propyl-3-(2-naphthyl)-benzamide was reacted with phosgene to provide a carbamoylchloride. Using Preparation Method 4, TMS protected S-benzyl-(L)-cysteine was prepared. The carbamoylchloride and TMS protected S-benzyl-(L)-cysteine were reacted using Preparation Method 5 to provide compound (14) as a colourless glassy oil (88%). NMR $^1$H (ppm, CDCl$_3$): 9.76 (d, J$^3$=6.98 Hz, 1H), 9.67 (br. s., 1H), 8.07 (s, 1H), 7.94 (t, J$^3$=8.49 Hz, 2H), 7.85 (d, J$^3$=7.32 Hz, 3H), 7.74 (d.d., J$^3$=8.50 Hz, J$^4$=1.5 Hz, 1H), 7.60-7.46 (m, 4H), 7.37-7.25 (m, 5H), 4.85-4.79 (m, 1H), 3.82 (s, 2H). 3.77 (m, 2H), 3.08-2.92 (m, 2H), 1.63 (sext., J$^3$=7.42 Hz, 2H), 0.78 (t, J$^3$=7.34 Hz, 3H).

Example 13

Compound (15)

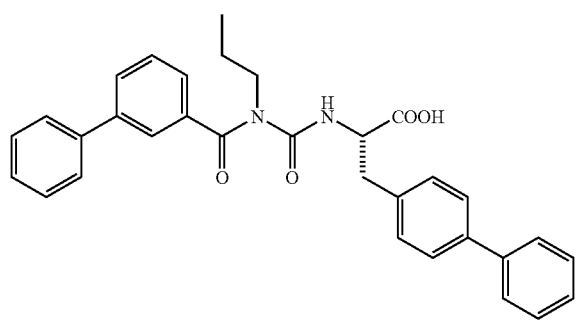

(15)

Using Preparation Method 3, N-n-propyl-3-phenylbenzamide from Example 1B was reacted with phosgene to provide a carbamoylchloride. Using Preparation Method 4, TMS protected (L)-4,4'-biphenylalanine was prepared. The carbamoylchloride and TMS protected (L)-4,4'-biphenylalanine were reacted using Preparation Method 5 to provide compound (15) as a colourless glassy oil (70%). NMR $^1$H (ppm, CDCl$_3$): 10.1 (br. s., 1H), 9.53 (d, J$^3$=6.91 Hz, 1H), 7.69 (d., J$^3$=7.82 Hz, 1H), 7.64 (s, 1H), 7.59-7.56 (m, 6H), 7.52-7.32 (m, 10H), 4.93-4.86 (m, 1H), 3.67 (m, 2H), 3.40-3.16 (m, 2H), 1.52 (sext., J$^3$=7.38 Hz, 2H), 0.70 (t, J$^3$=7.36 Hz, 3H).

Example 14

Compound (16)

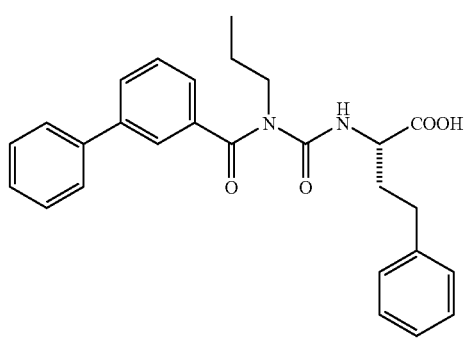

(16)

Using Preparation Method 3, N-n-propyl-3-phenylbenzamide from Example 1B was reacted with phosgene to provide a carbamoylchloride. Using Preparation Method 4, TMS protected (L)-homophenylalanine was prepared. The carbamoylchloride and TMS protected (L)-homophenylalanine were reacted using Preparation Method 5 to provide compound (16) as a colourless glassy oil (92%). NMR $^1$H (ppm, CDCl$_3$): 10.28 (br. s., 1H), 9.56 (d, J$^3$=7.02 Hz, 1H), 7.73-7.69 (m, 2H), 7.62-7.60 (m, 2H), 7.56-7.37 (m, 6H), 7.32-7.21 (m, 3H), 4.65-4.59 (m, 1H), 3.73 (m, 2H), 2.80 (t, J$^3$=8.00 Hz, 2H), 2.39-2.08 (m, 2H), 1.59 (sext., J$^3$=7.46 Hz, 2H), 0.76 (t, J$^3$=7.37 Hz, 3H).

Example 15

Compound (17)

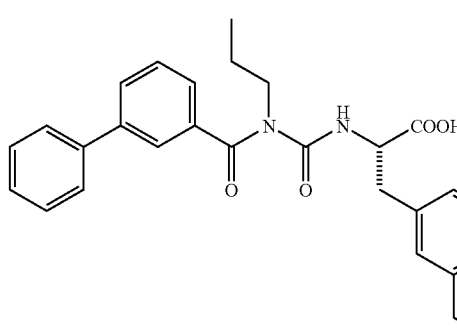

(17)

Using Preparation Method 3, N-n-propyl-3-phenylbenzamide from Example 1B was reacted with phosgene to provide a carbamoylchloride. Using Preparation Method 4, TMS protected (L)-2-naphthylalanine was prepared. The carbamoylchloride and TMS protected (L)-2-naphthylalanine were reacted using Preparation Method 5 to provide compound (17) as a colourless glassy oil (89%). NMR ¹H (ppm, CDCl₃): 11.00 (br. s., 1H), 9.56 (d, $J^3$=6.99 Hz, 1H), 7.84-7.80 (m, 3H), 7.76 (s, 1H), 7.60-7.57 (m, 3H), 7.50-7.40 (m, 7H), 7.38-7.32 (m, 1H), 5.01-4.94 (m, 1H), 3.67-3.62 (m, 2H), 3.55-3.26 (m, 2H), 1.46 (sext., $J^3$=7.38 Hz, 2H), 0.67 (t, $J^3$=7.36 Hz, 3H).

Example 16

Compound (18)

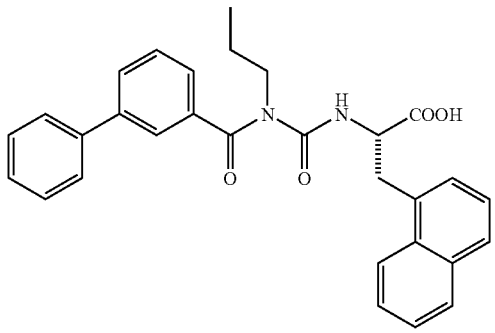

Using Preparation Method 3, N-n-propyl-3-phenylbenzamide from Example 1B was reacted with phosgene to provide a carbamoylchloride. Using Preparation Method 4, TMS protected (L)-1-naphthylalanine was prepared. The carbamoylchloride and TMS protected (L)-1-naphthylalanine were reacted using Preparation Method 5 to provide compound (18) as a colourless glassy oil (90%). NMR ¹H (ppm, CDCl₃): 10.9 (br. s., 1H), 9.56 (d, $J^3$=6.52 Hz, 1H), 8.19 (d., $J^3$=8.62 Hz, 1H), 7.87 (d.d., $J^3$=8.03 Hz, $J^4$=1.11 Hz, 1H), 7.79 (d.d., $J^3$=6.81 Hz, $J^4$=2.33 Hz, 1H), 7.67 (d.d.d., $J^3$=7.72 Hz, $J^4$=2.78 Hz, $J^4$=1.02 Hz, 1H), 7.62-7.56 (m, 4H), 7.53-7.37 (m, 8H), 5.00-4.97 (m, 1H), 3.94-3.3.87 (m, 1H), 3.63-3.58 (m, 2H), 3.52-3.45 (m, 1H), 1.46 (sext., $J^3$=7.55 Hz, 2H), 0.68 (t, $J^3$=7.35 Hz, 3H).

Example 17

Compound (19)

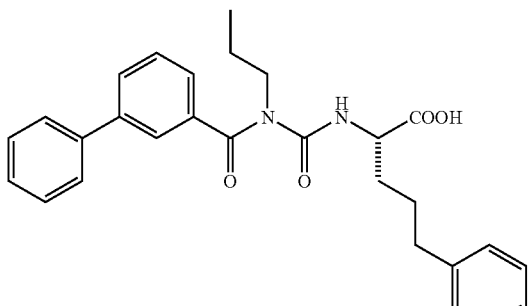

Using Preparation Method 3, N-n-propyl-3-phenylbenzamide from Example 1B was reacted with phosgene to provide a carbamoylchloride. Using Preparation Method 4, TMS protected (L)-2-amino-5-phenyl-pentanoic acid was prepared. The carbamoylchloride and TMS protected (L)-2-amino-5-phenyl-pentanoic acid were reacted using Preparation Method 5 to provide compound (19) as a colourless glassy oil (97%). NMR ¹H (ppm, CDCl₃): 9.44 (d, $J^3$=7.00 Hz, 1H), 9.1 (br. s., 1H), 7.70 (d.d.d., $J^3$=7.75 Hz, $J^4$=2.98 Hz, $J^4$=1.31 Hz, 1H), 7.67 (t., $J^4$=1.57 Hz, 1H), 7.60-7.57 (m, 2H), 7.52 (d, $J^3$=7.54 Hz, 1H), 7.48-7.38 (m, 5H), 7.29-7.22 (m, 1H), 7.19-7.14 (m, 3H), 4.61-4.55 (m, 1H), 3.71-3.67 (m, 2H), 2.67 (t, $J^3$=7.76 Hz, 2H), 2.08-1.92 (m, 2H), 1.92-1.72 (m, 2H), 1.55 (sext., $J^3$=7.52 Hz, 2H), 0.73 (t, $J^3$=7.36 Hz, 3H).

Example 18

Compound (20)

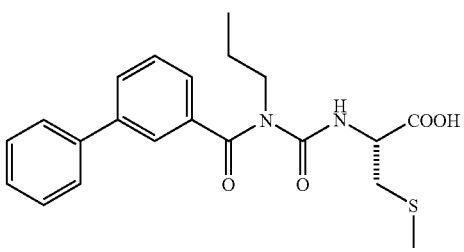

Using Preparation Method 3, N-n-propyl-3-phenylbenzamide from Example 1B was reacted with phosgene to provide a carbamoylchloride. Using Preparation Method 4, TMS protected S-methyl-(L)-cysteine was prepared. The carbamoylchloride and TMS protected S-methyl-(L)-cysteine were reacted using Preparation Method 5 to provide compound (20) as a colourless glassy oil (82%). NMR ¹H (ppm, CDCl₃): 9.85 (d, $J^3$=6.85 Hz, 1H), 7.70 (dt, $J^3$=7.71 Hz, $J^4$=1.79 Hz, 1H), 7.66 (t, $J^4$=1.34 Hz, 1H), 7.60-7.56 (m, 2H), 7.54-7.33 (m, 5H), 4.80-4.74 (m, 1H), 3.71 (m, 2H), 3.12-3.00 (m, 2H), 2.19 (s, 3H), 1.56 (sext., $J^3$=7.53 Hz, 2H), 0.73 (t, $J^3$=7.39 Hz, 3H).

Example 19

Compound (21)

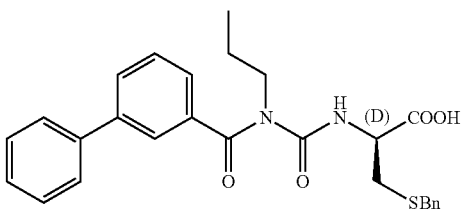

Using Preparation Method 3, N-n-propyl-3-phenylbenzamide from Example 1B was reacted with phosgene to provide a carbamoylchloride. Using Preparation Method 4, TMS protected S-benzyl-(D)-cysteine was prepared. The carbamoylchloride and TMS protected S-benzyl-(D)-cysteine were reacted using Preparation Method 5 to provide compound

(21) as a colourless glassy oil (78%). NMR $^1$H (ppm, CDCl$_3$): 9.70 (d, J$^3$=7.00 Hz, 1H), 9.2 (br. s., 1H), 7.73-7.67 (m, 2H), 7.62-7.57 (m, 2H), 7.54-7.38 (m, 6H), 7.36-7.27 (m, 4H), 4.80-4.74 (m, 1H), 3.79 (s, 2H), 3.71 (m, 2H), 3.04-2.88 (m, 2H), 1.58 (sext., J$^3$=7.53 Hz, 2H), 0.74 (t, J$^3$=7.35 Hz, 3H).

Example 20

Compound (22)

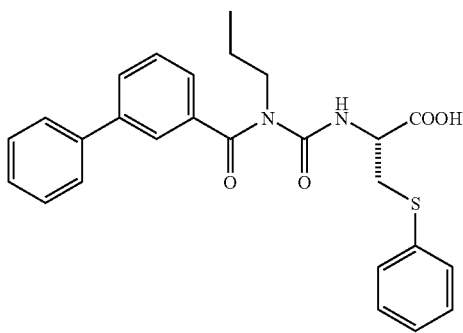

(22)

Using Preparation Method 3, N-n-propyl-3-phenylbenzamide from Example 1B was reacted with phosgene to provide a carbamoylchloride. Using Preparation Method 4, TMS protected S-phenyl-(L)-cysteine was prepared. The carbamoylchloride and TMS protected S-phenyl-(L)-cysteine were reacted using Preparation Method 5 to provide compound (22) as a colourless glassy oil. NMR $^1$H (ppm, CDCl$_3$): 9.74 (d, J$^3$=6.65 Hz, 1H), 7.70 (d, J$^3$=7.81 Hz, 1H), 7.62-7.57 (m, 3H), 7.53-7.44 (m, 4H), 7.38 (t, J$^3$=6.83 Hz, 2H), 7.28-7.22 (m, 4H), 4.77-4.72 (m, 1H), 3.63 (m, 2H), 3.58-3.24 (m, 2H), 1.50 (sext., J$^3$=7.53 Hz, 2H), 0.70 (t, J$^3$=7.36 Hz, 3H).

Example 21

Compound (23)

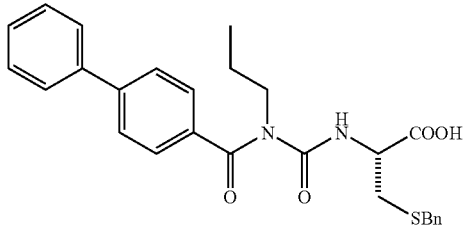

(23)

21A: N-n-propyl-4-phenylbenzamide

Using Preparation Method 2, N-n-propyl-4-bromobenzamide from Example 9A was reacted with phenylboronic acid. The resulting reaction mixture was purified using SiO$_2$ with CH$_2$Cl$_2$/Petroleum Ether 80:20 to CH$_2$Cl$_2$/AcOH 80:20 to give a white solid (71%). NMR $^1$H (ppm, CDCl$_3$): 7.82 (d, J$^3$=8.32 Hz, 2H), 7.63 (d, J$^3$=8.69 Hz, 2H), 7.59 (d, J$^3$=7.14 Hz, 2H), 7.45 (t, J$^3$=7.09 Hz, 2H), 7.39-7.34 (m, 1H), 6.14 (br. s., 1H), 3.47-3.41 (m, 2H), 1.65 (sext., J$^3$=7.18 Hz, 2H), 0.99 (t, J$^3$=7.37 Hz, 3H).

21B: Compound (23)

Using Preparation Method 3, N-n-propyl-4-phenylbenzamide was reacted with phosgene to provide a carbamoylchloride. Using Preparation Method 4, TMS protected S-benzyl-(L)-cysteine was prepared. The carbamoylchloride and TMS protected S-benzyl-(L)-cysteine were reacted using Preparation Method 5 to provide compound (23) as a colourless glassy oil (82%). NMR $^1$H (ppm, CDCl$_3$): 10.29 (br. s., 1H), 9.66 (d, J$^3$=7.05 Hz, 1H), 7.67 (d, J$^3$=8.3 Hz, 2H), 7.62 (d, J$^3$=7.00 Hz, 2H), 7.54 (d, J$^3$=8.32 Hz, 2H), 7.47 (t, J$^3$=7.00 Hz, 2H), 7.42-7.23 (m, 4H), 7.18-7.13 (m, 2H), 4.82-4.75 (m, 1H), 3.79 (s, 2H), 3.74 (m, 2H), 3.04-2.88 (m, 2H), 1.59 (sext., J$^3$=7.47 Hz, 2H), 0.76 (t, J$^3$=7.37 Hz, 3H).

Example 22

Compound (24)

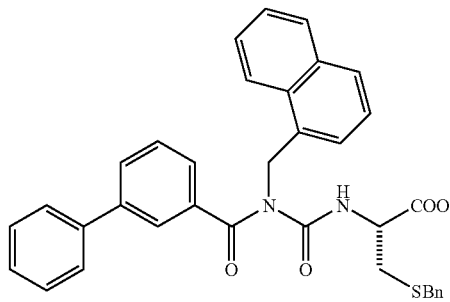

(24)

22A: N-naphthalenemethyl-3-bromobenzamide

Using Preparation Method 1, 3-bromobenzoic acid was reacted with 1-naphthylenemethylamine. The resulting reaction mixture was purified using SiO$_2$ with CH$_2$Cl$_2$ 100% to CH$_2$Cl$_2$/Ethyl Acetate 95:5 to give a white solid (78%). NMR $^1$H (ppm, CDCl$_3$): 8.05 (d, J$^3$=7.42 Hz, 1H), 7.91-7.88 (m, 2H), 7.84 (d, J$^3$=8.14 Hz, 1H), 7.64 (d, J$^3$=7.74 Hz, 1H), 7.60-7.42 (m, 5H), 7.25 (t, J$^3$=7.85 Hz, 1H), 6.26 (br. s., 1H), 5.07 (d, J$^3$=5.24 Hz, 1H).

22B: N-naphthalenemethyl-3-phenylbenzamide

Using Preparation Method 2, N-naphthalenemethyl-3-bromobenzamide was reacted with phenylboronic acid. The resulting reaction mixture was purified using SiO$_2$ with CH$_2$Cl$_2$/Petroleum Ether 95:5 to CH$_2$Cl$_2$/Ethyl Acetate 90:10 to give a white solid (100%). NMR $^1$H (ppm, CDCl$_3$): 8.08-8.04 (m, 2H), 7.88-7.85 (m, 1H), 7.80 (d, J$^3$=8.07 Hz, 1H), 7.67 (t, J$^3$=7.95 Hz, 2H), 7.56-7.46 (m, 5H), 7.43-7.33 (m, 5H), 6.88 (t, J$^3$=5.04 Hz, 1H), 5.03 (d, J$^3$=5.36 Hz, 1H). NMR $^{13}$C (ppm, CDCl$_3$): 167.2, 141.5, 140.0, 134.7, 133.8, 133.6, 131.4, 130.0, 128.8, 128.7, 128.71, 128.67, 128.5, 127.6, 127.0, 126.6, 126.5, 125.9, 125.8, 125.6, 125.3, 123.4, 42.2.

22C: Compound (24)

Using Preparation Method 3, N-naphthalenemethyl-3-phenylbenzamide was reacted with phosgene to provide a carbamoylchloride. Using Preparation Method 4, TMS protected S-benzyl-(L)-cysteine was prepared. The carbamoylchloride and TMS protected S-benzyl-(L)-cysteine were reacted using Preparation Method 5 to provide compound (24) as a colourless glassy oil (87%). NMR $^1$H (ppm, CDCl$_3$): 10.18 (br. s., 1H), 9.97 (d, J$^3$=7.25 Hz, 1H), 7.84 (d., J$^3$=7.73 Hz, 1H), 7.77 (d, J$^3$=7.98 Hz, 1H), 7.67-7.64 (d, J$^3$=8.14 Hz, 1H), 7.91-7.23 (m., 13H), 7.18 (d, J$^3$=6.9 Hz, 2H), 7.052-7.02 (m, 2H), 5.50 (s, 2H), 4.89-4.83 (m, 1H), 3.81 (s, 2H), 3.10-2.93 (m, 2H).

Example 23

Compound (25)

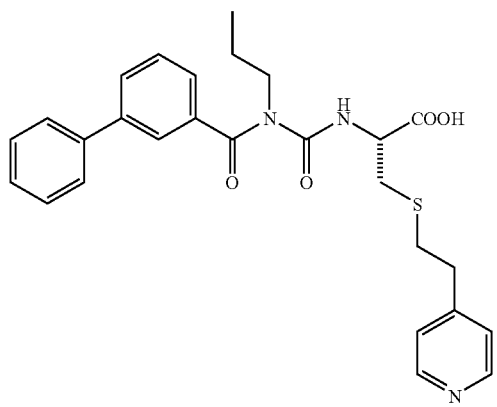

(25)

Using Preparation Method 3, N-n-propyl-3-phenylbenzamide from Example 1B was reacted with phosgene to provide a carbamoylchloride, Using Preparation Method 4, TMS protected S-ethylpyridyl-(L)-cysteine was prepared. The carbamoylchloride and TMS protected S-ethylpyridyl-(L)-cysteine were reacted using Preparation Method 5 to provide compound (25) as a colourless glassy oil (63%). NMR $^1$H (ppm, CDCl$_3$): 9.69 (br. s., 1H), 8.29 (br. s., 2H), 7.69-7.66 (m, 2H), 7.58-7.55 (m, 2H), 7.51-7.33 (m, 7H), 4.82 (br. s., 1H), 3.70 (br. s., 2H), 3.70 (br. m., 1H), 3.14-3.10 (m, 1H), 2.96-2.74 (m, 4H), 1.56 (br. sext., J$^3$=6.89 Hz, 2H), 0.73 (br. t., J$^3$=6.50 Hz, 3H).

Example 24

Compound (26)

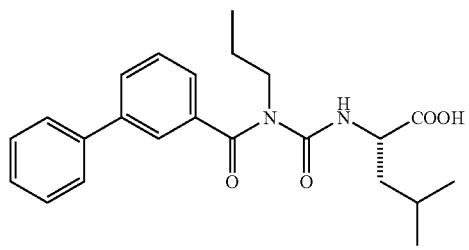

(26)

Using Preparation Method 3, N-n-propyl-3-phenylbenzamide from Example 1B was reacted with phosgene to provide a carbamoylchloride. Using Preparation Method 4, TMS protected (L)-leucine was prepared. The carbamoylchloride and TMS protected (L)-leucine were reacted using Preparation Method 5 to give a colourless glassy oil (89%). NMR $^1$H (ppm, CDCl$_3$): 9.35 (d, J$^3$=6.82 Hz, 1H), 7.69 (d, J$^3$=7.64 Hz, 1H), 7.65 (s, 1H), 7.58 (d., J$^3$=7.33 Hz, 2H), 7.53-7.34 (m, 5H), 4.56-4.52 (m, 1H), 3.69 (m, 2H), 1.80-1.68 (m, 2H), 1.58 (sext., J$^3$=7.52 Hz, 2H), 0.99-0.96 (m, 6H), 0.72 (t, J$^3$=7.37 Hz, 3H).

Example 25

Compound (27)

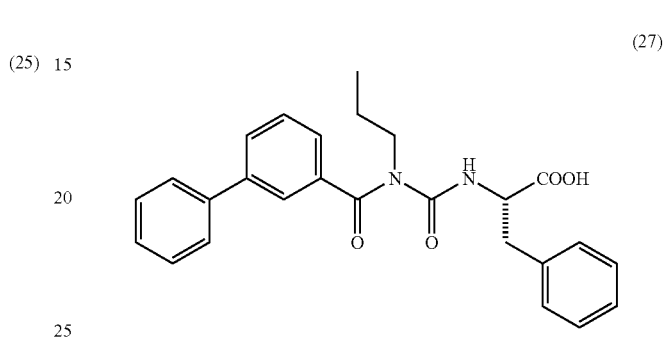

(27)

Using Preparation Method 3, N-n-propyl-3-phenylbenzamide from Example 1B was reacted with phosgene to provide a carbamoylchloride. Using Preparation Method 4, TMS protected (L)-phenylalanine was prepared. The carbamoylchloride and TMS protected (L)-phenylalanine were reacted using Preparation Method 5 to give a colourless glassy oil (85%). NMR $^1$H (ppm, CDCl$_3$): 9.45 (d, J$^3$=6.8 Hz, 1H), 9.44 (br. s., 1H), 7.69 (d, J$^3$=7.8 Hz, 1H), 7.62-7.57 (m, 3H), 7.38 (t, J$^3$=7.3 Hz, 2H), 7.33-7.26 (m, 5H), 4.87-4.80 (m, 1H), 3.66 (m, 2H), 3.34-3.11 (m, 2H), 1.51 (sext., J$^3$=7.3 Hz, 2H), 0.70 (t, J$^3$=7.3 Hz, 3H).

Example 26

Compound (28)

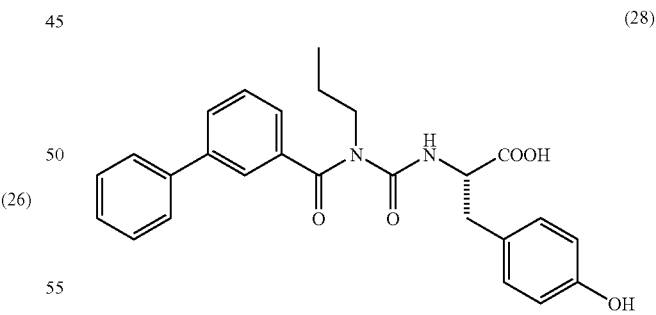

(28)

Using Preparation Method 3, N-n-propyl-3-phenylbenzamide from Example 1B was reacted with phosgene to provide a carbamoylchloride. Using Preparation Method 4, but using two equivalents of (N,O)-bistrimethylsilylacetamide, TMS protected (L)-tyrosine was prepared. The carbamoylchloride and TMS protected (L)-tyrosine were reacted using Preparation Method 5 to give a colourless glassy oil (85%). NMR $^1$H (ppm, CDCl$_3$): 9.43 (d, J$^3$=6.86 Hz, 1H), 7.68 (d, J$^3$=7.82 Hz, 1H), 7.61 (s, 1H), 7.59 (d., J$^3$=7.03 Hz, 2H), 7.51-7.34 (m, 5H), 7.06 (d, J$^3$=8.25 Hz, 2H), 6.71 (d, J$^3$=8.28 Hz, 2H), 4.80-4.73 (m, 1H), 3.65 (m, 2H), 3.18-3.03 (m, 2H), 1.51 (sext., $J^3$=7.44 Hz, 2H), 0.69 (t, $J^3$=7.34 Hz, 3H).

Example 27

Compound (29)

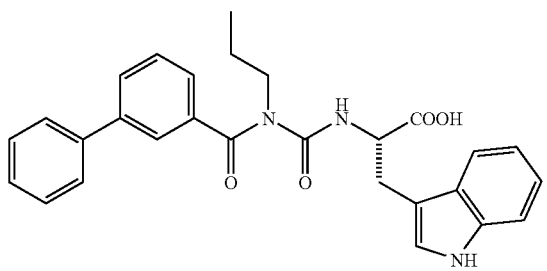

(29)

Using Preparation Method 3, N-n-propyl-3-phenylbenzamide from Example 1B was reacted with phosgene to provide a carbamoylchloride. Using Preparation Method 4, TMS protected (L)-tryptophan was prepared. The carbamoylchloride and TMS protected (L)-tryptophan were reacted using Preparation Method 5 to give a colourless glassy oil (85%). NMR $^1$H (ppm, CDCl$_3$): 9.95 (br. s., 1H), 9.49 (d, $J^3$=6.32 Hz, 1H), 8.31 (s, 1H), 7.67 (d, $J^3$=9.17 Hz, 1H), 7.64 (d, $J^3$=7.83 Hz, 1H), 7.57 (d, $J^3$=7.25 Hz, 4H), 7.50-7.36 (m, 4H), 7.32-7.25 (m, 2H), 7.16-7.08 (m, 2H), 4.91-4.85 (m, 1H), 3.65 (m, 2H), 3.49-3.30 (m, 2H), 1.52 (sext., $J^3$=7.40 Hz, 2H), 0.69 (t, $J^3$=7.36 Hz, 3H).

Example 28

Compound (30)

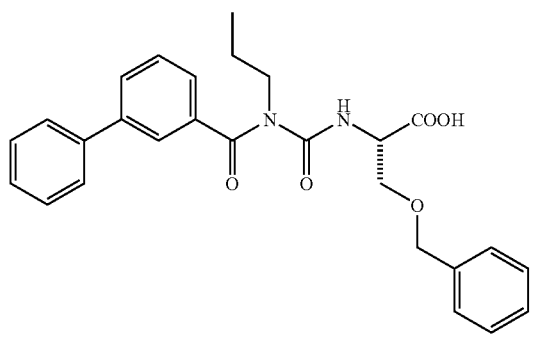

(30)

Using Preparation Method 3, N-n-propyl-3-phenylbenzamide from Example 1B was reacted with phosgene to provide a carbamoylchloride. Using Preparation Method 4, TMS protected O-benzyl-(L)-serine was prepared. The carbamoylchloride and TMS protected O-benzyl-(L)-serine were reacted using Preparation Method 5 to give a colourless glassy oil (72%). NMR $^1$H (ppm, CDCl$_3$): 9.66 (d, $J^3$=7.32 Hz, 1H), 9.19 (br. s., 1H), 7.72-7.69 (m, 2H), 7.60 (d, $J^3$=7.02 Hz, 1H), 7.54-7.38 (m, 5H), 7.34-7.27 (m, 5H), 4.79-4.75 (m, 1H), 4.58 (s, 2H), 4.01-3.96 (m, 1H), 3.82-3.77 (m, 2H), 3.71 (m, 2H), 1.58 (sext., $J^3$=7.39 Hz, 2H), 0.74 (t, $J^3$=7.33 Hz, 3H).

Example 29

Compound (31)

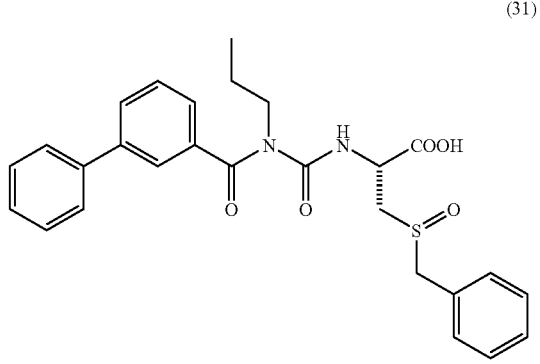

(31)

Meta-chloroperbenzoic acid (70 mg, Tech grade 77% purity) was added to a solution of compound (1) (134 mg, 0.28 mmol) in 1 mL of dry THF at 0° C. TLC showed complete reaction after 20 minutes. After concentration under vacuum, the residue was purified by flash chromatography using SiO$_2$ with CH$_2$Cl$_2$/MeOH/AcOH 99:0.5:0.5 to 89.5:10:0.5 to give compound (31) as a colourless film (66 mg, 48%). NMR $^1$H (ppm, CDCl$_3$): 9.71-9.64 (m, 1H), 7.63-7.23 (m, 14H), 4.94 (br. s., 1H), 4.28-4.07 (br. m., 2H), 3.64-3.17 (br. m., 4H), 1.50 (br. m., 2H), 0.68 (br. m., 3H).

Example 30

Compound (32)

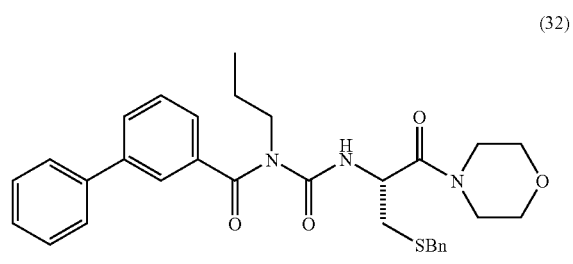

(32)

A mixture of compound (1) from Example 1 (121 mg, 0.25 mmol), 1-ethyl-3-(3-dimethylaminopropyl)carbodiimide hydrochloride (EDCI) (73 mg, 0.38 mmol), DMAP (2.53 mg), and morpholine (44.3 µL, 0.5 mmol) in 2 mL of dry DMF was stirred for 16 hours at room temperature. The reaction was then poured into 1N HCl. The acidic aqueous phase was extracted three times with ethyl acetate. The combined organic layers were washed with 1N HCl, water and brine, dried over Na$_2$SO$_4$ and concentrated. Purification by flash chromatography using SiO$_2$, CH$_2$Cl$_2$/MeOH 98:2 to 85:15 gave a yellow oil. NMR $^1$H (ppm, CDCl$_3$): 9.42 (d, $J^3$=7.96 Hz, 1H), 7.69-7.25 (m, 14H), 4.99-4.92 (m, 1H), 3.68-3.74

(m, 2H), 3.71 (m, 2H), 3.68-3.33 (br. m., 8H), 2.86-2.63 (m, 2H), 1.55 (hept., $J^3$=7.52 Hz, 2H), 0.74 (t, $J^3$=7.37 Hz, 3H).

Example 31

Compound (33)

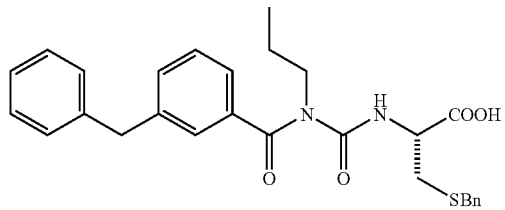

(33)

31A: 3-phenylmethylbenzoic acid

3-Phenylmethylbenzoic acid was prepared according to the method of Van Herwijnen et. al., 2001. 3-Phenylmethylbenzoic acid (904 mg, 4 mmol), powdered NaOH (700 mg), hydrazine hydrate (0.7 mL), and tri(ethylene glycol) (20 mL) were stirred at 190° C. for four hours. Upon cooling, the reaction mixture was washed twice with diethyl ether. Concentrated HCl was added dropwise to the aqueous phase until an acid solution was obtained. The resulting precipitate was filtered off, washed with water and dried to give pale yellow flakes (780 mg, 92%). NMR $^1$H (ppm, CDCl$_3$) 7.96-7.93 (m, 2H), 7.43-7.17 (m, 7H), 4.04 (s, 2H).

31B: N-n-propyl-(3-phenylmethyl)benzamide

Using Preparation Method 1, 3-phenylmethylbenzoic acid was reacted with propylamine. The resulting reaction mixture was purified using SiO$_2$, CH$_2$Cl$_2$/Petroleum Ether 80:20 to CH$_2$Cl$_2$/Ethyl Acetate 80:20 to give a white solid (53%). NMR $^1$H (ppm, CDCl$_3$): 7.61 (s, 1H), 7.56 (dt, $J^3$=6.84, $J^4$=1.93 Hz, 1H), 7.32-7.26 (m, 4H), 7.21-7.15 (m, 3H), 6.10 (br. s., 1H), 4.00 (s, 2H), 3.44-3.36 (m, 2H), 1.61 (sext., $J^3$=7.23 Hz, 2H), 0.96 (t, $J^3$=7.36 Hz, 3H).

31C: Compound (33)

Using Preparation Method 3, N-n-propyl-(3-phenylmethyl)benzamide was reacted with phosgene to provide a carbamoylchloride. Using Preparation Method 4, TMS protected S-benzyl-(L)-cysteine was prepared. The carbamoylchloride and TMS protected S-benzyl-(L)-cysteine were reacted using Preparation Method 5 to provide compound (33) as a colourless glassy oil (72%). NMR $^1$H (ppm, CDCl$_3$): 9.68 (br. s., 1H), 9.66 (d, $J^3$=6.94 Hz, 1H), 7.38-7.20 (m, 14H), 4.75-4.69 (m, 1H), 4.01 (s, 2H), 3.76 (s, 2H), 3.58 (m, 2H), 3.00-2.84 (m, 2H), 1.47 (sext., $J^3$=7.52 Hz, 2H), 0.66 (t, $J^3$=7.38 Hz, 3H).

Example 32

Compound (34)

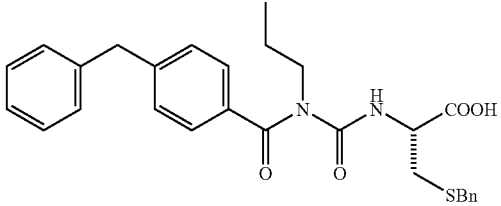

(34)

32A: 4-phenylmethyl benzoic acid

4-Phenylmethylbenzoic acid was prepared according to the method of Van Herwijnen et. al., 2001. 4-Benzoylbenzoic acid (452 mg, 2 mmol), powdered NaOH (350 mg), hydrazine hydrate (0.35 mL) and tri(ethylene glycol) (15 mL) were stirred at 190° C. for four hours.

Upon cooling, the reaction mixture was washed twice with diethyl ether. Concentrated HCl was added dropwise to the aqueous phase until an acidic solution was obtained. The resulting precipitate was filtered off, washed with water and dried to give white crystals (259 mg, 61%). NMR $^1$H (ppm, CDCl$_3$) 8.02, (d, $J^3$ 8.1 Hz, 2H), 7.32-7.16 (m, 7H), 4.04 (s, 2H).

32B: N-n-propyl-(4-phenylmethyl)benzamide

Using Preparation Method 1, 4-phenylmethylberzoic acid was reacted with propyl amine. The resulting reaction mixture was purified using SiO$_2$, CH$_2$Cl$_2$/Petroleum Ether 80:20 to CH$_2$Cl$_2$/Ethyl Acetate 80:20 to give a white solid (69%). NMR $^1$H (ppm, DMSO-d$_6$): 7.66 (d, $J^3$=8.22, 1H), 7.33-7.08 (m, 7H), 6.02 (br. s., 1H), 4.00 (s, 2H), 3.43-3.36 (m, 2H), 1.61 (sext., $J^3$=7.32 Hz, 2H), 0.96 (t, $J^3$=7.35 Hz, 3H).

32C: Compound (34)

Using Preparation Method 3, N-n-propyl(4-phenylmethyl)benzoic acid was reacted with phosgene to provide a carbamoylchloride. Using Preparation Method 4, TMS protected S-benzyl-(L)-cysteine was prepared. The carbamoylchloride and TMS protected S-benzyl-(L)-cysteine were reacted using Preparation Method 5 to provide compound (34) as a colourless glassy oil (75%). NMR $^1$H (ppm, CDCl$_3$): 10.27 (br. s, 1H), 9.62 (d, $J^3$=6.99 Hz, 1H), 7.38 (d, $J^3$=8.13 Hz, 2H), 7.33-7.22 (m, 12H), 4.76-4.70 (m, 1H), 4.02 (s, 2H), 3.76 (s, 2H), 3.67 (m, 2H), 3.01-2.85 (m, 2H), 1.53 (sext., $J^3$=7.47 Hz, 2H), 0.72 (t, $J^3$=7.38 Hz, 3H).

Example 33

Compound (35)

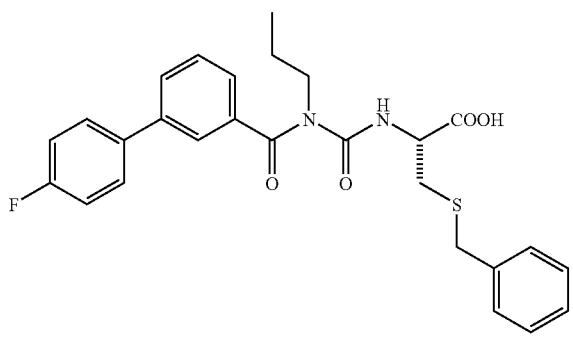

(35)

33A: N-n-propyl 3-((4'-fluoro)-phenyl)benzamide

Using Preparation Method 2, N-n-propyl-3-bromobenzamide from Example 1A as reacted with 4-fluorophenylboronic acid. The resulting reaction mixture was purified using SiO$_2$ with CH$_2$Cl$_2$/Petroleum Ether 80:20 to CH$_2$Cl$_2$/Ethyl Acetate 80:20 to give a white solid (70%). NMR $^1$H (ppm, CDCl$_3$): 7.94 (t, J$^4$=2.1 Hz, 1H), 7.66 (tt, J$^3$=7.8 Hz, J$^4$=0.9 Hz, 2H), 7.58-7.53 (m, 2H), 7.47 (t, J$^3$=7.8 Hz, 1H), 7.13 (t, J$^3$=9 Hz, 2H), 6.12 (br. s., 1H), 3.47-3.40 (m, 2H), 1.65 (sext., J$^3$=7.5 Hz, 2H), 0.99 (t, J$^3$=7.44 Hz, 3H).

33B: Compound (35)

Using Preparation Method 3, N-n-propyl-3-((4'-fluoro)-phenyl)benzamide was reacted with phosgene to provide a carbamoylchloride. Using Preparation Method 4, TMS protected S-benzyl-(L)-cysteine was prepared. The carbamoylchloride and TMS protected S-benzyl-(L)-cysteine were reacted using Preparation Method 5 to provide compound (35) as a colourless glassy oil (86%). NMR $^1$H (ppm, CDCl$_3$): 9.93 (br. s., 1H), 9.67 (d, J$^3$=6.92 Hz, 1H), 7.67-7.63 (m, 2H), 7.57-7.48 (m, 3H), 7.42 (d, J$^3$=7.61 Hz, 1H), 7.32-7.11 (m, 7H), 4.80-4.74 (m, 1H), 3.79 (s, 2H), 3.71 (m, 2H), 3.04-2.88 (m, 2H), 1.58 (sext., J$^3$=7.35 Hz, 2H), 0.74 (t, J$^3$=7.34 Hz, 3H).

Example 34

Compound (36)

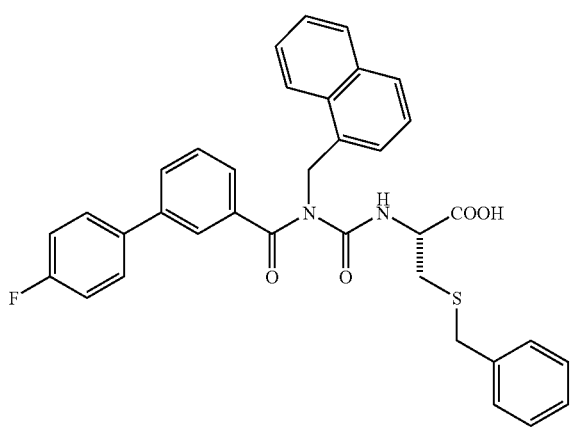

(36)

34A: N-naphthalenemethyl 3-(4'-fluorophenyl)benzamide

Using Preparation Method 2, N-naphthalenemethyl-3-bromobenzamide from Example 21A was reacted with 4-fluorophenyl boronic acid. The resulting reaction mixture was purified using SiO$_2$ with CH$_2$Cl$_2$ 100% to CH$_2$Cl$_2$/Ethyl Acetate 95:5 to give a white solid (71%). NMR $^1$H (ppm, CDCl$_3$): 8.08 (dd, J$^3$=9 Hz, J$^4$=2.1 Hz, 1H), 7.95 (t, J$^4$=2.1 Hz 1H), 7.90-7.87 (m, 1H), 7.83 (d, J$^3$=8.04 Hz, 1H), 7.65 (dt, J$^3$=9.3 Hz, J$^4$=1.2 Hz, 1H), 7.62 (dq, J$^3$=7.8 Hz, J$^4$=1.2 Hz, 1H), 7.57-7.48 (m, 5H), 7.46-7.39 (m, 2H), 7.09 (t, J$^3$=8.70 Hz, 2H), 6.46, (br. s., 1H), 5.08 (d, J$^3$=5.27 Hz, 1H).

34B: Compound (36)

Using Preparation Method 3, N-naphthalenemethyl 3-(4'-fluorophenyl)-benzamide was reacted with phosgene to provide a carbamoylchloride. Using Preparation Method 4, TMS protected S-benzyl-(L)-cysteine was prepared. The carbamoylchloride and TMS protected S-benzyl-(L)-cysteine were reacted using Preparation Method 5 to provide compound (36) to give a colourless glassy oil (72%). NMR $^1$H (ppm, CDCl$_3$): 9.64 (d., J$^3$=7.25 Hz, 1H), 8.1 (br. s., H), 7.84 (d, J$^3$=6.9 Hz, 1H), 7.77 (d, J$^3$=7.71 Hz, 1H), 9.63 (d, J$^3$=8.42 Hz, 1H), 7.49-7.29 (m, 13H), 6.90 (d, J$^3$=6.6 Hz, 1H), 4.81 (br. s., 1H), 5.54-5.42 (m, 2H), 4.88-4.82 (m, 2H), 3.80 (s, 2H), 3.10-2.92 (m, 2H).

Example 35

Compound (37)

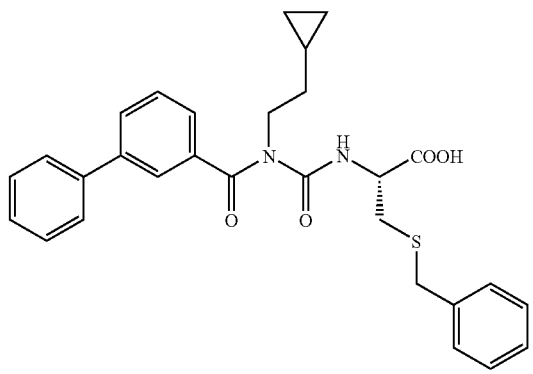

(37)

35A: N-(2-cyclopropyl)ethyl-3-phenylbenzamide

Using Preparation Method 1, 3-phenylbenzoic acid was reacted with (2-cyclopropyl)ethylamine. The resulting reaction mixture was purified using SiO$_2$ with CH$_2$Cl$_2$ 100%. A white crystalline solid was obtained (69%). NMR $^1$H (ppm, CDCl$_3$): 7.97 (s, 1H), 7.69 (d, J$^3$=7.7 Hz, 2H), 7.60 (d, J$^3$=7.2 Hz, 2H), 7.51-7.33 (m, 4H), 6.29 (br. s., 1H), 3.60-3.53 (m, 2H), 1.54 (quart., J$^3$=7.0 Hz, 2H), 0.78-0.67 (m, 1H), 0.52-0.46 (m, 2H), 0.14-0.06 (m, 2H).

35B: Compound (37)

Using Preparation Method 3, N-(2-cyclopropyl)ethyl-3-phenylbenzamide was reacted with phosgene to provide a carbamoylchloride. Using Preparation Method 4, TMS protected S-benzyl-(L)-cysteine was prepared. The carbamoylchloride and TMS protected S-benzyl-(L)-cysteine were reacted using Preparation Method 5 to provide compound

(37) as a colourless oil (35%). NMR $^1$H (ppm, CDCl$_3$): 9.71 (d, J$^3$=6.9 Hz, 1H), 7.72-7.23 (m, 14H), 4.75-4.68 (m, 1H), 3.86 (t, J$^3$=7.2 Hz, 2H), 3.78 (s, 2H), 3.02-2.87 (m, 2H), 1.42 (quart., J$^3$=6.9 Hz, 2H), 0.40-0.27 (m, 3H), (−0.11)-(−0.15) (m, 2H).

Example 36

Compound (38)

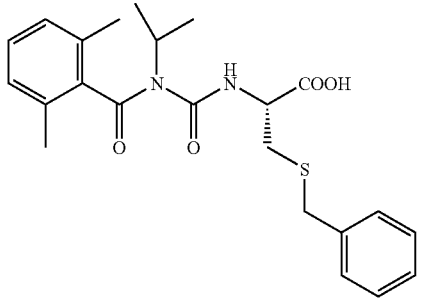

(38)

36A: N-isopropyl-2,6-dimethylbenzamide

Using Preparation Method 1, 2,6-dimethylbenzoic acid was reacted with isopropylamine. The resulting reaction mixture was purified using SiO$_2$ with CH$_2$Cl$_2$/MeOH 99:1. A white crystalline solid was obtained (73%). NMR $^1$H (ppm, CDCl$_3$): 7.15-7.10 (m, 1H), 6.99 (d, J$^3$=7.57 Hz, 2H), 5.44 (br. s., 1H), 4.40-4.24 (m, 1H), 2.31 (s, 6H), 1.24 (d, J$^3$=6.58 Hz, 6H).

36B: Compound (38)

Using Preparation Method 3, N-isopropyl-2,6-dimethylbenzamide was reacted with phosgene to provide a carbamoylchloride. Using Preparation Method 4, TMS protected S-benzyl-(L)-cysteine was prepared. The carbamoylchloride and TMS protected S-benzyl-(L)-cysteine were reacted using Preparation Method 5 to provide compound (38) as a colourless glassy oil (35%). NMR $^1$H (ppm, CDCl$_3$): 9.98 (d, J$^3$=6.76 Hz, 1H), 7.33-7.27 (m, 5H), 7.06-7.04 (m, 3H), 4.78-4.72 (m, 1H), 3.88-3.79 (m, 1H), 3.79 (s, 2H), 3.05-2.87 (m, 2H), 2.30 (s, 6H), 1.39 (d, J$^3$=6.69 Hz, 6H).

Example 37

Compound (39)

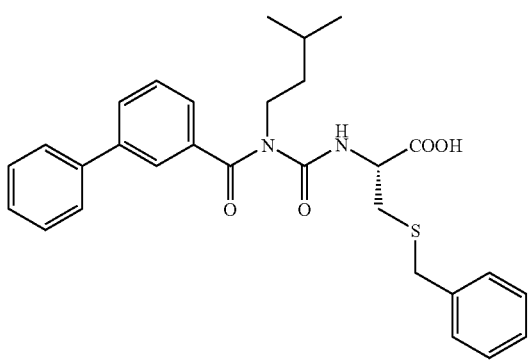

(39)

37A: N-isoamyl-3-phenylbenzamide

Using Preparation Method 1, 3-phenylbenzoic acid was reacted with isoamylamine. The resulting reaction mixture was purified using SiO$_2$ with CH$_2$Cl$_2$ 100%. An off-white crystalline solid was obtained (61%). NMR $^1$H (ppm, CDCl$_3$): 7.96 (s, 1H), 7.69 (d, J$^3$=8.3 Hz, 2H), 7.59 (d, J$^3$=7.2 Hz, 2H), 7.50-7.33 (m, 4H), 6.10 (br. s., 1H), 3.52-3.45 (m, 2H), 1.76-1.64 (m, 1H), 1.52 (quart., 2H), 0.95 (d, J$^3$=6.6 Hz, 6H).

37B: Compound (39)

Using Preparation Method 3, N-isoamyl-3-phenylbenzamide was reacted with phosgene to provide a carbamoylchloride. Using Preparation Method 4, TMS protected S-benzyl-(L)-cysteine was prepared. The carbamoylchloride and TMS protected S-benzyl-(L)-cysteine were reacted using Preparation Method 5 to provide compound (39) as a colourless oil (62%). NMR $^1$H (ppm, CDCl$_3$): 9.72 (d, J$^3$=6.8 Hz, 1H), 7.68-7.23 (m, 14H), 4.77-4.70 (m, 1H), 3.78-3.70 (m, 4H), 3.03-2.87 (m, 2H), 1.47-1.32 (m, 3H), 0.67 (d, J$^3$=6.1 Hz, 6H).

Example 38

Compound (40)

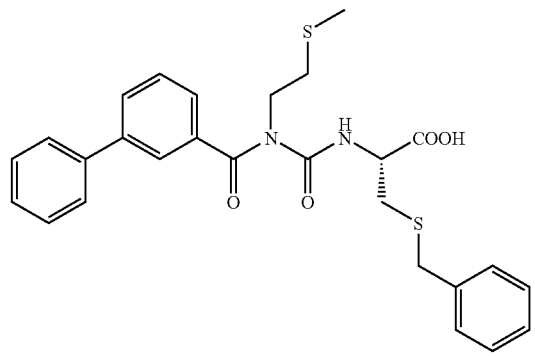

(40)

38A: N-(2-methylthio)ethyl-3-phenylbenzamide

Using Preparation Method 1, 3-phenylbenzoic acid was reacted with 2-(methylthio)ethylamine. The resulting reaction mixture was purified using SiO$_2$ with CH$_2$Cl$_2$ 100%. An white crystalline solid was obtained (65%). NMR $^1$H (ppm, CDCl$_3$): 8.00 (s, 1H), 7.72 (d, J$^3$=7.7 Hz, 2H), 7.60 (d, J$^3$=7.2 Hz, 2H), 7.52-7.34 (m, 4H), 6.62 (br. s., 1H), 3.72-3.65 (m, 2H), 2.77 (t, J$^3$=6.3 Hz, 2H), 2.14 (s, 3H).

38B: Compound (40)

Using Preparation Method 3, N-(2-methylthio)ethyl-3-phenylbenzamide was reacted with phosgene to provide a carbamoylchloride. Using Preparation Method 4, TMS protected S-benzyl-(L)-cysteine was prepared. The carbamoylchloride and TMS protected S-benzyl-(L)-cysteine were reacted using Preparation Method 5 to provide compound (40) as a colourless oil (62%). NMR $^1$H (ppm, CDCl$_3$): 9.62 (d, J$^3$=6.9 Hz, 1H), 7.71-7.11 (m, 14H), 4.75-4.68 (m, 1H), 3.97 (t, J$^3$=7.0 Hz, 2H), 3.78 (s, 2H), 3.02-2.87 (m, 2H), 2.63 (t, J$^3$=6.9 Hz, 2H), 1.79 (s, 3H).

Example 39

Compound (42)

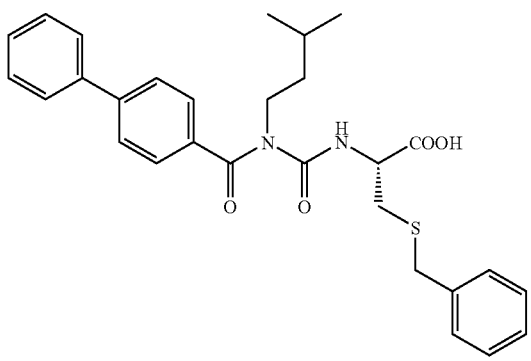

39A: N-isoamyl-4-phenylbenzamide

Using Preparation Method 1, 4-phenylbenzoic acid was reacted with isoamylamine. The resulting reaction mixture was purified using $SiO_2$ with $CH_2Cl_2$ 100%. A white crystalline solid was obtained (29%). NMR $^1$H (ppm, $CDCl_3$): 7.81 (d, $J^3$=8.3 Hz, 2H), 7.65-7.58 (m, 4H), 7.47-7.34 (m, 3H), 6.06 (br. s., 1H), 3.53-3.36 (m, 2H), 1.74-1.65 (m, 1H), 1.52 (quart., $J^3$=6.7 Hz, 2H), 0.96 (d, $J^3$=6.6 Hz).

39B: Compound (42)

Using Preparation Method 3, N-isoamyl-4-phenylbenzamide was reacted with phosgene to provide a carbamoylchloride. Using Preparation Method 4, TMS protected S-benzyl-(L)-cysteine was prepared. The carbamoylchloride and TMS protected S-benzyl-(L)-cysteine were reacted using Preparation Method 5 to provide compound (42) as a colourless oil (55%). NMR $^1$H (ppm, $CDCl_3$): 9.70 (d, $J^3$=6.8 Hz, 1H), 7.68-7.15 (m, 14H), 4.76-4.69 (m, 1H), 3.79-3.73 (m, 4H), 3.01-2.86 (m, 2H), 1.47-1.34 (m, 3H), 0.70 (d, $J^3$=6.0 Hz, 6H).

Example 40

Compound (43)

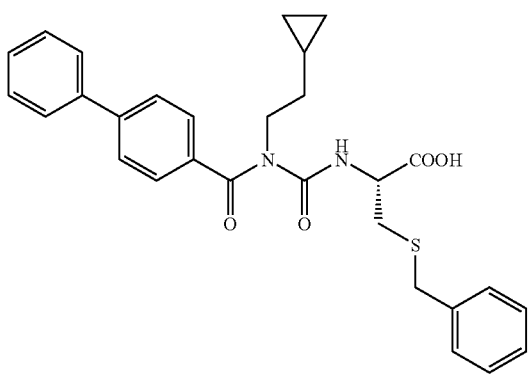

40A: N-(2-cyclopropyl)ethyl-4-phenylbenzamide

Using Preparation Method 1, 4-phenylbenzoic acid was reacted with (2-cyclopropyl)ethylamine. The resulting reaction mixture was purified using $SiO_2$ with $CH_2Cl_2$ 100%. A white crystalline solid was obtained (29%). NMR $^1$H (ppm, $CDCl_3$): 7.82 (d, $J^3$=8.2 Hz, 2H), 7.64 (d, $J^3$=8.4 Hz, 2H), 7.60 (d, $J^3$=7.5 Hz, 2H), 7.47-7.34 (m, 3H), 6.26 (br. s., 1H), 3.60-3.53 (m, 2H), 1.54 (quart., $J^3$=6.8 Hz, 2H), 0.76-0.71 (m, 1H), 0.51-0.48 (m, 2H), 0.13-0.11 (m, 2H).

40B: Compound (43)

Using Preparation Method 3, N-(2-cyclopropyl)ethyl-4-phenylbenzamide was reacted with phosgene to provide a carbamoylchloride. Using Preparation Method 4, TMS protected S-benzyl-(L)-cysteine was prepared. The carbamoylchloride and TMS protected S-benzyl-(L)-cysteine were reacted using Preparation Method 5 to provide compound (43) as a colourless oil (47%). NMR $^1$H (ppm, $CDCl_3$): 9.70 (d, $J^3$=6.9 Hz, 1H), 7.68-7.15 (m, 14H), 4.73-4.69 (m, 1H), 3.88 (t, $J^3$=7.2 Hz, 2H), 3.78 (s, 2H), 3.02-2.86 (m, 2H), 1.44 (quart., $J^3$=6.9 Hz., 2H), 0.46-0.29 (m, 3H), (−0.08)-(−0.12) (m, 2H).

Example 41

Compound (44)

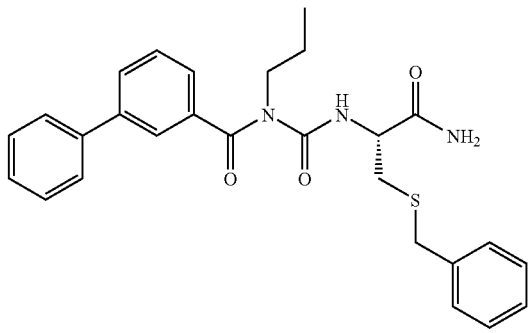

Compound (1) from example 1A (171 mg, 0.36 mmol) was dissolved in dry $CH_2Cl_2$ (2.5 mL) with DMF (0.25 mL). The solution was cooled to 0° C. and stirred under nitrogen. Oxalyl chloride (46 μL, 70 mg, 0.55 mmol) was added via syringe and stirring was applied at room temperature for two hours. The solvent and any excess oxalyl chloride were removed under reduced pressure. The orange residue was dissolved in dry $CH_2Cl_2$ (1 mL) and added via syringe to ammonia solution (25%, 2 mL) at 0° C. The mixture was stirred for one hour, and then neutralized with 10% citric acid. The product was extracted with $CH_2Cl_2$ three times, and the organic layers were washed with water, then brine, and were then dried over $MgSO_4$ and concentrated. The product was purified using $SiO_2$ with $CH_2Cl_2$/EtOAc 90:10. A colourless oil was obtained (72 mg, 42%). NMR $^1$H (ppm, $CDCl_3$): 9.44 (d, $J^3$=7.2 Hz, 1H), 7.66-7.19 (m, 14H), 6.44 (br. s., 1H), 6.03 (br. s., 1H), 4.60-4.53 (m, 1H), 3.79 (s, 2H), 3.69 (t, $J^3$=7.5 Hz, 2H), 2.96-2.80 (m, 2H), 1.56 (sext., $J^3$=7.5 Hz, 2H), 0.74 (t, $J^3$=7.4 Hz, 3H).

Example 42

Compound (45)

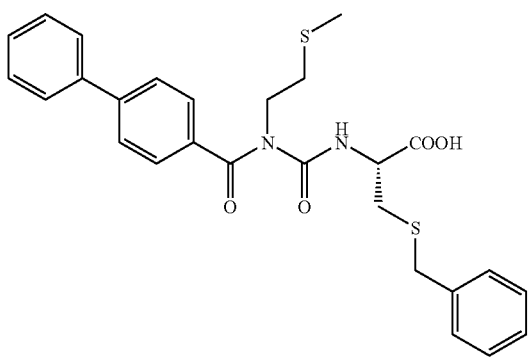

42A: N-(2-methylthio)ethyl-4-phenylbenzamide

Using Preparation Method 1, 4-phenylbenzoic acid was reacted with 2-(methylthio)ethylamine. The resulting reaction mixture was purified using SiO$_2$ with CH$_2$Cl$_2$ 100%. A white crystalline solid was obtained. NMR $^1$H (ppm, CDCl$_3$): 7.50-7.35 (m, 3H), 7.85 (d, J$^3$=8.1 Hz, 2H), 7.65 (d, J$^3$=8.4 Hz, 2H), 7.60 (d, J$^3$=8.0 Hz, 2H), 6.61 (br. s., 1H), 3.72-3.65 (m, 2H), 2.77 (t, J$^3$=6.4 Hz, 2H), 2.15 (s, 3H).

42B: Compound (45)

Using Preparation Method 3, N-(2-methylthio)ethyl-4-phenylbenzamide was reacted with phosgene to provide a carbamoylchloride. Using Preparation Method 4, TMS protected S-benzyl-(L)-cysteine was prepared. The carbamoylchloride and TMS protected S-benzyl-(L)-cysteine were reacted using Preparation Method 5 to provide compound (45) as an off-white solid (38%). NMR $^1$H (ppm, CDCl$_3$): 9.55 (d, J$^3$=6.9 Hz, 1H), 7.68-7.23 (m, 14H), 4.76-4.69 (m, 1H), 4.00 (t, J$^3$=6.9 Hz, 2H), 3.78 (s, 2H), 3.02-2.87 (m, 2H), 2.65 (t, J$^3$=7.0 Hz, 2H), 1.85 (s, 3H).

Example 43

Compound (46)

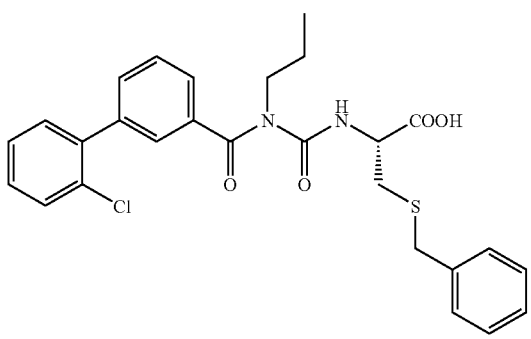

43A: N-N-propyl-3-(2'-chloro)-phenylbenzamide

Using Preparation Method 2, N-n-propyl-3-bromobenzamide from example 1A was reacted with 2-chloro-phenyl boronic acid. The resulting reaction mixture was purified using SiO$_2$ with Petroleum ether/CH$_2$Cl$_2$ 5:95 to CH$_2$Cl$_2$ 100% to AcOEt/CH$_2$Cl$_2$ 5:95. A white crystalline solid was obtained (79%). NMR $^1$H (ppm, CDCl$_3$): 7.80 (s, 1H), 7.76 (d. t., J$^3$=7.7 Hz, J$^4$=1.3 Hz, 1H), 7.52 (d. t., J$^3$=7.8 Hz, J$^4$=1.4 Hz, 1H), 7.44-7.38 (m, 2H), 7.29-7.20 (m, 3H), 6.61 (br. s., 1H), 3.41-3.33 (m, 2H), 1.56 (sext., J$^3$=7.2 Hz, 2H), 0.92 (t, J$^3$=7.4 Hz, 3H).

43B: Compound (46)

Using Preparation Method 3, N-n-propyl-3-(2'-chloro)-phenylbenzamide was reacted with phosgene to provide a carbamoylchloride. Using Preparation Method 4, TMS protected S-benzyl-(L)-cysteine was prepared. The carbamoylchloride and TMS protected S-benzyl-(L)-cysteine were reacted using Preparation Method 5 to provide compound (46) as a colourless oil (46%). NMR $^1$H (ppm, CDCl$_3$): 9.68 (d, J$^3$=6.8 Hz, 1H), 7.55-7.17 (m, 13H), 4.74-4.67 (m, 1H), 3.78 (s, 2H), 3.73 (t, J$^3$=7.5 Hz, 2H), 3.02-2.86 (m, 2H), 1.55 (sext., J$^3$=7.5 Hz, 2H), 0.73 (t, J$^3$=7.4 Hz, 3H).

Example 44

Compound (47)

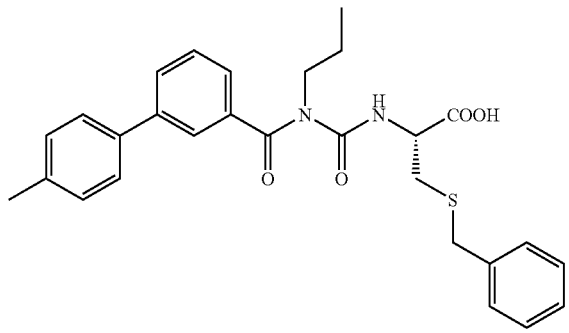

44A: N-n-propyl-3-(4'-tolyl)-benzamide

Using Preparation Method 2, N-n-propyl-3-bromobenzamide from example 1A was reacted with 4-tolylboronic acid. The resulting reaction mixture was purified using SiO$_2$ with AcOEt/CH$_2$Cl$_2$ 10:90. A white crystalline solid was obtained (78%). NMR $^1$H (ppm, CDCl$_3$): 7.99 (s, 1H), 7.69 (d, J$^3$=7.7 Hz, 1H), 7.64 (d, J$^3$=7.8 Hz, 1H), 7.46 (d, J$^3$=7.9 Hz, 2H), 7.39 (d, J$^3$=7.7 Hz, 1H), 7.21 (d, J$^3$=7.6 Hz, 2H), 6.74 (br. s., 1H), 3.42-3.35 (m, 2H), 2.36 (s, 3H), 1.61 (sext., J$^3$=7.2 Hz, 2H), 0.94 (t, J$^3$=7.4 Hz, 3H).

44B: Compound (47)

Using Preparation Method 3, N-n-propyl-3-(4'-tolyl)-benzamide was reacted with phosgene to provide a carbamoylchloride. Using Preparation Method 4, TMS protected S-benzyl-(L)-cysteine was prepared. The carbamoylchloride and TMS protected S-benzyl-(L)-cysteine were reacted using Preparation Method 5 to provide compound (47) as a colourless solid (71%). NMR$^1$H (ppm, CDCl$_3$): 9.73 (d, J$^3$=6.9 Hz, 1H), 9.64 (br. s., 1H), 7.70-7.68 (m, 2H), 7.52-7.47 (m, 3H), 7.41-7.23 (m, 5H), 4.82-4.76 (m, 1H), 3.79 (s, 2H), 3.72 (t, J$^3$=7.5 Hz, 2H), 3.05-2.89 (m, 2H), 2.40 (s, 3H), 1.58 (sext., J$^3$=7.4 Hz, 2H), 0.74 (t, J$^3$=7.3 Hz, 3H).

Example 45

Compound (48)

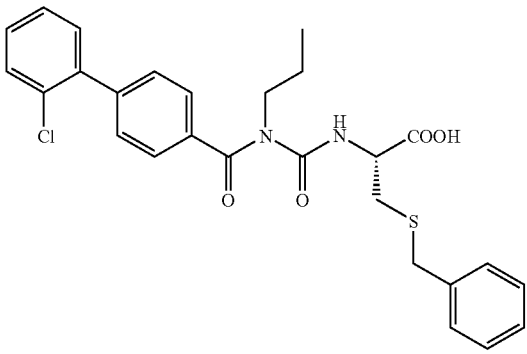

(48)

45A: N-n-propyl-4-(2'-chloro)-phenylbenzamide

Using Preparation Method 2, N-n-propyl-4-bromobenzamide from example 9A was reacted with 2-chloro-phenyl boronic acid. The resulting reaction mixture was purified using $SiO_2$ with Petroluem ether/$CH_2Cl_2$ 5:95 to $CH_2Cl_2$ 100% to AcOEt/$CH_2Cl_2$ 5:95. A white crystalline solid was obtained (81%). NMR $^1$H (ppm, $CDCl_3$): 7.82 (d, $J^3$=8.53 Hz, 2H), 7.46-7.43 (m, 3H), 7.28-7.26 (m, 3H), 6.59 (br. s., 1H), 3.44-3.37 (m, 2H), 1.63 (sext., $J^3$=7.2 Hz, 2H), 0.92 (t, $J^3$=7.4 Hz, 3H).

45B: Compound (48)

Using Preparation Method 3, N-n-propyl-4-(2'-chloro)-phenylbenzamide was reacted with phosgene to provide a carbamoylchloride. Using Preparation Method 4, TMS protected S-benzyl-(L)-cysteine was prepared. The carbamoylchloride and TMS protected S-benzyl-(L)-cysteine were reacted using Preparation Method 5 to provide compound (48) as a colourless oil (63%). NMR $^1$H (ppm, $CDCl_3$): 9.63 (d, $J^3$=6.9 Hz, 1H), 7.52-7.23 (m, 13H), 4.76-4.69 (m, 1H), 3.79 (s, 2H), 3.72 (t, $J^3$=7.5 Hz, 2H), 3.02-2.87 (m, 2H), 1.57 (sext., $J^3$=7.4 Hz, 2H), 0.76 (t, $J^3$=7.4 Hz, 3H).

Example 46

Compound (49)

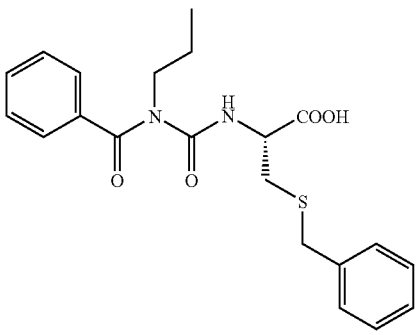

(49)

46A: N-n-propylbenzamide

A solution of benzoyl chloride (116 μL, 1 mmol) in 1 mL of dry $CH_2Cl_2$ was treated successively at 0° C. with triethylamine (167 μL, 1.2 mmol) and n-propylamine (124 μL, 1.5 mmol). The reaction was stirred at room temperature for two hours. The resulting reaction mixture was diluted with $CH_2Cl_2$ washed with 2M HCl, followed by saturated $NaHCO_3$, then brine. The resulting solution was then dried over $MgSO_4$. The residue was purified using $SiO_2$ with $CH_2Cl_2$/Petroluem ether 95:5 to $CH_2Cl_2$ 100%. A white solid was obtained (166 mg, quantitative yield). NMR $^1$H (ppm, $CDCl_3$): 7.74 (d, $J^3$=8.1 Hz, 2H), 7.41 (t. t., $J^3$=7.2 Hz, $J^4$=1.3 Hz, 1H), 7.33 (t. t., $J^3$=7.6 Hz, $J^4$=1.6 Hz, 2H), 5.23 (br. s., 1H), 3.36-3.30 (m, 2H), 1.57 (sext., $J^3$=7.2 Hz, 2H), 0.90 (t, $J^3$=7.4 Hz, 3H).

46B: Compound (49)

Using Preparation Method 3, N-n-propylbenzamide was reacted with phosgene to provide a carbamoylchloride. Using Preparation Method 4, TMS protected S-benzyl-(L)-cysteine was prepared. The carbamoylchloride and TMS protected S-benzyl-(L)-cysteine were reacted using Preparation Method 5 to provide compound (49) as a colourless oil (78%). NMR $^1$H (ppm, $CDCl_3$): 9.67 (d, $J^3$=6.7 Hz, 1H), 7.48-7.22 (m, 10H), 4.74-4.67 (m, 1H), 3.78 (s, 2H), 3.65 (t, $J^3$=7.5 Hz, 2H), 3.02-2.86 (m, 2H), 1.53 (sext., $J^3$=7.5 Hz, 2H), 0.71 (t, $J^3$=7.4 Hz, 3H).

Example 47

Compound (50)

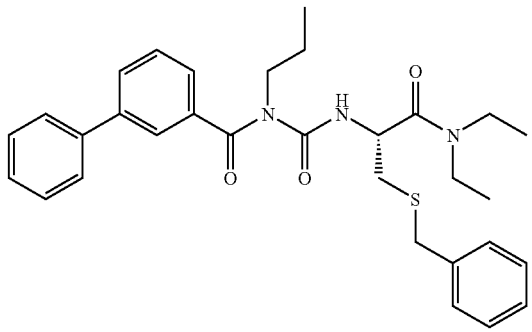

(50)

Compound (1) from example 1A (171 mg, 0.36 mmol) was dissolved in dry $CH_2Cl_2$ (2.5 mL) with DMF (0.25 mL). The solution was cooled to 0° C. and stirred under nitrogen. Oxalyl chloride (46 μL, 70 mg, 0.55 mmol) was added via syringe and stirring was applied at room temperature for two hours. The solvent and any excess oxalyl chloride were removed under reduced pressure. The orange residue was dissolved in dry $CH_2Cl_2$ (1 mL) and added via syringe to a solution of diethylamine (83 μL, 59 mg, 0.8 mmol) in dry $CH_2Cl_2$ (2 mL) at 0° C. The mixture was stirred for 16 hours, and then neutralized with 10% citric acid. The product was extracted with $CH_2Cl_2$ three times, and the organic layers were washed with water, then brine, and were then dried over $MgSO_4$ and concentrated. The product was purified using $SiO_2$ with $CH_2Cl_2$/EtOAc 90:10. A colourless oil was obtained (38 mg, 20%). NMR $^1$H (ppm, $CDCl_3$): 9.25 (d, $J^3$=3=8.2 Hz, 1H), 7.71-7.22 (m, 14H), 5.01-4.94 (m, 1H), 3.77-3.67 (m, 4H), 3.56-3.40 (m, 2H), 3.36-3.18 (m, 2H), 2.85-2.65 (m, 2H), 1.57 (sext., $J^3$=7.4 Hz, 2H), 1.16 (t, $J^3$=7.2 Hz, 3H), 1.10 (t, $J^3$=7.1 Hz, 3H), 0.75 (t, $J^3$=7.4 Hz, 3H).

Example 48

Compound (52)

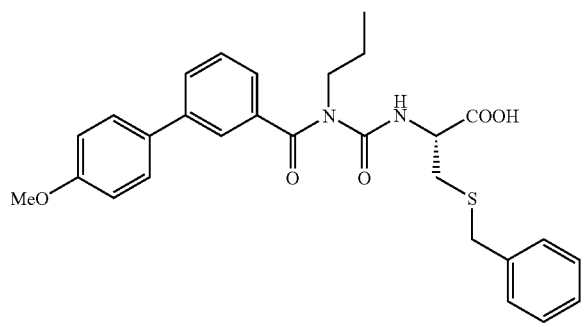

(52)

48A: N-n-propyl-3-(4'-methoxy)-phenylbenzamide

Using Preparation Method 2, N-n-propyl-3-bromobenzamide from Example 1A was reacted with 4-methoxyphenylboronic acid. The resulting reaction mixture was purified using SiO$_2$ with AcOEt/CH$_2$Cl$_2$ 10:90. A white crystalline solid was obtained (52%). NMR $^1$H (ppm, CDCl$_3$): 7.93 (s, 1H), 7.75-7.62 (m, 2H), 7.54 (d, J$^3$=38.8 Hz, 2H), 7.45 (t, J$^3$=3=7.9 Hz, 1H), 6.97 (d, J$^3$=8.8 Hz, 2H), 6.15 (br. s., 1H), 3.84 (s, 3H), 3.47-3.40 (m, 2H), 1.65 (sext., J$^3$=7.3 Hz, 2H), 0.99 (t, J$^3$=7.4 Hz, 3H).

48B: Compound (52)

Using Preparation Method 3, N-n-propyl-3-(4'-methoxy)-phenylbenzamide was reacted with phosgene to provide a carbamoylchloride. Using Preparation Method 4, TMS protected S-benzyl-(L)-cysteine was prepared. The carbamoylchloride and TMS protected S-benzyl-(L)-cysteine were reacted using Preparation Method 5 to provide compound (52) as a colourless oil (32%). NMR $^1$H (ppm, CDCl$_3$): 9.70 (d, J$^3$=7.0 Hz, 1H), 9.19 (br. s., 1H), 7.66-7.20 (m, 11H), 6.98 (d, J$^3$=8.7 Hz, 2H), 4.79-4.73 (m, 1H), 3.84 (s, 3H), 3.78 (s, 2H), 3.70 (t, J$^3$=7.5 Hz, 2H), 3.03-2.87 (m, 2H), 1.56 (sext., J$^3$=7.4 Hz, 2H), 0.73 (t, J$^2$=7.4 Hz, 3H).

Example 49

Compound (55)

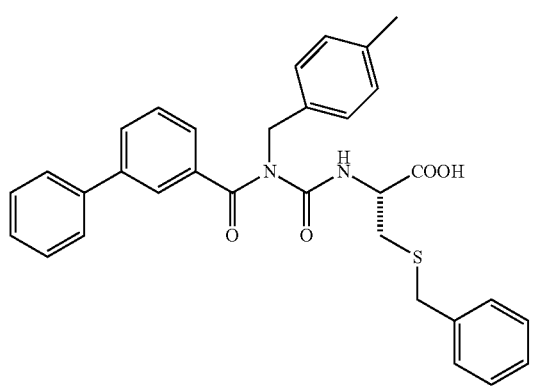

(55)

49A: Biphenyl-3-carboxylic acid 4-methyl-benzylamide

Using preparation method 1, 3-phenylbenzoic acid (125 mg, 0.63 mmol) was reacted with 4-methylbenzylamine (96 mg, 0.7 mmol). The product was purified by flash chromatography on SiO$_2$ using CH$_2$Cl$_2$/hexanes 50:50 then CH$_2$Cl$_2$ 100%. White crystals were obtained (115 mg, 58%). NMR $^1$H (ppm, CDCl$_3$): 7.99 (s, 1H), 7.73-7.69 (m, 2H), 7.58 (dd, J$^3$=7.0 Hz, J$^4$=1.4 Hz, 2H), 7.48 (t, J$^3$=7.8 Hz, 1H), 7.43 (t, J$^3$=7.6 Hz, 2H), 7.35 (tt, J$^3$=7.2 Hz, J$^4$=2.4 Hz, 1H), 7.29 (d, J$^3$=8.6 Hz, 2H), 6.88 (d, J$^3$=8.7 Hz, 2H), 6.36 (br. s, 1H), 4.59 (d, J$^3$=5.5 Hz, 2H), 3.79 (s, 3H).

49B: Compound (55)

Using Preparation Method 3, compound 49A (79 mg, 0.25 mmol) was reacted with phosgene to provide a carbamoylchloride. Using Preparation Method 4, TMS protected S-benzyl-(L)-cysteine (64 mg, 0.3 mmol) was prepared. The carbamoylchloride and TMS protected S-benzyl-(L)-cysteine were reacted using Preparation Method 5 to provide compound (55) as a colourless oil (60 mg, 43%). NMR $^1$H (ppm, CDCl$_3$): 9.78 (d, J$^3$=7.1 Hz, 1H), 8.60 (br. s, 1H), 7.66 (d, J$^3$=7.8 Hz, 1H), 7.47-7.20 (m, 13H), 6.94 (d J$^3$=8.6 Hz, 2H), 6.76 (d, J$^3$=8.7 Hz, 2H), 4.95 (s, 2H), 4.85-4.78 (m, 1H), 3.77 (s, 2H), 3.72 (s, 3H), 3.06-2.89 (m, 2H).

Example 50

Compound (56)

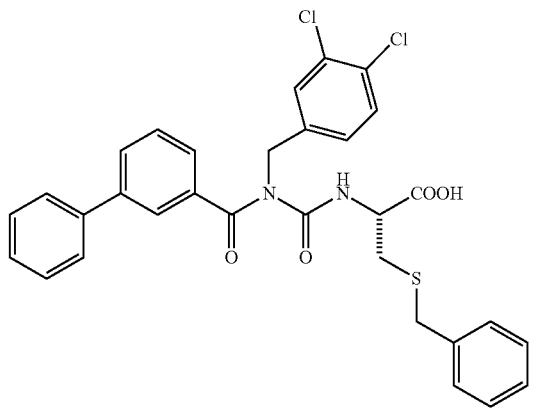

(56)

50A: Biphenyl-3-carboxylic acid 3,4-dichloro-benzylamide

Using preparation method 1, 3-phenylbenzoic acid (125 mg, 0.63 mmol) was reacted with 3,4-dichlorobenzylamine (123 mg, 0.7 mmol). The product was purified by flash chromatography on SiO$_2$ using CH$_2$Cl$_2$/hexanes 50:50 then CH$_2$Cl$_2$ 100%. White crystals were obtained (111 mg, 50%). NMR $^1$H (ppm, CDCl$_3$): 8.00 (s, 1H), 7.73 (dd, J$^3$=7.7 Hz, J$^4$=1.6 Hz, 2H), 7.59 (d, J$^3$=7.3 Hz, 2H), 7.50 (t, J$^3$=7.7 Hz, 1H), 7.46-7.34 (m, 6H), 7.19 (dd, J$^3$=8.2 Hz, J$^4$=1.8 Hz, 1H), 6.54 (br. s, 1H), 4.61 (d, J$^3$=5.9 Hz, 2H).

50B: Compound (56)

Using Preparation Method 3, compound 50A (89 mg, 0.25 mmol) was reacted with phosgene to provide a carbamoylchloride. Using Preparation Method 4, TMS protected S-benzyl-(L)-cysteine (64 mg, 0.3 mmol) was prepared. The carbamoylchloride and TMS protected S-benzyl-(L)-cysteine were reacted using Preparation Method 5 to provide compound (56) as white glassy solid (106 mg, 72%). NMR $^1$H (ppm, CDCl$_3$): 9.71 (d, J$^3$=7.1 Hz, 1H), 8.69 (br. s, 1H), 7.69 (d, J$^3$=7.7 Hz, 1H), 7.48-7.16 (m, 14H), 7.13 (d, J$^4$=1.8 Hz, 1H), 6.90 (dd, J$^3$=8.3 Hz, J$^4$=1.8 Hz, 1H), 4.94 (s, 2H), 4.83-4.77 (m, 1H), 3.78 (s, 2H), 3.06-2.89 (m, 2H).

Example 51

Compound (57)

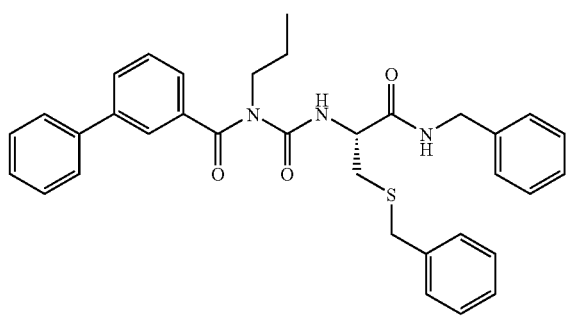

(57)

Compound (1) from Example 1A (171 mg, 0.36 mmol) was dissolved in dry CH$_2$Cl$_2$ (2.5 mL) with DMF (0.25 mL). The solution was cooled to 0° C. and stirred under nitrogen. Oxalyl chloride (46 µL, 70 mg, 0.55 mmol) was added via syringe and stirring was applied at room temperature for two hours. The solvent and any excess oxalyl chloride were removed under reduced pressure. The orange residue was dissolved in dry CH$_2$Cl$_2$ (1 mL) and added via syringe to a solution of benzylamine (88 µL, 86 mg, 0.8 mmol) in dry CH$_2$Cl$_2$ (2 mL) at 0° C. The mixture was stirred for 16 hours, and then neutralized with 10% citric acid. The product was extracted with CH$_2$Cl$_2$ three times, and the organic layers were washed with water, then brine, and were then dried over MgSO$_4$ and concentrated. The product was purified using SiO$_2$ with CH$_2$Cl$_2$/EtOAc 90:10. A colourless oil was obtained (81 mg, 44%). NMR $^1$H (ppm, CDCl$_3$): 9.45 (d, J$^3$=7.3 Hz, 1H), 7.71-7.19 (m, 19H), 6.71 (t, J$^3$=5.6 Hz, 1H), 4.61-4.39 (m, 3H), 3.76 (s, 2H), 3.68 (t, J$^3$=7.6 Hz, 2H), 3.01-2.84 (m, 2H), 1.53 (sext., J$^3$=7.5 Hz 2H), 0.72 (t, J$^3$=7.4 Hz, 3H).

Example 52

Compound (58)

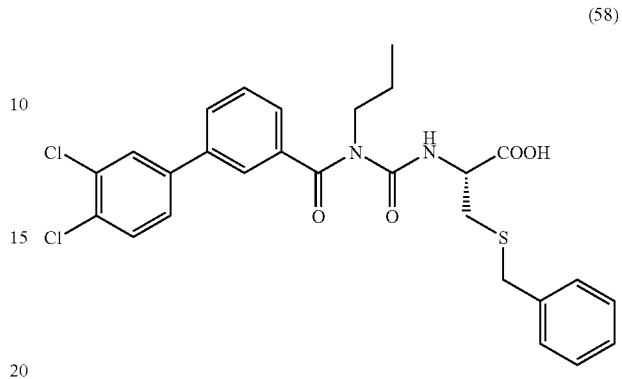

(58)

52A: N-n-propyl-3-(3',4'-dichloro)-phenylbenzamide

Using Preparation Method 2, N-n-propyl-3-bromobenzamide from Example 1A was reacted with 3,4-dichlorophenylboronic acid. The resulting reaction mixture was purified using SiO$_2$ with AcOEt/CH$_2$Cl$_2$ 10:90. A white crystalline solid was obtained (83%). NMR $^1$H (ppm, CDCl$_3$): 7.93 (d, J$^4$=1.6 Hz, 1H), 7.72-7.69 (m, 1H), 7.64 (d, J$^4$=2.0 Hz, 1H), 7.62-7.58 (m, 1H), 7.47-7.42 (m, 2H), 7.37 (d. d., J$^3$=8.4 Hz, J$^4$=2.1 Hz, 1H), 6.51 (br. s., 1H), 3.44-3.35 (m, 2H), 1.63 (sext., J$^3$=7.3 Hz, 2H), 0.96 (t, J$^3$=7.4 Hz, 3H).

52B: Compound (58)

Using Preparation Method 3, N-n-propyl-3-(3',4'-dichloro)-phenylbenzamide was reacted with phosgene to provide a carbamoylchloride. Using Preparation Method 4, TMS protected S-benzyl-(L)-cysteine was prepared. The carbamoylchloride and TMS protected S-benzyl-(L)-cysteine were reacted using Preparation Method 5 to provide compound (58) as a colourless oil (82%). NMR $^1$H (ppm, CDCl$_3$): 10.65 (br. s., 1H), 9.63 (d, J$^3$=7.1 Hz, 1H), 7.66-7.14 (m, 12H), 4.81-4.75 (m, 1H), 3.78 (s, 2H), 3.69 (t, J$^3$=7.5 Hz, 2H), 3.04-2.88 (m, 2H), 1.57 (sext., J$^3$=7.5 Hz, 2H), 0.74 (t, J$^3$=7.4 Hz, 3H).

Example 53

Compound (59)

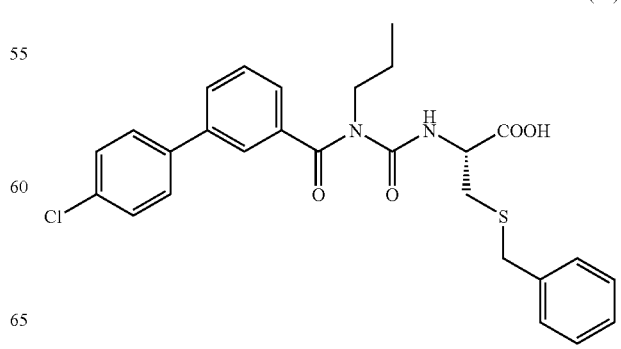

(59)

53A: N-n-propyl-3-(4'-chloro)-phenylbenzamide

Using Preparation Method 2, N-n-propyl-3-bromobenzamide from Example 1A was reacted with 4-chlorophenylboronic acid. The resulting reaction mixture was purified using SiO$_2$ with AcOEt/CH$_2$Cl$_2$ 10:90. A white crystalline solid was obtained (79%). NMR $^1$H (ppm, CDCl$_3$): 7.95 (s, 1H), 7.69 (d, J$^3$=7.7 Hz, 1H), 7.57 (d, J$^3$=7.7 Hz, 1H), 7.43 (d. t., J$^3$=8.6 Hz, J$^4$=2.2 Hz, 2H), 7.35 (t., J$^3$=7.7 Hz, 1H), 7.31 (d. t., J$^3$=8.6 Hz, J$^4$=2.2 Hz, 2H), 6.95 (br. s., 1H), 3.39-3.32 (m, 2H), 1.59 (sext., J$^3$=7.3 Hz, 2H), 0.91 (t, J$^3$=7.3 Hz, 3H).

53B: Compound (59)

Using Preparation Method 3, N-n-propyl-3-(4'-chloro)-phenylbenzamide was reacted with phosgene to provide a carbamoylchloride. Using Preparation Method 4, TMS protected S-benzyl-(L)-cysteine was prepared. The carbamoylchloride and TMS protected S-benzyl-(L)-cysteine were reacted using Preparation Method 5 to provide compound (59) as a colourless oil (80%). NMR $^1$H (ppm, CDCl$_3$): 10.0 (br. s., 1H), 9.65 (d, J$^3$=7.0 Hz, 1H), 7.66-7.23 (m, 13H), 4.81-4.75 (m, 1H), 3.78 (s, 2H), 3.69 (t, J$^3$=7.4 Hz, 2H), 3.04-2.87 (m, 2H), 1.57 (sext., J$^3$=7.3 Hz, 2H), 0.73 (t, J$^3$=7.4 Hz, 3H).

Example 54

Compound (60)

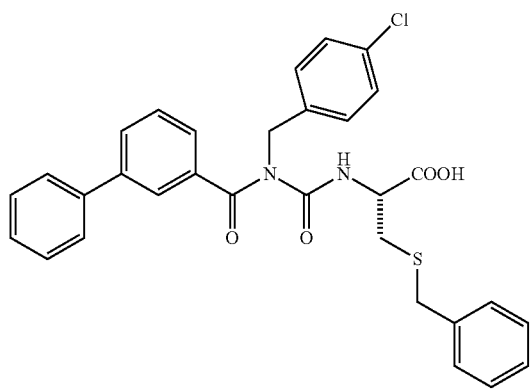

(60)

54A: Biphenyl-4-carboxylic acid 4-chloro-benzylamide

Using preparation method 1, 3-phenylbenzoic acid (125 mg, 0.63 mmol) was reacted with 4-chlorobenzylamine (99 mg, 0.7 mmol). The product was purified by flash chromatography on SiO$_2$ using CH$_2$Cl$_2$/hexanes 50:50 then CH$_2$Cl$_2$ 100%. White crystals were obtained (103 mg, 51%). NMR $^1$H (ppm, CDCl$_3$): 7.99 (t, J$^4$=1.6 Hz, 1H), 7.72 (dd, J$^3$=7.1 Hz, J$^4$=1.1 Hz, 2H), 7.58 (dd, J$^3$=7.1 Hz, J$^4$=1.5 Hz, 2H), 7.51-7.21 (m, 8H), 6.48 (br. s, 1H), 4.62 (d, J$^3$=5.8 Hz, 2H).

54B: Compound (60)

Using Preparation Method 3, compound 54A (80 mg, 0.25 mmol) was reacted with phosgene to provide a carbamoylchloride. Using Preparation Method 4, TMS protected S-benzyl-(L)-cysteine (64 mg, 0.3 mmol) was prepared. The carbamoylchloride and TMS protected S-benzyl-(L)-cysteine were reacted using Preparation Method 5 to provide compound (60) as white glassy solid (98 mg, 70%). NMR $^1$H (ppm, CDCl$_3$): 9.76 (d, J$^3$=6.9 Hz, 1H), 8.95 (br. s, 1H), 7.67 (d, J$^3$=7.5 Hz, 1H), 7.45-7.16 (m, 15H), 6.97 (d, J$^3$=8.0 Hz, 2H), 4.96 (s, 2H), 4.82-4.80 (m, 1H), 3.78 (s, 2H), 3.07-2.89 (m, 2H).

Example 55

Compound (61)

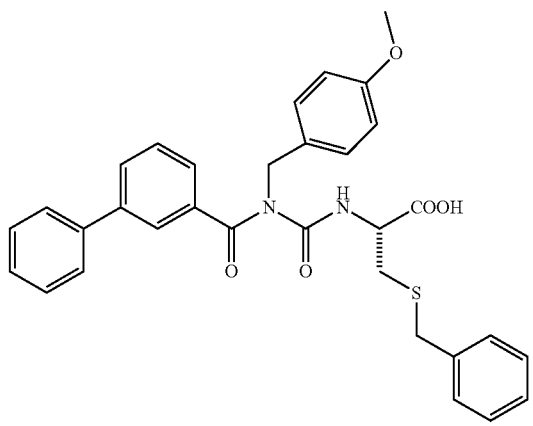

(61)

55A: Biphenyl-3-carboxylic acid 4-methoxy-benzylamide

Using preparation method 1,3-phenylbenzoic acid (125 mg, 0.63 mmol) was reacted with 4-methoxybenzylamine (123 mg, 0.7 mmol). The product was purified by flash chromatography on SiO$_2$ using CH$_2$Cl$_2$/hexanes 50:50 then CH$_2$Cl$_2$ 100%. White crystals were obtained (89 mg, 47%). NMR $^1$H (ppm, CDCl$_3$): 7.99 (t, J$^4$=1.5 Hz, 1H), 7.73-7.69 (m, 2H), 7.59 (dd, J$^3$=8.1 Hz, J$^4$=1.0 Hz, 2H), 7.48 (t, J$^3$=7.7 Hz, 1H), 7.44 (t, J$^3$=7.6 Hz, 2H), 7.35 (tt, J$^3$=7.2 Hz, J$^4$=2.4 Hz, 1H), 7.26 (d, J$^3$=7.3 Hz, 2H), 7.16 (d, J$^3$=7.8 Hz, 2H), 6.36 (br. s, 1H), 4.62 (d, J$^3$=5.5 Hz, 2H), 2.33 (s, 3H).

55B: Compound (61)

Using Preparation Method 3, compound 53A (75 mg, 0.25 mmol) was reacted with phosgene to provide a carbamoylchloride. Using Preparation Method 4, TMS protected S-benzyl-(L)-cysteine (64 mg, 0.3 mmol) was prepared. The carbamoylchloride and TMS protected S-benzyl-(L)-cysteine were reacted using Preparation Method 5 to provide compound (61) as a yellow oil (47 mg, 35%). NMR $^1$H (ppm, CDCl$_3$): 9.83 (d, J$^3$=7.1 Hz, 1H), 8.70 (br. s, 1H), 7.65 (d, J$^3$=7.8 Hz, 1H), 7.46-7.21 (m, 13H), 7.05 (d, J$^3$=7.9 Hz, 2H), 6.93 (d, J$^3$=7.9 Hz, 2H), 4.97 (s, 2H), 4.86-4.80 (m, 1H), 3.78 (s, 2H), 3.07-2.89 (m, 2H), s, 2.35 (s, 3H).

Example 56

Compound (62)

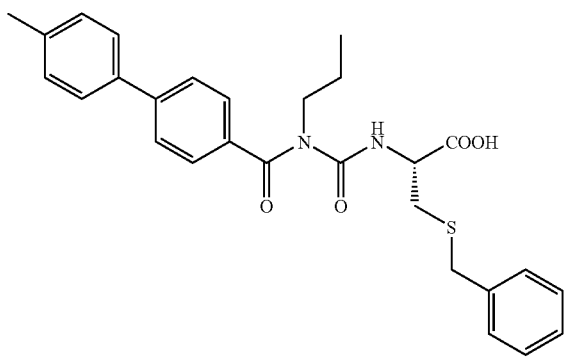

56A: N-n-propyl-4-(4'-tolyl)-benzamide

Using Preparation Method 2, N-n-propyl-4-bromobenzamide from Example 9A was reacted with 4-tolylboronic acid. The resulting reaction mixture was purified using SiO$_2$ with AcOEt/CH$_2$Cl$_2$ 10:90. A white crystalline solid was obtained (72%). NMR $^1$H (ppm, CDCl$_3$): 7.81 (d, J$^3$=8.3 Hz, 2H), 7.61 (d, J$^3$=38.4 Hz, 2H), 7.49 (d, J$^3$=8.1 Hz, 2H), 7.25 (d, J$^3$=7.9 Hz, 2H), 6.25 (br. s., 1H), 3.46-3.39 (m, 2H), 2.39 (s, 3H), 1.65 (sext., J$^3$=7.3 Hz, 2H), 0.98 (t, J$^3$=7.4 Hz, 3H).

56B: Compound (62)

Using Preparation Method 3, N-n-propyl-4-(4'-tolyl)-benzamide was reacted with phosgene to provide a carbamoylchloride. Using Preparation Method 4, TMS protected S-benzyl-(L)-cysteine was prepared. The carbamoylchloride and TMS protected S-benzyl-(L)-cysteine were reacted using Preparation Method 5 to provide compound (62) as a colourless solid (74%). NMR $^1$H (ppm, CDCl$_3$): 9.64 (d, J$^3$=7.2 Hz, 1H), 8.72 (br. s., 1H), 7.63 (d, J$^3$=8.4 Hz, 2H), 7.51 (d, J$^3$=6.6 Hz, 2H), 7.49 (d, J$^3$=6.6 Hz, 2H), 7.33-7.18 (m, 7H), 4.77-4.73 (m, 1H), 3.78 (s, 2H), 3.71 (t, J$^3$=7.5 Hz, 2H), 3.02-2.92 (m, 2H), 2.40 (s, 3H), 1.56 (sext., J$^3$=7.4 Hz, 2H), 0.75 (t, J$^3$=7.3 Hz, 3H).

Example 57

Compound (63)

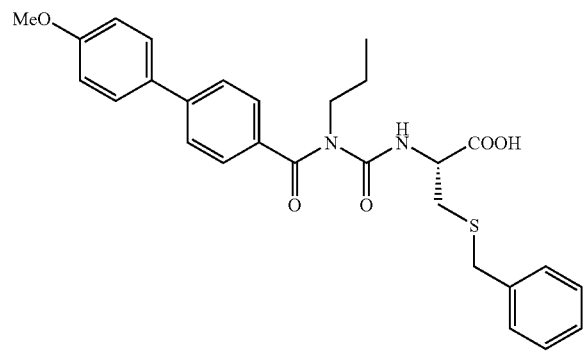

57A: N-n-propyl-4-(4'-methyl)-phenylbenzamide

Using Preparation Method 2, N-n-propyl-4-bromobenzamide from Example 9A was reacted with 4-methoxyphenylboronic acid. The resulting reaction mixture was purified using SiO$_2$ with AcOEt/CH$_2$Cl$_2$ 10:90. A white crystalline solid was obtained (56%). NMR $^1$H (ppm, CDCl$_3$): 7.79 (d, J$^3$=8.4 Hz, 2H), 7.58 (d, J$^3$=8.5 Hz, 2H), 7.53 (d, J$^3$=8.8 Hz, 2H), 6.97 (d, J$^3$=8.8 Hz, 2H), 6.29 (br. s., 1H), 3.84 (s, 3H), 3.45-3.39 (m, 2H), 1.64 (sext., J$^3$=7.4 Hz, 2H), 0.98 (t, J$^3$=7.4 Hz, 3H).

57B: Compound (63)

Using Preparation Method 3, N-n-propyl-4-(4'-methoxy)-phenylbenzamide was reacted with phosgene to provide a carbamoylchloride. Using Preparation Method 4, TMS protected S-benzyl-(L)-cysteine was prepared. The carbamoylchloride and TMS protected S-benzyl-(L)-cysteine were reacted using Preparation Method 5 to provide compound (63) as a colourless solid (64%). NMR $^1$H (ppm, CDCl$_3$): 9.56 (d, J$^3$=7.2 Hz, 1H), 8.84 (br. s., 1H), 7.69-7.19 (m, 11H), 6.99 (d, J$^3$=9.0 Hz, 2H), 4.80-4.74 (m, 1H), 3.84 (s, 3H), 3.77 (s, 2H), 3.73 (t, J$^3$=7.5 Hz, 2H), 3.03-2.85 (m, 2H), 1.58 (sext., J$^3$7.4 Hz, 2H), 0.75 (t, J$^3$=7.4 Hz, 3H).

Example 58

Compound (64)

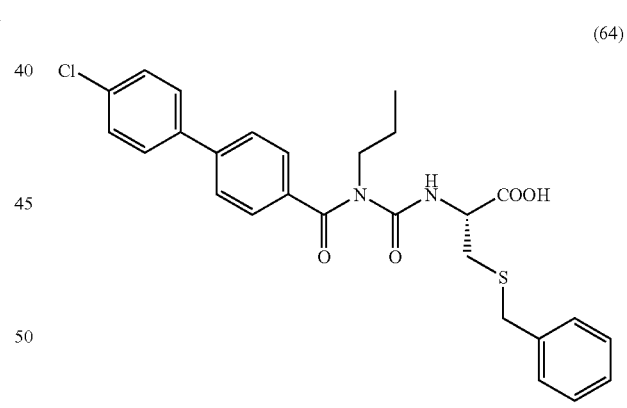

58A: N-n-propyl-4-(4'-chloro)-phenylbenzamide

Using Preparation Method 2, N-n-propyl-4-bromobenzamide from example 9A was reacted with 4-chlorophenylboronic acid. The resulting reaction mixture was purified using SiO$_2$ with AcOEt/CH$_2$Cl$_2$ 10:90. A white crystalline solid was obtained (50%). NMR $^1$H (ppm, CDCl$_3$): 7.81 (d, J$^3$=8.2 Hz, 2H), 7.56 (d, J$^3$=8.2 Hz, 2H), 7.49 (d, J$^3$=38.4 Hz, 2H), 7.39 (d, J$^3$=8.6 Hz, 2H), 6.34 (br. s., 1H), 3.45-3.38 (m, 2H), 1.64 (sext., J$^3$=7.3 Hz, 2H), 0.97 (t, J$^3$=7.4 Hz, 3H).

58B: Compound (64)

Using Preparation Method 3, N-n-propyl-4-(4'-chloro)-phenylbenzamide was reacted with phosgene to provide a carbamoylchloride. Using Preparation Method 4, TMS protected S-benzyl-(L)-cysteine was prepared. The carbamoylchloride and TMS protected S-benzyl-(L)-cysteine were reacted using Preparation Method 5 to provide compound (64) as a colourless oil (61%). NMR $^1$H (ppm, CDCl$_3$): 9.62 (d, $J^3$=7.0 Hz, 1H), 9.24 (br. s., 1H), 7.64 (d, $J^3$=8.1 Hz, 2H), 7.54-7.50 (m, 4H), 7.42 (d, $J^3$=8.6 Hz, 2H), 7.33-7.14 (m, 5H), 4.80-4.74 (m, 1H), 3.78 (s, 2H), 3.71 (t, $J^3$=7.4 Hz, 2H), 3.03-2.87 (m, 2H), 1.57 (sext., $J^3$=7.4 Hz, 2H), 0.75 (t, $J^3$=7.4 Hz, 3H).

Example 59

Compound (65)

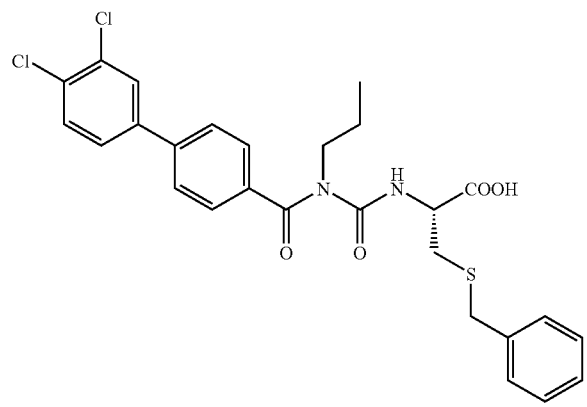

(65)

59A: N-n-propyl-4-(3',4'-dichloro)-phenylbenzamide

Using Preparation Method 2, N-n-propyl-4-bromobenzamide from example 9A was reacted with 3,4-dichlorophenylboronic acid. The resulting reaction mixture was purified using SiO$_2$ with AcOEt/CH$_2$Cl$_2$ 10:90. A white crystalline solid was obtained (92%). NMR $^1$H (ppm, CDCl$_3$): 7.83 (d, $J^3$=8.5 Hz, 2H), 7.67 (d, $J^4$=2.0 Hz, 1H), 7.58 (d, $J^3$=8.5 Hz, 2H), 7.51 (d, $J^3$=8.3 Hz, 1H), 7.41 (d.d., $J^3$=8.3 Hz, $J^4$=2.1 Hz, 1H), 6.17 (br. s., 1H), 3.47-3.40 (m, 2H), 1.65 (sext., $J^3$=7.3 Hz, 2H), 0.99 (t, $J^3$=7.4 Hz, 3H).

59B: Compound (65)

Using Preparation Method 3, N-n-propyl-4-(3',4'-dichloro)-phenylbenzamide was reacted with phosgene to provide a carbamoylchloride. Using Preparation Method 4, TMS protected S-benzyl-(L)-cysteine was prepared. The carbamoylchloride and TMS protected S-benzyl-(L)-cysteine were reacted using Preparation Method 5 to provide compound (65) as a colourless oil (12%). NMR $^1$H (ppm, CDCl$_3$): 9.37 (br. s., 1H), 7.56-7.13 (m, 7H), 4.61 (br. s., 1H), 3.68-3.44 (m, 4H), 3.01-2.81 (m, 2H), 1.48-1.45 (m, 2H), 0.65 (t, $J^3$=7.2 Hz, 3H).

Example 60

Compound (66)

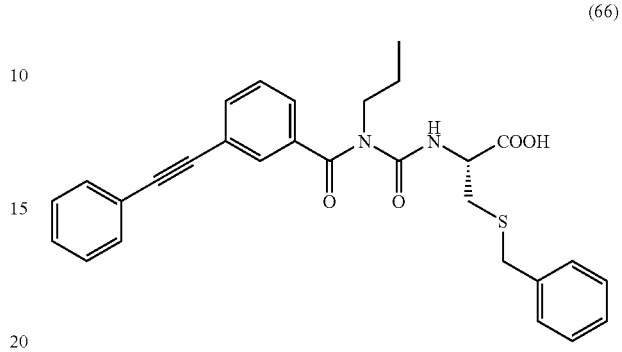

(66)

60A: N-n-propyl-3-iodobenzamide

Using Preparation Method 1, 3-iodobenzoic acid was reacted with n-propylamine. The resulting reaction mixture was purified using SiO$_2$ with CH$_2$Cl$_2$/petroleum ether 95:5 to CH$_2$Cl$_2$/AcOEt 95:5 to give N-n-propyl-3-iodobenzamide as an off-white solid (82%). NMR $^1$H (ppm, CDCl$_3$): 8.07 (t, $J^4$=1.6 Hz, 1H), 7.80 (d. t., $J^3$=7.9 Hz, $J^4$=1.1 Hz, 1H), 7.69 (d. t., $J^3$=7.8 Hz, $J^4$=1.1 Hz, 1H), 7.15 (t, $J^3$=7.8 Hz, 1H), 6.06 (br. s., 1H), 3.43-3.36 (m, 2H), 1.62 (sext., $J^3$=7.3 Hz, 2H), 0.97 (t, $J^3$=7.4 Hz, 3H).

60B: N-n-propyl-3-phenylethynyl-benzamide

A mixture of N-n-propyl-3-iodobenzamide, phenylacetylene (1.5 eq.) and Pd(PPh$_3$)$_2$Cl$_2$ (5 mol %) in piperidine (3 eq.) was heated at 70° C. for 30 minutes in a sealed tube. The solidified residue was dissolved with CH$_2$Cl$_2$ and water and poured onto HCl 2N. The acidic phase was extracted three times with CH$_2$Cl$_2$. The combined organic layers were washed once with HC 2N, twice with saturated NaHCO$_3$, once with water and once with brine. The organic layer was then dried over MgSO$_4$ and concentrated. The resulting residue was purified using SiO$_2$ with CH$_2$Cl$_2$/petroleum ether 80:20 to CH$_2$Cl$_2$ 100% to give N-n-propyl-3-phenylethynyl-benzamide as a yellow solid (Quantitative yield). NMR $^1$H (ppm, CDCl$_3$): 7.88 (s, 1H), 7.74-7.68 (m, 1H), 7.63-7.60 (m, 1H), 7.53-7.50 (m, 2H), 7.42-7.33 (m, 4H), 6.22 (br. s., 1H), 3.44-3.38 (m, 2H), 1.64 (sext., $J^3$=7.3 Hz, 2H), 0.98 (t, $J^3$=7.3 Hz, 3H).

60C: Compound (66)

Using Preparation Method 3, N-n-propyl-3-phenylethynyl-benzamide was reacted with phosgene to provide a carbamoylchloride. Using Preparation Method 4, TMS protected S-benzyl-(L)-cysteine was prepared. The carbamoylchloride and TMS protected S-benzyl-(L)-cysteine were reacted using Preparation Method 5 to provide compound (66) as a colourless oil (68%). NMR $^1$H (ppm, CDCl$_3$): 9.62 (d, $J^3$=6.9 Hz, 1H), 7.64-7.21 (m, 14H), 4.75-

4.69 (m, 1H), 3.78 (s, 2H), 3.67 (t, $J^3$=7.5 Hz, 2H), 3.02-2.87 (m, 2H), 1.54 (sext., $J^3$=7.4 Hz, 2H), 0.74 (t, $J^3$=7.4 Hz, 3H).

Example 61

Compound (67)

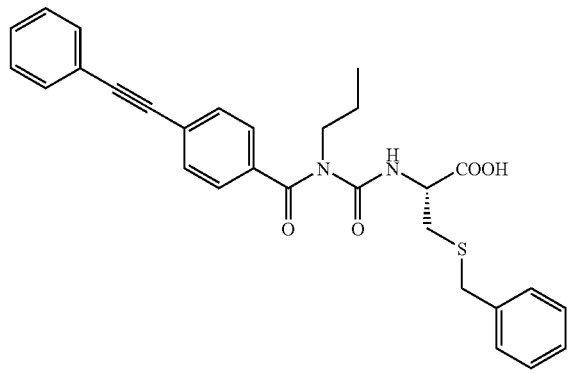

61A: N-n-propyl-4-phenylethynyl-benzamide

A mixture of N-n-propyl-4-bromobenzamide from Example 9A, phenylacetylene (1.5 eq.) and Pd(PPh$_3$)$_2$Cl$_2$ (5 mol %) in piperidine (3 eq.) was heated at 70° C. for 30 minutes in a sealed tube. The solidified residue was dissolved with CH$_2$Cl$_2$ and water and poured onto HCl 2N. The acidic phase was extracted three times with CH$_2$Cl$_2$. The combined organic layers were washed once with HCl 2N, twice with saturated NaHCO$_3$, once with water and once with brine. The organic layer was then dried over MgSO$_4$ and concentrated. The resulting residue was purified using SiO$_2$ with CH$_2$Cl$_2$/petroleum ether 80:20 to CH$_2$Cl$_2$ 100% to give N-n-propyl-3-phenylethynyl-benzamide as a yellow solid (Quantitative yield). NMR $^1$H (ppm, CDCl$_3$): 7.73 (d. $J^3$=8.4 Hz, 2H), 7.63-7.51 (m, 5H), 7.36-7.32 (m, 2H), 6.10 (br. s., 1H), 3.45-3.37 (m, 2H), 1.64 (sext., J=7.2 Hz, 2H), 0.99 (t, $J^3$=7.4 Hz, 3H).

61B: Compound (67)

Using Preparation Method 3, N-n-propyl-4-phenylethynyl-benzamide was reacted with phosgene to provide a carbamoylchloride. Using Preparation Method 4, TMS protected S-benzyl-(L)-cysteine was prepared. The carbamoylchloride and TMS protected S-benzyl-(L)-cysteine were reacted using Preparation Method 5 to provide compound (67) as a colourless oil (60%). NMR $^1$H (ppm, CDCl$_3$): 9.60 (d, $J^3$=6.6 Hz, 1H), 7.61-7.24 (m, 14H), 4.75-4.69 (m, 1H), 3.78 (s, 2H), 3.66 (t, $J^3$=7.4 Hz, 2H), 3.02-2.87 (m, 2H), 1.54 (sext., $J^3$=7.4 Hz, 2H), 0.73 (t, $J^3$=7.4 Hz, 3H).

Example 62

Compound (70)

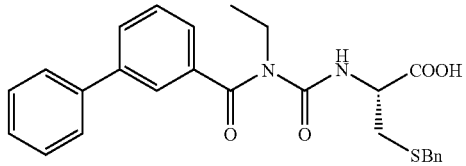

62A: Methyl 3-phenylbenzoate

Using Preparation Method 2, Methyl 3-bromobenzoate (3.86 g, 18.6 mmol) was reacted with phenyl boronic acid (2.4 g, 20.5 mmol) in the presence of 5 mol % Pd(PPh$_3$)$_4$, 18 mL of 2N Na$_2$CO$_3$, 9.4 mL of Ethanol and 37 mL of toluene. The resulting reaction mixture was purified using SiO$_2$ with hexane/diethyl ether 98:2 to give a colourless thick oil (389 g, 96%). NMR $^1$H (ppm, CDCl$_3$): 8.29 (s, 1H), 8.03 (d, $J^3$=7.8 Hz, 1H), 7.79 (d, $J^3$=7.8 Hz, 1H), 7.63 (d, $J^3$=7.2 Hz, 2H), 7.54-7.26 (m, 4H), 3.96 (s, 3H). MS: M+1 463.2.

62B: N-ethyl 3-phenylbenzamide

Trimethylaluminum (920 µL of 2M solution in toluene, 1.84 mmol) was added drop wise to a suspension of ethylamine hydrochloride (151 mg, 1.84 mmol) in 2.76 mL of dry toluene at 0° C. The reaction was then warmed to room temperature and stirred until no gas evolution was observed. The clear solution was then canulated onto a solution of Methyl 3-phenylbenzoate in 6 mL of toluene. The reaction was then heated to 80° C. and stirred for 18 hours. The reaction mixture was then carefully treated with 5% HCl at 0° C. The aqueous layer was extracted three times with ethyl acetate. The combined organic layers were washed with brine, dried over Na$_2$SO$_4$ and concentrated. The oil obtained was purified by flash chromatography using SiO$_2$ with CH$_2$Cl$_2$/MeOH 99:1 to give a pale yellow oil (129 mg, 62%). NMR $^1$H (ppm, CDCl$_3$): 8.0 (s, 1H), 7.72 (d, $J^3$=8.1 Hz, 2H), 7.61 (d, $J^3$=5.4 Hz, 2H), 7.52-7.35 (m, 4H), 6.14 (br. s., 1H), 3.58-3.49 (m, 2H), 1.28 (t, $J^3$=7.5 Hz, 3H).

62C: Compound (70)

Using Preparation Method 3, N-ethyl 3-phenylbenzamide was reacted with phosgene to provide a carbamoylchloride. Using Preparation Method 4, TMS protected S-benzyl-(L)-cysteine was prepared. The carbamoylchloride and TMS protected S-benzyl-(L)-cysteine were reacted using Preparation Method 5 to provide compound (70) as a colourless glassy oil (65%). NMR $^1$H (ppm, CDCl$_3$): 9.72 (d, $J^3$=6.9 Hz, 1H), 9.57 (br. s., 1H), 7.75-7.73 (m, 2H), 7.70-7.69 (m, 2H), 7.61-7.22 (m, 10H), 4.79 (m, 1H), 3.84-3.78 (m, 4H), 3.04-2.95 (m, 2H), 1.16 (t, 3H).

Example 63

Compound (71)

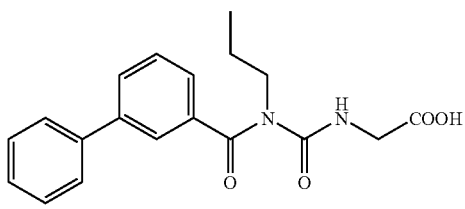

Using Preparation Method 3, N-n-propyl-3-phenylbenzamide from Example 1B was reacted with phosgene to provide a carbamoylchloride. Using Preparation Method 4, TMS protected glycine was prepared. The carbamoylchloride and TMS protected glycine were reacted using Preparation Method 5 to give a colourless glassy oil (82%). NMR $^1$H (ppm, CDCl$_3$): 9.50 (t, J$^3$=5.14 Hz, 1H), 7.70 (d, J$^3$=6.52 Hz, 1H), 7.64 (s, 1H), 7.59-7.37 (m, 7H), 4.17 (d, J$^3$=5.41 Hz, 2H), 3.69 (m, 2H), 1.55 (sext., J$^3$=7.49 Hz, 2H), 0.72 (t, J$^3$=7.41 Hz, 3H).

Example 64

Compound (72)

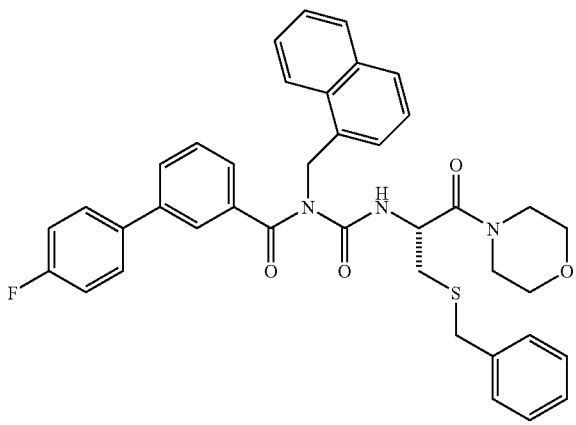

A mixture of compound (36) from Example (34) (105 mg, 0.18 mmol), EDCI (52 mg, 0.36 mmol), DMAP (1.8 mg), and morpholine (31 µL, 0.27 mmol) in 1.8 mL of dry DMF was stirred for 16 hours at room temperature. The reaction was then poured onto 1N HCl. The acidic aqueous phase was extracted three times with ethyl acetate and the combined organic layers were washed with 1N HCl, water and brine and dried over Na$_4$SO$_4$. After concentration the reaction product was purified by flash chromatography using SiO$_2$ with CH$_2$Cl$_2$/MeOH 98:2 to give compound (72) as a pale yellow oil (27 mg, 23%). NMR $^1$H (ppm, CDCl$_3$): 9.75 (d., J$^3$=8.15 Hz, 1H), 7.85 (d, J$^3$=7.87 Hz, 1H), 7.78 (d, J$^3$=7.84 Hz, 1H), 9.65 (d, J$^3$=7.85 Hz, 1H), 7.49-7.23 (m, 13H), 6.90 (d, J$^3$=6.95 Hz, 1H), 5.53-5.37 (m, 2H), 5.04-4.93 (m, 1H), 3.83-3.72 (m, 2H), 3.67-3.54 (m, 4H), 3.52-3.44 (m, 2H), 3.40-3.25 (m, 2H), 2.87-2.70 (m, 2H).

Example 65

Compound (74)

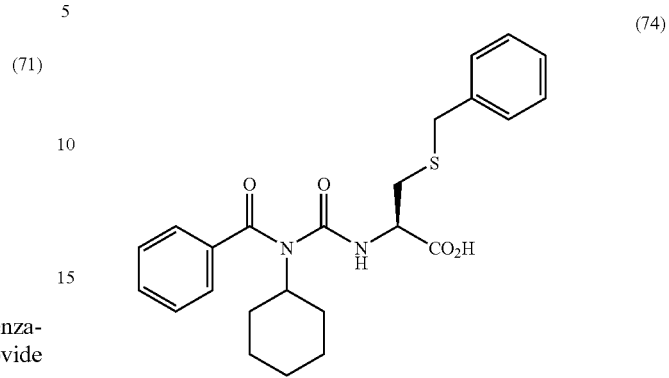

65A: N-cyclohexylbenzamide

Cyclohexylamine (8.5 mL, 0.1 mole) was added drop wise to a solution of benzoylchloride (1.17 mL, 10 mmol) in 35 mL of dry THF at 0° C. The reaction was then stirred at room temperature for 3 hours. After that time water was added and the mixture was poured onto crushed ice. A white solid precipitated. It was collected by filtration and rinsed thoroughly with water. The solid was then dried under vacuum (1.63 g, 80%). NMR $^1$H (ppm, CDCl$_3$): 7.72 (d, J$^3$=6.78 Hz, 2H), 7.48-7.36 (m, 3H), 6.02 (br. d., J$^3$=6.58 Hz, 1H), 4.00-3.89 (m, 1H), 2.03-1.99 (m, 2H), 1.79-1.71 (m, 3H), 1.44-1.37 (m, 2H), 1.25-1.15 (m, 3H).

65B: Compound (74)

Using Preparation Method 3, N-cyclohexylbenzamide was reacted with phosgene to give a carbamoylchloride. Using Preparation Method 4, TMS protected S-benzyl-(L)-cysteine was prepared. The carbamoylchloride and TMS protected S-benzyl-(L)-cysteine were reacted using Preparation Method 5 to give a colourless glassy oil (65%). NMR $^1$H (ppm, CDCl$_3$): 10.51 (br. s., 1H), 7.82 (d, J$^3$=7.11 Hz, 1H), 7.5 (d.d., J$^3$=6.55 Hz, J$^4$=1.61 Hz, 2H), 7.45-7.33 (m, 3H), 7.31-7.19 (m, 5H), 4.57-4.50 (m, 1H), 4.01-3.92 (m, 1H), 3.64 (s, 2H), 2.69 (br. s., 2H), 2.14-2.05 (m, 2H), 1.86-1.77 (m, 4H), 1.54 (br. s., 1H), 1.12 (br. s., 3H).

Example 66

Compound (75)

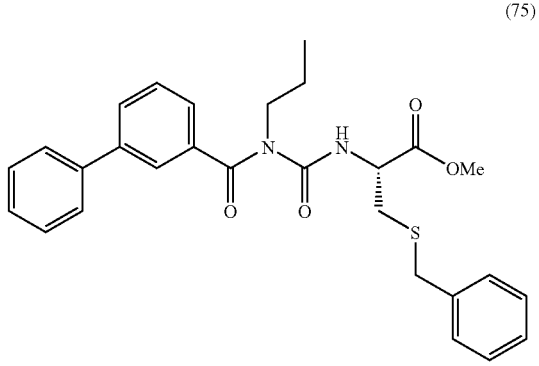

Compound (1) from example 1A (171 mg, 0.36 mmol) was dissolved in dry CH$_2$Cl$_2$ (2.5 mL) with DMF (0.25 mL). The solution was cooled to 0° C. and stirred under nitrogen. Oxalyl chloride (46 µL, 70 mg, 0.55 mmol) was added via syringe and stirring was applied at room temperature for two hours. The solvent and any excess oxalyl chloride were removed under reduced pressure. The orange residue was dissolved in CH$_2$Cl$_2$ (1 mL) and was added dropwise to a mixture of methanol (0.5 mL) in CH$_2$Cl$_2$ (2 mL). After stirring for 16 hours at room temperature, the reaction mixture was diluted with 10% citric acid and extracted three times with CH$_2$Cl$_2$. The combined organic layers were washed with water and then brine, dried over MgSO$_4$ and concentrated. The oil obtained was purified using SiO$_2$ with CH$_2$Cl$_2$/EtOAc 90:10. A colourless oil was obtained (89 mg, 51%). NMR $^1$H (ppm, CDCl$_3$): 9.65 (d, J$^3$=7.2 Hz, 1H), 7.71-7.20 (m, 14H), 4.80-4.74 (m, 1H), 3.77 (s, 2H), 3.76 (s, 3H), 3.70 (t, J$^3$=7.5 Hz, 2H), 2.99-2.84 (m, 2H), 1.57 (sext., J$^3$=7.5 Hz, 2H), 0.74 (t, J$^3$=7.4 Hz, 3H).

Example 67

Compound (80)

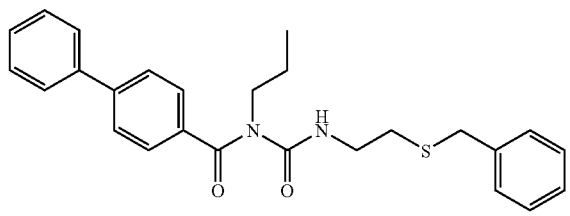

(80)

67A: 2-(N-Boc-amino)-ethanol

To a solution of ethanolamine (500 mg, 8.2 mmol) in 10 mL of dry CH$_2$Cl$_2$ was added DMAP (50 mg, 0.4 mmol), triethylamine (1.25 mL, 9 mmol) and Boc$_2$O (1.96 g, 90 mmol). The reaction was stirred overnight at room temperature. The reaction mixture was then washed with 10% citric acid, saturated NaHCO$_3$ and brine, dried over MgSO$_4$ and concentrated. A clear oil was obtained which was used without further purification (1 g, 76%). NMR $^1$H (ppm, CDCl$_3$): 5.07 (br. s., 1H), 3.64-3.63 (m, 2H), 3.24-3.23 (m, 2H), 2.9 (br. s., 1H), 1.40 (s, 9H).

67B: N-Boc-2-Tosyl-ethylamine

Pyridine (1.5 mL, 18.5 mmol) was added to 2-(N-Boc-amino)-ethanol (280 mg, 1.7 mmol) at 0° C. Tosyl chloride (1.65 g, 8.7 mmol) was then added and the reaction was allowed to stir at 0° C. overnight. The resulting cloudy reaction was diluted with Et$_2$O and washed with water, saturated NaHCO$_3$ and brine, dried over MgSO$_4$ and concentrated. The resulting white solid was purified using SiO$_2$ with AcOEt/petroleum ether 20:80 to 30:70. A white solid was obtained (250 mg, 46%). NMR $^1$H (ppm, CDCl$_3$): 7.77 (d, J$^3$=8.3 Hz, 2H), 7.33 (d, J$^3$=8.0 Hz, 2H), 4.82 (br. s., 1H), 4.05 (t, J$^3$=5.08 Hz, 2H), 3.38-3.33 (m, 2H), 2.43 (s, 3H), 1.39 (s, 9H).

67C: N-Boc-2-Benzylsulfanyl-ethylamine

N-Boc-2-Tosyl-ethylamine (100 mg, 0.32 mmol) was added to a mixture of benzylmercaptan (45 mL, 0.38 mmol) and Cs$_2$CO$_3$ (68 mg, 0.21 mmol) in 1.6 mL of dry DMF. The reaction was stirred for 18 hours after which time the reaction mixture was poured onto water. The aqueous layer was extracted three times with AcOEt. The combined organic layers were washed with water, saturated NaHCO$_3$ and brine, dried over Na$_2$SO$_4$ and concentrated. The residue was purified using SiO$_2$ with AcOEt/Petroleum ether 5:95 to 15:75. A yellow oil was obtained (72 mg, 83%). NMR $^1$H (ppm, CDCl$_3$): 7.31-7.25 (m, 5H), 4.79 (br. s., 1H), 3.70 (s, 2H), 3.25 (m, 2H), 2.55-2.53 (m, 2H), 1.43 (s, 9H).

67D: 2-Benzylsulfanyl-ethylammonium trifluoroacetate

N-Boc-2-Benzylsulfanyl-ethylamine (56 mg, 0.21 mmol) in 1 mL dry CH$_2$Cl$_2$ was treated with 0.5 mL of TFA at 0° C. After reaction completion (checked by TLC), the reaction mixture was concentrated in vacuo. The residue was dissolved in toluene and concentrated. This procedure was repeated two more times and the residue was dried under high vacuum and used directly in the next step without further purification.

67E: Compound (80)

Using Preparation Method 3, N-n-propyl-3-phenylbenzamide (42 mg, 0.175 mmol) from Example 1B was reacted with phosgene to provide a carbamoylchloride. To a solution of carbamoylchloride (0.175 mmol) in 2 mL of acetonitrile was added a solution of 2-benzylsulfonyl-ethylammonium trifluoroacetate (56 mg, 0.21 mmol) and triethylamine (33 µL, 0.22 mmol) in 1 mL of acetonitrile at 0° C. The reaction was then stirred at room temperature for 16 hours. The reaction mixture was then diluted with ethyl acetate and poured onto 2N HCl. The aqueous phase was extracted three times with ethyl acetate. The combined organic phases were washed with brine, dried over MgSO$_4$ and concentrated. The residue was purified using Silica gel with CH$_2$Cl$_2$ 100% to give compound (80) as a colourless oil (55 mg, 73%). NMR $^1$H (ppm, CDCl$_3$): 9.18 (br. s., 1H), 7.68-7.30 (m, 14H), 3.75 (s, 2H), 3.69 (t, J$^3$=7.5 Hz, 2H), 3.54-3.47 (m, 2H), 2.63 (t, J$^3$=6.8 Hz, 2H), 1.57 (sext., J$^3$=7.4 Hz, 2H), 0.73 (t, J$^3$=7.4 Hz, 3H).

Example 68

Compound (81)

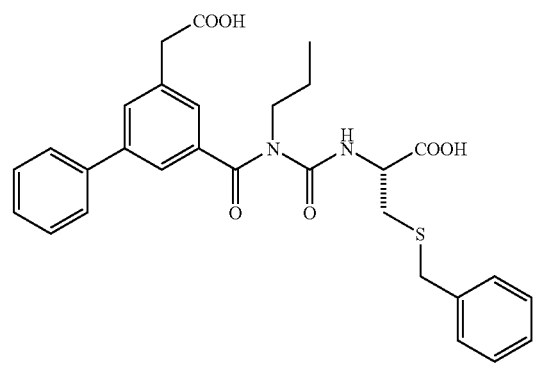

(81)

68A: 5-Bromo-isophthalic acid dimethyl ester

Prepared from 5-Amino-isophthalic acid dimethyl ester according to Brummer et al., 1998.

68B: 5-Bromo-isophthalic acid monomethyl ester

Prepared from 68A according to Chen et al., 2000.

68C: 5-Bromo-N-propyl-isophthalamic acid methyl ester

Using Preparation Method 1, 68B (350 mg, 1.3 mmol) was reacted with n-propylamine (160 µL, 1.95 mmol). The resulting reaction mixture was purified using $SiO_2$ with $CH_2Cl_2$/AcOEt 99:1 to 95:5 to give 64C as a white solid (257 mg, 66%). NMR $^1$H (ppm, $CDCl_3$): 8.27 (s, 2H), 8.13 (s., 1H), 6.30 (br. s., 1H), 3.92 (s, 3H), 3.44-3.37 (m, 2H), 1.65 (sext., $J^3$=7.2 Hz, 2H), 0.97 (t, $J^3$=7.4 Hz, 3H).

68D: 5-Propylcarbamoyl-biphenyl-3-carboxylic acid methyl ester

Using Preparation Method 2, 68C (247 mg, 0.82 mmol) was reacted with phenyl boronic acid (109 mg, 0.9 mmol) in the presence of 5 mol % $Pd(PPh_3)_4$, 0.82 mL of 2N $Na_2CO_3$, 0.43 mL of Ethanol and 1.8 mL of toluene. The resulting reaction mixture was purified using $SiO_2$ with $CH_2Cl_2$/AcOEt 98:2 to 90:10 to give a greenish oil (284 g, quant.). NMR $^1$H (ppm, $CDCl_3$): 8.37 (t, $J^4$=1.64 Hz, 1H), 8.27 (d. t., $J^3$=6.03 Hz, $J^4$=1.75 Hz, 1H), 7.63 (d, $J^3$=6.97 Hz, 1H), 7.49-7.36 (m, 5H), 6.27 (br. s., 1H), 3.49-3.42 (m, 2H), 1.64 (sext., $J^3$=7.25 Hz, 2H), 1.00 (t., $J^3$=7.37 Hz, 3H).

68E: 5-Propylcarbamoyl-biphenyl-3-carboxylic acid

A solution of NaOH (44 mg, 1.1 mmol) in 372 µL of MeOH was added to a solution of 68D (284 mg, 0.96 mmol) in 1.8 mL of acetone. The reaction was stirred at room temperature for 16 hrs after which time 10 mg of NaOH and 200 µL of MeOH were added. The reaction was stirred for 72 hrs. The reaction mixture was then concentrated in vacuo and the residue obtained was dissolved in water and a few drops of concentrated HCl were added till pH ~1. An off-white solid appeared. It was collected by filtration and extensively rinsed with water. The solid was then dried in vacuo (194 mg, 72%). NMR $^1$H (ppm, $CD_3OD$): 8.43 (t., $J^4$=1.63 Hz, 1H), 8.38 (t., $J^4$=1.73 Hz, 1H), 8.27 (t., $J^4$=1.78 Hz, 1H), 7.71-7.67 (m, 2H), 7.48 (m, 2H), 7.39 (t.t., $J^3$=7.34 Hz, $J^4$=1.36 Hz 1H), 3.39-3.34 (m, 2H), 1.65 (sext., $J^3$=7.18 Hz, 2H), 0.98 (t., $J^3$=7.34 Hz, 3H).

68F: 5-(2-Diazo-acetyl)-biphenyl-3-carboxylic acid propylamide 68E (194 mg, 0.69 mmol) was suspended in 1.5 mL of toluene with 11 µL of dry DMF. Oxalyl chloride (72 µL, 0.82 mmol) was then added dropwise at 0° C. leading to a gas evolution. After the addition, the reaction was stirred at room temperature for 2 hours. After that time, the reaction mixture was concentrated. The residue was dissolved in THF. At 0° C., triethylamine (95 µL, 0.69 mmol) was added followed by trimethylsilyldiazomethane (582 µL of a 2 M solution in $Et_2O$). The reaction was then stirred at room temperature for 16 hours. The reaction mixture was then concentrated and the residue was purified using $SiO_2$ with $CH_2Cl_2$/AcOEt 98:2 to 85:15. An orange oil was obtained (100 mg, 48%). NMR $^1$H (ppm, $CDCl_3$): 8.14 (t., $J^4$=1.68 Hz, 1H), 8.06 (t., $J^4$=1.60 Hz, 1H), 8.03 (t., $J^4$=1.68 Hz, 1H), 7.59-7.55 (m, 2H), 7.46-7.34 (m, 3H), 6.51 (br.s., 1H), 6.01 (s, 1H), 3.46-3.39 (m, 2H), 1.64 (sext., $J^3$=7.24 Hz, 2H), 0.97 (t., $J^3$=7.37 Hz, 3H).

68G: (5-Propylcarbamoyl-biphenyl-3-yl)-acetic acid methyl ester

A freshly prepared solution of $Ag(PhCO_2)$ in $NEt_3$ (0.5 g in 5 mL, filtered) was added to a solution of 68F (100 mg, 0.33 mmol) in 1 mL of dry MeOH. The reaction vessel was then sonicated for 2 minutes. The reaction mixture was then filtered through a pad of celite and the celite was rinsed with MeOH. The filtrate was concentrated and the residue was purified using $SiO_2$ with $CH_2Cl_2$/AcOEt 98:2 to 90:10. A yellowish oil was obtained (50 mg, 50%). NMR $^1$H (ppm, $CDCl_3$): 7.86 (s, 1H), 7.61-7.60 (m, 3H), 7.57 (s, 1H), 7.46-7.33 (m, 3H), 6.16 (br. s, 1H), 3.72 (s, 2H), 3.70 (s, 3H), 3.46-3.39 (m, 2H), 1.64 (sext., $J^3$=3=7.43 Hz, 2H), 0.98 (t., $J^3$6=7.50 Hz, 3H).

68H: (5-Propylcarbamoyl-biphenyl-3-yl)-acetic acid

A solution of LiOH (800 µL of a 2 M solution in $H_2O$) was added to a solution of 68G (50 mg, 0.16 mmol) in 4 mL of a 3:1 mixture MeOH/$H_2O$. After 1 hour, the reaction was complete as shown by TLC. The reaction mixture was then concentrated and the residue was dissolved in water and HCl 10% was then added. As no product precipitated, the aqueous solution was extracted 3 times with AcOEt. The combined organic layers were washed with brine, dried over $MgSO_4$ and concentrated. A white foamy solid was obtained and used in the next step without further purification (47 mg, quantitative). NMR $^1$H (ppm, DMSO-$d_6$): 7.86 (s, 1H), 7.61-7.60 (m, 3H), 7.57 (s, 1H), 7.46-7.33 (m, 3H), 6.16 (br, s, 1H), 3.72 (s, 2H), 3.70 (s, 3H), 3.46-3.39 (m, 2H), 1.64 (sext., $J^3$=7.43 Hz, 2H), 0.98 (t., $J^3$=7.50 Hz, 3H).

68I: Compound (81)

Using Preparation Method 3 with 2.2 equivalents of TMSOTf and $NEt_3$, 68H was reacted with phosgene to provide a carbamoylchloride. Using Preparation Method 4, Trimethylsilyl (TMS) protected S-benzyl-(L)-cysteine was prepared. The carbamoylchloride and TMS-protected S-benzyl-(L)-cysteine were reacted using Preparation Method 5 to provide compound (81) as a white solid (40%). NMR $^1$H (ppm, $CDCl_3$): 9.56 (d, $J^3$=7.12 Hz, 1H), 9.5 (br. s, 1H), 7.59-7.55 (m, 4H), 7.44-7.36 (m, 4H), 7.30-7.24 (m, 5H), 4.74 (m, 1H), 3.76 (s, 2H), 3.74 (s, 2H), 3.66 (m, 2H), 3.01-2.86 (m, 2H), 1.57 (sext., $J^3$=7.44 Hz, 2H), 0.73 (t, $J^3$=7.28 Hz, 3H).

Example 69

Compound (82)

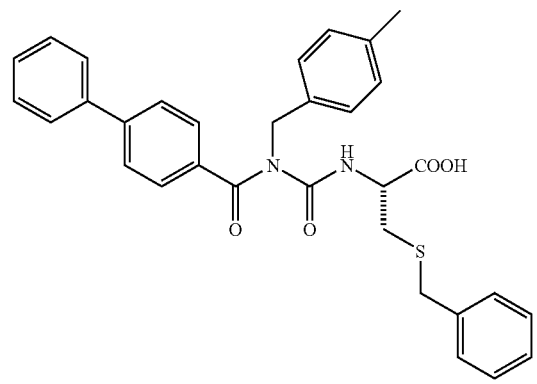

(82)

69A: N-(4-methyl)-benzyl-4-phenylbenzamide

Using preparation method 1, 4-phenylbenzoic acid (125 mg, 0.63 mmol) was reacted with 4-methylbenzylamine (85 mg, 0.7 mmol). The product was purified by flash chromatography on $SiO_2$ using $CH_2Cl_2$/hexanes 50:50 then pure $CH_2Cl_2$. White crystals were obtained (107 mg, 57%). NMR $^1H$ (ppm, $CDCl_3$): 7.84 (d, $J^3$=8.1 Hz, 2H), 7.63 (d, $J^3$=8.2 Hz, 2H), 7.59 (d, $J^3$=7.2 Hz, 2H), 7.44 (t, $J^3$=7.3 Hz, 2H), 7.36 (t, $J^3$=7.2 Hz, 1H), 7.26 (d, $J^3$=7.6 Hz, 2H), 7.16 (d, $J^3$=7.6 Hz, 2H), 6.34 (br. s, 1H), 4.62 (d, $J^3$=5.3 Hz, 2H), 1.55 (s, 3H).

69B: Compound (82)

Using preparation method 3, compound 69A (75 mg, 0.25 mmol) was reacted with phosgene to give a carbamoyl chloride. Using preparation method 4, the carbamoyl chloride and TMS-protected S-benzyl-(L)-cysteine (64 mg, 0.3 mmol) were reacted using preparation method 5. The product was purified by flash chromatography on $SiO_2$, using $CH_2Cl_2$ 100%, then $CH_2Cl_2/CH_3COOH$ 99.5:0.5, then $CH_2Cl_2/CH_3COOH/MeOH$ 99:0.5:0.5. A yellow oil was obtained (47 mg, 35%). NMR $^1H$ (ppm, $CDCl_3$): 9.46 (br. s, 1H), 7.40-6.86 (m, 18H), 5.05-4.99 (m, 1H), 4.62 (br. s, 2H), 3.62 (br. s, 2H), 3.03-2.86 (m, 2H), 2.15 (s, 3H).

Example 70

Compound (83)

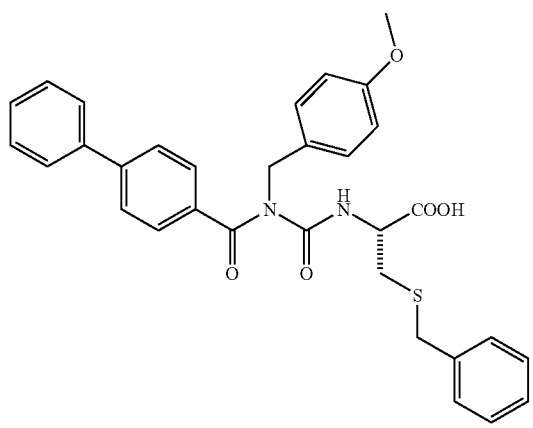

(83)

70A: N-(4-methoxy)-benzyl-4-phenylbenzamide

Using preparation method 1, 4-phenylbenzoic acid (125 mg, 0.63 mmol) was reacted with 4-methoxybenzylamine (96 mg, 0.7 mmol). The product was purified by flash chromatography on $SiO_2$ using $CH_2Cl_2$/hexanes 50:50 then pure $CH_2Cl_2$. White crystals were obtained (87 mg, 44%). NMR $^1H$ (ppm, $CDCl_3$): 7.84 (d, $J^3$=8.3 Hz, 2H), 7.63 (d, $J^3$=8.4 Hz, 2H), 7.59 (d, $J^3$=7.1 Hz, 2H), 7.44 (t, $J^3$=7.3 Hz, 2H), 7.36 (t, $J^3$=7.2 Hz, 1H), 7.29 (d, $J^3$=8.6 Hz, 2H), 6.88 (d, $J^3$=8.6 Hz, 2H), 6.34 (br. s, 1H), 4.59 (d, $J^3$=5.4 Hz, 2H), 3.80 (s, 3H).

70B: Compound (83)

Using preparation method 3, compound 70A (79 mg, 0.25 mmol) was reacted with phosgene to give a carbamoyl chloride. Using preparation method 4, the carbamoyl chloride and TMS-protected S-benzyl-(L)-cysteine (64 mg, 0.3 mmol) were reacted using preparation method 5. The product was purified by flash chromatography on $SiO_2$, using $CH_2Cl_2$ 100%, then $CH_2Cl_2/CH_3COOH$ 99.5:0.5, then $CH_2Cl_2/CH_3COOH/MeOH$ 99:0.5:0.5. A colourless oil was obtained (26 mg, 19%). NMR $^1H$ (ppm, $CDCl_3$): 9.63 (br. s, 1H), 7.56-6.73 (m, 18H), 4.96 (d, $J^3$=5.8 Hz, 2H), 4.77-4.73 (m, 1H), 3.76-3.72 (m, 5H), 3.02-2.88 (m, 2H).

Example 71

Compound (84)

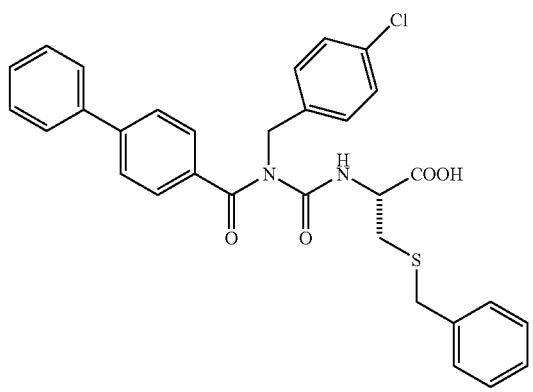

(84)

71A: N-(4-chloro)-benzyl-4-phenylbenzamide

Using preparation method 1, 4-phenylbenzoic acid (125 mg, 0.63 mmol) was reacted with 4-chlorobenzylamine (99 mg, 0.7 mmol). The product was purified by flash chromatography on $SiO_2$ using $CH_2Cl_2$/hexanes 50:50 then $CH_2Cl_2$ 100%. White crystals were obtained (102 mg, 50%). NMR $^1H$ (ppm, $CDCl_3$): 7.86-7.84 (m, 2H), 7.66-7.58 (m, 4H), 7.47-7.23 (m, 7H), 6.42 (br. s, 1H), 4.63 (br. s, 2H).

71B: Compound (84)

Using preparation method 3, compound 71A (80 mg, 0.25 mmol) was reacted with phosgene to give a carbamoyl chloride. Using preparation method 4, the carbamoyl chloride and TMS-protected S-benzyl-(L)-cysteine (64 mg, 0.3 mmol) were reacted using preparation method 5. The product was purified by flash chromatography on $SiO_2$, using $CH_2Cl_2$ 100%, then $CH_2Cl_2/CH_3COOH$ 99.5:0.5, then $CH_2Cl_2/CH_3COOH/MeOH$ 99:0.5:0.5. A colourless oil was obtained (18 mg, 13%). NMR $^1H$ (ppm, $CDCl_3$): 9.62 (d, $J^3$=7.0 Hz, 1H), 7.59-7.55 (m, 4H), 7.47-7.37 (m, 5H), 7.30-7.20 (m, 7H), 6.99 (d, $J^3$ 8.3 Hz, 2H), 4.98 (s, 2H), 4.79-4.72 (m, 1H), 3.77 (s, 2H), 3.04-2.87 (m, 2H).

Example 72

Compound (85)

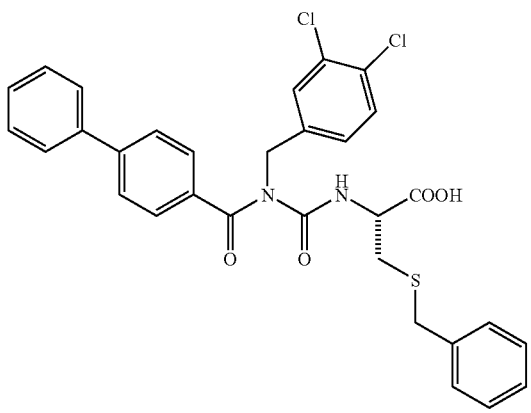

72A: Biphenyl-4-carboxylic acid 3,4-dichloro-benzylamide

Using preparation method 1, 4-phenylbenzoic acid (125 mg, 0.63 mmol) was reacted with 3,4-dichlorobenzylamine (123 mg, 0.7 mmol). The product was purified by flash chromatography on SiO$_2$ using CH$_2$Cl$_2$/hexanes 50:50 then CH$_2$Cl$_2$ 100%. White crystals were obtained (210 mg, 94%). NMR $^1$H (ppm, CDCl$_3$): 7.87-7.82 (m, 2H), 7.67-7.56 (m, 4H), 7.48-7.36 (m, 5H), 7.19 (tt, J$^3$=7.8 Hz, J$^4$=2.1 Hz, 1H), 6.51 (br. s, 1H), 4.61 (m, 2).

72B: Compound (85)

Using preparation method 3, compound 72A (89 mg, 0.25 mmol) was reacted with phosgene to give a carbamoyl chloride. Using preparation method 4, the carbamoyl chloride and TMS-protected S-benzyl-(L)-cysteine (64 mg, 0.3 mmol) were reacted using preparation method 5. The product was purified by flash chromatography on SiO$_2$, using CH$_2$Cl$_2$ 100%, then CH$_2$Cl$_2$/CH$_3$COOH 99.5:0.5, then CH$_2$Cl$_2$/CH$_3$COOH/MeOH 99:0.5:0.5. A yellow oil was obtained (77 mg, 52%). NMR $^1$H (ppm, CDCl$_3$): 9.60 (d, J$^3$=7.2 Hz, 1H), 7.60 (d, J$^3$=8.5 Hz, 2H), 7.57 (d, J$^3$=7.5 Hz, 2H), 7.47-7.38 (m, 5H), 7.33-7.24 (m, 6H), 7.12 (d, J$^4$=2.0 Hz, 1H), 6.92 (dd, J$^3$=8.1 Hz, J$^4$=2.4 Hz, 1H), 4.96 (s, 2H), 4.79-4.73 (m, 1H), 3.77 (s, 2H), 3.04-2.87 (m, 2H).

Example 73

Compound (86)

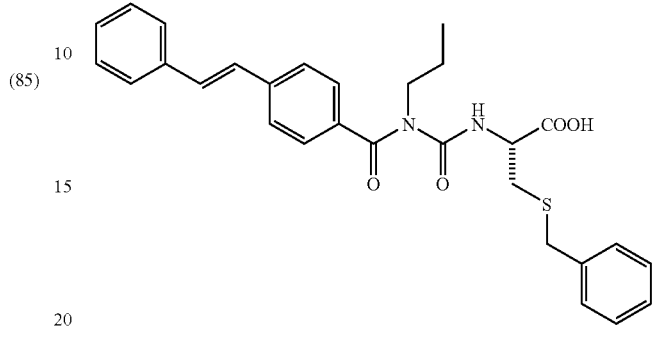

(86)

73A: 4-Styryl-benzoic acid methyl ester

Methyl 4-(bromomethyl)benzoate (458 mg, 2 mmol) was added to dry toluene (8 mL) along with triphenylphosphine (609 mg, 2.2 mmol). Under nitrogen, reflux conditions were applied for three hours and the mixture was then permitted to cool to room temperature. The fine white solid was filtered off, washed thoroughly with EtOAc, and dried under vacuum (967 mg). This solid was stirred in dry THF (4 mL) under nitrogen, and potassium t-butoxide (246 mg, 2.18 mmol) was added. The bright orange mixture was heated under reflux for one hour. Upon cooling, benzaldehyde (202 µL, 212 mg, 1.2 mmol) in dry THF (2 mL) was added. Further heating under reflux was applied for thirty minutes. The reaction mixture was diluted with water and extracted with EtOAc. The organic layers were combined, washed with water and then brine, dried over MgSO$_4$ and concentrated. The product was purified by flash chromatography on SiO$_2$ using EtOAc/hexanes 10:90. A white solid was obtained (97 mg, 20%).

73B: 4-Styryl-benzoic acid 73A (80 mg, 0.34 mmol) was suspended in EtOH (0.5 mL) and aqueous NaOH (1 M, 2 mL) and was heated to 80° C. for one hour. Upon cooling to room temperature, the solution was acidified with HCl (concentrated), was cooled to 0° C., and was filtered. The white crystalline precipitate was dried under vacuum (75 mg, quant.). NMR $^1$H (ppm, CDCl$_3$): 7.93 (d, J$^3$=8.3 Hz, 2H), 7.56-7.53 (m, 4H), 7.33 (t, J$^3$=7.4 Hz, 2H), 7.27-7.11 (m, 3H).

73C: N-Propyl-4-styryl-benzamide

Using preparation method 1, 73B (67 mg, 0.3 mmol) was reacted with n-propylamine (27 µL, 19.5 mg, 0.33 mmol). The product was purified by flash chromatography on SiO$_2$ using CH$_2$Cl$_2$/EtOAc 80:20. White crystals were obtained (48 mg, 61%). NMR $^1$H (ppm, CDCl$_3$): 7.74 (d, J$^3$=8.4 Hz, 2H), 7.53 (d, J$^3$ 8.1 Hz, 2H), 7.51 (d, J$^3$=6.4 Hz, 2H), 7.35 (t, J$^3$=7.1 Hz, 2H), 7.27 (tt, J$^3$=7.2 Hz, J$^4$=2.4 Hz, 1H), 7.17 (d, J$^3$=16 Hz, 1H), 7.09 (d, J$^3$=16 Hz, 1H), 6.21 (br. s, 1H), 3.45-3.38 (m, 2H), 1.64 (sext., J$^3$=7.3 Hz, 2H), 0.98 (t, J$^3$=7.4 Hz, 3H).

73D: Compound (86)

Using preparation method 3, compound 73C (48 mg, 0.18 mmol) was reacted with phosgene to give a carbamoyl chloride. Using preparation method 4, the carbamoyl chloride and TMS-protected S-benzyl-(L)-cysteine (64 mg, 0.3 mmol) were reacted using preparation method 5. Purification using $CH_2Cl_2$ 100%, then $CH_2Cl_2/CH_3COOH$ 99.5:0.5, then $CH_2Cl_2/CH_3COOH/MeOH$ 99:0.5:0.5 gave compound (86) as a yellow oil (35 mg, 39%). NMR $^1H$ (ppm, $CDCl_3$): 9.62 (d, $J^3$=7.0 Hz, 1H), 7.58-7.12 (m, 16H), 4.77-4.71 (m, 1H), 3.78 (s, 2H), 3.73-3.68 (m, 2H), 1.56 (sext., $J^3$=7.4 Hz, 2H), 0.74 (t, $J^3$=7.4 Hz, 3H).

Example 74

Compound (87)

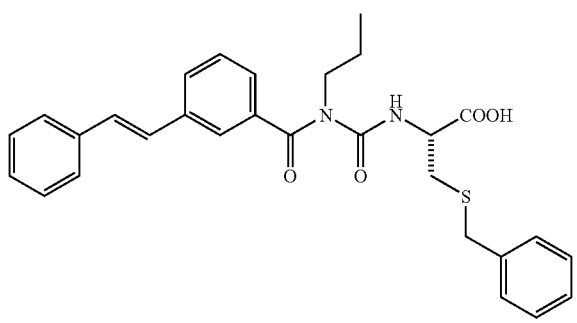

(87)

74A: 3-Styryl-benzoic acid methyl ester

Methyl 3-bromobenzoate (458 mg, 2 mmol), 1-styreneboronic acid pinacoyl ester (484 mg, 2.1 mmol), $Na_2CO_3$ (222 mg, 2.1 mmol), tetrakis(triphenylphosphino)palladium (116 mg, 0.1 mmol), water (4 mL) and 1,2-dimethoxyethane (6 mL) were stirred with reflux conditions for one hour, under nitrogen. The reaction mixture was diluted with water and was extracted three times with EtOAc. The organic layers were combined, washed with water and then brine, dried over $MgSO_4$ and concentrated. The product was purified by trituration with $Et_2O$. White crystals were obtained (393 mg, 82%). NMR $^1H$ (ppm, $CDCl_3$): 8.19 (t, $J^4$=1.6 Hz, 1H), 7.91 (dt, $J^3$=7.7 Hz, $J^4$=1.3 Hz, 1H), 7.67 (d, $J^3$=7.8 Hz, 1H), 7.52 (d, $J^3$=7.3 Hz, 2H), 7.42 (t, $J^3$=7.9 Hz, 1H), 7.36 (t, $J^3$=7.4 Hz, 2H), 7.30-7.26 (m, 1H), 7.19 (d, $J^3$=16.3 Hz, 1H), 7.11 (d, $J^3$=16.4 Hz, 1H), 3.06 (s, 3H).

74B: 3-Styryl-benzoic acid 74A (357 mg, 1.5 mmol) was suspended in EtOH (2 mL) and aqueous NaOH (1 M, 6 mL) and was heated to 80° C. for thirty minutes. Upon cooling to room temperature, the solution was acidified with HCl (concentrated), was cooled to 0° C., and was filtered. The white crystalline precipitate was dried under vacuum (303 mg, 90%). NMR $^1H$ (ppm, $CDCl_3$): 8.26 (s, 1H), 7.99 (d, $J^3$=7.7 Hz, 1H), 7.73 (d, $J^3$=8.2 Hz, 1H), 7.53 (d, $J^3$=7.3 Hz, 2H), 7.46 (td, $J^3$=7.7 Hz, $J^4$=2.2 Hz, 1H), 7.37 (t, $J^3$=7.4 Hz, 2H), 7.30-7.24 (m, 1H), 7.21 (d, $J^3$=17 Hz, 1H), 7.13 (d, $J^3$=16 Hz, 1H).

74C: N-Propyl-3-styryl-benzamide

Using preparation method 1, 74B (224 mg, 1 mmol) was reacted with n-propylamine (90 µL, 65 mg, 1.1 mmol). The product was purified by flash chromatography on $SiO_2$ using $CH_2Cl_2$/hexanes 40:60 to $CH_2Cl_2$/hexanes 60:40. White crystals were obtained (154 mg, 58%). NMR $^1H$ (ppm, $CDCl_3$): 7.92 (s, 1H), 7.60 (t, $J^3$=7.7 Hz, 2H), 7.51 (d, $J^3$=7.8 Hz, 2H), 7.40 (t, $J^3$=7.6 Hz, 1H), 7.36 (t, $J^3$=7.5 Hz, 2H), 7.29-7.26 (m, 1H), 7.18 (d, $J^3$=16.4 Hz, 1H), 7.10 (d, $J^3$=16.3 Hz, 1H), 6.12 (br. s, 1H), 3.47-3.40 (m, 2H), 1.65 (sext., $J^3$=7.2 Hz, 2H), 1.00 (t, $J^3$=7.4 Hz, 3H).

74D: Compound (87)

Using preparation method 3, compound 74C (66 mg, 0.25 mmol) was reacted with phosgene to give a carbamoyl chloride. Using preparation method 4, the carbamoyl chloride and TMS-protected S-benzyl-(L)-cysteine (64 mg, 0.3 mmol) were reacted using preparation method 5. Purification using $CH_2Cl_2$ 100%, then $CH_2Cl_2/CH_3COOH$ 99.5:0.5, then $CH_2Cl_2/CH_3COOH/MeOH$ 99:0.5:0.5 gave compound (87) as a colourless oil (68 mg, 54%). NMR $^1H$ (ppm, $CDCl_3$): 9.69 (d, $J^3$=7.0 Hz, 1H), 7.61-7.24 (m, 14H), 7.16 (d, $J^3$=18.3 Hz, 1H), 7.08 (d, $J^3$=16.2 Hz, 1H), 4.80-4.74 (m, 1H), 3.79 (s, 2H), 3.70 (t, $J^3$=7.5 Hz, 2H), 3.04-2.87 (m, 2H), 1.57 (sext., $J^3$=7.4H, 2H), 0.74 (t, $J^3$=7.4 Hz, 3H).

Example 75

Compound (88)

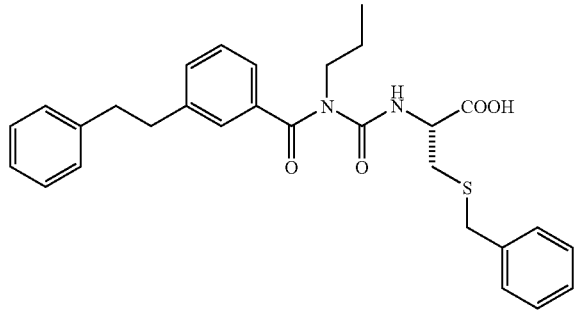

(88)

75A: 3-Trifluoromethanesulfonyloxy-benzoic acid methyl ester

Methyl 3-hydroxybenzoate (1.52 g, 10 mmol) was dissolved in dry $CH_2Cl_2$ (25 mL) along with 4-dimethylaminopyridine (244 mg, 2 mmol) and 2,4,6-collidine (1.6 mL, 1.45 g, 12 mmol). The solution was immersed in a dry ice/ $CH_3CN$ bath, and stirred under nitrogen. Triflic anhydride (2 mL, 3.36 g, 12 mmol) was added by dropping funnel. The reaction mixture was permitted to reach room temperature and stirring was maintained for thirty minutes. The reaction mixture was quenched with citric acid (10%) and was extracted three times with $CH_2Cl_2$. The combined organic layers were washed with water and then brine, were dried over $MgSO_4$ and were concentrated. The product was purified by flash chromatography on $SiO_2$ using EtOAc/hexanes 3:97. A colourless oil was obtained (2.50 g, 88%). NMR $^1H$ (ppm, CDCl$_3$): 8.09 (d, J$^3$=10.9 Hz, 1H), 7.92 (s, 1H), 7.57 (t, J$^3$=9.2 Hz, 1H), 7.46 (d, J$^3$=8.3 Hz, 1H), 3.94 (s, 3H).

75B: 3-Phenethyl-benzoic acid methyl ester 75A (1.14 g, 4 mmol), N-methylpyrrolidinone (2.2 mL), Fe(acac)$_3$ (70 mg, 0.2 mmol) and dry THF (25 mL) were stirred under nitrogen at room temperature. Phenethylmagnesium bromide (1.0 M in THF, 5 mL) was added by syringe. After stirring for fifteen minutes, HCl (1 M, 10 mL) was slowly added. The mixture was diluted with water and extracted three times with EtOAc. The organic layers were combined, washed with water and then brine, were dried over MgSO$_4$ and were concentrated. Purification was achieved using flash chromatography on SiO$_2$ with hexanes/toluene 50:50. A colourless oil was obtained (660 mg, 69%). NMR $^1$H (ppm, CDCl$_3$): 7.96-7.85 (m, 2H), 7.33-7.15 (m, 7H), 3.91 (s, 3H), 2.97-2.93 (m, 4H).

75C: 3-Phenethyl-benzoic acid 75B (660 mg, 2.75 mmol) was suspended in EtOH (2 mL) and aqueous NaOH (1 M, 6 mL) and was heated to 80° C. for thirty minutes. Upon cooling to room temperature, the solution was acidified with HCl (concentrated), was cooled to 0° C., and was filtered. The white crystalline precipitate was dried under vacuum (356 mg, 57%). NMR $^1$H (ppm, CDCl$_3$): 7.96-7.91 (m, 2H), 7.40-7.36 (m, 2H), 7.30-7.15 (n, 5H), 3.02-2.90 (m, 4H).

75D: 3-Phenethyl-N-propyl-benzamide

Using preparation method 1, 75C (226 mg, 1 mmol) was reacted with n-propylamine (90 μL, 65 mg, 1.1 mmol). No purification was necessary. White crystals were obtained (107 mg, 40%). NMR $^1$H (ppm, CDCl$_3$): 7.96-7.89 (m, 2H), 7.56-7.12 (m, 7H), 6.03 (br. s, 1H), 3.42-3.38 (m, 2H), 3.04-2.87 (m, 4H), 1.63 (sext., J$^3$=7.3 Hz, 2H), 0.98 (t, J$^3$=7.4 Hz, 3H).

75E: Compound (88)

Using preparation method 3, compound 75D (67 mg, 0.25 mmol) was reacted with phosgene to give a carbamoyl chloride. Using preparation method 4, the carbamoyl chloride and TMS-protected S-benzyl-(L)-cysteine cysteine (60 mg, 0.28 mmol) were reacted using preparation method 5. Purification using CH$_2$Cl$_2$ 100%, then CH$_2$Cl$_2$/CH$_3$COOH 99.5:0.5, then CH$_2$Cl$_2$/CH$_3$COOH/MeOH 99:0.5:0.5 gave compound (88) as a colourless oil was obtained (45 mg, 36%). NMR $^1$H (ppm, CDCl$_3$): 9.69 (d, J$^3$=6.9 Hz, 1H), 7.41-7.11 (m, 14H), 4.76-4.79 (m, 1H), 3.78 (s, 2H), 3.58 (t, J$^3$=7.5 Hz, 2H), 3.02-2.86 (m, 2H), 1.50 (sext., J$^3$=7.5 Hz, 2H), 0.70 (t, J$^3$=7.4 Hz, 3H).

Example 76

Compound (89)

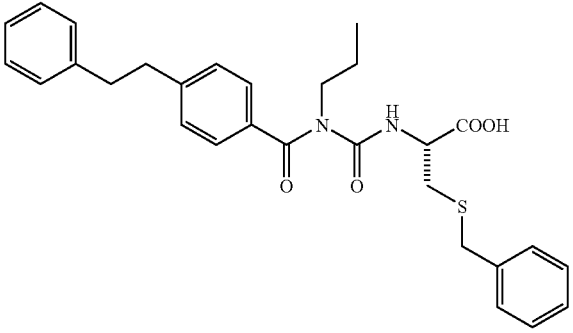

(89)

76A: 4-Trifluoromethanesulfonyloxy-benzoic acid methyl ester

Methyl 4-hydroxybenzoate (1.52 g, 10 mmol) was dissolved in dry CH$_2$Cl$_2$ (25 mL) along with 4-dimethylaminopyridine (244 mg, 2 mmol) and 2,4,6-collidine (1.6 mL, 1.45 g, 12 mmol). The solution was immersed in a dry ice/CH$_3$CN bath, and stirred under nitrogen. Triflic anhydride (2 mL, 3.36 g, 12 mmol) was added by syringe. The reaction mixture was permitted to reach room temperature and stirring was maintained for thirty minutes. The reaction mixture was quenched with NaHCO$_3$ (conc.) and was extracted three times with CH$_2$Cl$_2$. The combined organic layers were washed with water and then brine, were dried over MgSO$_4$ and were concentrated. The product was purified by flash chromatography on SiO$_2$ using hexanes/toluene 50:50. A colourless oil was obtained (2.52 g, 88%). NMR $^1$H (ppm, CDCl$_3$): 8.13 (d, J$^3$=8.9 Hz, 2H), 7.34 (d, J$^3$=8.9 Hz, 2H), 3.93 (s, 3H).

76B: 4-Phenethyl-benzoic acid methyl ester 76A (2.27 g, 8 mmol), N-methylpyrrolidinone (4.4 mL), Fe(acac)$_3$ (140 mg, 0.4 mmol) and dry THF (50 mL) were stirred under nitrogen at room temperature. Phenethylmagnesium bromide (1.0 M in THF, 10 mL) was added by syringe. After stirring for fifteen minutes, HCl (1 M, 20 mL) was slowly added. The mixture was diluted with water and extracted three times with EtOAc. The organic layers were combined, washed with water and then brine, were dried over MgSO$_4$ and were concentrated. Purification was achieved using flash chromatography on SiO$_2$ with hexanes/toluene 50:50. A colourless oil was obtained (1.575 g, 82%). NMR $^1$H (ppm, CDCl$_3$): 7.94 (d, J$^3$ 8.2 Hz, 2H), 7.29-7.13 (m, 7H), 3.89 (s, 3H), 3.01-2.89 (m, 4H).

76C: 4-Phenethyl-benzoic acid 76B (1.20 g, 5 mmol) was suspended in EtOH (4 mL) and aqueous NaOH (1 M, 10 mL) and was heated to 75° C. for one hour. Upon cooling to room temperature, the solution was acidified with HCl (conc.), was cooled to 0° C., and was filtered. The white crystalline precipitate was dried under vacuum (835 mg, 74%). NMR $^1$H (ppm, CDCl$_3$): 8.00 (d, J$^3$=8.2 Hz, 2H), 7.29-7.13 (m, 9H), 3.01-2.91 (m, 4H).

76D: 4-Phenethyl-N-propyl-benzamide

Using preparation method 1, 76C (226 mg, 1 mmol) was reacted with n-propylamine (90 µL, 65 mg, 1.1 mmol). No purification was necessary. White crystals were obtained (103 mg, 39%). NMR $^1$H (ppm, CDCl$_3$): 7.65 (d, J$^3$=8.1 Hz, 2H), 7.28-7.12 (m, 7H), 6.05 (br. s, 1H), 3.44-3.38 (m, 2H), 3.01-2.92 (m, 4H), 1.63 (sext., J$^3$=7.3 Hz, 2H), 0.98 (t, J$^3$=7.4 Hz, 3H).

76E: Compound (89)

Using preparation method 3, compound 76D (67 mg, 0.25 mmol) was reacted with phosgene to give a carbamoyl chloride. Using preparation method 4, the carbamoyl chloride and TMS-protected S-benzyl-(L)-cysteine cysteine (60 mg, 0.28 mmol) were reacted using preparation method 5. Purification using CH$_2$Cl$_2$ 100%, then CH$_2$Cl$_2$/CH$_3$COOH 99.5:0.5, then CH$_2$Cl$_2$/CH$_3$COOH/MeOH 99:0.5:0.5 gave compound (89) as a colourless oil was obtained (20 mg, 16%). NMR $^1$H (ppm, CDCl$_3$): 9.66 (br. s, 1H), 7.36-7.11 (m, 14H), 4.71 (br. s, 1H), 3.76 (s, 2H), 3.64 (br. s, 2H) 2.92 (br. s, 6H), 1.50 (br. s, 2H), 0.70 (br. s, 3H).

Example 77

Compound (90)

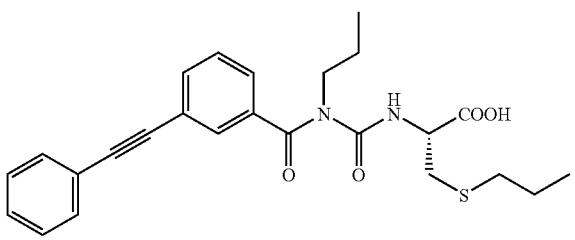

(90)

77A: Boc-(S)-propyl-L-cysteine

Using preparation method 6, cysteine (242 mg, 2 mmol) was reacted with propyl iodide (219 µL, 2.2 mmol) to provide Boc-(S)-propyl-L-cysteine as thick pale yellow oil (474 mg, 90%). NMR $^1$H (ppm, DMSO-d$_6$): 4.27 (br. t., J$^3$=6.97 Hz, 1H), 3.00-2.77 (m, 2H), 2.54 (t., J$^3$=7.19 Hz, 2H), 1.59 (sex., J$^3$=7.28 Hz, 2H), 1.45 (s, 9H), 0.98 (t., J$^3$=7.31 Hz, 3H).

77B: Compound (90)

Using preparation method 3, compound from example 60B (445 mg, 1.7 mmol) was reacted with phosgene to provide a carbamoylchloride. This carbamoyl chloride was dissolved in acetonitrile to obtain a 0.4 M solution. Using preparation method 7, compound 77A (58 mg, 0.22 mmol) was deprotected and reacted with 660 µL of the carbamoylchloride solution. The reaction was then stirred at room temperature for 10 min. Purification by flash chromatography using CH$_2$Cl$_2$/Pet. Et. 80:20 then CH$_2$Cl$_2$ 100% then CH$_2$Cl$_2$/MeOH/AcOH 99:0.5:0.5 to give compound (90) as a pale yellow oil (25 mg, 25%). NMR $^1$H (ppm, CDCl$_3$): 9.62 (d, J$^3$=6.7 Hz, 1H), 7.63-7.60 (m, 2H), 7.54-7.51 (m, 2H), 7.43-7.40 (m, 2H), 7.36-7.34 (m, 3H), 4.78-4.71 (m, 1H), 3.70-3.62 (m, 2H), 3.13-3.00 (m, 2H), 2.57 (t., J$^3$=7.24 Hz, 2H), 1.68-1.48 (m, 4H), 0.97 (t, J$^3$=7.30 Hz, 3H), 0.74 (t, J$^3$=7.35 Hz, 3H). MS (−ESI): M−H$^-$ 451.1.

Example 78

Compound (91)

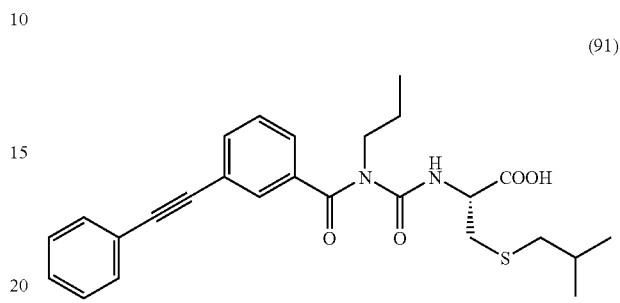

(91)

78A: Boc-(S)-isobutyl-L-cysteine

Using preparation method 6, cysteine (242 mg, 2 mmol) was reacted with 2-methyl-1-bromopropane (239 µL, 2.2 mmol) to provide Boc-(S)-isobutyl-L-cysteine as thick pale yellow oil (510 mg, 92%). NMR $^1$H (ppm, DMSO-d$_6$): 4.27 (br. t., J$^3$=7.06 Hz, 1H), 2.99-2.77 (m, 2H), 2.44 (d, J$^3$=6.81 Hz, 2H), 1.75 (hept., J$^3$=6.71 Hz, 1H), 1.44 (s, 9H), 0.99 (d, J$^3$=6.62 Hz, 6H).

78B: Compound (91)

Using preparation method 7, compound 78A (62 mg, 0.22 mmol) was deprotected and reacted with 670 µL of the carbamoylchloride solution from example 77B. The reaction was then stirred at room temperature for 10 min. Purification by HPLC semi-preparative to give compound (91) as a colourless oil (25 mg, 24%). NMR $^1$H (ppm, CDCl$_3$): 9.62 (d, J$^3$=6.84 Hz, 1H), 7.64-7.61 (m, 2H), 7.54-7.50 (m, 2H), 7.43-7.40 (m, 2H), 7.36-7.33 (m, 3H), 4.78-4.72 (m, 1H), 3.70-3.65 (m, 2H), 3.10-2.99 (m, 2H), 2.47 (d, J$^3$=6.85 Hz, 2H), 1.80 (hept., J$^3$=6.69 Hz, 1H), 1.54 (sex., J$^3$=7.51 Hz, 2H), 0.97 (d, J$^3$=6.64 Hz, 6H), 0.74 (t, J$^3$=7.37 Hz, 3H). MS (+ESI): M+H$^+$ 467.1.

Example 79

Compound (92)

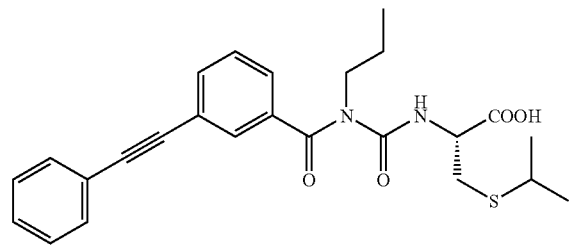

(92)

79A: Boc-(S)-isopropyl-L-cysteine

Using preparation method 6, cysteine (242 mg, 2 mmol) was reacted with 2-bromopropane (207 µL, 2.2 mmol) to provide Boc-(S)-propyl-L-cysteine as thick pale yellow oil (480 mg, 91%). NMR $^1$H (ppm, DMSO-d$_6$): 4.28 (br. t., $J^3$=6.95 Hz, 1H), 3.03-2.80 (m, 3H), 1.44 (s, 9H), 1.24 (d, $J^3$=6.8 Hz, 6H).

79B: Compound (92)

Using preparation method 7, compound 79A (56 mg, 0.21 mmol) was deprotected and reacted with 640 µL of the carbamoylchloride solution from example 77B. The reaction was then stirred at room temperature for 10 min. Purification by HPLC semi-preparative to give compound (92) as a colourless yellow oil (25 mg, 24%). NMR $^1$H (ppm, CDCl$_3$): 9.60 (d, $J^3$=6.80 Hz, 1H), 7.63-7.60 (m, 2H), 7.54-7.50 (m, 2H), 7.46-7.40 (m, 2H), 7.36-7.32 (m, 3H), 4.78-4.72 (m: 1H), 3.70-3.65 (m, 2H), 3.14-2.94 (m, 3H), 1.54 (sex., $J^3$=7.48 Hz, 2H), 1.27 (d, $J^3$=6.69 Hz, 6H), 0.74 (t, $J^3$=7.37 Hz, 3H). MS (–ESI): M–H$^-$ 451.1.

Example 80

Compound (93)

(93)

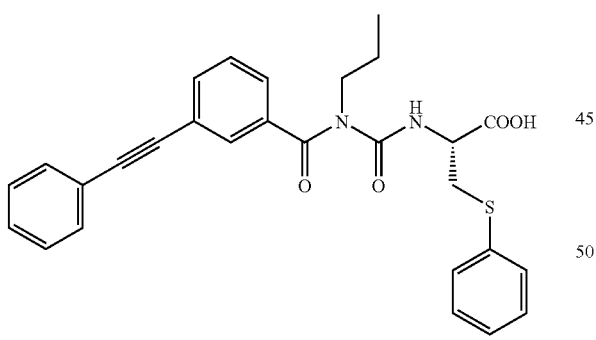

Using preparation method 8, carbamoylchloride from example 77B was reacted with S-phenyl-L-cysteine. Purification by flash chromatography using CH$_2$Cl$_2$/Pet.Et. 80:20, then CH$_2$Cl$_2$ 100% then CH$_2$Cl$_2$/MeOH/AcOH 99:0.5:0.5 gave compound (93) as a pale yellow oil (43 mg, 44%). NMR $^1$H (ppm, CDCl$_3$): 9.66 (d, $J^3$=6.86 Hz, 1H), 7.63-7.60 (m, 1H), 7.56-7.52 (m, 3H), 7.47-7.40 (m, 2H), 7.42-7.34 (m, 5H), 7.39-7.21 (m, 3H), 4.80-4.74 (m, 1H), 3.62-3.57 (m, 2H), 3.56-3.31 (m, 2H), 1.48 (sex., $J^3$=7.46 Hz, 2H), 0.71 (t, $J^3$=7.31 Hz, 3H). MS (–ESI): M–H$^-$ 402.0.

Example 81

Compound (94)

(94)

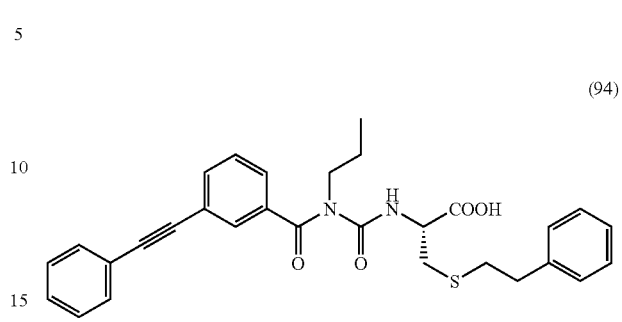

81A: Boc-(S)-phenethyl-L-cysteine

Using preparation method 6, cysteine (242 mg, 2 mmol) was reacted with 2-bromopropane (207 µL, 2.2 mmol) to provide Boc-(S)-phenethyl-L-cysteine as thick pale yellow oil (586 mg, 90%). NMR $^1$H (ppm, DMSO-d$_6$): 7.24-7.13 (m, 5H), 4.30-4.26 (m, 1H), 3.00-2.76 (m, 6H), 1.41 (s, 9H).

81B: Compound (94)

Using preparation method 7, compound 81A (78 mg, 0.24 mmol) was deprotected and reacted with 528 µL of the carbamoylchloride solution from example 77B. The reaction was then stirred at room temperature for 10 min. Purification by flash chromatography using CH$_2$Cl$_2$/Pet.Et. 80:20, then CH$_2$Cl$_2$ 100% then CH$_2$Cl$_2$/MeOH/AcOH 99:0.5:0.5 gave compound (94) as a pale yellow oil (63 mg, 51%). NMR $^1$H (ppm, CDCl$_3$): 9.67 (d, $J^3$=6.88 Hz, 1H), 7.63-7.58 (m, 2H), 7.54-7.51 (m, 2H), 7.42 (t, $J^3$=7.58 Hz, 1H), 7.36-7.34 (m, 3H), 7.26-7.7.24 (m, 1H), 7.21-7.17 (m, 3H), 4.80-4.74 (m, 1H), 3.69-3.64 (m, 2H), 3.15-3.00 (m, 2H), 2.92-2.80 (m, 4H), 1.49 (sex., $J^3$=7.43 Hz, 2H), 0.72 (t, $J^3$=7.34 Hz, 3H). MS (–ESI): M–H$^-$ 513.7.

Example 82

Compound (95)

(95)

82A: Boc-(S)-phenylpropyl-L-cysteine

Using preparation method 6, cysteine (242 mg, 2 mmol) was reacted with 1-bromo-3-phenylpropane (334 µL, 2.2 mmol) to provide Boc-(S)-phenylpropyl-L-cysteine as thick pale yellow oil (638 mg, 94%). NMR $^1$H (ppm, DMSO-d$_6$): 7.26-7.10 (m, 5H), 4.27-4.24 (m, 1H), 3.02-2.78 (m, 2H), 2.69 (t, J³=7.32, 2H), 2.55 (t, J³=7.31 Hz, 2H), 1.84 (q, J³=7.43 Hz, 2H), 1.41 (s, 9H).

82B: Compound (95)

Using preparation method 7, compound 82A (48 mg, 0.14 mmol) was deprotected and reacted with 423 µL of the carbamoylchloride solution from example 77B. The reaction was then stirred at room temperature for 10 min. Purification by semi-preparative HPLC to give compound (95) as colourless oil (29 mg, 39%). NMR ¹H (ppm, CDCl₃): 9.66 (d, J³=3=6.76 Hz, 1H), 7.64-7.59 (m, 2H), 7.54-7.50 (m, 2H), 7.46-7.33 (m, 5H), 7.28-7.23 (m, 2H), 7.18-7.14 (m, 3H), 4.78-4.72 (m, 1H), 3.70-3.64 (m, 2H), 3.13-3.00 (m, 2H), 2.69 (t, J³=1=7.40 Hz, 2H), 2.60 (t, J³=7.18 Hz, 2H), 1.91 (q, J³=7.57 Hz, 2H), 1.53 (sex., J³=7.49 Hz, 2H), 0.73 (t, J³=7.35 Hz, 3H). MS (–ESI): M–H⁻ 529.2.

Example 83

Compound (96)

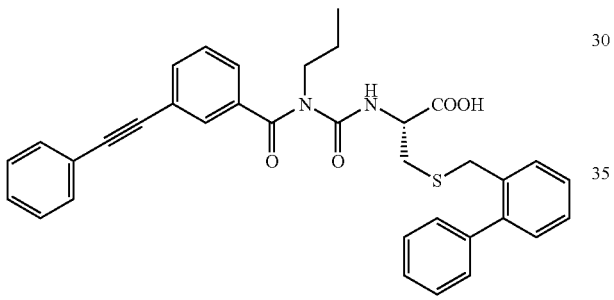

(96)

83A: Boc-(S)-biphenyl-2-ylmethyl-L-cysteine

Using preparation method 6, cysteine (35.5 mg, 0.25 mmol) was reacted with 2-biphenyl-2-ylmethylbromide (50.5 µL, 0.28 mmol) to provide Boc-(S)-biphenyl-2-ylmethyl-L-cysteine as thick pale yellow oil (252 mg, 65%). NMR ¹H (ppm, CDCl₃): 9.86 (br. s, 1H), 7.42-7.18 (m, 9H), 5.20 (d, J³=7.05 Hz 1H), 4.44 (br s., 1H), 3.77-3.67 (m, 2H), 2.96 (m, 2H), 1.43 (s, 9H).

83B: Compound (96)

Using preparation method 7, compound 83A (47 mg, 0.12 mmol) was deprotected and reacted with 360 µL of the carbamoylchloride solution from example 77B. The reaction was then stirred at room temperature for 10 min. Purification by semi-preparative HPLC to give compound (96) as colourless oil (6 mg, 9%). NMR ¹H (ppm, CDCl₃): 9.55 (d, J³=3=6.70 Hz, 1H), 7.64-7.58 (m, 2H), 7.54-7.50 (m, 2H), 7.46-7.23 (m, 14H), 4.59-4.53 (m, 1H), 3.76 (s, 2H), 3.67-3.62 (m, 2H), 3.07-3.85 (m,2H), 1.52 (sex., J³=7.48 Hz, 2H), 0.73 (t, J³=7.40 Hz, 3H). MS (+ESI): M+H⁺ 577.1.

Example 84

Compound (97)

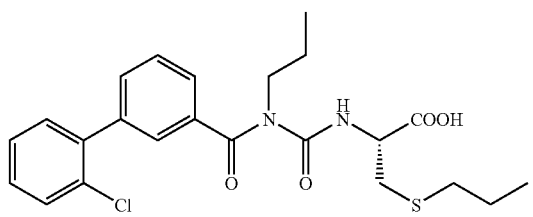

(97)

Using preparation method 3, compound from example 43A (527 mg, 1.93 mmol) was reacted with phosgene to provide a carbamoylchloride. This carbamoylchloride was dissolved in acetonitrile to obtain a 2 M solution. Using preparation method 7, compound 77A (45 mg, 0.17 mmol) was deprotected and reacted with 374 µL of the carbamoylchloride solution. The reaction was then stirred at room temperature for 10 min. Purification by semi-preparative HPLC afforded compound (97) as a colourless oil. NMR ¹H (ppm, CDCl₃): 9.67 (d, J³=6.81 Hz, 1H), 7.54-7.51 (m, 3H), 7.48-7.44 (m, 2H), 7.32-7.28 (m, 3H), 4.93 (br. s, 1H), 4.77-4.71 (m, 1H), 3.75-3.70 (m, 2H), 3.12-2.98 (m, 2H), 2.56 (t., J³=7.27 Hz, 2H), 1.66-1.49 (m, 4H), 0.96 (t, J³=7.30 Hz, 3H), 0.73 (t, J³=7.34 Hz, 3H). MS (+ESI): M+H⁺ 463.5.

Example 85

Compound (98)

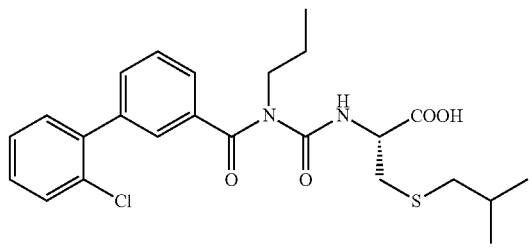

(98)

Using preparation method 3, compound from example 43A (112 mg, 0.407 mmol) was reacted with phosgene to provide a carbamoylchloride. This carbamoylchloride was dissolved in acetonitrile to obtain a 2 M solution. Using preparation method 7, compound 78A (102 mg, 0.37 mmol) was deprotected and reacted with 814 µL of the carbamoylchloride solution. The reaction was then stirred at room temperature for 10 min. Purification by semi-preparative HPLC afforded compound (98) as a colourless oil. NMR ¹H (ppm, CDCl₃): 9.67 (d, J³=6.73 Hz, 1H), 7.54-7.44 (m, 5H), 7.32-7.28 (m, 3H), 4.93 (br. s, 1H), 4.76-4.70 (m, 1H), 4.4 (br. s., 2H), 3.75-3.70 (m, 2H), 3.11-2.98 (m, 2H), 2.47 (d, J³=6.82 Hz, 2H), 1.80 (hept., J³=6.69 Hz, 1H), 1.54 (sex., J³=7.46 Hz, 2H), 0.96 (d, J³=6.63 Hz, 6H), 0.73 (t, J³=7.36 Hz, 3H). MS (+ESI): M+H⁺ 477.5.

Example 86

Compound (99)

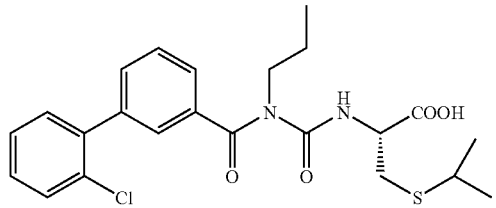

(99)

Using preparation method 3, compound from example 43A (69 mg, 0.26 mmol) was reacted with phosgene to provide a carbamoylchloride. This carbamoyl chloride was dissolved in acetonitrile to obtain a 2 M solution. Using preparation method 7, compound 79A (60 mg, 0.23 mmol) was deprotected and reacted with 506 µL of the carbamoylchloride solution. The reaction was then stirred at room temperature for 10 min. Purification by semi-preparative HPLC afforded compound (99) as a colourless oil. NMR $^1$H (ppm, CDCl$_3$): 9.67 (d, J$^3$=6.76 Hz, 1H), 7.54-7.51 (m, 3H), 7.48-7.43 (m, 2H), 7.32-7.30 (m, 3H), 4.78-4.72 (m, 1H), 3.75-3.70 (m, 2H), 3.07 (t, J$^3$=6.55 Hz, 2H), 3.01 (hept., J$^3$=6.67 Hz, 1H), 1.55 (sex., J$^3$=7.52 Hz, 2H), 1.26 (d, J$^3$=6.69 Hz, 6H), 0.73 (t, J$^3$=7.39 Hz, 3H). MS (+ESI): M+H$^+$ 463.1.1.

Example 87

Compound (100)

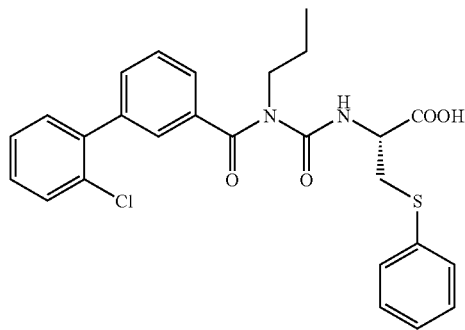

(100)

Using preparation method 3, compound from example 43A (61 mg, 0.22 mmol) was reacted with phosgene to provide a carbamoylchloride. This carbamoylchloride was dissolved in acetonitrile to obtain a 2 M solution. Using preparation method 8, this carbamoylchloride was reacted with S-phenyl-L-cysteine. Purification by semi-preparative HPLC afforded compound (100) as a colourless oil. NMR $^1$H (ppm, CDCl$_3$): 9.72 (d, J$^3$=6.75 Hz, 1H), 7.52-7.41 (m, 7H), 7.32-7.31 (m, 2H), 7.28-7.17 (m, 4H), 4.80-4.71 (m, 1H), 4.5 (br. s., 2H), 3.67-3.62 (m, 2H), 3.57-3.38 (m, 2H), 1.49 (sex., J$^3$=7.55 Hz, 2H), 0.70 (t, J$^3$=7.37 Hz, 3H). MS (+ESI): M+H$^+$ 497.5.

Example 88

Compound (101)

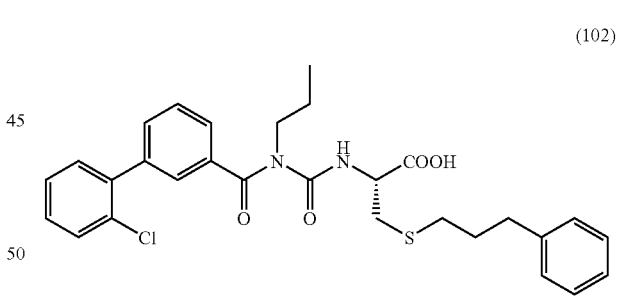

(101)

Using preparation method 3, compound from example 43A (72 mg, 0.27 mmol) was reacted with phosgene to provide a carbamoylchloride. This carbamoylchloride was dissolved in acetonitrile to obtain a 2 M solution. Using preparation method 7, compound 81A (77 mg, 0.24 mmol) was deprotected and reacted with 528 µL of the carbamoylchloride solution. The reaction was then stirred at room temperature for 10 min. Purification by flash chromatography using CH$_2$Cl$_2$/Pet.Et. 80:20, then CH$_2$Cl$_2$ 100% then CH$_2$Cl$_2$/MeOH/AcOH 99:0.5:0.5 gave compound (101) as a pale yellow oil. NMR $^1$H (ppm, CDCl$_3$): 9.73 (d, J$^3$=6.90 Hz, 1H), 8.05 (br. s., 1H), 7.56-7.44 (m, 5H), 7.33-7.31 (m, 3H), 7.27-7.23 (m, 2H), 7.19-7.15 (m, 3H), 4.82-4.76 (m, 1H), 3.75-3.70 (m, 2H), 3.16-2.97 (m, 2H), 2.92-2.80 (m, 4H), 1.52 (sex., J$^3$=7.49 Hz, 2H), 0.73 (t, J$^3$=7.35 Hz, 3H). MS (−ESI): M−H$^−$ 523.3.

Example 89

Compound (102)

(102)

Using preparation method 3, compound from example 43A (118 mg, 0.43 mmol) was reacted with phosgene to provide a carbamoylchloride. This carbamoylchloride was dissolved in acetonitrile to obtain a 2 M solution. Using preparation method 7, compound 82A (131 mg, 0.39 mmol) was deprotected and reacted with 858 µL of the carbamoylchloride solution. The reaction was then stirred at room temperature for 10 min. Purification by flash chromatography using CH$_2$Cl$_2$/Pet.Et. 80:20, then CH$_2$Cl$_2$ 100% then CH$_2$Cl$_2$/MeOH/AcOH 99:0.5:0.5 gave compound (102) as a pale yellow oil. NMR $^1$H (ppm, CDCl$_3$): 9.72 (d, J$^3$=6.86 Hz, 1H), 9.00 (br. s., 1H), 7.53-7.44 (m, 5H), 7.33-7.30 (m, 3H), 7.27-7.25 (m, 2H), 7.17-7.15 (m, 3H), 4.81-4.75 (m, 1H), 3.76-3.71 (m, 2H), 3.15-3.01 (m, 2H), 2.70 (t, J$^3$=7.38 Hz, 2H), 2.61 (t, J³=7.17 Hz, 2H), 1.91 (q, J³=7.47 Hz, 2H), 1.56 (sex., J³=7.41 Hz, 2H), 0.74 (t, J³=7.35 Hz, 3H). MS (−ESI): M−H⁺: 537.5.

Example 90

Compound (103)

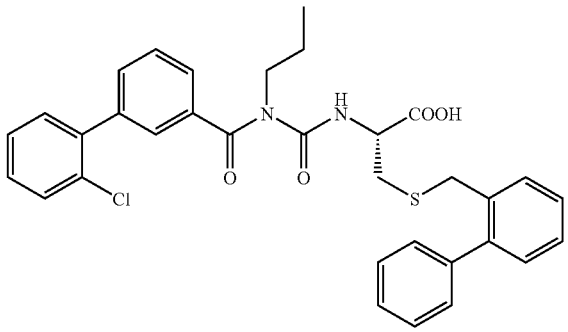

(103)

Using preparation method 3, compound from example 43A (45 mg, 0.17 mmol) was reacted with phosgene to provide a carbamoylchloride. This carbamoylchloride was dissolved in acetonitrile to obtain a 2 M solution. Using preparation method 7, compound 83A (58 mg, 0.15 mmol) was deprotected and reacted with 330 μL of the carbamoylchloride solution. The reaction was then stirred at room temperature for 10 min. Purification by semi-preparative HPLC gave compound (103) as colourless oil. NMR ¹H (ppm, CDCl₃): 9.60 (d, J³=6.68 Hz, 1H), 7.54-7.44 (m, 5H), 7.40-7.23 (m, 12H), 4.67 (br. s., 1H), 4.58-4.52 (m, 1H), 3.75 (s, 2H), 3.73-3.68 (m, 2H), 3.06-2.84 (m, 2H), 1.50 (sex., J³=7.59 Hz, 2H), 0.71 (t, J³=7.34 Hz, 3H). MS (−ESI): M−H⁻ 585.7.

Example 91

Compound (104)

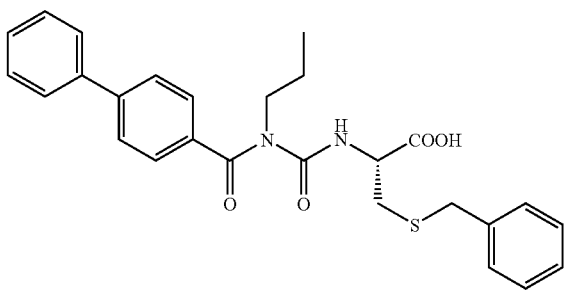

(104)

91A: 1-Biphenyl-3-yl-2-diazo-ethanone

A mixture of 3-phenylbenzoic acid (595 mg, 3 mmol) and thionyl chloride (1 mL) was heated at 60° C. for 2.5 hours. After this time, the thionyl chloride was removed under vaccum. Toluene was then added and the resulting solution was concentrated. This procedure was repeated two more times. The oily residue was then dissolved in dry THF. At 0° C., triethylamine (304 μL, 3 mmol) and trimethylsilyldiazomethane were added successively. The reaction was then stirred for 20 hours at room temperature. The reaction was concentrated. Purification of the residue by flash chromatography using CH₂Cl₂/AcOEt 95:5 to 85:15 gave the compound as a yellow thick oil (141 mg, 21%). NMR ¹H (ppm, CDCl₃): 7.98 (t., J³=1.37 Hz, 1H), 7.74-7.67 (m, 2H), 7.60-7.57 (m, 2H), 7.50-7.24 (m, 4H), 5.95 (s, 1H). MS (+ESI): M+H⁺: 222.9.

91B: Biphenyl-3-yl-acetic acid methyl ester 2 mL of a freshly prepared and filtered solution of Ag(Ph-COO) in triethylamine (500 mg in 5 mL), was added to a solution of compound 91A in 2 mL of methanol. The dark solution was sonicated for 2 minutes. The reaction mixture was then filtered through a pad of silica gel. The residue was rinsed with methanol. The combined filtrates were concentrated and the residue was purified by flash chromatography using Pet. Et./AcOEt 98:2 to 96:4 to give the compound as a colourless oil (141 mg, quant.). NMR ¹H (ppm, CDCl₃): 7.58 (d., J³=7.22 Hz, 2H), 7.50-7.48 (m, 2H), 7.45-7.42 (m, 2H), 7.40 (d., J³=2.51 Hz, 1H), 7.37-7.31 (m, 1H), 7.28-7.25 (m, 1H), 3.70 (s, 3H), 3.69 (s, 2H).

91C: Biphenyl-3-yl-acetic acid 3.5 mL of a 2 M LiOH solution in methanol was added to a solution of compound 91B in 3:1 MeOH/H₂O solution. The reaction was stirred at room temperature for 20 hours. The mixture was concentrated under vacuum and the residue dissolved in water. 10% HCl was then added leading to a white precipitate. The solids were collected, washed thoroughly with water and dried (125 mg, 95%). NMR ¹H (ppm, MeOD): 7.58 (d., J³=7.26 Hz, 2H), 7.52-7.47 (m, 2H), 7.43-7.37 (m, 3H), 7.34-7.24 (m, 2H), 3.66 (s, 2H). MS (−ESI): M−H⁺: 211.

91D: 2-Biphenyl-3-yl-N-propyl-acetamide

EDAC.HCl (114 mg, 0.59 mmol) was added to a mixture of compound 91C (125 mg, 0.59 mmol), propylamine (49 μL, 0.59 mmol) and HOBT (80 mg, 0.59 mmol) in 1 mL of CH₃CN. The reaction was stirred for 72 hours. After this time, the mixture was diluted with AcOEt. The organic layer was washed three times with HCl 2N, three times with NaOH 2N, dried over MgSO₄ and concentrated. A with solid was obtained (100 mg, 67%). NMR ¹H (ppm, CDCl₃): 7.57 (d., J³=7.05 Hz, 2H), 7.52-7.32 (m, 6H), 7.23 J³=7.94 Hz, 1H), 5.65 (br. s., 1H), 3.62 (s, 2H), 3.20-3.13 (m, 2H), 1.44 (sex. J³=7.21 Hz, 2H), 0.83 (t, J³=7.43 Hz, 3H). NMR ¹³C (ppm, CDCl₃): 170.9, 141.9, 140.5, 135.5, 129.3, 128.8, 128.2, 127.5, 127.0, 126.0, 43.8, 41.3, 22.7, 11.2. MS (+ESI): M+H⁺: 254.3.

91E: Compound (104)

Using Preparation Method 8, compound 91D (51 mg, 0.2 mmol) and S-benzyl-(L)-cysteine (96 mg, 0.22 mmol) were reacted. Purification using CH₂Cl₂ 100% then CH₂Cl₂/MeOH 99.5:0.5 then CH₂Cl₂/MeOH/AcOH 99:0.5:0.5 provided compound (104) as a colourless oil (34 mg, 35%). NMR ¹H (ppm, CDCl₃): 9.87 (d, J³=6.40 Hz, 1H), 7.57-7.50 (m, 3H), 7.44-7.39 (m, 3H), 7.35-7.31 (m, 1H), 7.27-7.20 (m, 6H), 4.90 (br. s., 1H), 4.68-4.62 (m, 2H), 3.95 (s, 2H), 3.76-3.70 (m, 2H), 3.72 (s, 2H), 2.96-2.78 (m, 2H), 1.65 (sex., J³=7.71 Hz, 2H), 0.93 (t, J³=7.26 Hz, 3H). MS (−ESI): M−H⁺: 489.9.

Example 92

Compound (105)

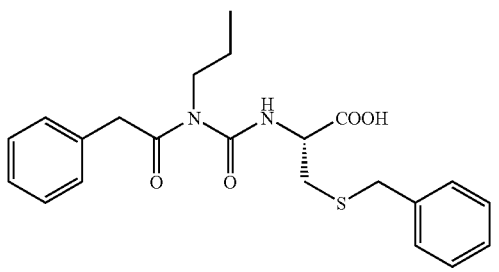

(105)

92A: 2-Phenyl-N-propyl-acetamide

EDAC.HCl (959 mg, 5 mmol) was added to a mixture of phenylacetic acid (681 mg, 5 mmol), propylamine (411 µL, 5 mmol) and HOBT (676 mg, 5 mmol) in 5 mL of CH$_3$CN. The reaction was stirred for 72 hours. After this time, the mixture was diluted with AcOEt. The organic layer was washed three times with HCl 2N, three times with NaOH 2N, dried over MgSO$_4$ and concentrated. A with solid was obtained (576 mg, 65%). NMR $^1$H (ppm, CDCl$_3$): 7.39-7.24 (m, 5H), 5.38 (br. s., 1H), 3.57 (s, 2H), 3.20-3.13 (m, 2H), 1.45 (sex. J$^3$=7.19 Hz, 2H), 0.83 (t, J$^3$=7.40 Hz, 3H).

92B: Compound (105)

Using Preparation Method 8, compound 92A (36 mg, 0.2 mmol) and S-benzyl-(L)-cysteine (96 mg, 0.22 mmol) were reacted. Purification using CH$_2$Cl$_2$ 100% then CH$_2$Cl$_2$/MeOH 99.5:0.5 then CH$_2$Cl$_2$/MeOH/AcOH 99:0.5:0.5 provided compound (105) as a colourless oil (26 mg, 31%). NMR $^1$H (ppm, CDCl$_3$): 9.87 (d, J$^3$=6.88 Hz, 1H), 7.37-7.18 (m, 10H), 6.9 (br. s., 1H), 4.69-4.63 (m, 2H), 3.88 (s, 2H), 3.72 (s, 2H), 3.72-3.67 (m, 2H), 2.96-2.78 (m, 2H), 1.62 (sex., J$^3$=7.06 Hz, 2H), 0.92 (t, J$^3$=7.35 Hz, 3H). MS (−ESI): M−H$^+$: 413.3.

Example 93

Compound (106)

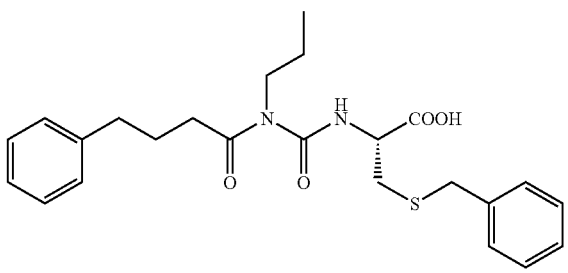

(106)

93A: 4-Phenyl-N-propyl-butyramide

EDAC.HCl (959 mg, 5 mmol) was added to a mixture of phenylacetic acid (821 mg, 5 mmol), propylamine (411 µL, 5 mmol) and HOBT (676 mg, 5 mmol) in 5 mL of CH$_3$CN. The reaction was stirred for 72 hours. After this time, the mixture was diluted with AcOEt. The organic layer was washed three times with HCl 2N, three times with NaOH 2N, dried over MgSO$_4$ and concentrated. A with solid was obtained (698 mg, 68%). NMR $^1$H (ppm, CDCl$_3$): 7.26-7.21 (m, 2H), 7.17-7.12 (m, 3H), 6.02 (br. s., 1H), 3.18-3.12 (m, 2H), 2.61 (t, J$^3$=7.49 Hz, 2H), 2.15 (t, J$^3$=7.14 Hz, 2H), 1.93 (q, J$^3$=7.36 Hz, 2H), 1.47 (sex. J$^3$=7.32 Hz, 2H), 0.88 (t, J$^3$=7.37 Hz, 3H).

93B: Compound (106)

Using Preparation Method 8, compound 93A (44 mg, 0.2 mmol) and S-benzyl-(L)-cysteine (96 mg, 0.22 mmol) were reacted. Purification using CH$_2$Cl$_2$ 100% then CH$_2$Cl$_2$/MeOH 99.5:0.5 then CH$_2$Cl$_2$/MeOH/AcOH 99:0.5:0.5 provided compound (106) as a colourless oil (32 mg, 36%). NMR $^1$H (ppm, CDCl$_3$): 9.97 (d, J$^3$=6.88 Hz, 1H), 7.33-7.24 (m, 6H), 7.23-7.16 (m, 4H), 4.69-4.63 (m, 2H), 3.74 (s, 2H), 3.59-3.54 (m, 2H), 2.97-2.81 (m, 2H), 2.69 (t, J$^3$=7.39 Hz, 2H), 2.50 (t, J$^3$=7.25 Hz, 2H), 2.02 (q, J$^3$=7.28 Hz, 2H), 1.51 (sex. J$^3$=7.87 Hz, 2H), 0.84 (t, J$^3$=7.35 Hz, 3H). MS (−ESI): M−H$^+$: 442.0.

Example 94

Compound (107)

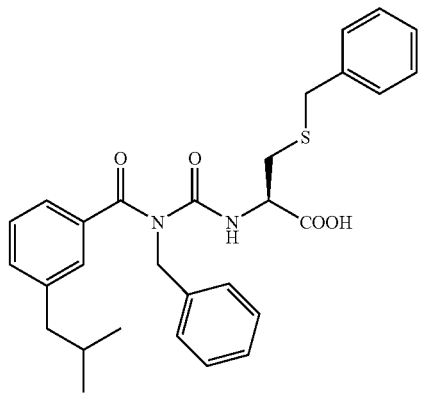

(107)

94A: 3-Isobutyl-benzoic acid methyl ester

Compound from example 76A (1.62 g, 6 mmol), N-methylpyrrolidinone (3.4 mL), Fe(acac)$_3$ (140 mg, 0.4 mmol) and dry THF (35 mL) were stirred under nitrogen at room temperature. Isobutylmagnesium bromide (2.0 M in Et$_2$O, 3.6 mL) was added by syringe. After stirring for fifteen minutes, HCl (2 M, 20 mL) was slowly added. The mixture was diluted with water and extracted three times with EtOAc. The organic layers were combined, washed with water and then brine, were dried over MgSO$_4$ and were concentrated. Purification was achieved using flash chromatography on SiO$_2$ with hexanes/toluene 75:25. A colourless oil was obtained (1.07 g, 93%). NMR $^1$H (ppm, CDCl$_3$): 7.94-7.89 (m, 2H), 7.39-7.33 (m, 2H), 3.89 (s, 3H), 2.51 (d, J$^3$=7.2 Hz, 2H), 1.94-1.85 (m, 1H), 0.89 (t, J$^3$=6.6 Hz, 6H).

94B: 3-Isobutyl-benzoic acid 94A (1.07 g, 5.5 mmol) was suspended in EtOH (10 mL) and aqueous NaOH (1 M, 20 mL) and was heated to 80° C. for forty-five minutes. Upon cooling to room temperature, the solution was acidified with HCl (conc.), was cooled to 0° C., and was filtered. The white crystalline precipitate was dried under vacuum (262 mg, 27%). NMR $^1$H (ppm, CDCl$_3$): 7.94-7.89 (m, 2H), 7.39-7.33 (m, 2H), 2.53 (d, J$^3$=7.2 Hz, 2H), 1.94-1.85 (m, 1H), 0.90 (t, J$^3$=6.6 Hz, 6H).

94C: 3-Isobutyl-N-benzyl-benzamide

Using preparation method 1, 94B (131 mg, 0.74 mmol) was reacted with benzylamine (120 μL, 118 mg, 1.1 mmol). Purification by flash chromatography on SiO$_2$ using CH$_2$Cl$_2$/hexanes 50:50 then CH$_2$Cl$_2$ 100% afforded white crystals (1.60 mg, 81%). NMR $^1$H (ppm, CDCl$_3$): 7.58-7.54 (m, 2H), 7.36-7.24 (m, 7H), 6.35 (br. s, 1H), 4.64 (d, J$^3$=5.7 Hz, 2H), 2.50 (d, J$^3$=7.2 Hz, 2H), 1.92-1.82 (m, 1H), 0.88 (t, J$^3$=6.6 Hz, 6H).

94D: Compound (107)

Using Preparation Method 8, compound 94C (67 mg, 0.25 mmol) and S-benzyl-(L)-cysteine (60 mg, 0.28 mmol) were reacted. Purification using CH$_2$Cl$_2$ 100% then CH$_2$Cl$_2$/MeOH 99.5:0.5 then CH$_2$Cl$_2$/MeOH/AcOH 99:0.5:0.5 provided compound (107) as a colourless oil (74 mg, 59%). NMR $^1$H (ppm, CDCl$_3$): 9.79 (d, J$^3$ 7.1 Hz, 1H), 7.45 (br. s, 1H), 7.31-7.01 (m, 14H), 4.97 (s, 2H), 4.82-4.75 (m, 1H), 3.77 (s, 2H), 3.02-2.87 (m, 2H), 2.38 (d, J$^3$=7.2 Hz, 2H), 1.75-1.66 (m, 1H), 0.82 (d, J$^3$=6.6 Hz, 6H). MS (−ESI): M−H$^+$: 503.7.

Example 95

Compound (108)

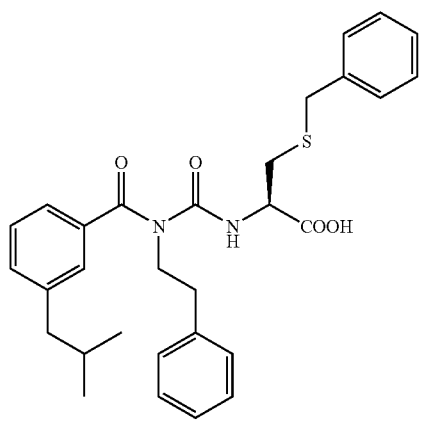

(108)

95A: 3-Isobutyl-N-phenethyl-benzamide

Using preparation method 1, 94B (131 mg, 0.74 mmol) was reacted with phenethylamine (138 μL, 133 mg, 1.1 mmol). Purification by flash chromatography on SiO$_2$ using CH$_2$Cl$_2$/hexanes 50:50 then CH$_2$Cl$_2$ 100% afforded white crystals were obtained (177 mg, 86%). NMR $^1$H (ppm, CDCl$_3$): 7.50 (s, 1H), 7.47 (dt, J$^3$=7.0 Hz, J$^4$=1.8 Hz, 1H), 7.33-7.21 (m, 7H), 6.28 (br. s, 1H), 3.72-3.66 (m, 2H), 2.92 (t, J$^3$=7.0 Hz, 2H), 2.48 (d, J$^3$=7.2 Hz, 2H), 1.90-1.81 (m, 1H), 0.88 (d, J$^3$=6.6 Hz, 6H).

95B: Compound (108)

Using Preparation Method 8, compound 95A (70 mg, 0.25 mmol) and S-benzyl-(L)-cysteine (60 mg, 0.28 mmol) were reacted. Purification using CH$_2$Cl$_2$ 100% then CH$_2$Cl$_2$/MeOH 99.5:0.5 then CH$_2$Cl$_2$/MeOH/AcOH 99:0.5:0.5 provided compound (108) as a colourless oil (27 mg, 21%). NMR $^1$H (ppm, CDCl$_3$): 9.72 (d, J$^3$=7.1 Hz, 1H), 7.32-7.15 (m, 10H), 7.06 (d, J$^3$=7.2 Hz, 1H), 6.99 (s, 1H), 6.90-6.88 (m, 2H), 6.32 (br. s, 1H), 4.81-4.75 (m, 1H), 3.93 (t, J$^3$=7.3 Hz, 2H), 3.80 (s, 2H), 3.05-2.77 (m, 2H), 2.79 (t, J$^3$=7.3 Hz, 2H), 2.46 (d, J$^3$=7.2 Hz, 2H), 1.89-1.79 (m, 1H), 0.87 (d, J$^3$=7.5 Hz, 6H). MS (−ESI): M−H$^+$: 517.5.

Example 96

Compound (109)

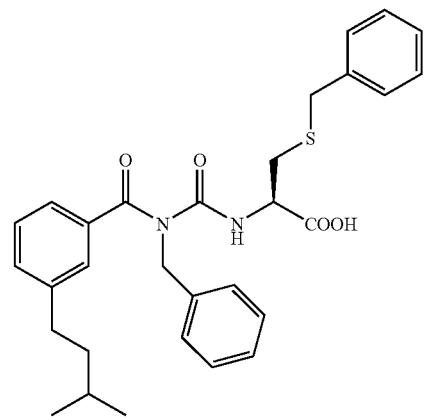

(109)

96A: 3-Isopentyl-benzoic acid methyl ester

Compound from example 76A (1.42 g, 5 mmol), N-methylpyrrolidinone (2.8 mL), Fe(acac)$_3$ (120 mg, 0.34 mmol) and dry THF (30 mL) were stirred under nitrogen at room temperature. Isopentylmagnesium bromide (0.46 M in THF, 13 mL) was added by syringe. After stirring for fifteen minutes, HCl 2N (25 mL) was slowly added. The mixture was diluted with water and extracted three times with EtOAc. The organic layers were combined, washed with water and then brine, were dried over MgSO$_4$ and were concentrated. Purification was achieved using flash chromatography on SiO$_2$ with hexanes/EtOAc 98:2. A colourless oil was obtained (848 mg, 82%). NMR $^1$H (ppm, CDCl$_3$): 7.85-7.81 (m, 2H), 7.37-7.29 (m, 2H), 3.90 (s, 3H), 2.67-2.61 (m, 2H), 1.62-1.46 (m, 3H), 0.92 (d, J=6.3 Hz, 6H).

96B: 3-Isopentyl-benzoic acid 96A (824 mg, 4 mmol) was suspended in EtOH (4 mL) and aqueous NaOH (1 M, 20 mL) and was heated under reflux conditions for sixty minutes. Upon cooling to room temperature, the solution was acidified with HCl (conc.), was cooled to 0° C., and was filtered. The white crystalline precipitate was dried under vacuum (633 mg, 82%). NMR $^1$H (ppm, CDCl$_3$): 7.94-7.91 (m, 2H), 7.42 (d, J$^3$=7.6 Hz, 1H), 7.36 (t, J$^3$=7.7 Hz, 1H), 2.69-2.64 (m, 2H), 1.62-1.49 (m, 3H), 0.94 (d, J$^3$=6.3 Hz, 6H).

96C: 3-Isopentyl-N-benzyl-benzamide

Using preparation method 1, 96B (288 mg, 1.5 mmol) was reacted with benzylamine (240 µL, 236 mg, 2.2 mmol). Purification by flash chromatography on SiO$_2$ using CH$_2$Cl$_2$/hexanes 50:50 then CH$_2$Cl$_2$ 100% afforded white crystals (316 mg, 74%). NMR $^1$H (ppm, CDCl$_3$): 7.62 (s, 1H), 7.56-7.53 (m, 1H), 7.36-7.27 (m, 7H), 6.35 (br. s, 1H), 4.64 (d, J$^3$=5.7 Hz, 2H), 2.66-2.60 (m, 2H), 1.64-1.46 (m, 3H), 0.92 (d, J$^3$=6.3 Hz, 6H).

96D: Compound (109)

Using Preparation Method 8, compound 96C (71 mg, 0.25 mmol) and S-benzyl-(L)-cysteine (60 mg, 0.28 mmol) were reacted. Purification using CH$_2$Cl$_2$ 100% then CH$_2$Cl$_2$/MeOH 99.5:0.5 then CH$_2$Cl$_2$/MeOH/AcOH 99:0.5:0.5 provided compound (109) as a colourless oil (55 mg, 42%). NMR $^1$H (ppm, CDCl$_3$): 9.80 (d, J$^3$=7.2 Hz, 1H), 7.43 (br. s, 1H), 7.35-7.13 (m, 11H), 7.08 (s, 1H), 7.00 (d, J$^3$=6.4 Hz, 2H), 4.96 (s, 2H), 4.82-4.75 (m, 1H), 3.77 (s, 2H), 3.04-2.87 (m, 2H), 2.53-2.47 (m, 2H), 1.54-1.45 (m, 1H), 1.34 (quart., J$^3$=7.6 Hz, 2H), 0.88 (d, J$^3$=6.5 Hz, 6H). MS (−ESI): M−H$^+$: 517.5.

Example 97

Compound (110)

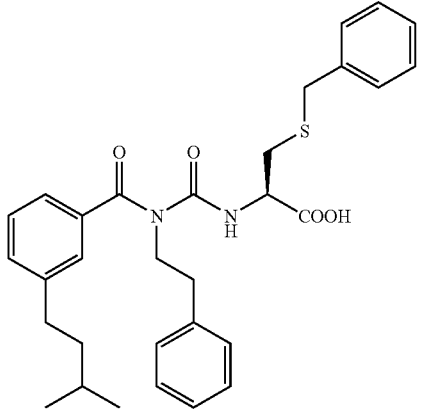

(110)

97A: 3-Isopentyl-N-phenethyl-benzamide

Using preparation method 1, 96B (288 mg, 1.5 mmol) was reacted with phenethyl amine (276 µL, 266 mg, 2.2 mmol). Purification by flash chromatography on SiO$_2$ using CH$_2$Cl$_2$/hexanes 50:50 then CH$_2$Cl$_2$ 100% afforded white crystals (330 mg, 74%). NMR $^1$H (ppm, CDCl$_3$): 7.52 (s, 1H), 7.44-7.41 (m, 1H), 7.34-7.22 (m, 7H), 6.09 (br. s, 1H), 3.74-3.67 (m, 2H), 2.92 (t, J$^3$=6.9 Hz, 2H), 2.64-2.59 (m, 2H), 1.63-1.40 (m, 3H), 0.92 (d, J$^3$=6.3 Hz, 6H).

97B: Compound (110)

Using Preparation Method 8, compound 97A (74 mg, 0.25 mmol) and S-benzyl-(L)-cysteine (60 mg, 0.28 mmol) were reacted. Purification by flash chromatography on SiO$_2$ using CH$_2$Cl$_2$ 100% then CH$_2$Cl$_2$/MeOH 99.5:0.5 then CH$_2$Cl$_2$/MeOH/AcOH 99:0.5:0.5 provided compound (110) as a colourless oil (77 mg, 58%). NMR $^1$H (ppm, CDCl$_3$): 9.73 (d, J$^3$=7.0 Hz, 1H), 7.38-7.16 (m, 10H), 7.10-6.89 (m, 4H), 6.12 (br. s, 1H), 4.82-4.75 (m, 1H), 3.92 (t, J$^3$=7.2 Hz, 2H), 3.80 (s, 2H), 3.05-2.88 (m, 2H), 2.80 (t, J$^3$=7.2 Hz, 2H), 2.62-2.56 (m, 2H), 1.59-1.43 (m, 3H), 0.92 (d, J$^3$=6.4 Hz, 6H). MS (−ESI): M−H$^+$: 531.5.

Example 98

Compound (111)

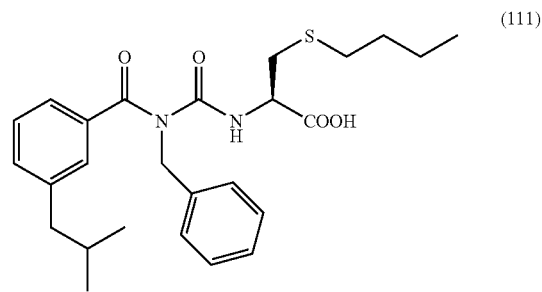

(111)

Using preparation method 9, (L)-cysteine (30 mg, 0.25 mmol) was treated with 1-iodobutane (28 µL, 46 mg, 0.25 mmol), and then treated with the carbamoylchloride of 94C. Purification by flash chromatography on SiO$_2$ using CH$_2$Cl$_2$ 100% then CH$_2$Cl$_2$/MeOH 99.5:0.5 then CH$_2$Cl$_2$/MeOH/AcOH 99:0.5:0.5 provided compound (111) as a colourless oil (37 mg, 31%). NMR $^1$H (ppm, CDCl$_3$): 9.77 (d, J$^3$=7.0 Hz, 1H), 7.34-7.13 (m, 6H), 7.06 (s, 1H), 6.99 (d, J$^3$=6.3 Hz, 2H), 6.39 (br. s, 1H), 4.96 (s, 2H), 4.82-4.76 (m, 1H), 3.14-2.99 (m, 2H), 2.58 (t, J$^3$=7.3 Hz, 2H), 2.37 (d, J$^3$=7.2 Hz, 2H), 1.76-1.64 (m, 1H), 1.56 (quint., J$^3$=7.5 Hz, 2H), 1.38 (sext., J$^3$=7.4 Hz, 2H), 0.88 (t, J$^3$=7.2 Hz, 3H), 0.81 (d, J$^3$=6.6 Hz, 6H). MS (−ESI): M−H$^+$: 469.4.

Example 99

Compound (112)

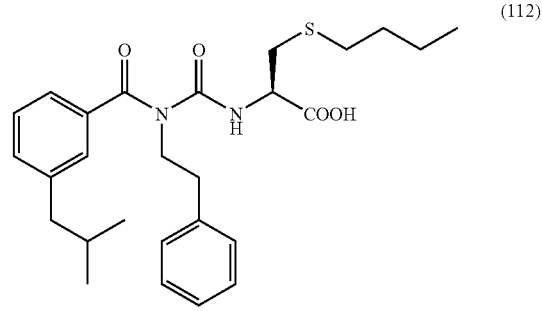

(112)

Using preparation method 9, cysteine (30 mg, 0.25 mmol) was treated with 1-iodobutane (28 μL, 46 mg, 0.25 mmol), and then treated with the carbamoylchloride of 95A. Purification by flash chromatography on SiO₂ using CH₂Cl₂ 100% then CH₂Cl₂/MeOH 99.5:0.5 then CH₂Cl₂/MeOH/AcOH 99:0.5:0.5 provided compound (112) as a colourless oil (24 mg, 20%). NMR ¹H (ppm, CDCl₃): 9.72 (d, J³=6.9 Hz, 1H), 7.30-7.16 (m, 5H), 7.03 (d, J³=7.3 Hz, 1H), 6.99 (s, 1H), 6.90-6.87 (m, 2H), 5.71 (br. s, 1H), 4.82-4.76 (m, 1H), 3.92 (t, J³=7.3 Hz, 2H), 3.16-3.00 (m, 2H), 2.81 (t, J³=7.3 Hz, 2H), 2.61 (t, J³=7.3 Hz, 2H), 2.46 (d, J³ 7.1 Hz, 2H), 1.88-1.78 (m, 1H), 1.56 (quint., J³=7.4 Hz, 2H), 1.39 (sext., J³=7.5 Hz, 2H), 0.92-0.86 (m, 9H). MS (-ESI): M-H⁺: 483.5.

Example 100

Compound (113)

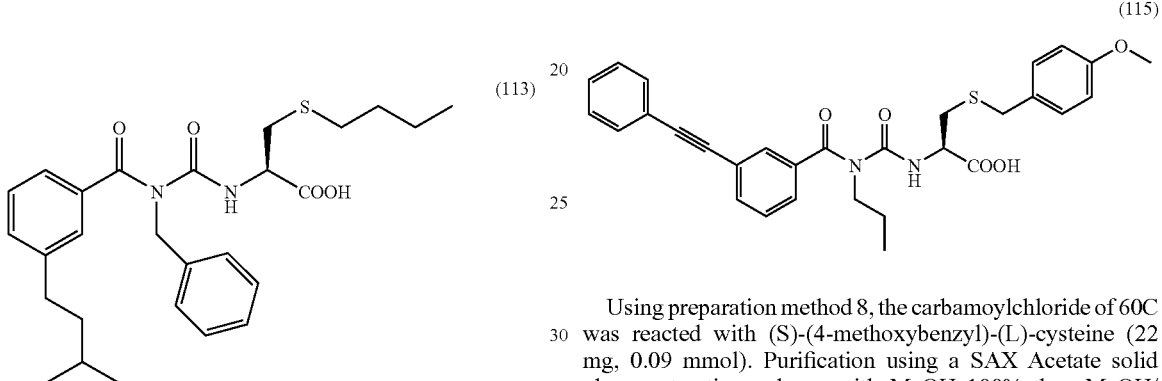

Using preparation method 9, cysteine (30 mg, 0.25 mmol) was treated with 1-iodobutane (28 μL, 46 mg, 0.25 mmol), and then treated with the carbamoylchloride of 96C. Purification by flash chromatography on SiO₂ using CH₂Cl₂ 100% then CH₂Cl₂/MeOH 99.5:0.5 then CH₂Cl₂/MeOH/AcOH 99:0.5:0.5 provided compound (113) as a colourless oil (38 mg, 31%). NMR ¹H (ppm, CDCl₃): 9.78 (d J³=6.9 Hz, 1H), 7.24-7.14 (m, 6H), 7.07 (s, 1H), 6.99 (d, J³=6.8 Hz, 2H), 6.70 (br. s, 1H), 4.95 (s, 2H), 4.82-4.76 (m, 1H), 3.14-3.00 (m, 2H), 2.58 (t, J³=7.2 Hz, 2H), 2.52-2.47 (m, 2H), 1.76-1.64 (m, 1H), 1.61-1.29 (m, 7H), 0.91-0.86 (m, 9H). MS (-ESI): M-H⁺: 483.5.

Example 101

Compound (114)

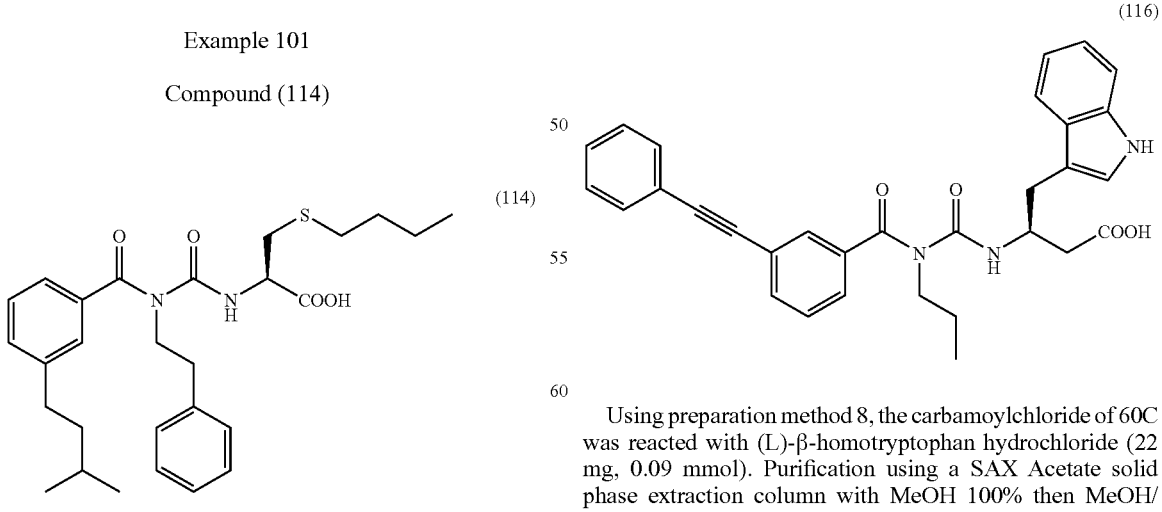

Using preparation method 9, cysteine (30 mg, 0.25 mmol) was treated with 1-iodobutane (28 μL, 46 mg, 0.25 mmol), and then treated with the carbamoylchloride of 97A. Purification by flash chromatography on SiO₂ using CH₂Cl₂ 100% then CH₂Cl₂/MeOH 99.5:0.5 then CH₂Cl₂/MeOH/AcOH 99:0.5:0.5 provided compound (114) as a colourless oil (48 mg, 39%). NMR ¹H (ppm, CDCl₃): 9.73 (d, J³=6.9 Hz, 1H), 8.02 (br. s, 1H), 7.29-7.16 (m, 5H), 7.02 (d, J³=3.7 Hz, 1H), 6.98 (s, 1H), 6.90 (d, J³=4.8 Hz, 2H), 4.84-4.77 (m, 1H), 3.92 (t, J³=7.1 Hz, 2H), 3.15-3.01 (m, 2H), 2.80 (t, J³=7.1 Hz, 2H), 2.63-2.56 (m, 4H), 1.63-1.33 (m, 7H), 0.92-0.87 (m, 9H). MS (-ESI): M-H⁺: 497.4.

Example 102

Compound (115)

Using preparation method 8, the carbamoylchloride of 60C was reacted with (S)-(4-methoxybenzyl)-(L)-cysteine (22 mg, 0.09 mmol). Purification using a SAX Acetate solid phase extraction column with MeOH 100% then MeOH/AcOH 85:15 provided compound (115) as a colourless oil (16 mg, 34%). NMR ¹H (ppm, CDCl₃): 9.61 (d, J³=6.9 Hz, 1H), 7.63-7.33 (m, 9H), 7.23 (d, J³=8.5 Hz, 2H), 6.83 (d, J³=8.6 Hz, 2H), 4.80 (br. s), 4.76-4.70 (m, 1H), 3.77 (s, 3H), 3.74 (s, 2H), 3.70-3.65 (m, 2H), 3.01-2.86 (m, 2H), 1.54 (sext., J³=7.4 Hz, 2H), 0.74 (t, J³=7.4 Hz, 3H). MS (-ESI): M-H⁺: 529.3.

Example 103

Compound (116)

Using preparation method 8, the carbamoylchloride of 60C was reacted with (L)-β-homotryptophan hydrochloride (22 mg, 0.09 mmol). Purification using a SAX Acetate solid phase extraction column with MeOH 100% then MeOH/AcOH 85:15 provided compound (116) as a colourless oil (8 mg, 18%). NMR ¹H (ppm, CDCl₃): 9.19 (d, J³=7.8 Hz, 1H), 8.11 (br. s, 1H), 7.68 (d, J³=7.4 Hz, 1H), 7.59 (d, J³=7.7 Hz, 1H), 7.53-7.10 (m, 12H), 4.67-4.58 (m, 1H), 3.64-3.59 (m, 2H), 3.31-3.06 (m, 2H), 2.72-2.58 (m, 2H), 1.48 (sext., $J^3$=7.5 Hz, 2H), 0.70 (t, $J^3$=7.4 Hz, 3H). MS (−ESI): M−H$^+$: 506.3.

Example 104

Compound (117)

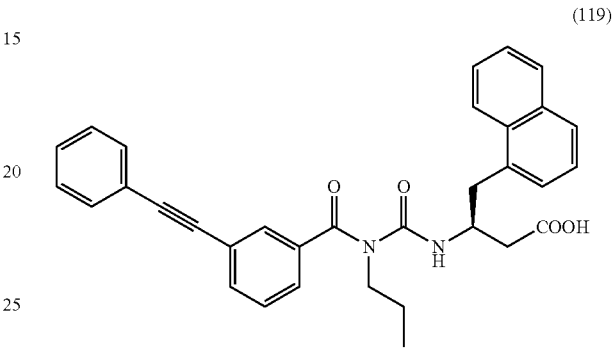

Using Preparation Method 3, compound 60B (26 mg, 0.1 mmol) was reacted with phosgene to provide a carbamoylchloride. Using Preparation Method 4, (L)-3-benzothienylalanine (23 mg, 0.105 mmol) was protected. The carbamoylchloride and TMS protected (L)-3-benzothienylalanine were reacted using Preparation Method 5. Purification using a SAX Acetate solid phase extraction column with MeOH 100% then MeOH/AcOH 85:15 provided compound (117) as a colourless oil (28 mg, 55%). NMR $^1$H (ppm, CDCl$_3$): 9.50 (d, $J^3$=6.7 Hz, 1H), 7.84 (t, $J^3$=7.1 Hz, 2H), 7.61-7.51 (m, 4H), 7.42-7.12 (m, 8H), 6.00 (br. s, 1H), 4.96-4.89 (m, 1H), 3.62-3.34 (m, 4H), 1.46 (sext., $J^3$=7.4 Hz, 2H), 0.68 (t, $J^3$=7.4 Hz, 3H). MS (−ESI): M−H$^+$: 509.2.

Example 105

Compound (118)

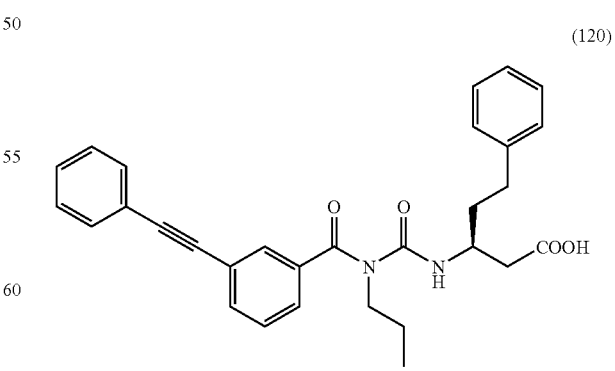

Using Preparation Method 3, compound 60B (26 mg, 0.1 mmol) was reacted with phosgene to provide a carbamoylchlioride. Using Preparation Method 4, (L)-3-amino-4-(2-naphthyl)-butyric acid hydrochloride (28 mg, 0.105 mmol) was protected. The carbamoylchloride and TMS protected (S)-3-amino-4-(2-naphthyl)-butyric acid were reacted using Preparation Method 5. Purification using a SAX Acetate solid phase extraction column with MeOH 100% then MeOH/AcOH 85:15 provided compound (118) as a colourless oil (16 mg, 31%). NMR 1H (ppm, CDCl$_3$): 9.24 (d, $J^3$=8.0 Hz, 1H), 7.80-7.15 (m, 16H), 4.66-4.54 (m, 1H), 3.59-3.54 (m, 2H), 3.19-3.06 (m, 2H), 2.67 (d, $J^3$=5.7 Hz, 2H), 1.38 (sext., $J^3$=7.5 Hz, 2H), 0.63 (t, $J^3$=7.4 Hz, 3H). MS (−ESI): M−H$^+$: 517.4.

Example 106

Compound (119)

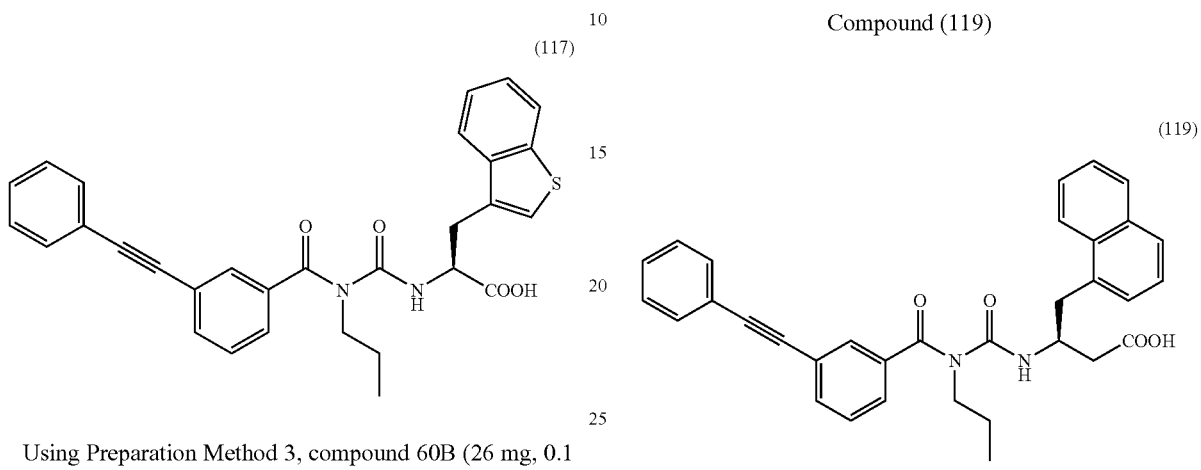

Using Preparation Method 3 compound 60B (26 mg, 0.1 mmol) was reacted with phosgene to provide a carbamoylchloride. Using Preparation Method 4, (L)-3-amino-4-(1-naphthyl)-butyric acid hydrochloride (28 mg, 0.105 mmol) was protected. The carbamoylchloride and TMS protected (S)-3-amino-4-(1-naphthyl)-butyric acid were reacted using Preparation Method 5. Purification using a SAX Acetate solid phase extraction column with MeOH 100% then MeOH/AcOH 85:15 provided compound (119) as a colourless oil (24 mg, 46%). NMR $^1$H (ppm, CDCl$_3$): 9.30 (d, $J^3$=7.8 Hz, 1H), 8.28 (d, $J^3$=8.4 Hz, 1H), 7.83 (d, $J^3$=8.1 Hz, 1H), 7.74 (dd, $J^3$=7.3 Hz, $J^4$=2.0 Hz, 1H), 7.60-7.15 (m, 13H), 5.80 (br. s, 1H), 4.71-4.65 (m, 1H), 3.62-3.32 (m, 4H), 2.73-2.59 (m, 2H), 1.44 (sext., $J^3$=7.4 Hz, 2H), 0.69 (t, $J^3$=7.4 Hz, 3H). MS (−ESI): M−H$^+$: 517.3.

Example 107

Compound (120)

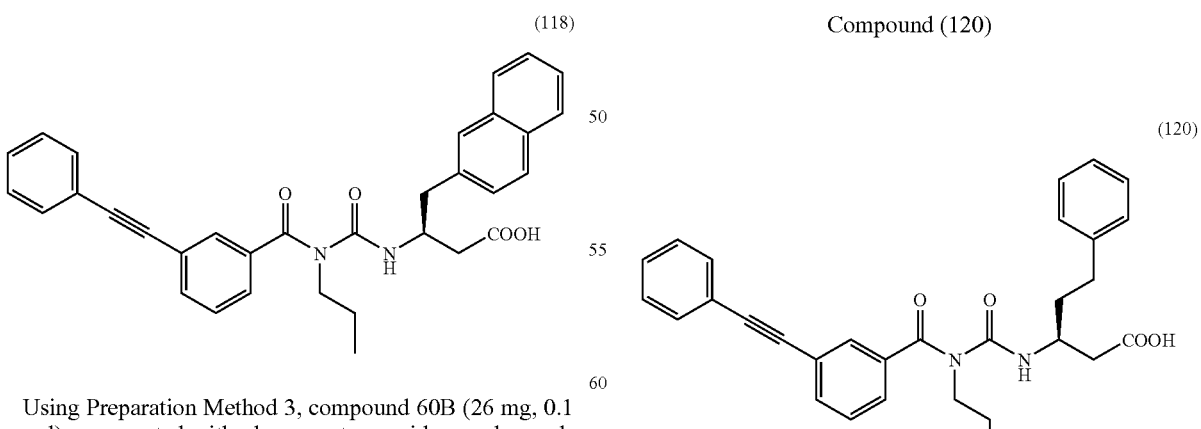

Using Preparation Method 3, compound 60B (26 mg, 0.1 mmol) was reacted with phosgene to provide a carbamoylchloride. Using Preparation Method 4, (L)-3-amino-5-phenylpentanoic acid hydrochloride (24 mg, 0.105 mmol) was protected. The carbamoylchloride and TMS protected (S)-3-amino-5-phenylpentanoic acid were reacted using Preparation Method 5. Purification using a SAX Acetate solid phase extraction column with MeOH 100% then MeOH/AcOH 85:15 provided compound (120) as a colourless oil (15 mg, 31%). NMR $^1$H (ppm, CDCl$_3$): 9.15 (d, J$^3$ 8.2 Hz, 1H), 7.59 (d, J$^3$=8.4 Hz, 2H), 7.53-7.50 (m, 2H), 7.42-7.22 (m, 6H), 7.16 (d, J3=7.4 Hz, 4H), 5.01 (br. s, 1H), 4.27-4.24 (m, 1H), 3.66-3.61 (m, 2H), 2.72-2.61 (m, 4H), 2.04-1.91 (m, 2H), 1.52 (sext., J$^3$=7.4 Hz, 2H), 0.72 (t, J$^3$=7.4 Hz, 3H). MS (–ESI): M–H$^+$: 481.4.

Example 108

Compound (121)

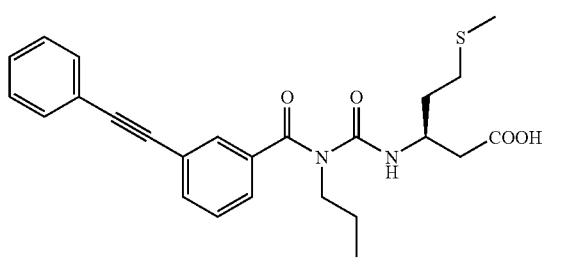

Using Preparation Method 3, compound 60B (26 mg, 0.1 mmol) was reacted with phosgene to provide a carbamoylchloride. Using Preparation Method 4, (L)-β-homomethionine hydrochloride (21 mg, 0.105 mmol) was protected. The carbamoylchloride and TMS protected (L)-β-homomethionine were reacted using Preparation Method 5. Purification using a SAX Acetate solid phase extraction column with MeOH 100% then MeOH/AcOH 85:15 provided compound (121) as a colourless oil (15 mg, 33%). NMR $^1$H (ppm, CDCl$_3$): 7.60 (d, J$^3$=9.0 Hz, 1H), 7.53-7.50 (m, 2H), 7.42 (t, J$^3$=7.6 Hz, 1H), 7.37-7.33 (m, 4H), 4.42-4.31 (m, 1H), 3.68-3.63 (m, 2H), 2.75-2.60 (m, 2H), 2.55 (br. s, 2H), 2.10 (br. s, 3H), 2.01-1.87 (m, 2H), 1.53 (sext., J$^3$=7.4 Hz, 2H), 0.69 (t, J$^3$=7.4 Hz, 3H). MS (–ESI): M–H$^+$: 451.3.

Example 109

Compound (122)

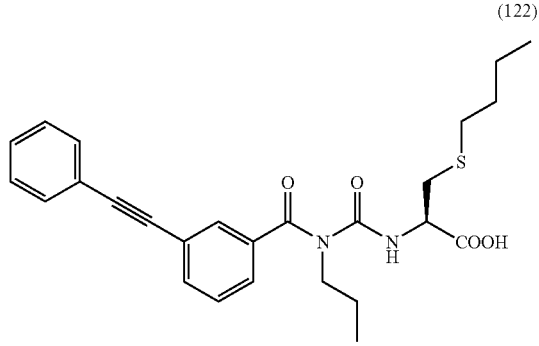

Using preparation method 9, (L)-cysteine (12 mg, 0.1 mmol) was treated with 1-bromobutane (11 μL, 14 mg, 0.1 mmol), and then treated with the carbamoylchloride prepared in 60C. Purification using a SAX Acetate solid phase extraction column with MeOH 100% then MeOH/AcOH 85:15 provided compound (122) as a colourless oil (15 mg, 32%). NMR $^1$H (ppm, CDCl$_3$): 9.61 (d, J$^3$=6.8 Hz, 1H), 7.63-7.60 (m, 2H), 7.53-7.50 (m, 2H), 7.45-7.33 (m, 5H), 4.97 (br. s, 1H), 4.77-4.71 (m, 1H), 3.70-3.65 (m, 2H), 3.13-2.99 (m, 2H), 2.58 (t, J$^3$=7.3 Hz, 2H), 1.61-1.50 (m, 4H), 1.38 (sext., J$^3$=7.4 Hz, 2H), 0.89 (t, J$^3$=7.3 Hz, 3H), 0.74 (t, J$^3$=7.4 Hz, 3H). MS (–ESI): M–H$^+$: 465.5.

Example 110

Compound (123)

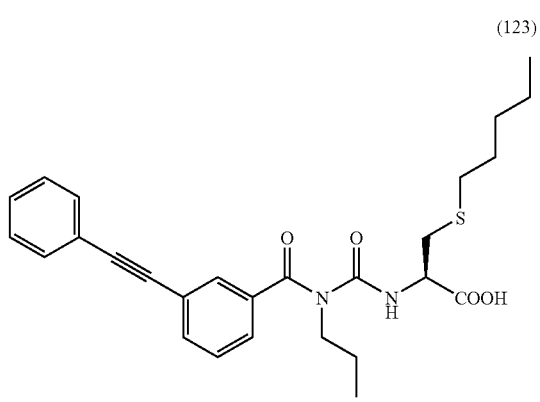

Using preparation method 9, (L)-cysteine (12 mg, 0.1 mmol) was treated with 1-bromopentane (12 μL, 15 mg, 0.1 mmol), and then treated with the carbamoylchloride prepared in 60C. Purification using a SAX Acetate solid phase extraction column with MeOH 100% then MeOH/AcOH 85:15 provided compound (123) as a colourless oil (10 mg, 21%). NMR $^1$H (ppm, CDCl$_3$): 9.59 (d, J$^3$=6.7 Hz, 1H), 7.63-7.60 (m, 2H), 7.53-7.50 (m, 2H), 7.45-7.33 (m, 5H), 4.75-4.69 (m, 1H), 4.42 (br. s, 1H), 3.70-3.65 (m, 2H), 3.13-2.99 (m, 2H), 2.58 (t, J$^3$=7.4 Hz, 2H), 1.60-1.50 (m, 4H), 1.36-1.31 (m, 4H), 0.87 (t, J$^3$=7.0 Hz, 3H), 0.73 (t, J$^3$=7.4 Hz, 3H). MS (–ESI): M–H$^+$: 479.3.

Example 111

Compound (124)

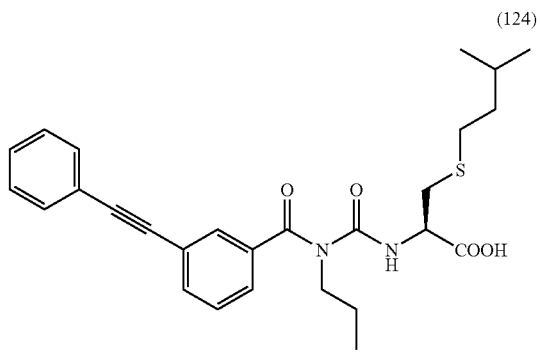

Using preparation method 9, (L)-cysteine (12 mg, 0.1 mmol) was treated with 1-bromo-3-methylbutane (12.5 μL, 15 mg, 0.1 mmol), and then treated with the carbamoylchloride prepared in 60C. Purification using a SAX Acetate solid phase extraction column with MeOH 100% then MeOH/ AcOH 85:15 provided compound (124) as a colourless oil (11 mg, 23%). NMR $^1$H (ppm, CDCl$_3$): 9.57 (d, J$^3$=6.7 Hz, 1H), 7.62-7.59 (m, 2H), 7.53-7.50 (m, 2H), 7.44-7.32 (m, 5H), 4.81 (br. s, 1H), 4.71-4.65 (m, 1H), 3.68-3.63 (m, 2H), 3.13-2.95 (m, 2H), 2.60-2.55 (m, 2H), 1.71-1.42 (m, 5H), 0.87 (d, J$^3$=6.5 Hz, 6H), 0.72 (t, J$^3$=7.4 Hz, 3H). MS (-ESI): M-H$^+$: 479.4.

Example 112

Compound (125)

Example 113

Compound (126)

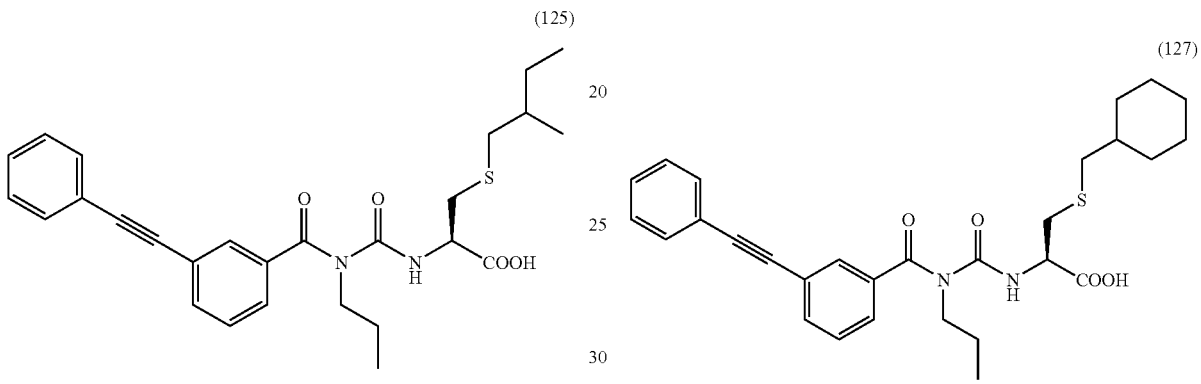

Using preparation method 9, (L)-cysteine (12 mg, 0.1 mmol) was treated with 1-bromo-2-methylbutane (12.5 µL, 15 mg, 0.1 mmol), and then treated with the carbamoylchloride prepared in 60C. Purification using a SAX Acetate solid phase extraction column with MeOH 100% then MeOH/ AcOH 85:15 provided compound (125) as a colourless oil (7 mg, 15%). NMR $^1$H (ppm, CDCl$_3$): 9.62 (d, J$^3$=6.9 Hz, 1H), 7.63-7.60 (m, 2H), 7.53-7.50 (m, 2H), 7.46-7.36 (m, 5H), 4.75-4.71 (m, 1H), 3.70-3.65 (m, 2H), 3.05-3.03 (m, 2H), 2.61-2.43 (m, 2H), 1.55-1.30 (m, 4H), 1.24-1.12 (m, 1H), 0.96 (d, J$^3$=6.5 Hz, 3H), 0.87 (t, J$^3$=7.3 Hz, 3H), 0.74 (t, J$^3$=7.3 Hz, 3H). MS (-ESI): M-H$^+$: 479.3.

Example 113

Compound (126)

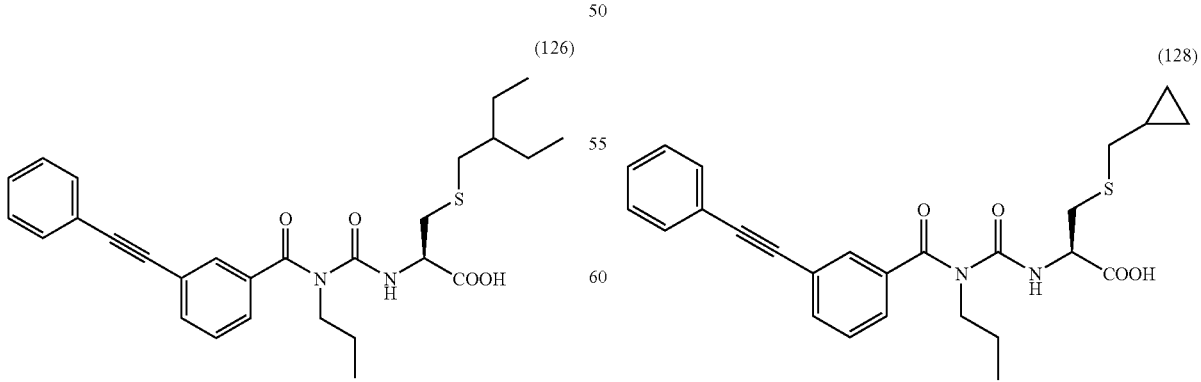

Using preparation method 9, (L)-cysteine (12 mg, 0.1 mmol) was treated with 1-bromo-2-ethylbutane (14 µL, 16.5 mg, 0.1 mmol), and then treated with the carbamoylchloride prepared in 60C. Purification using a SAX Acetate solid phase extraction column with MeOH 100% then MeOH/ AcOH 85:15 provided compound (126).as a colourless oil (8 mg, 16%). NMR $^1$H (ppm, CDCl$_3$): 9.58 (d, J$^3$=6.3 Hz, 1H), 7.62-7.59 (m, 2H), 7.53-7.50 (m, 2H), 7.45-7.34 (m, 5H), 4.70-4.66 (m, 1H), 3.68-3.63 (m, 2H), 3.17-2.91 (m, 2H), 2.56 (d, J$^3$=4.9 Hz, 2H), 1.53 (sext., J$^3$=7.6 Hz, 2H), 1.48-1.24 (m, 5H), 0.87 (t, J$^3$=6.9 Hz, 6H), 0.73 (t, J$^3$=7.3 Hz, 3H). MS (-ESI): M-H$^+$: 493.3.

Example 114

Compound (127)

Using preparation method 9, (L)-cysteine (12 mg, 0.1 mmol) was treated with (bromomethyl)cyclohexane (14 µL, 18 mg, 0.1 mmol), and then treated with the carbamoylchloride prepared in 60C. Purification using a SAX Acetate solid phase extraction column with MeOH 100% then MeOH/ AcOH 85:15 provided compound (127) as a colourless oil (11 mg, 22%). NMR $^1$H (ppm, CDCl$_3$): 9.55 (d, J$^3$=6.0 Hz, 1H), 7.62-7.59 (m, 2H), 7.53-7.50 (m, 2H), 7.44-7.34 (m, 5H), 5.17 (br. s, 1H), 4.71-4.65 (m, 1H), 3.68-3.63 (m, 2H), 3.16-3.00 (m, 2H), 2.49 (d, J$^3$=9.5 Hz, 2H), 1.83-1.36 (m, 8H), 1.23-1.12 (m, 3H), 0.96-0.86 (m, 4H), 0.72 (t, J$^3$ 7.3 Hz, 3H). MS (-ESI): M-H$^+$: 505.2.

Example 115

Compound (128)

Using preparation method 9, (L)-cysteine (12 mg, 0.1 mmol) was treated with (bromomethyl)cyclopropane (10 µL, 14 mg, 0.1 mmol), and then treated with the carbamoylchloride prepared in 60C. Purification using a SAX Acetate solid phase extraction column with MeOH 100% then MeOH/AcOH 85:15 provided compound (128) as a colourless oil (7 mg, 15%). NMR $^1$H (ppm, CDCl$_3$): 9.61 (d, J$^3$=6.5 Hz, 1H), 7.63-7.60 (m, 2H), 7.53-7.50 (m, 2H), 7.45-7.35 (m, 5H), 4.78-4.72 (m, 1H), 3.70-3.65 (m, 2H), 3.21-3.04 (m, 2H), 2.54 (d, J$^3$=6.9 Hz, 2H), 1.54 (sext., J$^3$=7.1 Hz, 2H), 1.05-0.95 (m, 1H), 0.74 (t, J$^3$=7.3 Hz, 3H), 0.57 (d, J$^3$=8.1 Hz, 2H), 0.22 (d, J$^3$=4.4 Hz, 2H). MS (−ESI): M−H$^+$: 463.2.

Example 116

Compound (129)

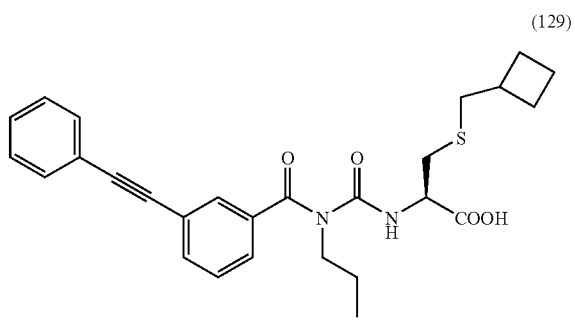

Using preparation method 9, (L)-cysteine (12 mg, 0.1 mmol) was treated with (bromomethyl)cyclobutane (11 µL, 15 mg, 0.1 mmol), and then treated with the carbamoylchloride prepared in 60C. Purification using a SAX Acetate solid phase extraction column with MeOH 100% then MeOH/AcOH 85:15 provided compound (129) as a colourless oil (6 mg, 13%). NMR $^1$H (ppm, CDCl$_3$): 9.60 (d, J$^3$=7.1 Hz, 1H), 7.63-7.60 (m, 2H), 7.53-7.50 (m, 2H), 7.46-7.35 (m, 5H), 4.75-4.70 (m, 1H), 3.70-3.65 (m, 2H), 3.20-2.97 (m, 2H), 2.66 (d, J$^3$=7.5 Hz, 2H), 2.49 (sept., J$^3$=7.5 Hz, 1H), 1.92-1.68 (m, 4H), 1.54 (sext. J$^3$=7.4 Hz, 2H), 0.74 (t, J$^3$=7.3 Hz, 3H). MS (−ESI): M−H$^+$: 477.3.

Example 117

Compound (130)

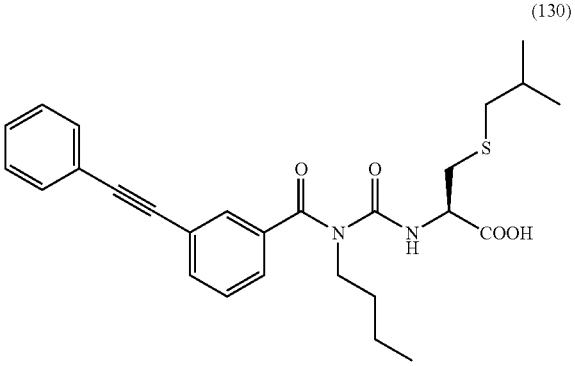

117A: Methyl 3-iodobenzoate 3-iodobenzoic acid (7.44 g, 30 mmol) was suspended in dry MeOH (40 mL) under nitrogen at 0° C. SOCl$_2$ (3.3 mL) was added over 5 minutes. Stirring continued at room temperature for 16 hours, after which the reaction mixture was concentrated. The residue was dissolved in EtOAc and was washed twice with NaHCO$_3$ (conc.). The organic solution was dried over MgSO$_4$, filtered and concentrated to yield a white crystalline solid (7.32 g, 93%). NMR $^1$H (ppm, CDCl$_3$): 8.36 (t, J$^4$=1.6 Hz, 1H), 7.98 (d, J$^3$=7.8 Hz, 1H), 7.86 (d, J$^3$=7.9 Hz, 1H), 7.16 (t, J$^3$=7.8 Hz, 1H), 3.90 (s, 3H).

117B: Methyl 3-phenylethynyl-benzoate

Methyl 3-iodobenzoate, phenylacetylene (1.5 eq.) and Pd(PPh$_3$)$_2$Cl$_2$ (5 mol %) in piperidine (3 eq.) was heated at 70° C. for 30 minutes. The solidified residue was dissolved with CH$_2$Cl$_2$ and water and poured onto HCl 2N. The acidic phase was extracted three times with CH$_2$Cl$_2$. The combined organic layers were washed twice with HCl 2N, once with water and once with brine. The organic layer was then dried over MgSO$_4$ and concentrated. The resulting residue was purified using SiO$_2$ with petroleum spirit/toluene 70:30 to give methyl 3-phenylethynyl-benzoate as a white solid (quantitative yield). NMR $^1$H (ppm, CDCl$_3$): 8.20 (t, J$^4$=1.7 Hz, 1H), 7.98 (d, J$^3$=7.9 Hz, 1H), 7.69 (d, J$^3$=7.6 Hz, 1H), 7.54-7.50 (m, 2H), 7.42 (t, J$^3$=7.8 Hz, 1H), 7.36-7.31 (m, 3H), 3.92 (s, 3H).

117C: 3-phenylethynyl-benzoic acid

Compound from example 117B (1.18 g, 5 mmol) was suspended in EtOH (10 mL) containing NaOH 2N (15 mL) and was stirred at 80° C. for sixty minutes. Upon cooling to room temperature the solution was acidified with HCl (conc.). The white precipitate was filtered off and dried under vacuum to give 3-phenylethynylbenzoic acid as a white solid (1.04 g, 94%). NMR $^1$H (ppm, CDCl$_3$): 8.27 (t, J$^4$=1.4 Hz, 1H), 8.06 (dt, J$^3$=7.8 Hz, J$^4$=1.3 Hz, 1H), 7.75 (dt, J$^3$=7.8 Hz, J$^4$=1.3 Hz, 1H), 7.56-7.53 (m, 2H), 7.47 (t, J$^3$=7.8 Hz, 1H), 7.37-7.34 (m, 3H).

117D: N-n-butyl-3-phenylethynyl-benzamide

Using preparation method 1, compound from example 117C (222 mg, 1 mmol) was treated with n-butylamine (110 µL, 1.1 mmol). Purification by flash chromatography with SiO$_2$ using CH$_2$Cl$_2$/EtOAc 97:3 gave N-n-butyl-3-phenylethynyl-benzamide as a white flaky solid (230 mg, 83%). NMR $^1$H (ppm, CDCl$_3$): 7.87 (s, 1H), 7.73 (d, J$^3$=7.8 Hz, 1H), 7.62 (d, J$^3$=7.6 Hz, 1H), 7.54-7.50 (m, 2H), 7.40 (t, J$^3$=7.8 Hz, 1H), 7.35-7.33 (m, 3H), 6.09 (br. s, 1H), 3.49-3.42 (m, 2H), 1.65-1.51 (m, 2H), 1.41 (sext., J$^3$=7.2 Hz, 2H), 0.95 (t, J$^3$=7.3 Hz, 3H).

117E: (S)-isobutyl-(L)-cysteine hydrochloride

Compound from example 78A was stirred in HCl 4N in 1,4-dioxane for 24 hours. The solvent was removed to obtain (S)-isobutyl-(L)-cysteine hydrochloride as a white solid. Quantitative yield.

117F: Compound (130)

Using preparation method 3, 117D (69 mg, 0.25 mmol) was reacted with phosgene to provide a carbamoylchloride.

Using preparation method 4, (S)-isobutyl-(L)-cysteine hydrochloride (64 mg, 0.3 mmol) was protected. The carbamoylchloride and TMS protected amino acid were reacted using Preparation Method 5. Purification by flash chromatography using $SiO_2$ with $CH_2Cl_2$ 100% then $CH_2Cl_2$/MeOH 99.5:0.5 then $CH_2Cl_2$/MeOH/AcOH 99:0.5:0.5 gave compound (130) as a pale yellow oil (22 mg, 18%). NMR $^1$H (ppm, $CDCl_3$): 9.61 (d, $J^3$=6.8 Hz, 1H), 8.76 (br. s, 1H), 7.61-7.59 (m, 2H), 7.52-7.50 (m, 2H), 7.45-7.34 (m, 5H), 4.77-4.74 (m, 1H), 3.72-3.67 (m, 2H), 3.10-2.98 (m, 2H), 2.47 (d, $J^3$=6.8 Hz, 2H), 1.84-1.74 (m, 1H), 1.50 (quin., $J^3$=6.6 Hz, 2H), 1.14 (sext., $J^3$=7.3 Hz, 2H), 0.97 (d. $J^3$=6.5 Hz, 6H), 0.75 (t, $J^3$=7.3 Hz, 3H). MS (+ESI): M+H$^+$: 481.7.

Example 118

Compound (131)

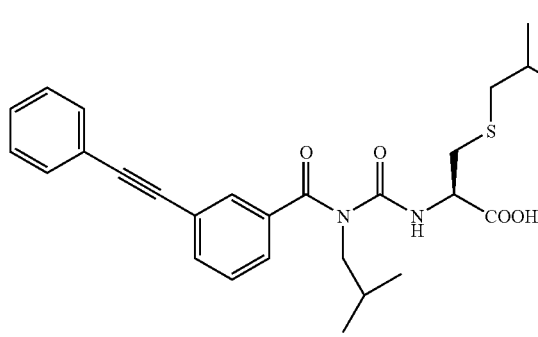

(131)

118A: N-isobutyl-3-phenylethynyl-benzamide

Using preparation method 1, compound from example 117C (222 mg, 1 mmol) was treated with isobutylamine (110 μL, 1.1 mmol). Purification by flash chromatography with $SiO_2$ using $CH_2Cl_2$/EtOAc 97:3 gave N-isobutyl-3-phenylethynyl-benzamide as a white flaky solid (192 mg, 69%). NMR $^1$H (ppm, $CDCl_3$): 7.87 (s, 1H), 7.73 (d, $J^3$=7.7 Hz, 1H), 7.63 (d, $J^3$=7.7 Hz, 1H), 7.53-7.51 (m, 2H), 7.41 (t, $J^3$=7.6 Hz, 1H), 7.35-7.33 (m, 3H), 6.16 (br. s, 1H), 3.30-3.26 (m, 2H), 1.94-1.83 (m, 1H), 0.98 (d, $J^3$=6.7 Hz, 6H).

118B: Compound (131)

Using preparation method 3, 118A (69 mg, 0.25 mmol) was reacted with phosgene to provide a carbamoylchloride. Using preparation method 4, (S)-isobutyl-(L)-cysteine hydrochloride (64 mg, 0.3 mmol) was protected. The carbamoylchloride and TMS protected amino acid were reacted using Preparation Method 5. Purification by flash chromatography using $SiO_2$ with $CH_2Cl_2$ 100% then $CH_2Cl_2$/MeOH 99.5:0.5 then $CH_2Cl_2$/MeOH/AcOH 99:0.5:0.5 gave compound (131) as a pale yellow oil (21 mg, 17%). NMR$^1$H (ppm, $CDCl_3$): 9.50 (d, $J^3$=6.8 Hz, 1H), 7.72-7.70 (m, 2H), 7.53-7.50 (m, 2H), 7.42-7.34 (m, 5H), 4.75-4.72 (m, 1H), 3.64 (d, $J^3$=7.2 Hz, 2H), 3.10-2.98 (m, 2H), 2.46 (d, $J^3$=6.7 Hz, 2H), 1.87-1.74 (m, 2H), 0.96 (d, $J^3$=6.6 Hz, 6H), 0.75 (t, $J^3$=6.6 Hz, 6H). MS (+ESI): M+H$^+$: 481.6.

Example 119

Compound (132)

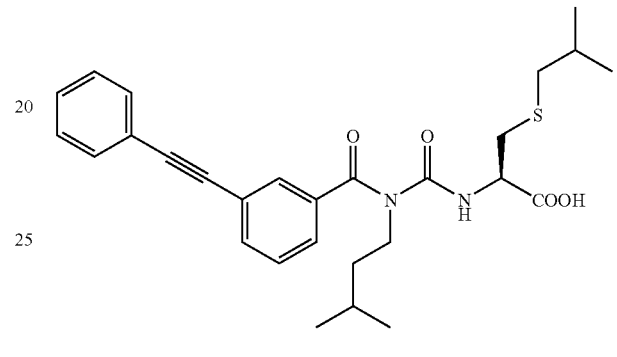

(132)

119A: N-isopentyl-3-phenylethynyl-benzamide

Using preparation method 1, compound from example 117C (222 mg, 1 mmol) was treated with isopentylamine (130 μL, 1.1 mmol). Purification by flash chromatography with $SiO_2$ using $CH_2Cl_2$/EtOAc 97:3 gave N-isopentyl-3-phenylethynyl-benzamide as a white flaky solid (184 mg, 63%). NMR $^1$H (ppm, $CDCl_3$): 7.86 (s, 1H), 7.73 (dt, $J^3$=7.7 Hz, $J^4$=1.3 Hz, 1H), 7.62 (dt, $J^3$=7.7 Hz, $J^4$=1.3 Hz, 1H), 7.54-7.51 (m, 2H), 7.40 (t, $J^3$=7.6 Hz, 1H), 7.35-7.32 (m, 3H), 6.06 (br. s, 1H), 3.51-3.44 (m, 2H), 1.73-1.64 (m, 1H), 1.51 (quart., $J^3$=7.3 Hz, 2H), 0.95 (d, $J^3$=6.7 Hz, 6H).

119B: Compound (132)

Using preparation method 3, 119A (73 mg, 0.25 mmol) was reacted with phosgene to provide a carbamoylchloride. Using preparation method 4, (S)-isobutyl-(L)-cysteine hydrochloride (64 mg, 0.3 mmol) was protected. The carbamoylchloride and TMS protected amino acid were reacted using Preparation Method 5. Purification by flash chromatography using $SiO_2$ with $CH_2Cl_2$ 100% then $CH_2Cl_2$/MeOH 99.5:0.5 then $CH_2Cl_2$/MeOH/AcOH 99:0.5:0.5 gave compound (132) as a pale yellow oil (18 mg, 15%). NMR $^1$H (ppm, $CDCl_3$): 9.64 (d, $J^3$=6.8 Hz, 1H), 7.61-7.59 (m, 2H), 7.53-7.50 (m, 2H), 7.45-7.33 (m, 5H), 4.78-4.72 (m, 1H), 3.73-3.67 (m, 2H), 3.10-2.88 (m, 2H), 2.47 (d, $J^3$=6.7 Hz, 2H), 1.84-1.71 (m, 1H), 1.51-1.38 (m, 3H), 0.97 (d, $J^3$=6.5 Hz, 6H), 0.75 (t, $J^3$=6.6 Hz, 6H). MS (+ESI): M+H$^+$: 495.6.

Example 120

Compound (133)

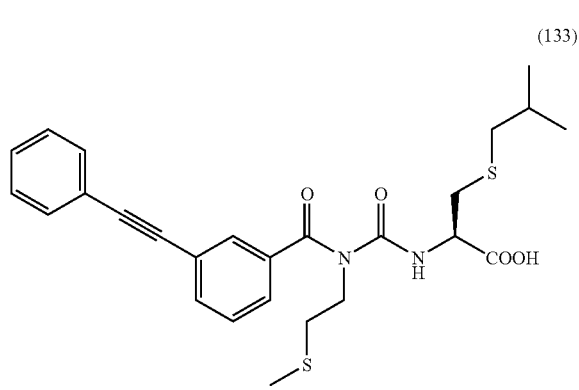

120A: N-(2-methylthio)ethyl-3-phenylethynyl-benzamide

Using preparation method 1, compound from example 117C (222 mg, 1 mmol) was treated with (2-methylthio)ethylamine (100 µL, 1.1 mmol). Purification by flash chromatography with SiO$_2$ using CH$_2$Cl$_2$/EtOAc 97:3 gave N-(2-methylthio)ethyl-3-phenylethynyl-benzamide as a white flaky solid (187 mg, 63%). NMR $^1$H (ppm, CDCl$_3$): 7.91 (t, J$^4$=1.5 Hz, 1H), 7.75 (dt, J$^3$=7.8 Hz, J$^4$=1.5 Hz, 1H), 7.64 (dt, J$^3$=7.8 Hz, J$^4$=1.3 Hz, 1H), 7.54-7.51 (m, 2H), 7.42 (t, J$^3$=7.8 Hz, 1H), 7.36-7.33 (m, 3H), 6.59 (br. s, 1H), 3.70-3.64 (m, 2H), 2.76 (t, J$^3$=6.3 Hz, 2H), 2.14 (s, 3H).

120B: Compound (133)

Using preparation method 3, 120A (73 mg, 0.25 mmol) was reacted with phosgene to provide a carbamoylchloride. Using preparation method 4, (S)-isobutyl-(L)-cysteine hydrochloride (64 mg, 0.3 mmol) was protected. The carbamoylchloride and TMS protected amino acid were reacted using Preparation Method 5. Purification by flash chromatography using SiO$_2$ with CH$_2$Cl$_2$ 100% then CH$_2$Cl$_2$/MeOH 99.5:0.5 then CH$_2$Cl$_2$/MeOH/AcOH 99:0.5:0.5 gave compound (133) as a pale yellow oil (22 mg, 18%). NMR $^1$H (ppm, CDCl$_3$): 9.54 (d, J$^3$=6.9 Hz, 1H), 8.41 (br. s, 1H), 7.63-7.61 (m, 2H), 7.53-7.50 (m, 2H), 7.44-7.34 (m, 5H), 4.78-4.72 (m, 1H), 3.95 (t, J$^3$=6.7 Hz, 2H), 3.10-2.90 (m, 2H), 2.63 (t, J$^3$=6.7 Hz, 2H), 2.47 (d, J$^3$=6.7 Hz, 2H), 1.84-1.72 (m, 4H), 0.97 (d, J$^3$=6.5 Hz, 6H). MS (+ESI): M+H$^+$: 499.5.

Example 121

Compound (134)

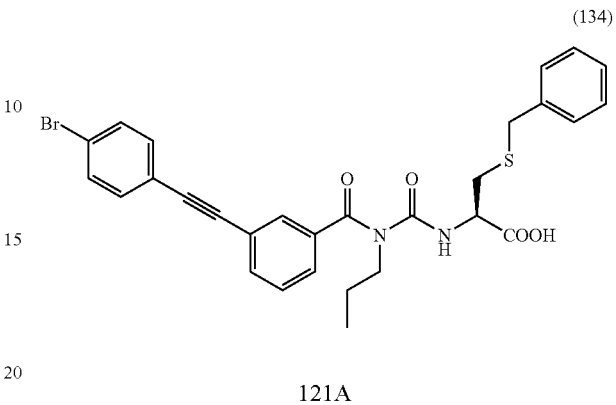

121A

Using preparation method 3, N-n-propyl-3-iodobenzamide (1.156 g, 4 mmol) was reacted with phosgene to provide a carbamoylchloride. Using preparation method 4, (S)-benzyl-(L)-cysteine hydrochloride was protected. The carbamoyl chloride and TMS protected amino acid were reacted using preparation method 5. Purification by flash chromatography using SiO$_2$ with CH$_2$Cl$_2$/MeOH 95:5 gave the compound as a pale amber oil (1.92 mg, 91%). NMR $^1$H (ppm, CDCl$_3$): 9.52 (d, J$^3$=7.0 Hz, 1H), 8.73 (br. s, 1H), 7.82-7.79 (m, 2H), 7.40 (d, J$^3$=7.7 Hz, 1H), 7.32-7.21 (m, 5H), 7.17 (t, J$^3$=7.9 Hz, 1H), 4.76-4.70 (m, 1H), 3.76 (s, 2H), 3.64-3.59 (m, 2H), 3.01-2.85 (m, 2H), 1.53 (sext., J$^3$=7.5 Hz, 2H), 0.73 (t, J$^3$=7.4 Hz, 3H). MS (+ESI): M+H$^+$: 527.3.

121B: Compound (134)

Using preparation method 10, 121A (100 mg, 0.19 mmol) was reacted with 4-bromophenylacetylene (54 mg, 0.3 mmol). Purification by passing through a SAX Acetate solid phase extraction column with MeOH 100% then MeOH/AcOH 85:15 gave compound (134) as an amber oil (74 mg, 67%). NMR $^1$H (ppm, CDCl$_3$): 9.60 (d, J$^3$=6.9 Hz, 1H), 8.72 (br. s, 1H), 7.60-7.22 (m, 13H), 4.77-4.71 (m, 1H), 3.78 (s, 2H), 3.69-3.64 (m, 2H), 3.02-2.86 (m, 2H), 1.54 (sext., J$^3$=7.4 Hz, 2H), 0.73 (t, J$^3$=7.4 Hz, 3H). MS (+ESI): M+H$^+$: 581.5.

Example 122

Compound (135)

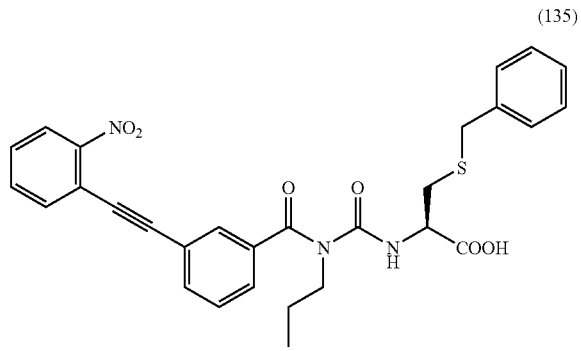

Using preparation method 10, 121A (100 mg, 0.19 mmol) was reacted with 2-nitrophenylacetylene (44 mg, 0.3 mmol). Purification by passing through a SAX Acetate solid phase extraction column with MeOH 100% then MeOH/AcOH 85:15 gave compound (135) as a yellow oil (68 mg, 66%). NMR $^1$H (ppm, CDCl$_3$): 9.65-9.56 (m, 1H), 9.25 (br. s, 1H), 7.72-7.22 (m, 13H), 4.76-4.71 (m, 1H), 3.78 (s, 2H), 3.71-3.64 (m, 2H), 2.98-2.86 (m, 2H), 1.63-1.51 (m, 2H), 0.74 (t, $J^3$=7.3 Hz, 3H). MS (+ESI): M+H$^+$: 546.6.

Example 123

Compound (136)

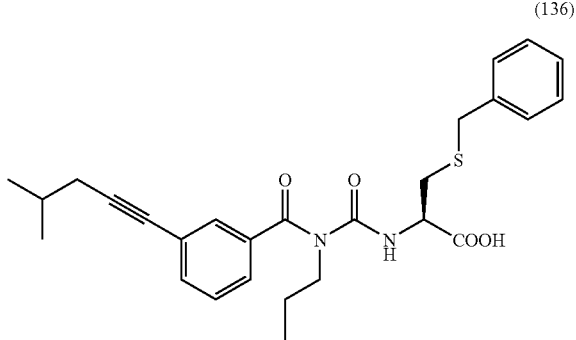

(136)

Using preparation method 10, 121A (100 mg, 0.19 mmol) was reacted with 4-methylpent-1-yne (35 µL, 25 mg, 0.3 mmol). Purification by passing through a SAX Acetate solid phase extraction column with MeOH 100% then MeOH/AcOH 85:15 gave compound (136) as a colourless oil (65 mg, 71%). NMR $^1$H (ppm, CDCl$_3$): 9.63 (d, $J^3$=6.9 Hz, 1H), 8.92 (br. s, 1H), 7.49-7.46 (m, 2H), 7.38-7.21 (m, 7H), 4.76-4.70 (m, 1H), 3.77 (s, 2H), 3.66-3.61 (m, 2H), 3.01-2.85 (m, 2H), 2.29 (d, $J^3$=6.5 Hz, 2H), 1.96-1.85 (m, 1H), 1.52 (sext., $J^3$=7.4 Hz, 2H), 1.03 (d, $J^3$=6.6 Hz, 6H), 0.72 (t, $J^3$=7.4 Hz, 3H). MS (+ESI): M+H$^+$: 481.8.

Example 124

Compound (137)

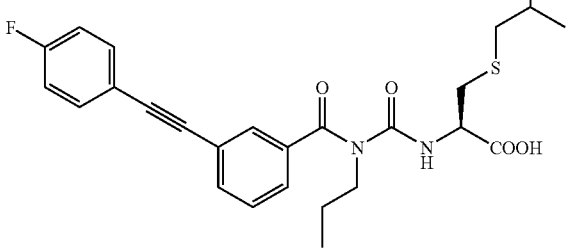

(137)

124A

Using preparation method 3, N-n-propyl-3-iodobenzamide (820 mg, 2.84 mmol) was reacted with phosgene to provide a carbamoylchloride. Using preparation method 4, (S)-isobutyl-(L)-cysteine hydrochloride was protected. The carbamoyl chloride and TMS protected amino acid were reacted using preparation method 5. Purification by flash chromatography using SiO$_2$ with CH$_2$Cl$_2$/MeOH 95:5 gave the compound as a pale amber oil (1.190 g, 85%). NMR $^1$H (ppm, CDCl$_3$): 9.53 (d, $J^3$=6.3 Hz, 1H), 7.85-7.79 (m, 2H), 7.41 (d, $J^3$=7.5 Hz, 1H), 7.18 (t, $J^3$=7.7 Hz, 1H), 4.75-4.69 (m, 1H), 3.60-3.55 (m, 2H), 3.06-2.96 (m, 2H), 2.47 (d, $J^3$=6.7 Hz, 2H), 1.84-1.75 (m, 1H), 1.54 (sext., $J^3$=7.6 Hz, 2H), 0.97 (d, $J^3$=6.6 Hz, 6H), 0.74 (t, $J^3$=7.5 Hz, 3H). MS (+ESI): M+H$^+$: 493.1.

124B

Using preparation method 10, 124A (49 mg, 0.1 mmol) was reacted with 4-fluorophenylacetylene (18 mg, 0.15 mmol). Purification by passing through a SAX Acetate solid phase extraction column with MeOH 100% then MeOH/AcOH 85:15 gave compound (137) as a golden oil (15 mg, 31%). NMR $^1$H (ppm, CDCl$_3$): 9.62 (d, $J^3$=6.9 Hz, 1H), 7.64-7.32 (m, 8H), 4.77-4.71 (m, 1H), 3.70-3.65 (m, 2H), 3.12-2.99 (m, 2H), 2.48 (d, $J^3$=6.9 Hz, 2H), 1.87-1.73 (m, 1H), 1.54 (sext., $J^3$=7.4 Hz, 2H), 0.97 (d, $J^3$=6.6 Hz, 6H), 0.74 (t, $J^3$=7.4 Hz, 3H). MS (+ESI): M+H$^+$: 485.3.

Example 125

Compound (138)

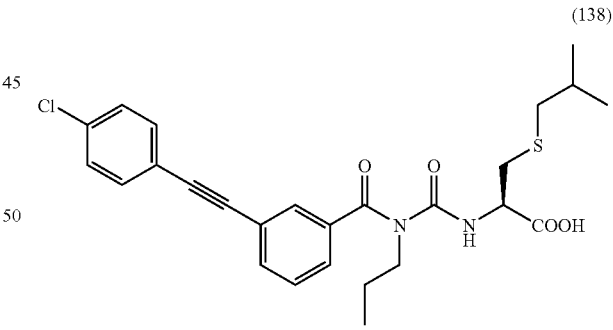

(138)

Using preparation method 10, 124A (49 mg, 0.1 mmol) was reacted with 4-chlorophenylacetylene (21 mg, 0.15 mmol). Purification by passing through a SAX Acetate solid phase extraction column with MeOH 100% then MeOH/AcOH 85:15 gave compound (138) as a golden solid (31 mg, 62%). NMR $^1$H (ppm, CDCl$_3$): 9.59 (d, $J^3$=6.9 Hz, 1H), 7.61-7.30 (m, 8H), 4.78-4.71 (m, 1H), 3.69-3.64 (m, 2H), 3.12-2.98 (m, 2H), 2.47 (d, $J^3$=6.9 Hz, 2H), 1.84-1.75 (m, 1H), 1.54 (sext., $J^3$=7.4 Hz, 2H), 0.96 (d, $J^3$=6.6 Hz, 6H), 0.73 (t, $J^3$=7.3 Hz, 3H). MS (+ESI): M+H$^+$: 501.3.

Example 126

Compound (139)

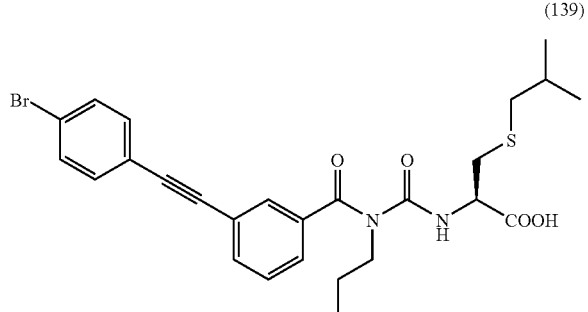

Using preparation method 10, 124A (49 mg, 0.1 mmol) was reacted with 4-bromophenylacetylene (27 mg, 0.15 mmol). Purification by passing through a SAX Acetate solid phase extraction column with MeOH 100% then MeOH/AcOH 85:15 gave compound (139) as a golden solid (20 mg, 37%). NMR H (ppm, CDCl$_3$): 9.59 (d, J$^3$=6.9 Hz, 1H), 7.62-7.59 (m, 2H), 7.49-7.36 (m, 6H), 4.78-4.72 (m, 1H), 3.69-3.64 (m, 2H), 3.12-2.99 (m, 2H), 2.47 (d, J$^3$=6.9 Hz, 2H), 1.87-1.73 (m, 1H), 1.54 (sext., J$^3$=7.5 Hz, 2H), 0.97 (d, J$^3$=6.6 Hz, 6H), 0.73 (t, J$^3$=7.4 Hz, 3H). MS (+ESI): M+H$^+$: 547.2.

Example 127

Compound (140)

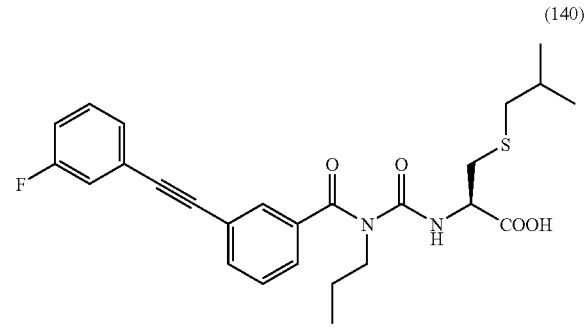

Using preparation method 10, 124A (49 mg, 0.1 mmol) was reacted with 3-fluorophenylacetylene (18 mg, 0.15 mmol). Purification by passing through a SAX Acetate solid phase extraction column with MeOH 100% then MeOH/AcOH 85:15 gave compound (140) as a golden solid (37 mg, 76%). NMR $^1$H (ppm, CDCl$_3$): 9.60-9.51 (m, 1H), 8.05-7.04 (m, 8H), 4.78-4.71 (m, 1H), 3.70-3.60 (m, 2H), 3.09-2.99 (m, 2H), 2.48-2.43 (m, 2H), 1.81-1.75 (m, 1H), 1.54 (sext., J$^3$=7.0 Hz, 2H), 0.97 (d, J$^3$=6.5 Hz, 6H), 0.74 (t, J$^3$=7.4 Hz, 3H). MS (+ESI): M+H$^+$: 485.1.

Example 128

Compound (141)

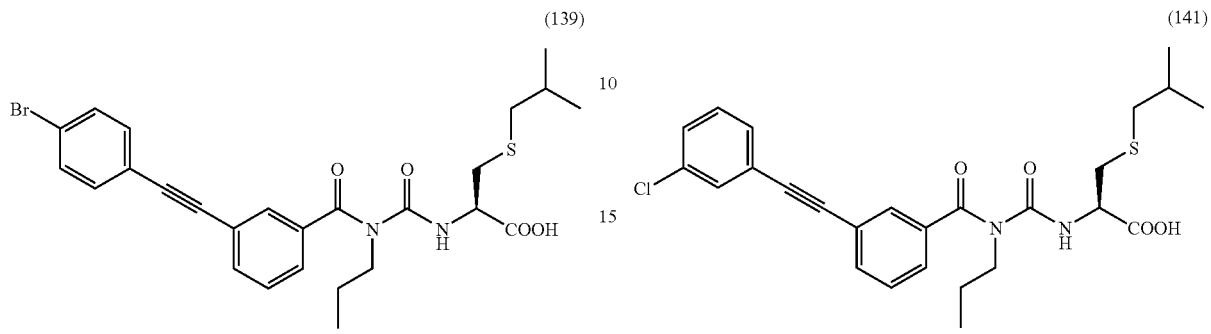

Using preparation method 10, 124A (49 mg, 0.1 mmol) was reacted with 3-chlorophenylacetylene (18 mg, 0.15 mmol). Purification by passing through a SAX Acetate solid phase extraction column with MeOH 100% then MeOH/AcOH 85:15 gave compound (141) as a golden solid (20 mg, 40%). NMR $^1$H (ppm, CDCl$_3$): 9.58 (d, J$^3$=6.9 Hz, 1H), 8.54 (br. s, 1H), 7.62-7.59 (m, 2H), 7.51-7.23 (m, 6H), 4.79-4.73 (m, 1H), 3.70-3.64 (m, 2H), 3.12-2.99 (m, 2H), 2.47 (d, J$^3$=6.6 Hz, 2H), 1.86-1.73 (m, 1H), 1.54 (sext., J$^3$=7.5 Hz, 2H), 0.97 (d, J$^3$=6.6 Hz, 6H), 0.74 (t, J$^3$=7.4 Hz, 3H). MS (+ESI): M+H$^+$: 501.2.

Example 129

Compound (142)

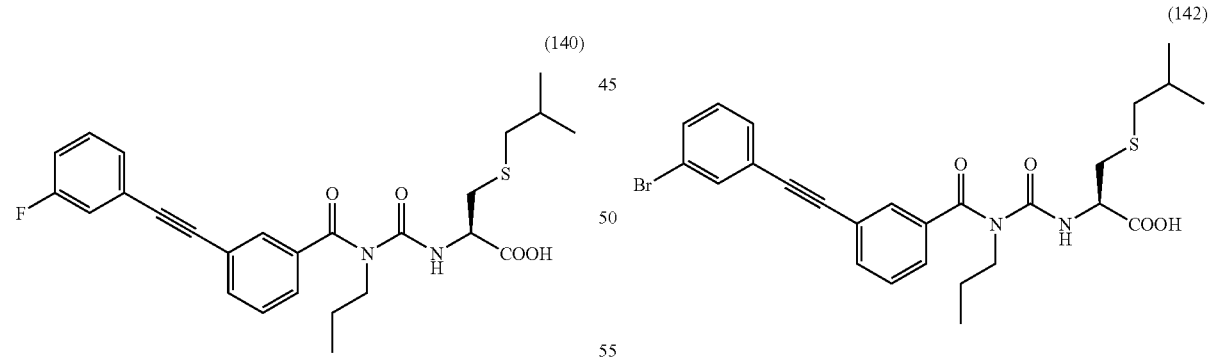

Using preparation method 10, 124A (49 mg, 0.1 mmol) was reacted with 3-bromophenylacetylene (27 mg, 0.15 mmol). Purification by passing through a SAX Acetate solid phase extraction column with MeOH 100% then MeOH/AcOH 85:15 gave compound (142) as an orange solid (32 mg, 59%). NMR $^1$H (ppm, CDCl$_3$): 9.58 (d, J$^3$=6.9 Hz, 1H), 8.69 (br. s, 1H), 7.67-7.59 (m, 3H), 7.48-7.41 (m, 4H), 7.21 (t, J$^3$=7.8 Hz, 1H), 4.79-4.73 (m, 1H), 3.70-3.64 (m, 2H), 3.12-2.99 (m, 2H), 2.47 (d, J$^3$=6.6 Hz, 2H), 1.86-1.73 (m, 1H), 1.54 (sext., J$^3$=7.5 Hz, 2H), 0.97 (d, J$^3$=6.6 Hz, 6H), 0.74 (t, J$^3$=7.4 Hz, 3H). MS (+ESI): M+H$^+$: 547.2.

Example 130

Compound (143)

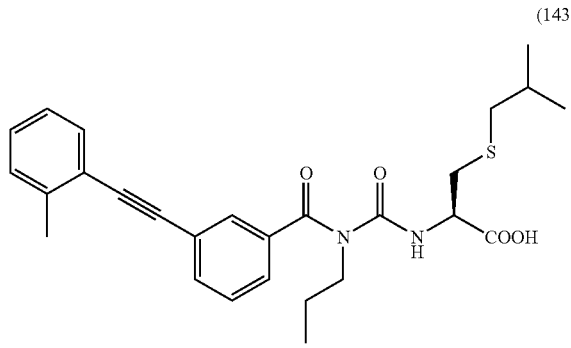

Using preparation method 10, 124A (49 mg, 0.1 mmol) was reacted with 2-ethynyltoluene (17.4 mg, 0.15 mmol). Purification by passing through a SAX Acetate solid phase extraction column with MeOH 100% then MeOH/AcOH 85:15 gave compound (143) as an off-white solid (20 mg, 42%). NMR $^1$H (ppm, CDCl$_3$): 9.63 (d, J$^3$=6.8 Hz, 1H), 8.40 (br. s, 1H), 7.63-7.60 (m, 2H), 7.49-7.37 (m, 3H), 7.27-7.13 (m, 3H), 4.79-4.73 (m, 1H), 3.70-3.65 (m, 2H), 3.13-2.99 (m, 2H), 2.51-2.47 (m, 5H), 1.84-1.74 (m, 1H), 1.55 (sext., J$^3$=7.4 Hz, 2H), 0.97 (d, J$^3$=6.6 Hz, 6H), 0.74 (t, J$^3$=7.4 Hz, 3H). MS (+ESI): M+H$^+$: 481.3.

Example 131

Compound (144)

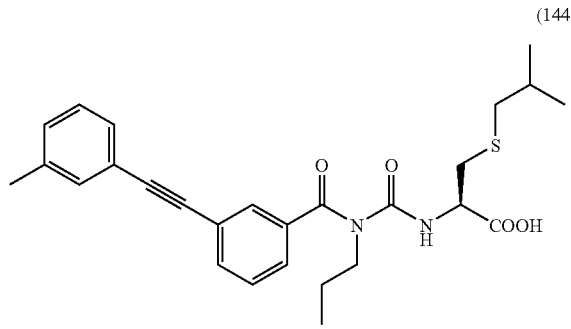

Using preparation method 10, 124A (49 mg, 0.1 mmol) was reacted with 3-ethynyltoluene (17.4 mg, 0.15 mmol). Purification by passing through a SAX Acetate solid phase extraction column with MeOH 100% then MeOH/AcOH 85:15 gave compound (144) as an amber solid (29 mg, 60%). NMR $^1$H (ppm, CDCl$_3$): 9.61 (d, J$^3$=6.9 Hz, 1H), 8.41 (br. s, 1H), 7.61-7.59 (m, 2H), 7.45-7.31 (m, 4H), 7.26-7.14 (m, 2H), 4.79-4.73 (m, 1H), 3.70-3.65 (m, 2H), 3.12-2.99 (m, 2H), 2.47 (d, J$^3$=7.0 Hz, 2H), 2.34 (s, 3H), 1.84-1.75 (m, 1H), 1.54 (sext., J$^3$=7.4 Hz, 2H), 0.97 (d, J$^3$=6.6 Hz, 6H), 0.74 (t, J$^3$=7.4 Hz, 3H). MS (+ESI): M+H$^+$: 493.1.

Example 132

Compound (145)

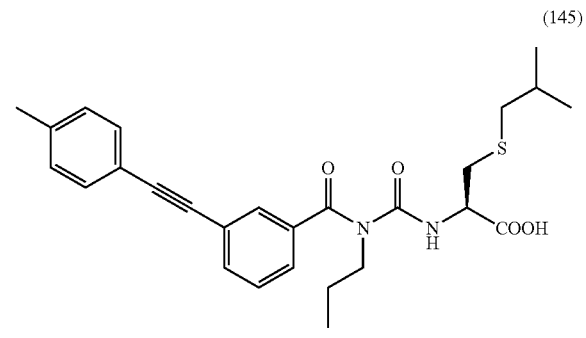

Using preparation method 10, 124A (49 mg, 0.1 mmol) was reacted with 4-ethynyltoluene (17.4 mg, 0.15 mmol). Purification by passing through a SAX Acetate solid phase extraction column with MeOH 100% then MeOH/AcOH 85:15 gave compound (145) as an amber solid (12 mg, 25%). NMR $^1$H (ppm, CDCl$_3$): 9.62 (d, J$^3$=5.9 Hz; 1H), 7.61-7.10 (m, 8H), 5.85 (br. s, 1H), 4.77-4.71 (m, 1H), 3.70-3.65 (m, 2H), 2.36-2.34 (m, 5H), 1.82-1.77 (m, 1H), 1.54 (sext., J$^3$=7.4 Hz, 2H), 0.97 (d, J$^3$=6.5 Hz, 6H), 0.73 (t, J$^3$=7.4 Hz, 3H). MS (+ESI): M+H$^+$: 481.3.

Example 133

Compound (146)

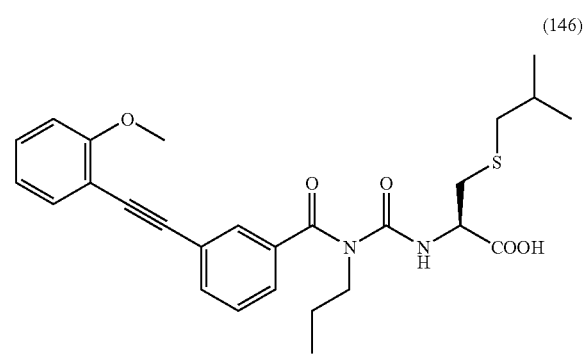

Using preparation method 10, 124A (49 mg, 0.1 mmol) was reacted with 2-methoxyphenylacetylene (20 mg, 0.15 mmol). Purification by passing through a SAX Acetate solid phase extraction column with MeOH 100% then MeOH/AcOH 85:15 gave compound (146) as an amber oil (7 mg, 14%). NMR $^1$H (ppm, CDCl$_3$): 9.56 (d, J$^3$=5.4 Hz, 1H), 7.65-6.89 (m, 8H), 4.76-4.70 (m, 1H), 4.56 (br. s, 1H), 3.91-3.88 (m, 5H), 3.71-3.66 (m, 2H), 1.81-1.72 (m, 1H), 1.54 (sext., J$^3$=7.4 Hz, 2H), 0.97 (d, J$^3$=6.5 Hz, 6H), 0.74 (t, J$^3$=7.4 Hz, 3H). MS (+ESI): M+H$^+$: 497.3.

Example 134

Compound (147)

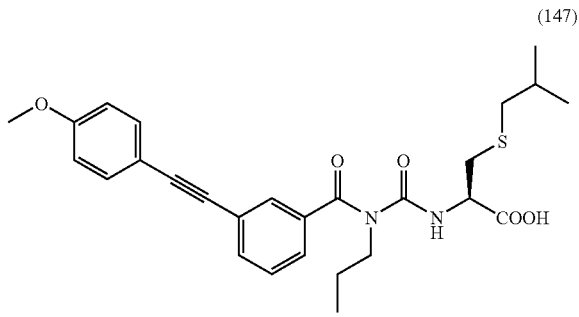

Using preparation method 10, 124A (49 mg, 0.1 mmol) was reacted with 4-methoxyphenylacetylene (20 mg, 0.15 mmol). Purification by passing through a SAX Acetate solid phase extraction column with MeOH 100% then MeOH/AcOH 85:15 gave compound (147) as an amber solid (5 mg, 10%). NMR $^1$H (ppm, CDCl$_3$): 9.62 (d, $J^3$=6.7 Hz, 1H), 7.65 (d, $J^3$=6.7 Hz, 2H), 7.47-7.35 (m, 4H), 6.87 (d, $J^3$=8.7 Hz, 2H), 5.90 (br. s, 1H), 4.78-4.72 (m, 1H), 3.82 (s, 3H), 3.70-3.65 (m, 2H), 3.13-3.00 (m, 2H), 2.48 (d, $J^3$=6.6 Hz, 2H), 1.85-1.76 (m, 1H), 1.54 (sext., $J^3$=7.3 Hz, 2H), 0.97 (d, $J^3$=6.6 Hz, 6H), 0.74 (t, $J^3$=7.4 Hz, 3H). MS (+ESI): M+H$^+$: 497.3.

Example 135

Compound (148)

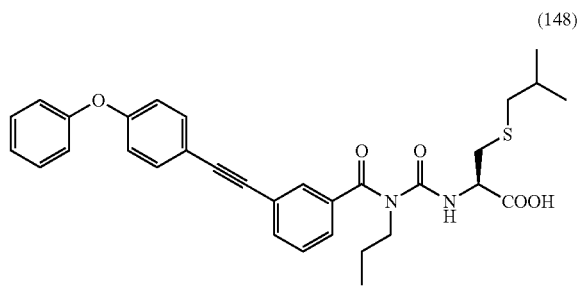

Using preparation method 10, 124A (49 mg, 0.1 mmol) was reacted with 4-phenoxyphenylacetylene (29.1 mg, 0.15 mmol). Purification by passing through a SAX Acetate solid phase extraction column with MeOH 100% then MeOH/AcOH 85:15 gave compound (148) as an amber oil (33 mg, 59%). NMR $^1$H (ppm, CDCl$_3$): 9.61 (d, $J^3$=6.8 Hz, 1H), 8.37 (br. s, 1H), 7.60-7.33 (m, 8H), 7.14 (t, $J^3$=8.1 Hz, 1H), 7.04-6.90 (m, 4H), 4.79-4.73 (m, 1H), 3.70-3.65 (m, 2H), 3.12-2.99 (m, 2H), 2.47 (d, $J^3$=6.9 Hz, 2H), 1.84-1.75 (m, 1H), 1.54 (sext., $J^3$=7.3 Hz, 2H), 0.97 (d, $J^3$=6.6 Hz, 6H), 0.73 (t, $J^3$=7.3 Hz, 3H). MS (+ESI): M+H$^+$: 559.4.

Example 136

Compound (149)

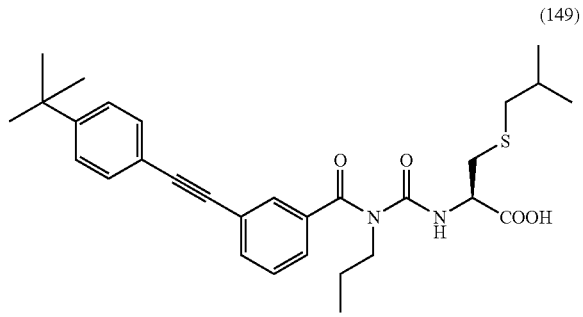

Using preparation method 10, 124A (49 mg, 0.1 mmol) was reacted with 4-tert-butylphenylacetylene (25 mg, 0.15 mmol). Purification by passing through a SAX Acetate solid phase extraction column with MeOH 100% then MeOH/AcOH 85:15 gave compound (149) as a colourless oil (3 mg, 6%). NMR $^1$H (ppm, CDCl$_3$): 9.62 (d, $J^3$=6.8 Hz, 1H), 7.62-7.35 (m, 8H), 4.75-4.71 (m, 1H), 3.70-3.65 (m, 2H), 3.12-2.99 (m, 2H), 2.48 (d, $J^3$=6.7 Hz, 2H), 1.84-1.75 (m, 1H), 1.54 (sext., $J^3$=7.3 Hz, 2H), 1.31 (s, 9H), 0.97 (d, $J^3$=6.4 Hz, 6H), 0.74 (t, $J^3$=7.2 Hz, 3H). MS (+ESI): M+H$^+$: 523.7.

Example 137

Compound (150)

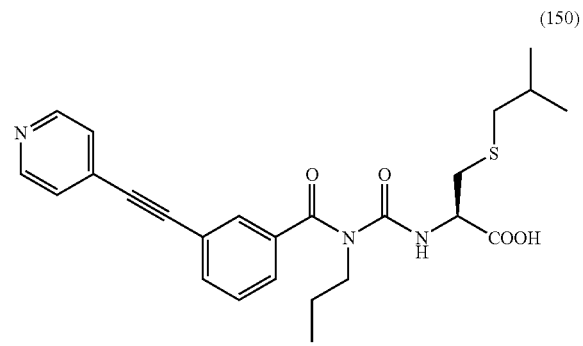

Using preparation method 10, 124A (49 mg, 0.1 mmol) was reacted with 4-ethynylpyridine hydrochloride (21 mg, 0.15 mmol). Purification by passing through a SAX Acetate solid phase extraction column with MeOH 100% then MeOH/AcOH 85:15 gave compound (150) as a red oil (10 mg, 21%). NMR $^1$H (ppm, CDCl$_3$): 9.50-9.35 (m, 1H), 7.81-7.14 (m, 8H), 4.76-4.70 (m, 1H), 3.70-3.65 (m, 2H), 3.12-2.99 (m, 2H), 2.46 (d, $J^3$=6.9 Hz, 2H), 1.82-1.73 (m, 1H), 1.54 (sext., $J^3$=7.2 Hz, 2H), 0.95 (d, $J^3$=6.6 Hz, 6H), 0.74 (m, 3H). MS (+ESI): M+H$^+$: 468.2.

Example 138

Compound (151)

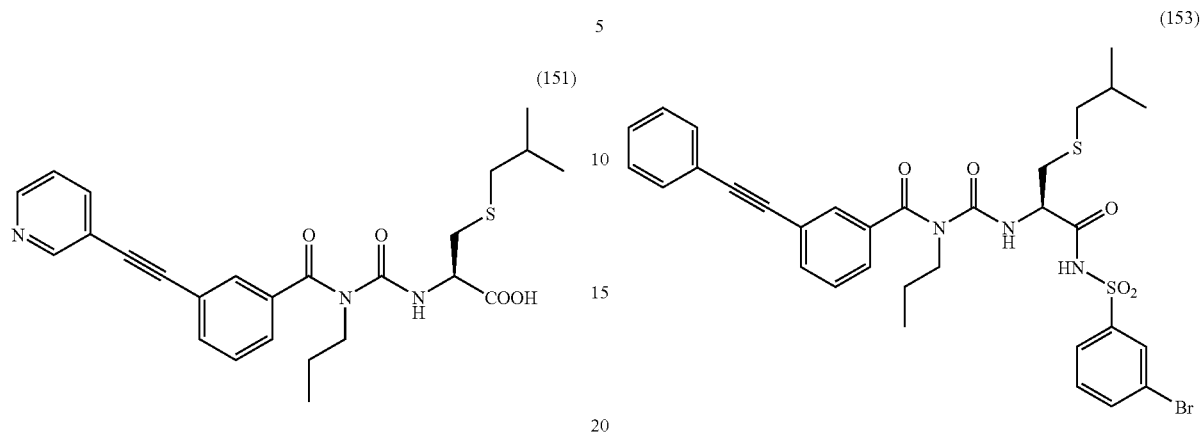

Using preparation method 10, 124A (49 mg, 0.1 mmol) was reacted with 3-ethynylpyridine (15 mg, 0.15 mmol). Purification by passing through a SAX Acetate solid phase extraction column with MeOH 100% then MeOH/AcOH 85:15 gave compound (151) as an amber oil (32 mg, 69%). NMR $^1$H (ppm, CDCl$_3$): 9.34 (d, $J^3$=6.8 Hz, 1H), 8.06 (d, $J^3$=7.6 Hz, 1H), 7.65-7.43 (m, 7H), 4.78-4.72 (m, 1H), 3.69-3.64 (m, 2H), 3.12-2.99 (m, 2H), 2.46 (d, $J^3$=6.6 Hz, 2H), 1.85-1.72 (m, 1H), 1.55 (sext., $J^3$=7.3 Hz, 2H), 0.95 (d, $J^3$=6.5 Hz, 6H), 0.75 (t, $J^3$=7.3 Hz, 3H). MS (+ESI): M+H$^+$: 468.3.

Example 139

Compound (152)

Compound from example 78B (47 mg, 0.1 mmol) was reacted with 4-bromobenzenesulfonamide (24 mg, 0.1 mmol) as described in preparation method 11, to obtain compound (152) as a colourless oil (51 mg, 75%). NMR $^1$H (ppm, CDCl$_3$): 9.83 (s, 1H), 9.59 (d, $J^3$=6.2 Hz, 1H), 8.14 (d, $J^3$=8.3 Hz, 2H), 7.72 (d, $J^3$=8.3 Hz, 2H), 7.60-7.34 (m, 9H), 4.55-4.52 (m, 1H), 3.71-3.65 (m, 2H), 2.99-2.87 (m, 2H), 2.39 (d, $J^3$=6.7 Hz, 2H), 1.78-1.70 (m, 1H), 1.52 (sext., $J^3$=7.5 Hz, 2H), 0.93 (d, $J^3$=6.6 Hz, 6H), 0.74 (t, $J^3$=7.4 Hz, 3H). MS (+ESI): M+H$^+$: 686.3.

Example 140

Compound (153)

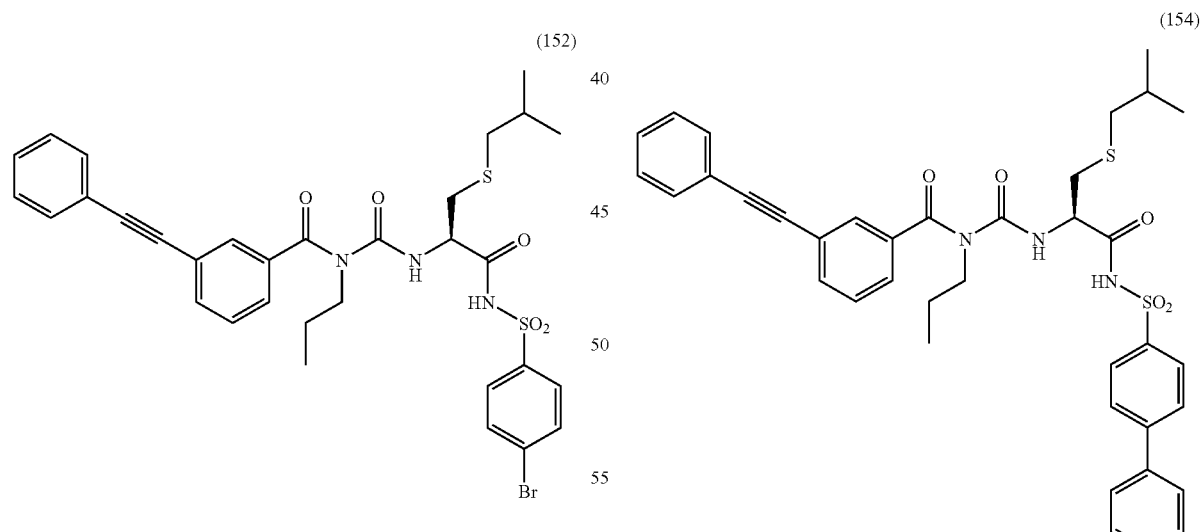

Compound from example 78B (47 mg, 0.1 mmol) was reacted with 3-bromobenzenesulfonamide (24 mg, 0.1 mmol) as described in preparation method 11, to obtain compound (153) as a colourless oil (61 mg, 89%). NMR $^1$H (ppm, CDCl$_3$): 9.90 (s, 1H), 9.58 (d, $J^3$=6.5 Hz, 1H), 8.18 (s, 1H), 8.03 (d, $J^3$=7.6 Hz, 1H), 7.85 (d, $J^3$=7.6 Hz, 1H), 7.72-7.62 (m, 2H), 7.53-7.50 (m, 2H), 7.43-7.33 (m, 6H), 4.53-4.47 (m, 1H), 3.70-3.65 (m, 2H), 2.97-2.82 (m, 2H), 2.38 (d, $J^3$=6.8 Hz, 2H), 1.78-1.70 (m, 1H), 1.52 (sext., $J^3$=7.5 Hz, 2H), 0.93 (d, $J^3$=6.6 Hz, 6H), 0.74 (t, $J^3$=7.4 Hz, 3H). MS (+ESI): M+H$^+$: 686.5.

Example 141

Compound (154)

141A: 4-phenylbenzenesulfonamide

Using preparation method 2, 4-bromobenzenesulfonamide (472 mg, 2 mmol) was reacted with phenylboronic acid (268 mg, 2.2 mmol). Purification by washing with hot toluene followed by filtration gave 4-phenylbenzenesulfonamide as an off-white crystalline solid (264 mg, 55%). NMR $^1$H (ppm, CDCl$_3$): 7.87 (d, J$^3$=8.6 Hz, 2H), 7.83 (d, J$^3$=8.7 Hz, 2H), 7.70 (d, J$^3$=7.2 Hz, 2H), 7.48 (t, J$^3$=7.3 Hz, 2H), 7.40 (t, J$^3$=7.1 Hz, 1H).

141B: Compound (154)

Compound from example 78B (47 mg, 0.1 mmol) was reacted with 4-phenylbenzenesulfonamide (23 mg, 0.1 mmol) as described in preparation method 11, to obtain compound (154) as a colourless oil (53 mg, 78%). NMR $^1$H (ppm, CDCl$_3$): 9.86 (s, 1H), 9.57 (d, J$^3$=6.3 Hz, 1H), 7.93 (d, J$^3$=8.6 Hz, 2H), 7.67-7.59 (m, 5H), 7.53-7.50 (m, 2H), 7.43 (t, J$^3$=7.6 Hz, 1H), 7.39-7.33 (m, 8H), 4.54-4.48 (m, 1H), 3.70-3.65 (m, 2H), 2.97-2.83 (m, 2H), 2.37 (d, J$^3$=6.8 Hz, 2H), 1.77-1.68 (m, 1H), 1.49 (sext., J$^3$=7.4 Hz, 2H), 0.92 (d, J$^3$=6.6 Hz, 6H), 0.73 (t, J$^3$=7.4 Hz, 3H). MS (+ESI): M+H$^+$: 682.6.

Example 142

Compound (155)

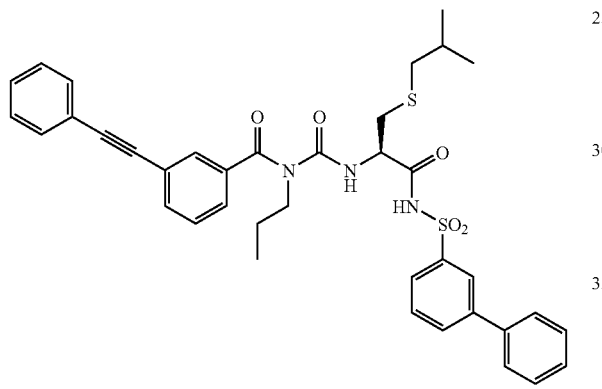

(155)

142A: 3-phenylbenzenesulfonamide

Using preparation method 2, 3-bromobenzenesulfonamide (236 mg, 1 mmol) was reacted with phenylboronic acid (134 mg, 1.1 mmol). Purification by flash chromatography on SiO$_2$ with CH$_2$Cl$_2$ gave 3-phenylbenzenesulfonamide as an off-white crystalline solid (155 mg, 66%). NMR $^1$H (ppm, d$_6$-DMSO): 8.11 (s, 1H), 7.84 (d, J$^3$=7.8 Hz, 1H), 7.70 (d, J$^3$=7.8 Hz, 1H), 7.56-7.53 (m, 2H), 7.48 (t, J$^3$=7.8 Hz, 1H), 7.43-7.34 (m, 3H), 5.10 (br. s, 2H).

142B: Compound (155)

Compound from example 78B (47 mg, 0.1 mmol) was reacted with 3-phenylbenzenesulfonamide (23 mg, 0.1 mmol) as described in preparation method 11, to obtain compound (155) as a colourless oil (48 mg, 70%). NMR $^1$H (ppm, CDCl$_3$): 9.85 (s, 1H), 9.56 (d, J$^3$=6.5 Hz, 1H), 8.28 (s, 1H), 8.05 (d, J$^3$=7.9 Hz, 1H), 7.83 (d, J$^3$=7.9 Hz, 1H), 7.62-7.34 (m, 15H), 4.54-4.48 (m, 1H), 3.64-3.57 (m, 2H), 2.97-2.83 (m, 2H), 2.37 (d, J$^3$=6.8 Hz, 2H), 1.76-1.67 (m, 1H), 1.49 (sext., J$^3$=7.4 Hz, 2H), 0.90 (d, J$^3$=6.6 Hz, 6H), 0.69 (t, J$^3$=7.4 Hz, 3H). MS (+ESI): M+H$^+$: 683.9.

Example 143

Compound (156)

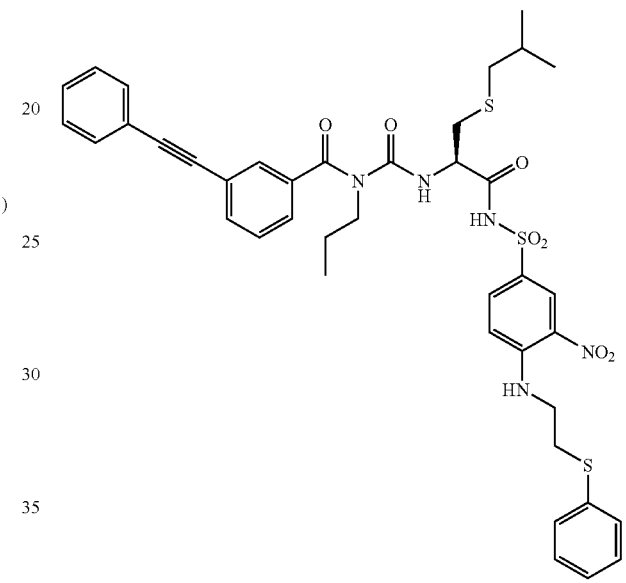

(156)

Compound from example 78B (47 mg, 0.1 mmol) was reacted with 3-nitro-4-(2-phenylthioethyl)aminobenzenesulfonamide (35 mg, 0.1 mmol) as described in preparation method 11, to obtain compound (156) as a yellow oil (68 mg, 85%). NMR $^1$H (ppm, CDCl$_3$): 9.89 (s, 1H), 9.58 (d, J$^3$=6.5 Hz, 1H), 8.79 (d, J$^4$=1.7 Hz, 1H), 8.65 (d, J$^3$=5.6 Hz, 1H), 8.02 (dd, J$^3$=9.2 Hz, J4=2.1 Hz, 1H), 7.61-7.24 (m, 14H), 6.78 (d, J$^3$=9.2 Hz, 1H), 4.53-4.47 (m, 1H), 3.70-3.65 (m, 2H), 3.57-3.50 (m, 2H), 3.18 (t, J$^3$=6.6 Hz, 2H), 2.94-2.85 (m, 2H), 2.40 (d, J$^3$=6.8 Hz, 2H), 1.78-1.69 (m, 1H), 1.49 (sext., J$^3$=7.4 Hz, 2H), 0.92 (d, J$^3$=6.6 Hz, 6H), 0.72 (t, J$^3$=7.4 Hz, 3H). MS (+ESI): M+H$^+$: 802.3.

Constrained Analogues

Example 144

Compound (157)

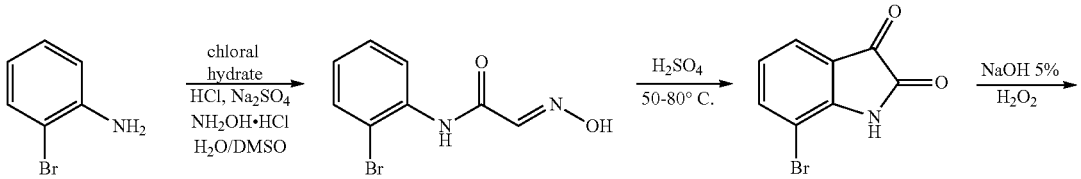

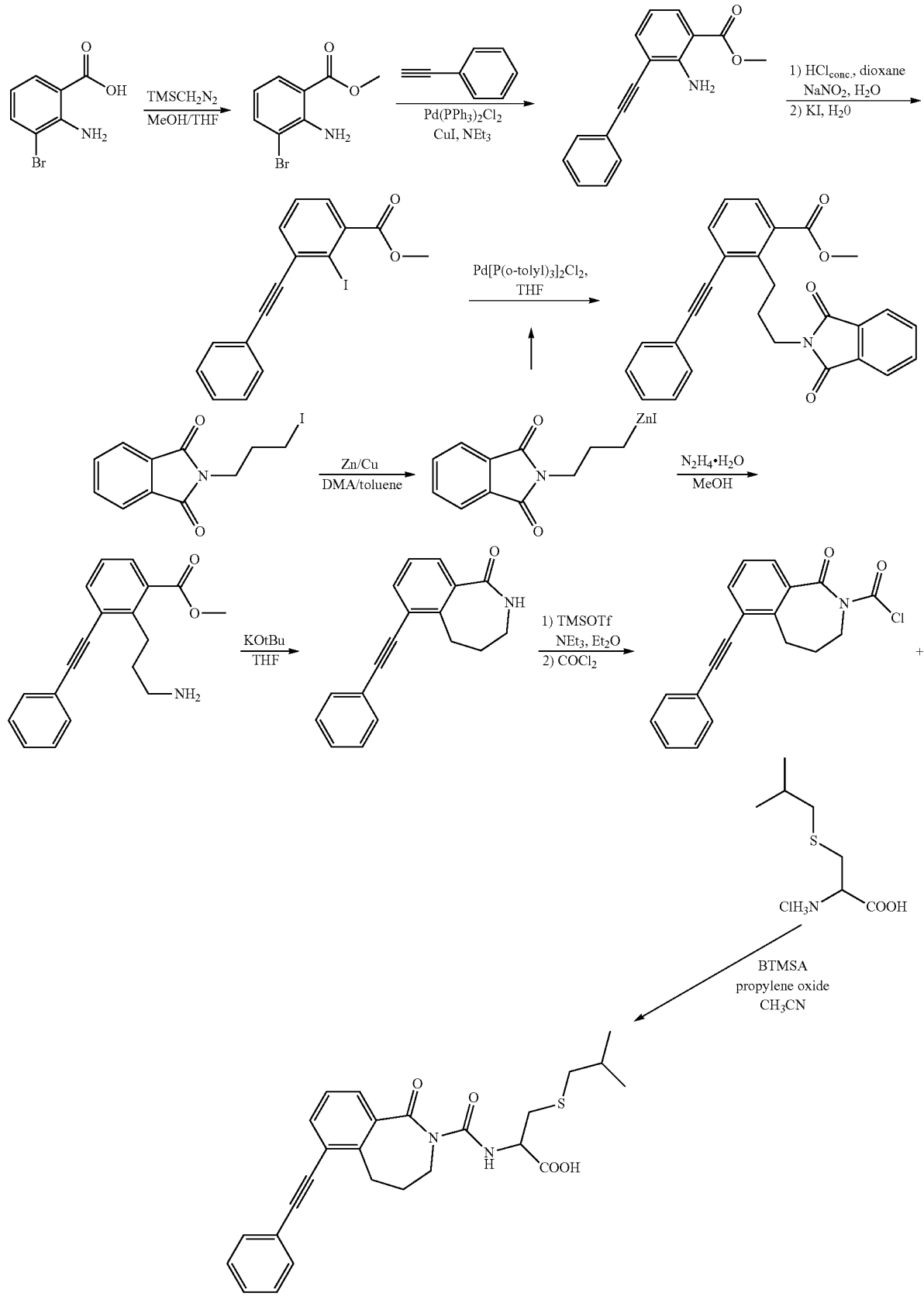

144A: N-(2-Bromo-phenyl)-2-hydroxyimino-acetamide. Chloral hydrate (11.6 g, 70 mmol) was added to a solution of sodium sulfate (18 g, 127 mmol) in 150 mL of water. $HCl_{conc.}$ (6 mL) was added to a suspension of 2-bromo aniline (10 g, 58 mmol) in 50 mL of water. A small amount of DMSO was added until the solution had cleared up. This mixture was then added to the previous solution followed by a solution of hydroxylamine hydrochloride (15 g, 216 mmol) in 70 mL of water. The mixture was heated slowly to reflux (over 90 minutes). Refluxed was then maintained for 10 minutes. The reaction was then cooled down to room temperature and filtered. The light brown solids were washed thoroughly with water and dried in vacuo. 7.95 g of solids was obtained (56%). NMR $^1$H (ppm, $CDCl_3$): 8.90 (br. s., 1H), 8.39 (d, $J^3$=8.1 Hz, 1H), 7.93 (br. s., 1H), 7.54 (d, $J^3$=8.1 Hz, 1H), 7.32 (t, $J^3$=7.8 Hz, 1H), 6.99 (t, $J^3$=7.5 Hz, 1H).

144B. 7-bromoisatin. N-(2-Bromo-phenyl)-2-hydroxyimino-acetamide from example 144A (7.8 g, 32 mmol) was added in small portions to 41 mL of sulfuric acid at 60° C. so as to keep the reaction temperature under 80° C. After addition the temperature was raised to 80° C. and the reaction was stirred at this temperature for 1 hr. The mixture was than cooled to room temperature and poured onto crushed ice. The red solids formed were isolated by filtration, rinsed thoroughly with water and dried in vacuo. 6.36 g of solid was obtained (88%). NMR $^1$H (ppm, acetone-$d^6$): 10.2 (br. s., 1H), 7.79 (d, $J^3$=8.1 Hz, 1H), 7.54 (d, $J^3$=7.3 Hz, 1H), 7.09 (t, $J^3$=8.01 Hz, 1H).

144C. 2-Amino-3-bromo-benzoic acid. $H_2O_2$ (30%, 141 mL) was added dropwise to a mixture of 7-bromoisatin from example 144B (6.3 g, 28.1 mmol) sodium hydroxide (5% in water, 141 mL). After the addition was finished, the reaction was stirred at 50° C. for 30 minutes. After that time 30 mL HCl 1N were added till pH 4. A white solid precipitated. It was collected by filtration and dried in vacuo. 2.66 g of solids were obtained (44%). NMR $^1$H (ppm, DMSO-$d^6$): 7.85 (m, 1H), 7.55 (m, 1H), 6.5 (m, 1H).

144D. Methyl 2-Amino-3-bromo-benzoate. Trimethylsylildiazomethane (2M solution in THF, 5.6 mL, 13.4 mmol) was added to a solution of 2-Amino-3-bromo-benzoic acid from example 144B (2.32 g, 11.1 mmol) in 1 mL of dry THF at 0° C. After 30 minutes at room temperature, the reaction mixture was concentrated and the crude residue was purified by flash chromatography on $SiO_2$ using Pet. Et./AcOEt 99:1 then 96:4 to afford a white solid (2.23 g, 86%). NMR $^1$H (ppm, $CDCl_3$): 7.83 (d, $J^3$=7.97 Hz, 1H), 7.55 (d, $J^3$=7.7 Hz, 1H), 6.51 (t, $J^3$=7.9 Hz, 1H), 3.87 (s, 3H). MS (+ESI): M+H$^+$ 230.0.

144E. Methyl 2-Amino-3-phenylethynyl-benzoate. Methyl 2-Amino-3-bromo-benzoate from example 144D (2.13 g, 9.26 mmol) and phenyl acetylene (4.33 mL, 37 mmol) were dissolved in 72 mL of triethylamine. CuI (109 mg, 0.6 mmol) and Pd(PPh$_3$)Cl$_2$ (224 mg, 0.32 mmol). The reaction was then stirred at 90° C. for 20 hours. After this time, the reaction was concentrated. The residue was diluted with AcOEt and the organic layer was washed three times with HCl 12%, then water and brine. It was dried over Na$_2$SO$_4$ and concentrated. The crude product was purified by flash chromatography on SiO, using Pet. Et./CH$_2$Cl$_2$ 90:10 to 70:30. 2.35 g of yellow oil was obtained (quantitative yield). NMR $^1$H (ppm, CDCl$_3$): 7.87 (dd, $J^3$=8.03 Hz, $J^4$=3.2 Hz, 1H), 7.56-7.49 (m, 3H), 7.39-7.31 (m, 3H), 6.61 (t, $J^3$=7.9 Hz, 1H), 5.65 (br. s., 1H), 3.87 (s, 3H). MS (+ESI): M+H$^+$ 252.1.

144F. Methyl 2-iodo-3-phenylethynyl-benzoate. Methyl 2-Amino-3-phenylethynyl-benzoate from example 144E (2.35 g, 9.35 mmol) was treated with 18.4 mL of concentrated HCl. 1 mL of dioxane was added to dissolve the precipitate. NaNO$_2$ (715 mg, 10.4 mmol) in solution in 12 mL of water was added dropwise at 0° C. The reaction was stirred at 0° C. for 1 hr. KI (16 g, 93.3 mmol) in solution in 13 mL of water was added and the reaction was then stirred at room temperature for 20 hours. After that time, the reaction mixture was concentrated. Dichloromethane and saturated NaHCO$_3$ were added. The aqueous layer was extracted 3 times with dichloromethane. The combined organic layers were washed with 10% sodium thiosulfate (two times), water and brine and dried over Na$_2$SO$_4$. After concentration the residue was purified by flash chromatography on SiO$_2$ using Pet. Et./AcOEt 98:2 then 95:5. 920 mg of brown oil were obtained (27%). NMR $^1$H (ppm, CDCl$_3$): 7.62-7.58 (m, 3H), 7.39-7.31 (m, 3H), 7.53 (dd, $J^3$=7.7 Hz, $J^4$=1.7 Hz, 1H), 7.37-7.32 (m, 4H), 3.94 (s, 3H).

144G. 2-[3-naphthylaminopropyl]-3-phenylethynyl-benzoic acid methyl ester. 1-iodo-3-naphtylaminopropane from example 144F (262 mg, 0.82 mmol) was placed in a flame dried schlenck flask and dissolved in a mixture of 4 mL of dry toluene and 0.5 mL of dry dimethylacetamide. 118 mg of Zn/Cu complex was then added and the mixture was placed in a sonicator bath. Sonication was applied for 2 hours after which TLC showed complete conversion of starting material. The reaction was left to decant and the supernatant was added to a solution of Methyl 2-iodo-3-phenylethynyl-benzoate (100 mg, 0.26 mmol) and Pd[P(o-tolyl)$_3$]Cl$_2$ (10.8 mg, 0.41 mmol) in 0.8 mL of dry THF. The reaction was stirred for 1 hour at room temperature. Saturated ammonium chloride was added and the reaction was diluted with AcOEt. HCl 2N was then added. The aqueous layer was extracted three times with AcOEt. The combined organic phases were washed with HCl 2N (two times), water and brine, then dried over Na$_2$SO$_4$ and concentrated. The residue was purified by flash chromatography on SiO$_2$ using Pet. Et./AcOEt 95:5 then 80:20. 92 mg of a white solid were obtained (80%). NMR $^1$H (ppm, CDCl$_3$): 7.78-7.75 (m, 3H), 7.66-7.60 (m, 3H), 7.49-7.46 (m, 2H), 7.31-7.29 (m, 3H), 7.21 (t, $J^3$=7.9 Hz, 1H), 3.85 (t, $J^3$=6.7 Hz, 1H), 3.82 (s, 3H), 3.26-3.21 (m, 2H), 2.14-2.04 (m, 2H).

144H. 2-[3-aminopropyl]-3-phenylethynyl-benzoic acid methyl ester. Hydrazine monohydrate (138 µL, 2.8 mmol) was added to a solution of 2-[3-naphthylaminopropyl]-3-phenylethynyl-benzoic acid methyl ester from example 144G (92 mg, 0.22 mmol) in 0.4 mL of methanol. The reaction was stirred at room temperature for 72 hours. HCl 6N was added till pH 1. The mixture was then concentrated to remove methanol and the solid residue was suspended in HCl 1N. It was filtered and the solid were rinsed with more HCl 1N. The acidic phase was washed three times with dichloromethane. Potassium carbonate was then added till pH 12 and the basic phase was extracted three times with dichloromethane. The combined organic layers were dried over Na$_2$SO$_4$ and concentrated. The white solid obtained was used in the next step without further purification.). MS (+ESI): M+H$^+$ 294.3.

144I. 6-Phenylethynyl-2,3,4,5-tetrahydro-benzo[c]azepin-1-one. 2-[3-aminopropyl]-3-phenylethynyl-benzoic acid methyl ester from example 144H (0.22 mmol) was dissolved in dr THF. Potassium terbutoxide (198 mg, 1.76 mmol) was added in one portion at 0° C. The ice bath was removed and the reaction was stirred at room temperature for 12 hours. Saturated ammonium chloride was added and the reaction was extracted three times with AcOEt. The combined organic layers were washed with water and brine, dried over Na$_2$SO$_4$ and concentrated. The residue was purified by preparative TLC using Pet. Et./AcOEt 60:40. 92 mg of a white solid were obtained. NMR $^1$H (ppm, CDCl$_3$): 7.67-7.63

(m, 2H), 7.54-7.50 (m, 2H), 7.36-7.25 (m, 3H), 7.25-7.13 (m, 1H), 6.54 (br. s., 1H), 3.22-3.11 (m, 3H), 2.11-2.03 (m, 3H). MS (+ESI): M+H$^+$ 262.1.

144J. Compound (157)

Using preparation method 3, 144I was reacted with phosgene to provide a carbamoylchloride. Using preparation method 4, (S)-isobutyl-(L)-cysteine hydrochloride was protected. The carbamoylchloride and TMS protected amino acid were reacted using Preparation Method 5.

Example 145

Compound (158)

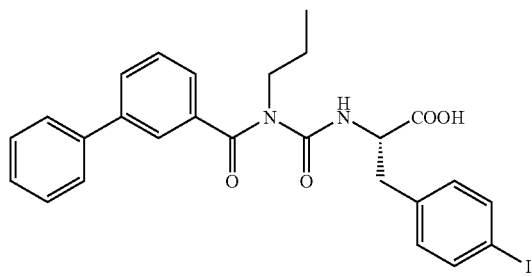

(158)

This synthesis was performed on Lantern™ solid phase.

145A

A solution of N-Fmoc-4-iodo-(L)-phenylalanine (62 mg, 0.24 mmol), diisopropylcarbodiimide (18.6 µL, 0.12 mmol) and DMAP (1.1 mg, 9 µmol) in dry DMF was added to HMP-lantern (2, 15 µmol loading each). The reaction was stood at room temperature for 2 hours. After that time, the lanterns were rinsed with DMF (3×3 min.) and CH$_2$Cl$_2$ (3×3 min.). The lanterns were then air-dried.

145B

The lanterns were then treated two times with 1 mL of a 20% piperidine solution in DMF (1×5 min., 1×25 min). After this, the lanterns were rinsed with DMF (3×5 min.), MeOH (3×5 min.) and CH$_2$Cl$_2$ (3×5 min.). The lanterns were dried in vacuo.

145C

To the deprotected lantern-supported compounds was added 0.5 mL of CH$_3$CN and 100 µL of propylene oxide. This mixture was treated at 0° C. with were treated with a solution of carbamoylchloride from Example 1B using Preparation Method 3 (0.3 mmol) in 0.5 mL of CH$_3$CN. The reaction was stood at room temperature for 16 hours. After that time, the lanterns were rinsed with CH$_3$CN (3×3 min.), MeOH (3×3 min.) and CH$_2$Cl$_2$ (3×3 min.).

145D: Compound (158)

On one lantern (15 µmol theoretical loading): The lantern was treated with a 20% TFA solution in CH$_2$Cl$_2$. The reaction was stood at room temperature for 1 hour. After this time the lantern was removed and the remaining solution was concentrated. The remaining residue was dissolved in a mixture CH$_3$CN/H$_2$O 90:10 and freeze-dried to give compound (158) as a white powder. HPLC analysis, (1 mL gradient 0% MeOH to 100% MeOH, run time: 18 minutes; retention time: 11.17 minutes) showed high purity was achieved. NMR $^1$H (CDCl$_3$, ppm): 9.51 (d, J$^3$=6.5 Hz, 1H), 7.71-7.37 (m, 11H), 7.01 (d, J$^3$=8.3 Hz, 1H), 4.77-4.76 (m, 1H), 3.67-3.62 (m, 2H), 3.23-3.07 (m, 2H), 1.49 (sext., J$^3$=7.71 Hz, 2H), 0.69 (t, J$^3$=7.4 Hz, 3H).

Example 146

Compound (15)

In this example, compound (15) from Example 13 was prepared using a solid phase synthesis on lantern using the following procedure.

146A

One lantern from Example 64C (15 µM theoretical loading) was swelled in 320 µL of dry DMF for 10 min. 80 µL of dry THF and 400 µL of dry diisopropylethylamine were added, followed by phenyl boronic acid (18 mg, 0.15 mmol) and Pd(Ph$_3$)$_4$ (3.5 mg, 20 mol %). The reaction was then stood under a nitrogen atmosphere for 18 hours. After this time, the lantern was successively rinsed with DMF (3×3 min.), sodium diethyldithiocarbamate DMF solution (sodium diethyldithiocarbamate 5 mg/mL, diisopropylethylamine 5 µL/mL, 3×3 min.), MeOH (3×3 min.) and CH$_2$Cl$_2$ (3×3 min.). The lantern was then air dried.

146B: Compound (15)

On the lantern from Example 65A (15 µmol theoretical loading): The lantern was treated with 1 mL of a 20% TFA solution in CH$_2$Cl$_2$. The reaction was stood at room temperature for 1 hour. After this time the lantern was removed and rinsed with CH$_2$Cl$_2$ for 5 minutes. The two solutions were combined and concentrated to give compound (15) as a yellowish film. Mass spectrometry (electrospray, positive ion): [M+H]$^+$: 507.2 (molecular weight: 506.22). HPLC analysis, (1 mL gradient 0% MeOH to 100% MeOH, run time: 18 minutes; retention time: 11.32 minutes) showed high purity was achieved and identical retention time compared to a sample of compound (15) from Example 13.

Biological Examples

Measurement of competition of benzoylurea compounds with Bim26-mer for a Bcl-2 binding site.

Alphascreen (Amplified Luminescent Proximity Homogenous Assay) is a bead based technology which measures the interaction between molecules. The assay consists of two hydrogel coated beads which, when bought into close proximity by a binding interaction, allow the transfer of singlet oxygen from a donor bead to an acceptor bead.

Upon binding and excitation with laser light at 680 nm, a photosensitiser in the donor bead converts ambient oxygen to a more excited singlet state. This singlet oxygen then diffuses across to react with a chemiluminescer in the acceptor bead. Fluorophores within the same bead are activated resulting in the emission of light at 580-620 nm.

Screening of the benzoylurea test compounds was performed using the Alphascreen GST (glutathione s-transferase) detection kit system. Test compounds were titrated into the assay which consisted of GST tagged Bcl$_w$ ΔC29 protein (0.05 nM Final concentration) and Biotinylated Bim BH3-26 peptide, Biotin-DLRPEIRIAQELRRIGDEFNE-TYTRR (3.0 nM Final concentration). For the GST tagged Bcl-x$_L$ assay, GST tagged Bcl-x$_L$ ΔC25 protein (0.6 nM Final concentration) and Biotinylated Bim BH3-26 peptide, Biotin-DLRPEIRIAQELRRIGDEFNETYTRR (5.0 nM Final concentration) were used. To this reaction mix anti-GST coated acceptor beads and Streptavidin coated donor beads, both at 15 μg/ml Final concentration, were added and the assay mixture incubated for 4 hours at room temperature before reading. Similarly when the Bcl-2 protein was Mcl-1, GST tagged Mcl-1 protein (0.4 nM Final concentration) and Biotinylated Bak BH3 peptide, Biotin-PSST-MGQVGRQLAIIGDDINRRYDSE-OH (4.0 nM Final concentration) were used.

Detailed Protocol:
1) prepare a 384 well with 4.75 μL of buffer and 0.25 μL of compounds (20 mM in DMSO) per well.
2) Mix the binding partners, in one tube add Bcl-w, Bcl-x$_L$ or Mcl-1 and the acceptor beads, in the second tube add Biotinylated BH3 peptide and the donor beads.
3) Pre-incubate the two pairs of binding partners for 30 minutes.
4) Add 1 μL of acceptor beads:Bcl-w, Bcl-x$_L$ or Mcl-1 protein mix to each well.
5) Seal the plate and incubate at room temperature for 30 minutes.
6) Add 10 μL of donor bead:BH3 peptide mix to each well.
7) Seal the plate, cover with foil and incubate for 4 hours.

Assay buffer contained 50 mM Hepes pH 7.4, 10 mM DTT, 100 mM NaCl, 0.05% Tween and 0.1 mg/ml casein. Bead dilution buffer contained 50 mM Tris, pH 7.5, 0.01% Tween and 0.1 mg/ml casein. The final DMSO concentration in the assay was 0.5%. Assays were performed in 384 well white Optiplates and analysed on the PerkinElmer Fusion alpha plate reader (Ex680, Em520-620 nM).

The GST Alphascreen detection kit and Optiplates were purchased from PerkinElmer.

The results of the binding assay are shown in Table 3.

TABLE 3

Binding affinities of Benzoylurea Compounds

| Compound No. | Bcl-wΔ29 IC$_{50}$ (μM) | Bcl-x$_L$Δ25 IC$_{50}$ (μM) | Mcl-1 IC$_{50}$ (μM) |
|---|---|---|---|
| (1) | 38[a] | 70.1 | — |
| (2) | 57 | 56.8 | — |
| (3) | 65 | 65.8 | — |
| (4) | 149 | 148 | — |
| (5) | 266 | 152.8 | — |
| (6) | 73 | 54.2 | — |
| (7) | 37 | 45.2 | — |
| (8) | 46 | 36.4 | — |
| (9) | 14[a] | — | — |
| (10) | 26[a] | — | — |
| (11) | 104 | — | — |
| (12) | 46[a] | — | — |
| (13) | 31 | — | — |
| (14) | 36 | — | — |
| (15) | 41 | — | — |
| (16) | 130 | — | — |
| (17) | 55 | — | — |
| (18) | 60 | — | — |
| (19) | 132 | — | — |
| (21) | 84 | — | — |
| (22) | 80 | — | — |
| (23) | 76 | — | — |
| (24) | 31.2 | — | — |
| (25) | 261 | — | — |
| (27) | 194 | — | — |
| (28) | 300 | — | — |
| (29) | 88 | — | — |
| (30) | 147 | — | — |
| (31) | 165 | — | — |
| (33) | 72 | — | — |
| (34) | 72 | — | — |
| (35) | 66 | — | — |
| (36) | 47 | — | — |
| (37) | 60 | — | — |
| (38) | 297 | — | — |
| (39) | 50 | — | — |
| (40) | 63 | — | — |
| (42) | 49 | — | — |
| (43) | 57 | — | — |
| (45) | 69 | — | — |
| (46) | 38 | — | — |
| (47) | 62 | — | — |
| (48) | 68 | — | — |
| (52) | 96 | — | — |
| (58) | 48 | — | — |
| (59) | 68 | — | — |
| (62) | 48 | — | — |
| (63) | 136 | — | — |
| (64) | 74 | — | — |
| (65) | 60 | — | — |
| (66) | 58 | — | — |
| (67) | 92 | — | — |
| (70) | 153 | — | — |
| (71) | n.b.[b] | — | — |
| (72) | n.b.[b] | — | — |
| (81) | 144 | — | — |
| (82) | 45 | 27 | 169 |
| (83) | 35 | 14 | 77 |
| (84) | 27 | 11 | 61 |
| (85) | 40 | n.b.[b] | 95 |
| (86) | 82 | 283 | n.b.[b] |
| (87) | 99 | 151 | 161 |
| (88) | 49 | 51 | 154 |
| (89) | 50 | 86 | 107 |
| (90) | 39 | 22 | 70 |
| (91) | 32 | 16 | 92 |
| (92) | 67 | 36 | n.b.[b] |
| (93) | 26 | 27 | 53 |
| (94) | 19 | 23 | 46 |
| (95) | 35 | 73 | 94 |
| (96) | 52 | 153 | 133 |
| (97) | 68 | 199 | 264 |
| (98) | 32 | 93 | 107 |
| (99) | 60 | 163 | 168 |
| (100) | 18 | 48 | 52 |
| (101) | 19 | 42 | 55 |
| (102) | 18 | 50 | 51 |
| (103) | 18 | 53 | 36 |
| (104) | 205 | 187 | 267 |
| (105) | 71 | 183 | 164 |
| (106) | 102 | 182 | 251 |
| (107) | 37 | 70 | 73 |
| (108) | 49 | 87 | 72 |
| (109) | 29 | 81 | 65 |
| (110) | 37 | 85 | 64 |
| (111) | 36 | 115 | 86 |
| (112) | 40 | 119 | 112 |
| (113) | 28 | 94 | 65 |
| (114) | 32 | 85 | 58 |
| (115) | — | 32 | — |
| (116) | — | 19 (26) | — |
| (117) | — | 35 (44) | — |
| (118) | — | 34 (39) | — |
| (119) | — | 67 (52) | — |
| (120) | — | 44 (46) | — |
| (121) | — | 141 (165) | — |
| (122) | — | 26 | — |
| (123) | — | 30 | — |
| (124) | — | 33 | — |

TABLE 3-continued

Binding affinities of Benzoylurea Compounds

| Compound No. | Bcl-wΔ29 IC$_{50}$ (µM) | Bcl-x$_L$Δ25 IC$_{50}$ (µM) | Mcl-1 IC$_{50}$ (µM) |
|---|---|---|---|
| (125) | — | 44 | — |
| (126) | — | 90 | — |
| (127) | — | 40 | — |
| (128) | — | 53 | — |
| (129) | — | 37 | — |
| (130) | — | 39 | — |
| (131) | — | 20 | — |
| (132) | — | 24 | — |
| (133) | — | 27 | — |
| (134) | — | 51 | 181 |
| (135) | — | 32 | 57 |
| (136) | — | 23 | 204 |
| (137) | — | 9.5 | 132 |
| (138) | — | 26 | 146 |
| (139) | — | 28 | 80 |
| (140) | — | 44 | n.b.[b] |
| (141) | — | 28 | 84 |
| (142) | — | 32 | 70 |
| (143) | — | 30 | 74 |
| (144) | — | 39 | 66 |
| (145) | — | 48 | 92 |
| (146) | — | 46 | n.b.[b] |
| (147) | — | 50 | 85 |
| (148) | — | 172 | 71 |
| (149) | — | 107 | — |
| (150) | — | n.b.[b] | — |
| (151) | — | 212 | — |
| (152) | — | 48 | — |
| (153) | — | 40 | — |
| (154) | — | 42 | — |
| (155) | — | 53 | — |
| (156) | — | 10 | — |

[a]Tested in a separate experiment;
[b]n.b. not binding in the assay conditions
[c]—not tested

Cell Based Assay

The efficacy of the compounds of the present invention can also be determined in cell based killing assays using a variety of cell lines and mouse tumor models. For example, their activity on cell viability can be assessed on a panel of cultured tumorigenic and non-tumorigenic cell lines, as well as primary mouse or human cell populations, e.g. lymphocytes. For these assays, 5,000-20,000 cells are cultured at 37° C. and 10% CO$_2$ in appropriate growth media, e.g.: 100 µL Dulbecco's Modified Eagle's medium supplemented with 10% foetal calf serum, asparaginase and 2-mercaptoethanol in the case of pre-B Eµ-Myc mouse tumors in 96 well plates. Cell viability and total cell numbers can be monitored over 1-7 days of incubation with 1 nM-100 µM of the compounds to identify those that kill at IC50<10 µM. Cell viability is determined by the ability of the cells to exclude propidum iodide (10 µg/mL by immunofluorescence analysis of emission wavelengths of 660-675 nm on a flow cytometer (BD FACScan). Alternatively, a high throughput calorimetric assay such as the Cell Titre 96. AQueous Non-Radioactive Cell Proliferation Assay (Promega) may be used. Cell death by apoptosis is confirmed by pre-incubation of the cells with 50 µM of a caspase inhibitor such as zVAD-fmk. Drug internalisation is confirmed by confocal microscopy of conjugates labelled with a fluorochrome such as Fitc.

The conjugates of the present invention can also be evaluated for the specificity of their targets and mode of action in vivo. For example, if a conjugate comprises a compound of the invention that binds with high selectivity to Bcl-2, it should not kill cells lacking Bcl-2. Hence, the specificity of action can be confirmed by comparing the activity of the compound in wild-type cells with those lacking Bcl-2, derived from Bcl-2-deficient mice.

Antibody Production

Antibodies suitable for preparation of conjugates may be prepared by techniques known in the art. See, for example, Galfre et. al., 1977.

Coupling Antibodies and Compounds of the Invention

The antibody is reacted with NHS-activated maleimide-ACP, sulfosuccinimidyl-4-[N-maleimidomethyl]cyclohexane-1-carboxylate, 4-succinimidyloxycarbonyl-α-methyl-α-(2-pyridyldithio)toluene or LC-SMPT to prepare an antibody decorated with multiple linkers. The antibody is then reacted with a thiol group on a thiol containing compound of the invention.

REFERENCES

G. P. Adams, J. E. McCartney, M. S. Tai, H. Oppermann, J. S. Huston, W. F. Stafford 3$^{rd}$, M. A. Bookman, I. Fand. L. L. Houston, L. M. Weiner, *Cancer Res.*, 1993, 53: 4026-34.

Ausubel et. al., Current Protocols in Molecular Biology, John Wiley & Sons Inc., 1994-1998.

J. B. Baell, D. C. S. Huang, *Biochem. Pharmacol.* 2002, 64, 851-863.

P. Bouillet, S. Cory, L. C. Zhang, A. Strasser, J. M. Adams, *Developmental Cell.* 2001, 1, 645.

N. D. Brewis, A. Phelan, N. Normand, E. Choolun, P. O'Hare, *Mol. Ther.*, 2003, 7(2), 262-70.

Brummer et al. *Synthesis*, 1998, 1742.

J. Carlsson, H. Dreven, R. Axen, *Biochem. J.*, 2001, 173: 723-37.

Chen et. al., *O.P.P.I. Briefs*, 2000, 32(4):381.

Coligan et. al., Current Protocols in Immunology, John Wiley & Sons, Inc., 1991.

S. Cory, J. A. Adams, *Nature Reviews/Cancer* 2002, 2, 647.

A. J. Cumber, E. S. Ward, G. Winter, G. D. Parnell, E. J. Wawrzynczak, *J. Immunol.*, 1992, 149: 120-126.

J. Davies, L. Riechmann, *FEBS Lett.*, 1994, 339: 285-290.

Deardon, C., *Biodrug*, 2002, 1b: 283-301.

D. J. Dunican and P. Doherty, *Biopolymers (Peptide Science)*, 2001, 60: 45-60.

S. S. Dharap and T. Minko, *Pharm. Res.*, 2003, 20 (6): 889-896.

A. Egle, P. Bouillet, A. W. Harris, S. Cory, *Blood*, 2003, 102, 135A.

G. Galfre, S. C. Howe, C. Milstein, G. W. Butcher, J. C. Howard, *Nature*, 1977, 266: 550-552.

R. Glockshuber, M. Malia, I. Pfitzinger, A. Plückthun, *Biochem.*, 1990, 29: 1363-1367.

A. C. Goulet, V. S. Goldmacher, J. M. Lambert, C. Baron, D. D. Roy, E. Kouassi, *Blood*, 1997, 90 (6): 2364-75.

D. R. Green, G. I. Evan, *Cancer Cell.* 2002, 1, 19.

C. Hamers-Casterman, T. Atarhouch, S. Muyldermans, G. Robinson, C. Hamers, E. B. Songa, N. Bendahman, R. Hamers, *Nature*, 1993, 363: 446-448.

M. G. Hinds, M. Lackmann, G. L. Skea, P. J. Harrison, D. C. S. Huang, C. L. Day, *EMBO J.* 2003, 22, 1497.

J. H. Horner, O. M. Musa, A. Bouvier, M. Newcomb, *Journal of the American Chemical Society* 1998, 120, 7738.

R. Ju, J. M. Lambert, L. R. Pierce, R. R. Traut, *Biochemistiy*, 1978, 17: 5399-5406.

S. H. Kaufmann, M. O. Hengartner, *Trends in Cell Biology.* 2001, 11, 526.

I. M. Klotz and R. E. Heiney, *Arch. Biochem. Biophys.*, 1962, 96: 605-612.

G. Köhler and C. Milstein, *Nature*, 1975, 256: 495-497.

S. A. Kostelny, M. S. Cole, J. Y. Tso, *J. Immunol.,* 1992, 148: 1547-1553.

A. Krebber, S. Bomhauser, J. Burmester, A. Honnerger, J. Wiluda, H. R. Bosshard, A. Plückthun, *J. Immunol. Methods,* 1997, 201(1): 35-55.

J. Ku, P. G. Schultz, *Proc. Natl. Acad. Sci. USA,* 1995, 92: 6552-6556.

A. Letai, M. C. Bassik, L. D. Walensky, M. D. Sorcinelli, S. Weiler, S. J. Korsmeyer, *Cancer cell,* 2002, 2(3): 183-92.

X. Liu, S. Dai, Y. Zhu, P. Marrack, J. Kappler, *Immunity.* 2003, 19, 341.

D. L. Ludwig, D. S. Pereira, Z. Zhu, D. J. Hicklin, P. Bohlen, *Oncogene,* 2003, 22 (56): 9097-9106.

A. J. Marks, M. Cooper, K. Orchard, N. I. Folarin, K. Ganeshaguru, A. V. Hoffbrand, A. B. Mehta, R. G. Wickremasinghe, Abstract, *Blood,* (11) 247, Part 1, Nov. 16, 2003.

S. W. Muchmore, M. Sattler, H. Liang, R. P. Meadows, J. E. Harlan, H. S. Yoon, D. Nettesheim, B. S. Chang, C. B. Thompson, S. L. Wong, S. L. Ng, S. W. Fesik, *Nature.* 1996, 381, 335.

E. Negishi and L. Anastasia, *Chem. Rev.,* 2003, 103, p 1979.

T. Oltersdorf, S. W. Elmore, A. R. Shoemaker, R. C. Armstrong, D. J. Augeri, B. A. Belli, M. Bruncko, T. L. Deckwerth, J. Dinges, P. J. Hajduk, M. K. Joseph, S. Kitada, S. J. Korsmeyer, A. R. Kunzer, A. Letai, C. Li, M. J. Mitten, D. G. Nettesheim, S. Ng, P. M. Nimmer, J. M. O'Connor, A. Oleksijew, A. M. Petros, J. C. Reed, W. Shen, S. K. Tahir, C. B. Thompson, K. J. Tomaselli, B. Wang, M. D. Wendt, H. Zhang, S. W. Fesik, S. H. Rosenberg, *Nature,* 2005, 435, 677-681.

P. Pack, A. Plückthun, *Biochem.,* 1992, 31: 1579-1584.

G. A. Patani and E. J. LaVoie, *Chem. Rev.,* 1996, 96, 3147-3176.

A. M. Petros, D. G. Nettesheim, Y. Wang, E. T. Olejniczak, R. P. Meadows, J. Mack, K. Swift, E. D. Matayoshi, H. Zhang, C. B. Thompson, S. W. Fesik, *Protein Science.* 2000, 9, 2528.

Plückthun et. al., Antibody Engineering: A practical approach. 203-252, 1996.

M. J. Poznansky, R. Singh, B. Singh, G. Fantus, *Science,* 1984, 223: 1304-1306.

Y. Reiter, U. Brinkmann, S. H. Jung, B. Lee, P. G. Kasprzyk, C. R. King, I. Pastan, *J. Biol. Chem.,* 1994a, 269: 18327-18331.

Y. Reiter, U. Brinkmann, R. J. Kreitman, S. H. Jung, B. Lee, I. Pastan, *Biochem.,* 1994b, 33: 5451-5459.

Y. Reiter, L. H. Pai, U. Brinkmann, Q. C. Wang, I. Pasian, *Cancer Res.,* 1994c, 54: 2714-2718.

P. Sapra and T. M. Allen, *Cancer Res.,* 2002, 62 (24): 7190-4.

M. Sattler, H. Liang, D. Nettesheim, R. P. Meadows, J. E. Harlan, M. Eberstadt, H. S. Yoon, S. B. Shuker, B. S. Chang, A. J. Minn, C. B. Thompson, S. W. Fesik, *Science.* 1997, 275, 983.

A. D. Schimmer, D. W. Hedley, S. Chow, N. A. Pham, A. Chakrabartly, D. Bouchard, T. W. Mak, M. R. Trus, M. D. Minden, *Cell Death Differ.,* 2001, 8(7): 725-733.

T. Seko, M. Kato, H. Kolino, S. Ono, K. Hashimura, H. Takimizu, K. Nakai, H. Maegawa, N. Katsube, M. Toda, *Bioorg. Med. Chem.,* 2003, 11:1901-1913.

S. Shangary and D. E. Johnson, *Biochemistry,* 2002, 41(30): 9485-95.

E. L. Snyder, B. R. Meade, C. C. Saenz, S. F. Dowdy, *PloS Biology,* 2004, 2, 0186-0193.

P. E. Thorpe, P. M. Wallace, P. P. Knowles, M. G. Relf, A. N. Brown, G. J. Watson, R. E. Knyba, E. J. Wawrzynczak, D. C. Blokey, *Cancer Res.,* 1987, 47: 5924-5931.

F. N. Uckun, W. E. Evans, C. J. Forsyth, K. G. Waddick, L. T. Ahlgren, L. M. Chelstrom, A. Burkhardt, J. Bolen, D. E. Meyers, *Science,* 1995, 267 (5199): 886-898.

H. W. G. Van Herwijnen and U. H. Brinker, *Journal of Organic Chemistry,* 2001, 66(8), 2874-2876.

D. Wang, S. Moore, *Biochemistry,* 1977, 16: 2937-2941.

D. Wang, Q. Li, W. Hudson, E. Berren, F. Uckun and J. H. Kersey, *Bioconjug. Chem.,* 1997, 8 (6): 878-84.

J. L. Wang, Z. J. Zhang, S. Choksi, S. Shan, Z. Lu, C. M. Croce, E. S. Alnemri, R. Komgold, Z. Huang, *Cancer. Res.,* 2000, 60(6): 498-502.

E. S. Ward, D. Gussow, A. D. Griffiths, P. T. Jones, G. Winter, *Nature,* 1989, 341: 544-546.

K. O. Webber, Y. Reiter, U. Brinkmann, R. Kreitman, I. Pastan, *Mol. Immunol.* 1995, 32: 249-258.

G. Winter and C. Milstein, *Nature,* 1991, 349: 293-9.

N. R. Worrell, A. J. Cumber, G. D. Parnell, A. Mirza, J. A. Forrester, W. C. Ross, *Anticancer Drug Design,* 1986, 1: 179-188.

H. Yin and A. D. Hamilton, *Bioorg. Med. Chem. Lett.,* 2004, 14, 1375-1379.

S. Yoshitake, Y. Yamada, E. Ishikawa, R. Masseyeff, *Eur. J. Biochem.,* 1979, 101: 395-399.

J. Y. Zhang *Nature Reviews/Drug Discovery* 2002, 1, 101.

The claims defining the invention are as follows:

1. A compound of formula (I):

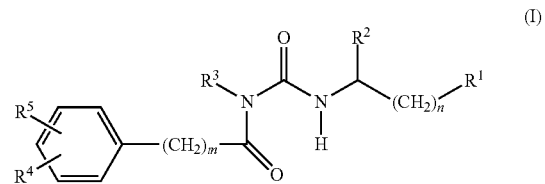

wherein $R^1$ is selected from $CO_2H$ or a carboxylic acid or carboxylate bioisostere;

$R^2$ is selected from an amino acid side chain and a group $$R^a\text{—}(CHR')_x\text{-}A\text{-}(CH_2)_y\text{—}$$

wherein A is a covalent bond or is selected from O, S, SO, $SO_2$ and $NR^6$, $R^a$ is H, cycloalkyl, cycloalkenyl, aryl, heterocyclyl, heteroaryl or $R^b$ where $R^b$ is

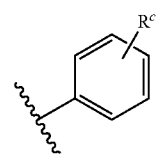

and $R^c$ is selected from heteroaryl, aryl, aryl($C_{2-6}$alkenyl), aryl($C_{2-6}$alkynyl), heteroaryl($C_{2-6}$alkenyl) and heteroaryl($C_{2-6}$alkynyl), R' is H or $C_{1-6}$alkyl, x and y are independently 0 or an integer from 1 to 6 provided that the sum of x and y is 1 to 6;

$R^3$ is selected from $C_{1-6}$alkyl, $C_{2-6}$alkenyl, $C_{2-6}$alkynyl, cycloalkyl, cycloalkenyl, aryl, heterocyclyl, heteroaryl and a group $$R^d\text{—}(CH_2)_p\text{—}W\text{—}(CH_2)_q\text{—}$$

wherein W is selected from a covalent bond, O, S and $NR^6$, $R^d$ is selected from H, cycloalkyl, cycloalkenyl, aryl, heterocyclyl and heteroaryl; p is an integer from 1 to 6, q is 0 or an integer from 1 to 5 provided that the sum of p and q is 1 to 6;

$R^4$ is selected from $C_{1-6}$alkyl, $C_{2-6}$alkenyl, $C_{2-6}$alkynyl, cycloalkyl, $C_{1-6}$alkyloxy, $C_{2-6}$alkenyloxy, $C_{2-6}$alkynyloxy, cycloalkoxy, $C_{1-6}$alkylthio, $C_{2-6}$alkenylthio, $C_{2-6}$alkynylthio, cycloalkylthio, halogen, aryl, aryl($C_{1-6}$alkyl)-, aryl($C_{2-6}$alkenyl), aryl($C_{2-6}$alkynyl), heterocyclyl, heterocyclyl($C_{1-6}$alkyl)-, heterocyclyl($C_{2-6}$alkenyl), heterocyclyl($C_{2-6}$alkynyl), heteroaryl, heteroaryl($C_{1-6}$alkyl)-, heteroaryl($C_{2-6}$alkenyl) and heteroaryl($C_{2-6}$ alkynyl);

$R^5$ is selected from H, halogen, $C_{1-6}$alkyl, $C_{2-6}$alkenyl, $C_{2-6}$alkynyl, $C_{1-6}$alkyloxy, $C_{2-6}$alkenyloxy, $C_{2-6}$alkynyloxy, $C_{1-6}$alkythio, $C_{2-6}$alkenylthio, $C_{2-6}$alkynylthio, CN and $C(R^7)_3$ or when $R^5$ is in the 2- or 5-position, $R^5$ and $R^3$ taken together may form a 5 to 10 membered ring;

$R^6$ is selected from H, $C_{1-6}$alkyl, $C_{2-6}$alkenyl and $C_{2-6}$alkynyl;

each $R^7$ is independently selected from H and halogen;

m is 0 or an integer from 1 to 6; and n is 0 or an integer from 1 to 3;

wherein each alkyl, alkenyl, alkynyl, cycloalkyl, aryl, heterocyclyl and heteroaryl is optionally substituted with one or more optional substituents;

and pharmaceutically acceptable salts and prodrugs thereof; with the proviso that when $R^1$ is COOH, $R^2$ is $C_6H_5$—$CH_2S$—$CH_2$—, $R^4$ is 3-$C_6H_5$ and $R^5$ is H, $R_3$ is not $CH_3CH_2$—.

2. A compound according to claim 1, wherein $R^1$ is $CO_2H$, tetrazole, tetrazolate or an acylbenzenesulfonamide.

3. A compound according to claim 2, wherein $R^1$ is $CO_2H$.

4. A compound according to claim 1, wherein $R^2$ is $R^a$—(CHR')$_x$-A-(CH$_2$)$_y$— in which $R^a$ is H, optionally substituted cycloalkyl or optionally substituted aryl, x is 0 or 1 to 4, R' is H or $C_{1-3}$alkyl, A is O, S or SO and y is 1 to 3.

5. A compound according to claim 1, wherein $R^2$ is $R^a$—(CHR')$_x$-A-(CH$_2$)$_y$— in which $R^a$ is optionally substituted aryl or optionally substituted heteroaryl, R' is H, the sum of x and y is 1 to 4 and A is a covalent bond.

6. A compound according to claim 1, wherein $R^3$ is $C_{1-6}$alkyl, optionally substituted cycloalkyl or a group $R^d$—(CH$_2$)$_p$—W—(CH$_2$)$_q$— in which $R^d$ is optionally substituted cycloalkyl, optionally substituted aryl, optionally substituted heterocyclyl or optionally substituted heteroaryl, W is a covalent bond and the sum of p and q is 1 to 3, or $R^d$ is H, W is O or S and the sum of p; and q is 2 to 4.

7. A compound according to claim 1, wherein $R^4$ is $C_{1-6}$alkyl, $C_{2-6}$alkenyl, $C_{2-6}$alkynyl, 3- or 4-aryl, aryl($C_{1-3}$alkyl)-, aryl($C_{2-3}$alkenyl)- or aryl($C_{2-3}$alkynyl)- wherein aryl is optionally substituted with one or more halogen, $C_{1-6}$alkyl, $C_{1-6}$alkoxy, trifluoromethyl, hydroxy($C_{1-6}$alkyl), CN or $C_{1-6}$acyl.

8. A compound according to claim 7, wherein $R^4$ is 3- or 4-phenyl, naphthyl or phenyl(ethynyl) in which the phenyl or naphthyl groups are optionally substituted.

9. A compound according to claim 1, wherein $R^5$ is hydrogen, halogen, methyl or methoxy.

10. A compound according to claim 9, wherein $R^5$ is hydrogen.

11. A compound according to claim 1, wherein m is 0.

12. A compound according to claim 1, wherein n is 0.

13. A compound according to claim 1, wherein said compound is a compound of formula (II)

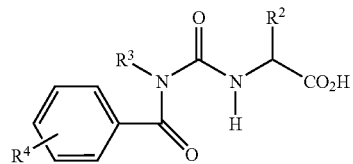

(II)

wherein $R^2$ and $R^3$ are as defined for formula (I) in claim 1 and $R^4$ is $C_{1-6}$alkyl, $C_{2-6}$alkenyl, $C_{2-6}$alkynyl, 3-phenyl, 3-(2-naphthyl), 3-(1-naphthyl), 3-benzyl, 4-phenyl, 4-benzyl, 3-(phenylethynyl) or 4-(phenylethynyl), wherein each phenyl, naphthyl or benzyl group is optionally substituted with one or more substituents selected from $C_{1-6}$alkyl, $C_{2-6}$alkenyl, $C_{2-6}$alkynyl, $C_{1-6}$alkoxy, $C_{2-6}$alkenyloxy and halogen, and pharmaceutically acceptable salts or prodrugs thereof, with the proviso that when $R^2$ is $C_6H_5$—$CH_2S$—$CH_2$— and $R^4$ is 3-phenyl, $R^3$ is not ethyl.

14. A compound according to claim 1, wherein said compound is a compound of formula (IIa)

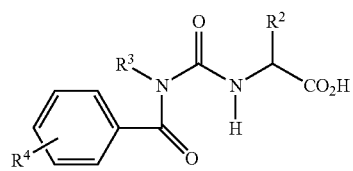

(IIa)

wherein $R^2$ is defined as above for formula (I) in claim 1, $R^3$ is selected from $C_{3-6}$alkyl, $C_{2-6}$alkenyl, $C_{2-6}$alkynyl, cycloalkyl, aryl, heterocyclyl, heteroaryl and a group

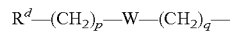

$R^d$—(CH$_2$)$_p$—W—(CH$_2$)$_q$— wherein W is selected from a covalent bond, 0, S or NR$^6$, $R^d$ is selected from H, cycloalkyl, cycloalkenyl, aryl, heterocyclyl and heteroaryl; p is an integer from 1 to 6, q is 0 or an integer from 1 to 5 provided that the sum of p and q is 1 to 6;

$R^4$ is $C_{1-6}$alkyl, $C_{2-6}$alkenyl, $C_{2-6}$alkynyl, 3-phenyl, 3-(2-naphthyl), 3-(1-naphthyl), 3-benzyl, 4-phenyl, 4-benzyl, 3-(phenylethynyl) or 4-(phenylethynyl), wherein each phenyl, naphthyl or benzyl group is optionally substituted with one or more substituents selected from $C_{1-6}$alkyl, $C_{2-6}$alkenyl, $C_{2-6}$alkynyl, $C_{1-6}$alkoxy, $C_{2-6}$alkenyloxy and halogen, and pharmaceutically acceptable salts or prodrugs thereof.

15. A composition comprising a compound according to claim 1 and a pharmaceutically acceptable carrier.

16. A composition comprising a compound according to claim 2 and a pharmaceutically acceptable carrier.

17. A composition comprising a compound according to claim 3 and a pharmaceutically acceptable carrier.

18. A composition comprising a compound according to claim 4 and a pharmaceutically acceptable carrier.

19. A composition comprising a compound according to claim 5 and a pharmaceutically acceptable carrier.

20. A composition comprising a compound according to claim 6 and a pharmaceutically acceptable carrier.

21. A composition comprising a compound according to claim 7 and a pharmaceutically acceptable carrier.

22. A composition comprising a compound according to claim 8 and a pharmaceutically acceptable carrier.

23. A composition comprising a compound according to claim 9 and a pharmaceutically acceptable carrier.

24. A composition comprising a compound according to claim 10 and a pharmaceutically acceptable carrier.

25. A composition comprising a compound according to claim 11 and a pharmaceutically acceptable carrier.

26. A composition comprising a compound according to claim 12 and a pharmaceutically acceptable carrier.

27. A composition comprising a compound according to claim 13 and a pharmaceutically acceptable carrier.

28. A composition comprising a compound according to claim 14 and a pharmaceutically acceptable carrier.

* * * * *